(12) United States Patent
Galley et al.

(10) Patent No.: US 8,354,441 B2
(45) Date of Patent: Jan. 15, 2013

(54) OXAZOLINE DERIVATIVES

(75) Inventors: Guido Galley, Rheinfelden (DE); Roger Norcross, Olsberg (CH); Alessandra Polara, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 45 days.

(21) Appl. No.: 12/938,401

(22) Filed: Nov. 3, 2010

(65) Prior Publication Data

US 2011/0112080 A1    May 12, 2011

(30) Foreign Application Priority Data

Nov. 11, 2009  (EP) .................................... 09175712

(51) Int. Cl.
*A61K 31/42*    (2006.01)
*C07D 263/08*    (2006.01)

(52) U.S. Cl. ......................... 514/377; 548/233
(58) Field of Classification Search ........................ None
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Eble | |
| 3,577,428 A | 5/1971 | Suh et al. | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahler et al. | |
| 4,146,647 A | 3/1979 | Lafon | |
| 4,311,840 A | 1/1982 | Condon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 6,268,389 B1 | 7/2001 | Esser et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |
| 2009/0209529 A1 | 8/2009 | Andreini et al. | |

FOREIGN PATENT DOCUMENTS

| | | |
|---|---|---|
| CA | 2246027 | 2/2000 |
| DE | 842065 | 6/1952 |
| DE | 1795517 | 2/1972 |
| DE | 2203373 | 8/1972 |
| DE | 2253555 | 11/1972 |
| DE | 2446758 | 4/1976 |
| DE | 2849537 | 5/1980 |
| DE | 0857483 | 8/1998 |
| EP | 0024829 | 3/1981 |
| EP | 0125410 | 11/1984 |
| EP | 0166937 | 1/1986 |
| EP | 0167459 | 1/1986 |
| EP | 0331374 | 9/1989 |
| EP | 0392929 | 10/1990 |
| EP | 0424059 | 4/1991 |
| EP | 0717037 | 6/1996 |
| EP | 0924209 | 6/1999 |
| EP | 1103243 | 5/2001 |
| EP | 1413576 | 4/2004 |
| ES | 323985 | 12/1966 |
| FR | 1355049 | 3/1964 |
| FR | 6551 | 12/1968 |
| GB | 877306 | 9/1961 |

(Continued)

OTHER PUBLICATIONS

PCT International Search Report PCT/EP2010/066960—Issued. Nov. 8, 2010.

(Continued)

*Primary Examiner* — Kamal Saeed
(74) *Attorney, Agent, or Firm* — George W. Johnston; Patricia S. Rocha-Tramaloni; Kimberly J. Prior

(57) ABSTRACT

The invention relates to compounds of formula I

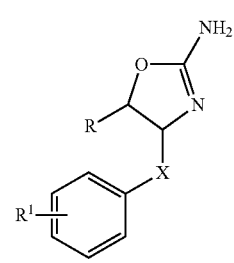

wherein the definitions of X, R and $R^1$ are as defined herein. The compounds of formula I have a good affinity to the trace amine associated receptors (TAARs), especially for TAAR1. The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

20 Claims, No Drawings

FOREIGN PATENT DOCUMENTS

| | | |
|---|---|---|
| GB | 1016514 | 1/1996 |
| WO | 96/22768 | 8/1996 |
| WO | 97/12874 | 4/1997 |
| WO | 98/12183 | 3/1998 |
| WO | 01/30762 | 5/2001 |
| WO | 01/81334 | 11/2001 |
| WO | 02/22801 | 3/2002 |
| WO | 02/40453 | 5/2002 |
| WO | 02/076950 | 10/2002 |
| WO | 03/092374 | 11/2003 |
| WO | 2004/014898 | 2/2004 |
| WO | 2006/119411 | 11/2006 |
| WO | 2007/024944 | 3/2007 |
| WO | 2007/085556 | 8/2007 |
| WO | 2008/092785 | 8/2008 |
| WO | 2008/098857 | 8/2008 |
| WO | 2010/010014 | 1/2010 |
| WO | 2010/042475 | 4/2010 |

OTHER PUBLICATIONS

Matsunaga, et al., Bioorganic & Medicinal Chemistry, p. 4314-4336 (2004), XP002444990.
Matsunaga, et al., Tetrahedron: Asymmetry, Elsevier Science Publishers, vol. 15, No. 13, pp. 2021-2028 (2004), XP004520137.
Ojida, A., et al., Tetrahedron: Asymmetry, Elsevier Science Publishers, vol. 15, No. 10, pp. 1555-1559 (2004), XP004508431.
Zhang, et al., Journal of Medicinal Chemistry, vol. 40, pp. 3014-3024 (1997), XP002108693.
Ojida et al., Org. Lett. 2002, 4, pp. 3051-3054 (Supporting document attached).
Khimiya Geterotsiklicheskikh Soedinenii, 1988, pp. 77-79 (English language abstract attached).
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Debernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at α-Adrenoceptors, J. Med. Chem. (1987), 30:1011-1017.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing α1A-Adrenoceptor Agonist, J. Med. Chem. (2004), 47: 3220-3235.
Carroll et al., In Vitro and In Vivo Characterization of Alpha-1A Selective Agonists and Their Utility for Stress Incontinence, Med, Chem. Res. (2004), 13:134-148.
Jetter et al., Synthesis of 4-Substituted Imidazoles via Palladium-Catalyzed Cross-Coupling Reactions, Synthesis (1998), 829-831.
Bagley et al., Synthesis and α2-Adrenergic Activities of Imidazole and Imidazolidine Analogues: In Vitro and In Vivo Selectivity, Medicinal Chemistry Research (1994), 4:346-364.
Lee et al., 4-[(N-Imidazol-2-ylmethyl)aniline]pyranopyridine Analogs as Novel Anti-Angiogenic Agents, Bull Korean Chem. Soc. (2005), 25: 619-628.
Agami et al., Tetrahedron 2001, vol. 57(1) pp. 195-200.
Ueda et al., Bioorganic & Medicinal Chem. Letters 2004, vol. 14(2) pp. 313-316.
Abstract corresponding to (EP0167459).
Abstract corresponding to (FR 6 551).
Cordi et al., Journal of Med. Chem. vol. 44(5) pp. 787-805 (2001) XP002475805.
Vassiliou et al., Synlett, 2003 pp. 2398-2400.
Schollkopf, U. Topics Curr. Chem. 1983 vol. 109 p. 65.
Hosseinzadeh et al., Tetrahedron Letters (2008) vol. 49 pp. 840-843.
Chen et al., Org. Letters (2008) vol. 10 pp. 4565-4568.
Strieter et al., J. Am. Chem. Sco. (2009) vol. 131 pp. 78-88.
U.S. Appl. No. 12/639,076, filed Dec. 16, 2009, Decoret et al.
U.S. Appl. No. 12/028,028, filed Feb. 8, 2008, Decoret et al.
U.S. Appl. No. 12/558,772, filed Sep. 14, 2009, Decoret et al.
Deutch et al., (1999) Neurotransmitters. In Fundamental Neuroscience (2nd ed.) pp. 193-234, Academic Press.
Wong, et al., (2001) Nat. Rev. Neurosci. 2, pp. 343-351.
Carlsson et al. (2001) Annu. Rev. Pharmacol. Toxicol. 41, pp. 237-260.
Tuite et al. (2003) Expert Opin. Investig. Drugs 12, pp. 1335-1352.
Castellanos et al., (2002) Nat. Rev. Neurosci. 3, pp. 617-628.
Usdin, E. and Sandler. M.; Editors, Psychopharmacology Series, vol. 1: Trace Amines and the Brain [Proceedings of a Study Group at the 14th Annual Meeting of the American College of Neuropsychoparmacology, San Juan, Puerto Rico] (1976) pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mosseau et al., (1995) Prog. Brain Res. 106, pp. 285-291.
McCormack et al. (1986) J. Neurosci. 6, pp. 94-101.
Dyck, L.E. (1989) Life Sci. 44, pp. 1149-1156.
Parker et al., (1988) J. Pharmacol. Exp. Ther. 245, pp. 199-210.
Lindemann et al. (2005) Genomics 85, pp. 372-385.
Habib et al., Synthesis, 1984, pp. 825-827.
Trani et al., J. Heterocycl. Chem. 11, pp. 257-262 (1974).
Abstract corresponding to (DE 842 065).
Bunzow, J.R., et al., Molecular Pharmacology, vol. 60(6), pp. 1181-1188 (2001), XP008008060.
Holt, Andrew, J. of Psychiatry & Neuroscience, vol. 28(6), pp. 409-414 (2003), XP002438693.
Timmermans, P B M W M, et al., Life Sciences, vol. 28, No. 6, pp. 653-660 (1981), XP002442517.
Prisinzano, Thomas, et al., Bioorganic & Medicinal Chemistry Letters, vol. 14, No. 18, pp. 4697-4699 (2004), XP002442518.
Olmos, G., et al , European Journal of Pharmacology, vol. 262, No. 1/2, pp. 41-48 (1994), XP000567119.
McLennan, P.L., European Journal of Pharmacology, vol. 69, No. 4, pp. 477-482 (1981), XP002442519.
Nathanson, J.A., Molecular Pharmacology, vol. 28., No. 3, pp. 254-268 (1985), XP009085722.
Hirashima, et al., Bioorganic and Medicinal Chemistry, vol. 10, No. 1, pp. 117-123 (2002), XP002442520.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Melloni et al., Eur. J. Med. Chem. vol. 26, pp. 207-213 (1991).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Yoshiya, et al., J. of Medicinal Chemistry, vol. 35(4), pp. 750-755 (1992), XP002151512.
Faust, J.A., et al., J. of Organic Chemistry, vol. 26, pp. 4044-4047 (1961), XP002442336.
Savola, J.M., et al., Drug Research, vol. 38(1), pp. 29-35 (1988), XP002033085.
U.S. Appl. No. 12/789,484, filed May 28, 2010.

OXAZOLINE DERIVATIVES

PRIORITY TO RELATED APPLICATION(S)

This application claims the benefit of European Patent Application No. 09175712.0, filed Nov. 11, 2009, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides compounds of formula

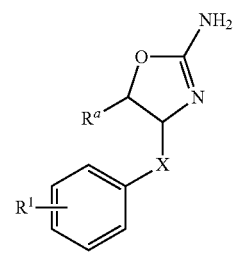

I wherein
R$^a$ is hydrogen or lower alkyl;
R$^1$ is a)

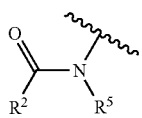

b)

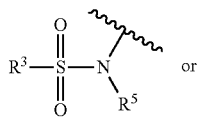 or c)

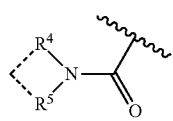

or is selected from the group consisting of

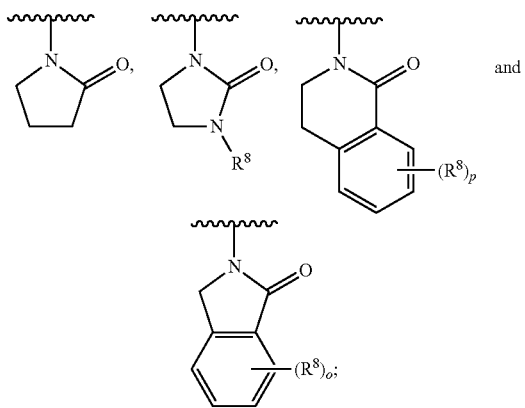 and

R$^8$ is hydrogen, halogen or aryl optionally substituted by halogen;
X is a bond, —(CH$_2$)$_n$—, —CHRCH$_2$—, —CHR(CH$_2$)$_2$—, —O—CHRCH$_2$— or

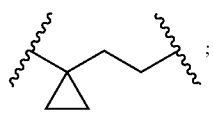 [SMILES: *CCC1(*)CC1]

R is lower alkyl or lower alkyl substituted by halogen;
R$^2$ is
  a) lower alkyl;
  b) hydrogen;
  c) NH-aryl, optionally substituted by one or more substituents selected from halogen and lower alkyl substituted by halogen;
  d) NH-heteroaryl, optionally substituted by one or more substituents selected from halogen and lower alkyl substituted by halogen;
  e) (CR'R")$_m$-cycloalkyl, optionally substituted by halogen, lower alkyl, lower alkyl substituted by halogen, halogen-substituted phenyl or heteroaryl;
  f) heterocycloalkyl, optionally substituted by halogen or lower alkyl substituted by halogen;
  g) (CR'R")$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen;
  h) (CR'R")$_m$-aryl, optionally substituted by halogen, lower alkyl substituted by halogen, lower alkoxy substituted by halogen, lower alkyl, alkynyl, lower alkoxy, CH$_2$-lower alkoxy or cyano; or
  i) —O(CH$_2$)$_o$-aryl, optionally substituted by halogen, lower alkoxy or lower alkyl substituted by halogen;
R' and R" are each independently hydrogen, lower alkoxy or lower alkyl; or together with the C-atom to which they are attached form a cycloalkyl group;
R$^3$ is aryl or heteroaryl, each of which is optionally substituted by one or more substituents selected from halogen and lower alkoxy;
R$^4$ is lower alkyl, aryl or heteroaryl, wherein aryl or heteroaryl are optionally substituted by one or more substituents selected from halogen, cyano and lower alkoxy;
R$^5$ is hydrogen, lower alkyl or aryl substituted by halogen:
  or R$^4$ and R$^5$ together with the N-atom to which they are attached form a heterocycloalkyl ring;
R$^6$ and R$^7$ are each independently hydrogen, lower alkyl or (CH$_2$)$_2$—O-lower alkyl;
m is 0, 1 or 2;
n is 1, 2 or 3;
o is 0 or 1; and
p is 0, 1 or 2;
and pharmaceutically suitable acid addition salts thereof.

The invention includes all racemic mixtures, all their corresponding enantiomers and/or optical isomers. In addition, all tautomeric forms of compounds of formula I are also encompassed by the present invention.

The preferred position of R$^1$ on the phenyl ring is para or meta.

Compounds of formula I have a good affinity to the trace amine associated receptors (TAARs), especially for TAAR1.

The compounds are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain compounds having selectivity for the TAAR1 receptor vs adrenergic receptors. The compounds of the present invention have selectivity for TAAR1 receptor over adrenergic receptors, in particular good selectivity vs the human and rat alpha1 and alpha2 adrenergic receptors.

The present invention provides new compounds of formula I and their pharmaceutically acceptable salts. It also provides pharmaceutical compositions containing such compounds and methods for the manufacture of such compounds and compositions. The invention further provides methods for the treatment of diseases related to the biological function of the trace amine associated receptors. In particular it provides methods for the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications are depression, psychosis, Parkinson's disease, diabetes, anxiety and attention deficit hyperactivity disorder (ADHD).

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above attached via an oxygen atom.

As used herein, the term "lower alkyl substituted by halogen" denotes a lower alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "lower alkoxy substituted by halogen" denotes a lower alkoxy group as defined above wherein at least on hydrogen atom is replaced by halogen.

The term "alkynyl" stands for a straight-chain or branched hydrocarbon residue comprising a triple bond and up to 7, preferably up to 4, carbon atoms, such as e.g. ethynyl or 2-propynyl.

The term "halogen" denotes chlorine, iodine, fluorine and bromine.

The term "cycloalkyl" denotes an alkylene ring containing from 3 to 6 carbon ring atoms.

The term "aryl", denotes an aromatic carbon ring, for example phenyl or naphthyl, preferably phenyl.

The term "heteroaryl" refers to an aromatic 5 to 6 membered monocyclic ring or 9 to 10 membered bicyclic ring which can comprise 1, 2 or 3 heteroatoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl, imidazo[4,5]pyridinyl, [1,6]naphthyridinyl, and isoquinolinyl. Preferred heteroaryl groups are pyridinyl, pyrazolyl, pyrimidinyl, benzoimidazolyl, quinolinyl and isoquinolinyl.

The term "heterocycloalkyl" refers to a non-aromatic 5 to 6 membered monocyclic ring which can comprise 1, 2 or 3 heteroatoms selected from nitrogen, oxygen and/or sulphur, such as piperidinyl, morpholinyl, tetrahydro-pyranyl, thiomorpholinyl or thiomorpholinyl-1,1-di-oxy.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

One embodiment of the invention provides compounds of formula IA

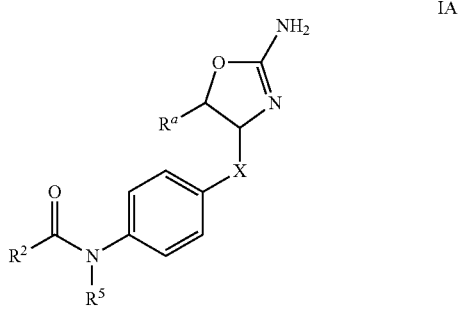

wherein —N($R^5$)—C(O)—$R^2$ is selected from the group consisting of

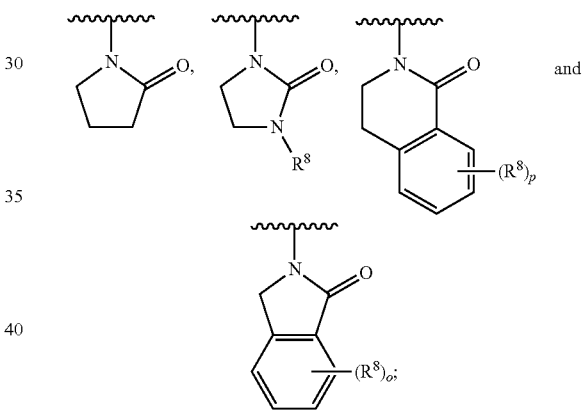

wherein
$R^8$ is hydrogen, halogen or aryl optionally substituted by halogen;
$R^a$ is hydrogen or lower alkyl;
X is a bond, —(CH$_2$)$_n$—, —CHRCH$_2$, —CHR(CH$_2$)$_2$—, —O—CHRCH$_2$— or

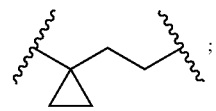 [SMILES: *CCC1(*)CC1]

R is lower alkyl or lower alkyl substituted by halogen; $R^2$ is
a) lower alkyl;
b) hydrogen;
c) NH-aryl, optionally substituted by one or more substituent selected from halogen and lower alkyl substituted by halogen;
d) NH-heteroaryl, optionally substituted by one or more substituent selected from halogen and lower alkyl substituted by halogen;

e) (CR'R")$_m$-cycloalkyl, optionally substituted by halogen, lower alkyl, lower alkyl substituted by halogen, halogen-substituted phenyl or heteroaryl;

f) heterocycloalkyl, optionally substituted by halogen or lower alkyl substituted by halogen;

g) (CR'R")$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen;

h) (CR'R")$_m$-aryl, optionally substituted by halogen, lower alkyl substituted by halogen, lower alkoxy substituted by halogen, lower alkyl, alkynyl, lower alkoxy, CH$_2$-lower alkoxy or cyano; or i) —O(CH$_2$)$_o$-aryl, optionally substituted by halogen, lower alkoxy or lower alkyl substituted by halogen;

R' and R" are each independently hydrogen, lower alkoxy or lower alkyl; or together with the C-atom to which they are attached form a cycloalkyl group;

R$^5$ is hydrogen, lower alkyl or aryl substituted by halogen:

R$^6$ and R$^7$ are each independently hydrogen, lower alkyl or (CH$_2$)$_2$—O-lower alkyl;

m is 0, 1 or 2;

n is 1, 2 or 3;

o is 0 or 1; and p is 0, 1 or 2;

or a pharmaceutically suitable acid addition salt thereof.

A further embodiment of the invention provides compounds of formula IB

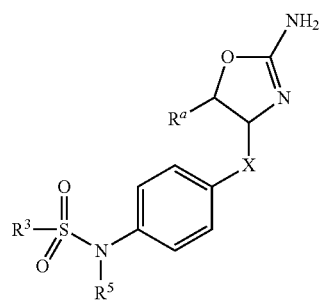

IB wherein

R$^a$ is hydrogen or lower alkyl;

X is a bond, —(CH$_2$)$_n$—, —CHRCH$_2$, —CHR(CH$_2$)$_2$—, —O—CHRCH$_2$— or

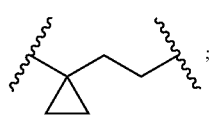 [SMILES: *CCC1(*)CC1]

;

R is lower alkyl or lower alkyl substituted by halogen;

R$^3$ is aryl or heteroaryl, each of which is optionally substituted by one or more substituents selected from halogen and lower alkoxy;

R$^5$ is hydrogen, lower alkyl or aryl substituted by halogen: and n is 1, 2 or 3;

or a pharmaceutically suitable acid addition salt thereof.

A further embodiment of the invention provides compounds of formula IC

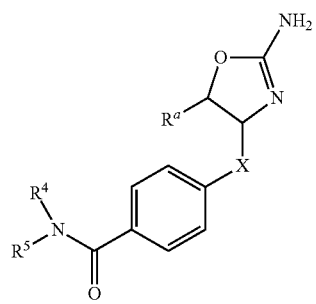

IC wherein

R$^a$ is hydrogen or lower alkyl;

X is a bond, —(CH$_2$)$_n$—, —CHRCH$_2$, —CHR(CH$_2$)$_2$—, —O—CHRCH$_2$— or

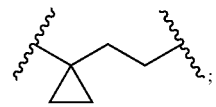 [SMILES: *CCC1(*)CC1]

;

R is lower alkyl or lower alkyl substituted by halogen;

R$^4$ is lower alkyl, aryl or heteroaryl, wherein aryl or heteroaryl is optionally substituted by one or more substituents selected from halogen, cyano and lower alkoxy;

R$^5$ is hydrogen, lower alkyl or aryl substituted by halogen:

or R$^4$ and R$^5$ together with the N-atom to which they are attached form a heterocycloalkyl ring; and n is 1, 2 or 3;

or a pharmaceutically suitable acid addition salt thereof.

One embodiment of the invention provides compounds of formula IA, wherein X is a bond, for example the following compound:

(RS)-1-[4-(2-Amino-4,5-dihydro-oxazol-4-yl)-phenyl]-3-(4-chloro-phenyl)-urea.

A further embodiment of the invention are compounds of formula IA, wherein X is —(CH$_2$)$_n$—, for example the following compounds 1-{4-[2-((S)-2-amino-4,5-dihydro-oxazol-4-yl)-ethyl]-phenyl}-3-(4-chloro-phenyl)-urea;

N-{4-[3-((S)-2-amino-4,5-dihydro-oxazol-4-yl)-propyl]-phenyl}-4-chloro-benzamide;

N-{4-[2-((S)-2-amino-4,5-dihydro-oxazol-4-yl)-ethyl]-phenyl}-4-chloro-benzamide;

1-{4-[2-((S)-2-amino-4,5-dihydro-oxazol-4-yl)-ethyl]-phenyl}-3-(3,4-dichloro-phenyl)-urea;

1-{4-[2-((S)-2-amino-4,5-dihydro-oxazol-4-yl)-ethyl]-phenyl}-3-(4-trifluoromethyl-phenyl)-urea;

N-{4-[2-((S)-2-amino-4,5-dihydro-oxazol-4-yl)-ethyl]-phenyl}-4-fluoro-benzamide;

N-{4-[2-((S)-2-amino-4,5-dihydro-oxazol-4-yl)-ethyl]-phenyl}-4-trifluoromethyl-benzamide;

N-{4-[2-((S)-2-amino-4,5-dihydro-oxazol-4-yl)-ethyl]-phenyl}-3-chloro-benzamide;

N-{4-[2-((S)-2-amino-4,5-dihydro-oxazol-4-yl)-ethyl]-phenyl}-6-chloro-nicotinamide;

5-chloro-pyridine-2-carboxylic acid {4-[2-((S)-2-amino-4,5-dihydro-oxazol-4-yl)-ethyl]-phenyl}-amide;

5-chloro-pyrimidine-2-carboxylic acid {4-[2-((S)-2-amino-4,5-dihydro-oxazol-4-yl)-ethyl]-phenyl}-amide;

1-{4-[2-((S)-2-amino-4,5-dihydro-oxazol-4-yl)-ethyl]-phenyl}-3-(5-chloro-pyridin-2-yl)-urea;

1-{4-[2-((S)-2-amino-4,5-dihydro-oxazol-4-yl)-ethyl]-phenyl}-3-(6-chloro-pyridin-3-yl)-urea;
4,4-difluoro-cyclohexanecarboxylic acid {4-[2-((S)-2-amino-4,5-dihydro-oxazol-4-yl)-ethyl]-phenyl}-amide;
1-methyl-cyclopropanecarboxylic acid {4-[2-((S)-2-amino-4,5-dihydro-oxazol-4-yl)-ethyl]-phenyl}-amide;
cyclopentanecarboxylic acid {4-[2-((S)-2-amino-4,5-dihydro-oxazol-4-yl)-ethyl]-phenyl}-amide;
3,3-difluoro-cyclobutanecarboxylic acid {4-[2-((S)-2-amino-4,5-dihydro-oxazol-4-yl)-ethyl]-phenyl}-amide;
cyclobutanecarboxylic acid {4-[2-((S)-2-amino-4,5-dihydro-oxazol-4-yl)-ethyl]-phenyl}-amide;
cyclopropanecarboxylic acid {4-[2-((S)-2-amino-4,5-dihydro-oxazol-4-yl)-ethyl]-phenyl}-amide;
cyclohexanecarboxylic acid {4-[2-((S)-2-amino-4,5-dihydro-oxazol-4-yl)-ethyl]-phenyl}-amide;
1-trifluoromethyl-cyclopropanecarboxylic acid {4-[2-((S)-2-amino-4,5-dihydro-oxazol-4-yl)-ethyl]-phenyl}-amide;
1-(4-chloro-phenyl)-cyclopropanecarboxylic acid {4-[2-((S)-2-amino-4,5-dihydro-oxazol-4-yl)-ethyl]-phenyl}-amide;
5-trifluoromethyl-pyridine-2-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-trifluoromethyl-nicotinamide;
1-{4-[2-((S)-2-amino-4,5-dihydro-oxazol-4-yl)-ethyl]-phenyl}-3-(4-fluoro-phenyl)-imidazolidin-2-one;
N-{4-[2-((S)-2-amino-4,5-dihydro-oxazol-4-yl)-ethyl]-phenyl}-2-(4-chloro-phenyl)-propionamide;
N-{4-[2-((S)-2-amino-4,5-dihydro-oxazol-4-yl)-ethyl]-phenyl}-4-cyano-benzamide;
N-{4-[2-((S)-2-amino-4,5-dihydro-oxazol-4-yl)-ethyl]-phenyl}-4-ethoxy-benzamide;
N-{4-[2-((S)-2-amino-4,5-dihydro-oxazol-4-yl)-ethyl]-phenyl}-4-propyl-benzamide;
N-{4-[2-((S)-2-amino-4,5-dihydro-oxazol-4-yl)-ethyl]-phenyl}-4-ethynyl-benz amide;
N-{4-[2-((S)-2-amino-4,5-dihydro-oxazol-4-yl)-ethyl]-phenyl}-4-methoxymethyl-benzamide;
N-{4-[2-((S)-2-amino-4,5-dihydro-oxazol-4-yl)-ethyl]-phenyl}-2-(4-ethoxy-phenyl)-acetamide;
N-{4-[2-((S)-2-amino-4,5-dihydro-oxazol-4-yl)-ethyl]-phenyl}-2-(4-methoxy-phenyl)-acetamide;
N-{4-[2-((S)-2-amino-4,5-dihydro-oxazol-4-yl)-ethyl]-phenyl}-2-(4-fluoro-phenyl)-acetamide;
N-{4-[2-((S)-2-amino-4,5-dihydro-oxazol-4-yl)-ethyl]-phenyl}-2-(4-chloro-phenyl)-acetamide;
N-{4-[2-((S)-2-amino-4,5-dihydro-oxazol-4-yl)-ethyl]-phenyl}-4-methoxy-benzamide;
N-{4-[2-((S)-2-amino-4,5-dihydro-oxazol-4-yl)-ethyl]-phenyl}-2-(4-chloro-phenyl)-isobutyramide;
N-{4-[2-((S)-2-amino-4,5-dihydro-oxazol-4-yl)-ethyl]-phenyl}-2-(4-bromo-phenyl)-2-methoxy-acetamide;
(S)-N-{4-[2-((S)-2-amino-4,5-dihydro-oxazol-4-yl)-ethyl]-phenyl}-2-methoxy-2-phenyl-acetamide;
N-{4-[2-((S)-2-amino-4,5-dihydro-oxazol-4-yl)-ethyl]-phenyl}-2-(4-chloro-phenyl)-2-methoxy-acetamide;
4-trifluoromethyl-cyclohexanecarboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-3-(2-chloro-phenyl)-propionamide;
N-{4-[2-((S)-2-amino-4,5-dihydro-oxazol-4-yl)-ethyl]-phenyl}-2-(3-trifluoromethyl-phenyl)-propionamide;
N-{4-[2-((S)-2-amino-4,5-dihydro-oxazol-4-yl)-ethyl]-phenyl}-2-(3-trifluoromethoxy-phenyl)-propionamide;
2-methoxy-pyrimidine-5-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-pyrazol-1-yl-nicotinamide;
1H-benzoimidazole-2-carboxylic acid {4-[2-((S)-2-amino-4,5-dihydro-oxazol-4-yl)-ethyl]-phenyl}-amide;
3,5-difluoro-pyridine-2-carboxylic acid {4-[2-((S)-2-amino-4,5-dihydro-oxazol-4-yl)-ethyl]-phenyl}-amide;
6-fluoro-pyridine-2-carboxylic acid {4-[2-((S)-2-amino-4,5-dihydro-oxazol-4-yl)-ethyl]-phenyl}-amide;
6-chloro-3-fluoro-pyridine-2-carboxylic acid {4-[2-((S)-2-amino-4,5-dihydro-oxazol-4-yl)-ethyl]-phenyl}-amide;
4-chloro-pyridine-2-carboxylic acid {4-[2-((S)-2-amino-4,5-dihydro-oxazol-4-yl)-ethyl]-phenyl}-amide;
quinoline-2-carboxylic acid {4-[2-((S)-2-amino-4,5-dihydro-oxazol-4-yl)-ethyl]-phenyl}-amide;
5-bromo-pyridine-2-carboxylic acid {4-[2-((S)-2-amino-4,5-dihydro-oxazol-4-yl)-ethyl]-phenyl}-amide;
isoquinoline-1-carboxylic acid {4-[2-((S)-2-amino-4,5-dihydro-oxazol-4-yl)-ethyl]-phenyl}-amide;
1-{4-[2-((S)-2-amino-4,5-dihydro-oxazol-4-yl)-ethyl]-phenyl}-3-(4-fluoro-phenyl)-urea;
1-{4-[2-((S)-2-amino-4,5-dihydro-oxazol-4-yl)-ethyl]-phenyl}-3-(3-chloro-phenyl)-urea;
(S)-N-(4-(2-(2-amino-4,5-dihydrooxazol-4-yl)ethyl)phenyl)-5-fluoropicolinamide;
N-{4-[2-((S)-2-amino-4,5-dihydro-oxazol-4-yl)-ethyl]-phenyl}-6-methoxy-nicotinamide;
N-{4-[2-((S)-2-amino-4,5-dihydro-oxazol-4-yl)-ethyl]-phenyl}-6-methyl-nicotinamide;
(S)-N-(4-(2-(2-amino-4,5-dihydrooxazol-4-yl)ethyl)phenyl)-2-fluoronicotinamide;
N-{4-[2-((S)-2-amino-4,5-dihydro-oxazol-4-yl)-ethyl]-phenyl}-5-fluoro-nicotinamide;
3-chloro-5-trifluoromethyl-pyridine-2-carboxylic acid {4-[2-((S)-2-amino-4,5-dihydro-oxazol-4-yl)-ethyl]-phenyl}-amide;
[1,6]naphthyridine-2-carboxylic acid {4-[2-((S)-2-amino-4,5-dihydro-oxazol-4-yl)-ethyl]-phenyl}-amide;
[1,8]naphthyridine-2-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-bromo-nicotinamide;
N-{4-[2-((S)-2-amino-4,5-dihydro-oxazol-4-yl)-ethyl]-phenyl}-2,5-difluoro-nicotinamide;
N-{4-[2-((S)-2-amino-4,5-dihydro-oxazol-4-yl)-ethyl]-phenyl}-5,6-dichloro-nicotinamide;
N-{4-[2-((S)-2-amino-4,5-dihydro-oxazol-4-yl)-ethyl]-phenyl}-2,6-difluoro-nicotinamide;
N-{4-[2-((S)-2-amino-4,5-dihydro-oxazol-4-yl)-ethyl]-phenyl}-6-cyano-nicotinamide;
6-bromo-pyridine-2-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-(2,2,2-trifluoro-ethoxy)-nicotinamide;
N-{4-[2-((S)-2-amino-4,5-dihydro-oxazol-4-yl)-ethyl]-phenyl}-2-methoxy-nicotinamide;
(S)-N-(4-(2-(2-amino-4,5-dihydrooxazol-4-yl)ethyl)phenyl)-5-methoxypicolinamide;
(S)-N-(4-(2-(2-amino-4,5-dihydrooxazol-4-yl)ethyl)phenyl)-5-cyanopicolinamide;
(S)-N-(4-(2-(2-amino-4,5-dihydrooxazol-4-yl)ethyl)phenyl)-6-fluoronicotinamide;
(S)-N-(4-(2-(2-amino-4,5-dihydrooxazol-4-yl)ethyl)phenyl)-6-chloropyridazine-3-carboxamide;
(S)-N-(4-(2-(2-amino-4,5-dihydrooxazol-4-yl)ethyl)phenyl)-2-(piperidin-1-yl)pyrimidine-5-carboxamide;
(S)-N-(4-(2-(2-amino-4,5-dihydrooxazol-4-yl)ethyl)phenyl)-5-chloronicotinamide;

(S)-N-(4-(2-(2-amino-4,5-dihydrooxazol-4-yl)ethyl)phenyl)-2-(3,4-dichlorophenyl)-2,2-difluoroacetamide;
(S)-N-(4-(2-(2-amino-4,5-dihydrooxazol-4-yl)ethyl)phenyl)-5-chloropyrazine-2-carboxamide;
(S)-N-(4-(2-(2-amino-4,5-dihydrooxazol-4-yl)ethyl)phenyl)-5-methoxypyrazine-2-carboxamide
(S)-N-(4-(2-(2-amino-4,5-dihydrooxazol-4-yl)ethyl)phenyl)-6-methoxypyrazine-2-carboxamide;
(S)-N-(4-(2-(2-amino-4,5-dihydrooxazol-4-yl)ethyl)phenyl)-5-methylpyrazine-2-carboxamide;
(S)-4-(2-(2-amino-4,5-dihydrooxazol-4-yl)ethyl)-N-(5-chloropyridin-2-yl)benzamide;
(S)-N-(4-(2-(2-amino-4,5-dihydrooxazol-4-yl)ethyl)phenyl)-4-chloro-2-fluorobenzamide;
(S)-N-(4-(2-(2-amino-4,5-dihydrooxazol-4-yl)ethyl)phenyl)-2,4-dichlorobenzamide;
(S)-N-(4-(2-(2-amino-4,5-dihydrooxazol-4-yl)ethyl)phenyl)-4-chloro-2-methoxybenzamide;
(S)-4-(2-(2-amino-4,5-dihydrooxazol-4-yl)ethyl)-N-(4-cyanophenyl)benzamide;
(S)-4-(2-(2-amino-4,5-dihydrooxazol-4-yl)ethyl)-N-(4-ethynylphenyl)benzamide;
{4-[2-((S)-2-amino-4,5-dihydro-oxazol-4-yl)-ethyl]-phenyl}-carbamic acid 4-chloro-benzyl ester;
{4-[2-((S)-2-amino-4,5-dihydro-oxazol-4-yl)-ethyl]-phenyl}-carbamic acid 4-methoxy-phenyl ester;
{4-[2-((S)-2-amino-4,5-dihydro-oxazol-4-yl)-ethyl]-phenyl}-carbamic acid 4-fluoro-phenyl ester;
{4-[2-((S)-2-amino-4,5-dihydro-oxazol-4-yl)-ethyl]-phenyl}-carbamic acid 3-trifluoromethyl-phenyl ester;
1-{4-[2-((S)-2-amino-4,5-dihydro-oxazol-4-yl)-ethyl]-phenyl}-3-(5-chloro-pyrimidin-2-yl)-urea;
(S)-N-(4-(2-(2-amino-4,5-dihydrooxazol-4-yl)ethyl)phenyl)-5-ethoxypicolinamide;
(S)-N-(4-(2-(2-amino-4,5-dihydrooxazol-4-yl)ethyl)phenyl)-5-chloro-4-methylpicolinamide;
(S)-N-(4-(2-(2-amino-4,5-dihydrooxazol-4-yl)ethyl)phenyl)-4-chloro-6-methylpicolinamide;
(S)-N-(4-(2-(2-amino-4,5-dihydrooxazol-4-yl)ethyl)phenyl)-4,6-dimethylpicolinamide;
(S)-N-(4-(2-(2-amino-4,5-dihydrooxazol-4-yl)ethyl)phenyl)-4,6-dichloropicolinamide;
(S)-N-(4-(2-(2-amino-4,5-dihydrooxazol-4-yl)ethyl)phenyl)-5-(trifluoromethyl)pyrazine-2-carboxamide;
(S)-N-(4-(2-(2-amino-4,5-dihydrooxazol-4-yl)ethyl)phenyl)-6-chloropyrazine-2-carboxamide;
(S)-N-(4-(2-(2-amino-4,5-dihydrooxazol-4-yl)ethyl)phenyl)-5-ethoxypyrazine-2-carboxamide;
(S)-N-(4-(2-(2-amino-4,5-dihydrooxazol-4-yl)ethyl)phenyl)-5-morpholinopyrazine-2-carboxamide;
(S)-N-(4-(2-(2-amino-4,5-dihydrooxazol-4-yl)ethyl)phenyl)-6-chloro-5-methoxypicolinamide;
(S)-N-(4-(2-(2-amino-4,5-dihydrooxazol-4-yl)ethyl)phenyl)-5-chlorothiophene-2-carboxamide;
(S)-N-(4-(2-(2-amino-4,5-dihydrooxazol-4-yl)ethyl)phenyl)-3-cyclopropylpropanamide;
(S)-N-(4-(2-(2-amino-4,5-dihydrooxazol-4-yl)ethyl)phenyl)-5-methylpicolinamide;
(S)-N-(4-(2-(2-amino-4,5-dihydrooxazol-4-yl)ethyl)phenyl)-2-methylisonicotinamide;
(S)-N-(4-(2-(2-amino-4,5-dihydrooxazol-4-yl)ethyl)phenyl)-2-chloroisonicotinamide;
(S)-N-(4-(2-(2-amino-4,5-dihydrooxazol-4-yl)ethyl)phenyl)-2-chloro-3-fluoroisonicotinamide;
(S)-N-(4-(2-(2-amino-4,5-dihydrooxazol-4-yl)ethyl)phenyl)-2,6-dichloroisonicotinamide;
(S)-N-(4-(2-(2-amino-4,5-dihydrooxazol-4-yl)ethyl)phenyl)-5-ethylpicolinamide;
(S)-N-(4-(2-(2-amino-4,5-dihydrooxazol-4-yl)ethyl)phenyl)-2,5-dimethyloxazole-4-carboxamide;
(S)-N-(4-(2-(2-amino-4,5-dihydrooxazol-4-yl)ethyl)phenyl)-2-(dimethylamino)-5-isopropylthiazole-4-carboxamide;
(S)-N-(4-(2-(2-amino-4,5-dihydrooxazol-4-yl)ethyl)phenyl)-2,6-dimethoxypyrimidine-4-carboxamide;
(S)-N-(4-(2-(2-amino-4,5-dihydrooxazol-4-yl)ethyl)phenyl)-5-methyloxazole-4-carboxamide;
(S)-N-(4-(2-(2-amino-4,5-dihydrooxazol-4-yl)ethyl)phenyl)-4-chloro-1-methyl-1H-pyrazole-3-carboxamide;
(S)-N-(4-(2-(2-amino-4,5-dihydrooxazol-4-yl)ethyl)phenyl)-1-(difluoromethyl)-1H-pyrazole-3-carboxamide;
(S)-N-(4-(2-(2-amino-4,5-dihydrooxazol-4-yl)ethyl)phenyl)-2-tert-butylisonicotinamide;
(S)-N-(4-(2-(2-amino-4,5-dihydrooxazol-4-yl)ethyl)phenyl)-2-isopropylisonicotinamide;
(S)-N-(4-(2-(2-amino-4,5-dihydrooxazol-4-yl)ethyl)phenyl)-2,4'-bipyridine-4-carboxamide;
(S)-N-(4-(2-(2-amino-4,5-dihydrooxazol-4-yl)ethyl)phenyl)-5-methylthiophene-2-carboxamide;
(S)-N-(4-(2-(2-amino-4,5-dihydrooxazol-4-yl)ethyl)phenyl)-4,5-dimethylthiophene-2-carboxamide;
2-ethyl-6-methoxy-pyrimidine-4-carboxylic acid {4-[2-((S)-2-amino-4,5-dihydro-oxazol-4-yl)-ethyl]-phenyl}-amide;
N-(4-(2-((4S,5S)-2-amino-5-methyl-4,5-dihydrooxazol-4-yl)ethyl)phenyl)-4-chlorobenzamide;
N-(4-(2-((4S,5R)-2-amino-5-methyl-4,5-dihydrooxazol-4-yl)ethyl)phenyl)-4-chlorobenzamide;
2-isopropyl-6-methoxy-pyrimidine-4-carboxylic acid {4-[2-((S)-2-amino-4,5-dihydro-oxazol-4-yl)-ethyl]-phenyl}-amide;
(S)-N-(4-(2-(2-amino-4,5-dihydrooxazol-4-yl)ethyl)phenyl)-5-ethylpyrazine-2-carboxamide;
(S)-N-(4-(2-(2-amino-4,5-dihydrooxazol-4-yl)ethyl)phenyl)-4-cyclopropyl-2-(trifluoromethyl)pyrimidine-5-carboxamide;
(S)-N-(4-(2-(2-amino-4,5-dihydrooxazol-4-yl)ethyl)phenyl)-6-ethylpyrazine-2-carboxamide;
(S)-N-(4-(2-(2-amino-4,5-dihydrooxazol-4-yl)ethyl)phenyl)-5-ethyloxazole-4-carboxamide;
(S)-N-(4-(2-(2-amino-4,5-dihydrooxazol-4-yl)ethyl)phenyl)-5-cyclopropyloxazole-4-carboxamide;
(S)-N-(4-(2-(2-amino-4,5-dihydrooxazol-4-yl)ethyl)phenyl)-5-isopropyloxazole-4-carboxamide;
(S)-N-(4-(2-(2-amino-4,5-dihydrooxazol-4-yl)ethyl)phenyl)-2-methyl-5-(trifluoromethyl)oxazole-4-carboxamide;
(S)-N-(4-(2-(2-amino-4,5-dihydrooxazol-4-yl)ethyl)phenyl)-2-ethyloxazole-4-carboxamide;
5-ethoxy-pyrazine-2-carboxylic acid {4-[2-((4S,5S)-2-amino-5-methyl-4,5-dihydro-oxazol-4-yl)-ethyl]-phenyl}-amide;
2-chloro-6-methoxy-pyrimidine-4-carboxylic acid {4-[2-((4S,5S)-2-amino-5-methyl-4,5-dihydro-oxazol-4-yl)-ethyl]-phenyl}-amide;
5-methyl-oxazole-4-carboxylic acid {4-[2-((4S,5S)-2-amino-5-methyl-4,5-dihydro-oxazol-4-yl)-ethyl]-phenyl}-amide;
5-trifluoromethyl-pyridine-2-carboxylic acid {4-[2-((4S,5S)-2-amino-5-methyl-4,5-dihydro-oxazol-4-yl)-ethyl]-phenyl}-amide;
5-ethyl-pyrazine-2-carboxylic acid {4-[2-((4S,5S)-2-amino-5-methyl-4,5-dihydro-oxazol-4-yl)-ethyl]-phenyl}-amide;

(S)-N-(4-(2-(2-amino-4,5-dihydrooxazol-4-yl)ethyl)phenyl)-6-isopropylpyrazine-2-carboxamide; and
2-chloro-6-methoxy-pyrimidine-4-carboxylic acid {4-[2-((S)-2-amino-4,5-dihydro-oxazol-4-yl)-ethyl]-phenyl}-amide.

An embodiment of the invention are further compounds of formula IA, wherein X is —CHRCH$_2$—, for example the following compounds
1-{4-[(S)-1-((S)-2-amino-4,5-dihydro-oxazol-4-ylmethyl)-propyl]-phenyl}-3-(4-fluoro-phenyl)-urea and
1-{4-[(S)-1-((S)-2-amino-4,5-dihydro-oxazol-4-ylmethyl)-propyl]-phenyl}-3-(4-trifluoromethyl-phenyl)-urea.

A further embodiment of the invention are compounds of formula IA, wherein X is —O—CHRCH$_2$, for example the following compound
N-{4-[(R)-1-((S)-2-amino-4,5-dihydro-oxazol-4-ylmethyl)-2,2,2-trifluoro-ethoxy]-phenyl}-4-chloro-benzamide.

A further embodiment of the invention are compounds of formula IA, wherein —N(R$^5$)—C(O)—R$^2$ is selected from the group consisting of

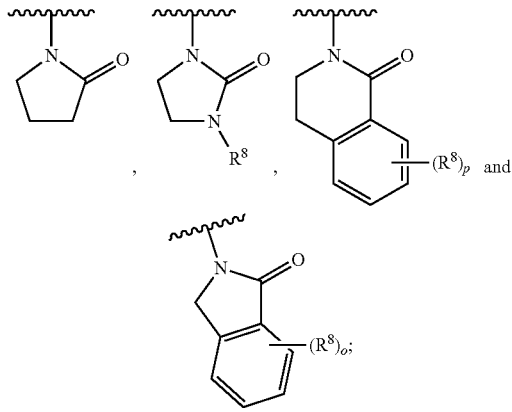

R$^8$ is hydrogen, halogen or aryl optionally substituted by halogen, for example the following compounds
1-(4-{1-[2-((S)-2-amino-4,5-dihydro-oxazol-4-yl)-ethyl]-cyclopropyl}-phenyl)-pyrrolidin-2-one;
1-{4-[2-((S)-2-amino-4,5-dihydro-oxazol-4-yl)-ethyl]-phenyl}-3-(4-fluoro-phenyl)-imidazolidin-2-one;
(S)-2-(4-(2-(2-aAmino-4,5-dihydrooxazol-4-yl)ethyl)phenyl)-5,6-dichloro-3,4-dihydroisoquinolin-1(2H)-one;
2-{4-[2-((S)-2-amino-4,5-dihydro-oxazol-4-yl)-ethyl]-phenyl}-6-chloro-2,3-dihydro-isoindol-1-one;
(S)-2-(4-(2-(2-amino-4,5-dihydrooxazol-4-yl)ethyl)phenyl)isoindolin-1-one;
(S)-2-(4-(2-(2-amino-4,5-dihydrooxazol-4-yl)ethyl)phenyl)-3,4-dihydroisoquinolin-1(2H)-one and
(S)-2-(4-(2-(2-amino-4,5-dihydrooxazol-4-yl)ethyl)phenyl)-6-chloro-3,4-dihydroisoquinolin-1(2H)-one.

An embodiment of the present invention are compounds of formula IB, wherein X is —(CH$_2$)$_n$—, for example the following compound
N-{4-[2-((S)-2-amino-4,5-dihydro-oxazol-4-yl)-ethyl]-phenyl}-3,4-dichloro-benzenesulfonamide.

A further embodiment of the invention are compounds of formula IC, wherein X is —(CH$_2$)$_n$—, for example the following compounds
4-[2-((S)-2-Amino-4,5-dihydro-oxazol-4-yl)-ethyl]-N-(4-chloro-phenyl)-benzamide and
(S)-4-(2-(2-Amino-4,5-dihydrooxazol-4-yl)ethyl)-N-(5-ethynylpyridin-2-yl)benzamide.

One further embodiment of the present invention provides compounds of formula I

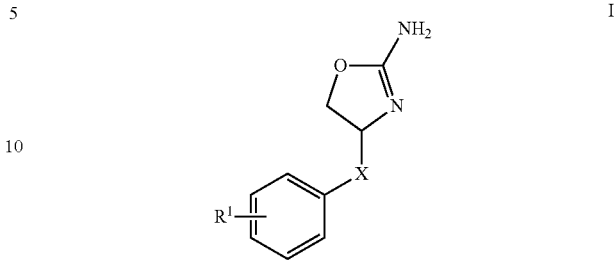

wherein
R$^1$ is a)

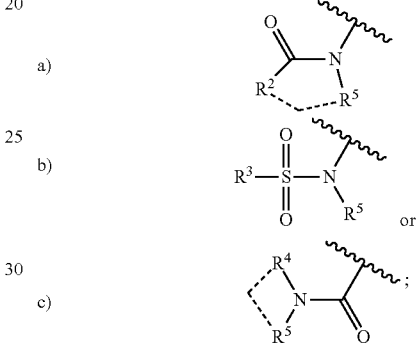

b)

c)

X is a bond, —(CH$_2$)$_n$—, —CHRCH$_2$, —CHR(CH$_2$)$_2$— or

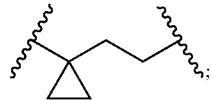 [SMILES: *CCC1(*)CC1]

R is lower alkyl; R$^2$ is
a) lower alkyl,
b) hydrogen,
c) NH-aryl, optionally substituted by one or more substituents selected from halogen and lower alkyl substituted by halogen,
d) NH-heteroaryl, optionally substituted by one or more substituents selected from halogen and lower alkyl substituted by halogen,
e) cycloalkyl, optionally substituted by halogen, lower alkyl, lower alkyl substituted by halogen, halogen-substituted phenyl or heteroaryl,
f) heterocycloalkyl, optionally substituted by halogen or lower alkyl substituted by halogen,
g) (CR'R")$_m$-heteroaryl, optionally substituted by halogen, lower alkoxy, lower alkyl substituted by halogen or heteroaryl, or
h) (CR'R")$_m$-aryl, optionally substituted by halogen, lower alkyl substituted by halogen, lower alkoxy substituted by halogen, lower alkyl, alkynyl, lower alkoxy, CH$_2$-lower alkoxy or cyano,
R' and R" are each independently hydrogen, lower alkoxy or lower alkyl;
R$^3$ is aryl or heteroaryl, each of which is optionally substituted by one or more halogen or lower alkoxy;

R⁴ is lower alkyl, aryl or heteroaryl, wherein aryl or heteroaryl is optionally substituted by one or more by halogen or lower alkoxy;
R⁵ is hydrogen, lower alkyl or aryl substituted by halogen:
or R² and R⁵ together with —(CH₂)₃— or with —N(R⁶)—(CH₂)₂— form a five membered ring; and
wherein R⁶ is hydrogen or aryl optionally substituted by halogen;
or R⁴ and R⁵ together with the N-atom to which they are attached form a heterocycloalkyl ring;
m is 0, 1 or 2 and
n is 1, 2 or 3;
or a pharmaceutically suitable acid addition salt thereof.

The present compounds of formula I and their pharmaceutically acceptable salts can be prepared by methods known in the art, for example, by processes described below, which process comprises a) reacting a compound of formula

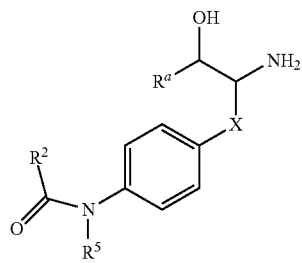

with cyanogen bromide
to obtain a compound of formula

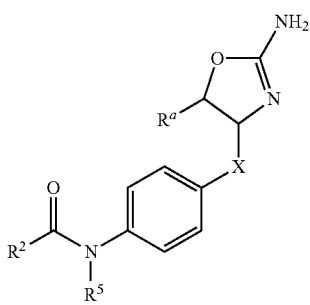

IA wherein the definitions are as described above, or
if desired, converting the compounds obtained into pharmaceutically acceptable acid addition salts, or b) reacting a compound of formula

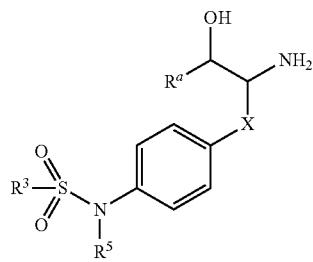

with cyanogen bromide
to obtain a compound of formula

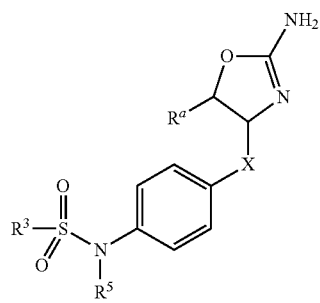

IB wherein the definitions are as described above, or
if desired, converting the compounds obtained into pharmaceutically acceptable acid addition salts or c) reacting a compound of formula

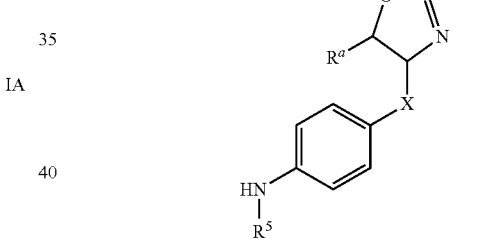

with R²C(O)OH or R²C(O)Cl
to obtain a compound of formula

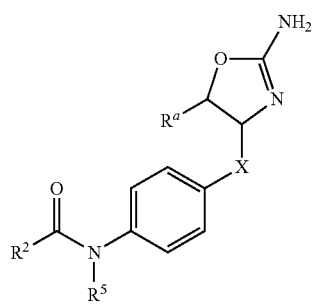

IA wherein the definitions are as described above, or d) reacting a compound of formula

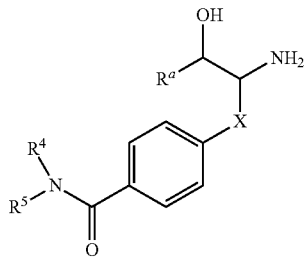

with cyanogen bromide
to obtain a compound of formula

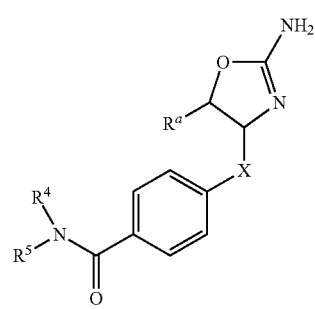

IC wherein the definitions are as described above, or if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-18. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 18, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

General Procedure

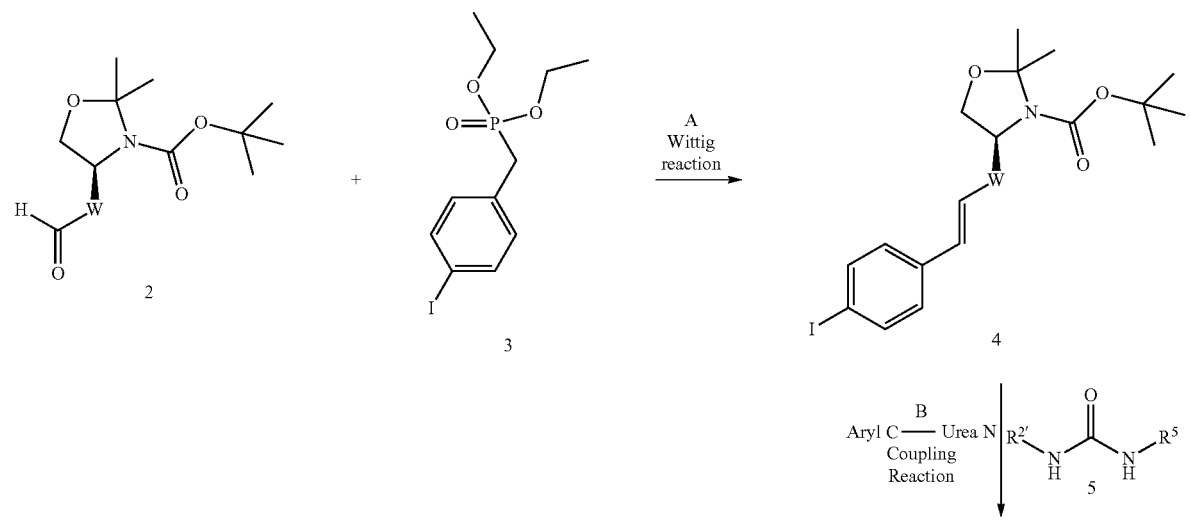

Scheme 1

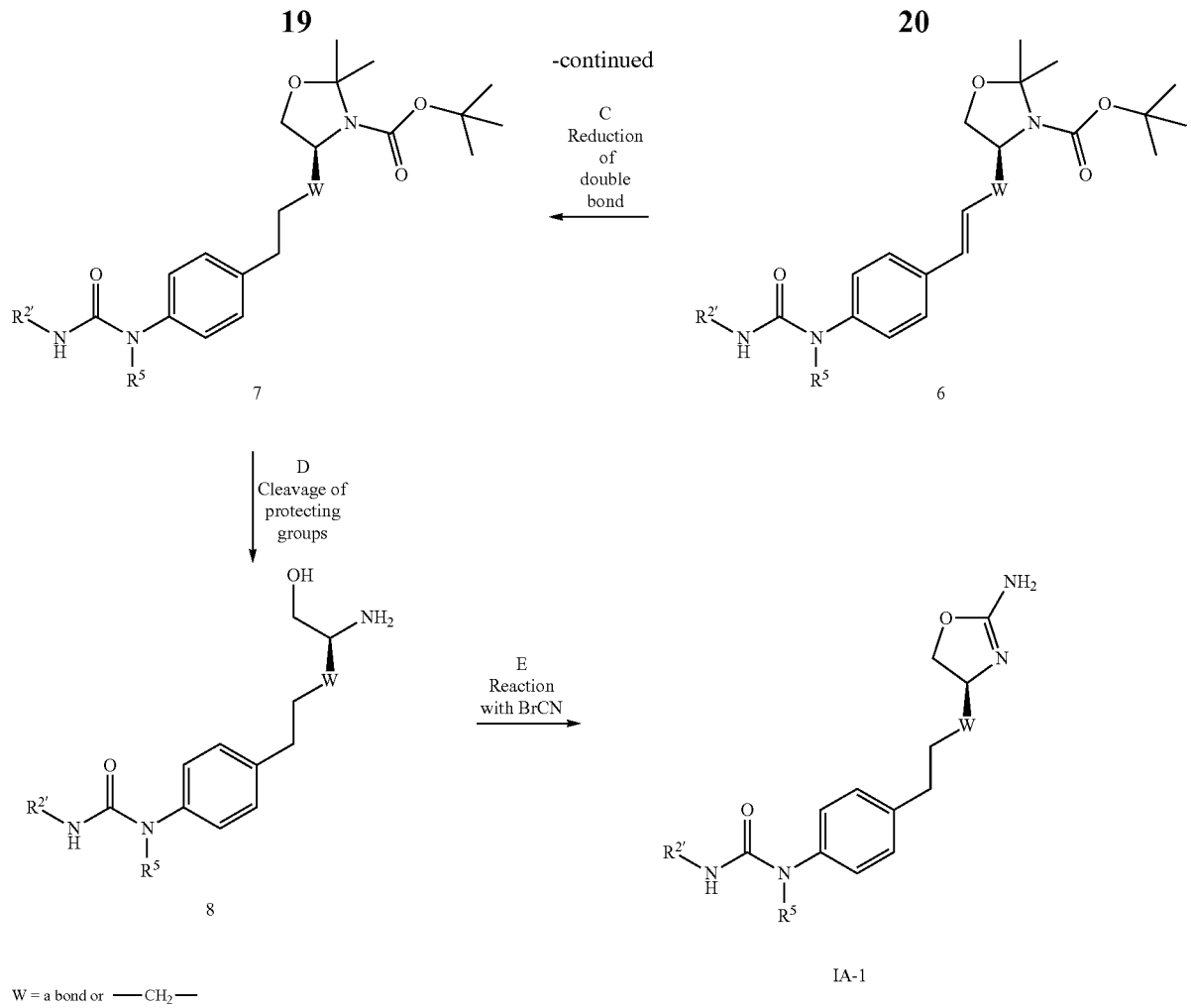

W = a bond or —CH₂—

$R^2$ is aryl or heteroaryl, each of which is optionally substituted by one or more substituents selected from halogen and lower alkyl substituted by halogen, W is a bond or —CH₂— and the other substituents are as described above.

Step A: Wittig reaction between aldehyde 2 (W=a bond: CAS 95715-87-0 or W=—CH₂—: CAS 147959-19-1) and (4-iodo-benzyl)-phosphonic acid diethyl ester 3 (CAS 173443-43-1) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethane, DMF, benzene, toluene or mixtures thereof at temperatures from −78° C. to 80° C. for 15 min-8 hrs and if appropriate optional addition of a crown ether for ylide generation and then condensing the ylide with the carbonyl compound in the same solvent at a temperature between 0 and 80° C. for 1-24 hrs. Alternatively, the base, the carbonyl compound and the optional crown ether can be added to the reaction mixture at the same time without pre-formation of the ylide at temperatures from −78° C. to 80° C.

Preferred conditions are ylide formation at −78° C. using LDA (prepared in situ from treatment of N,N-diisopropylamine with n-BuLi) as base and THF as solvent, reacting the phosphonic acid ester for 1 hour at −78° C., and then condensation with the carbonyl component warming to room temperature overnight.

Step B: C—N bond formation can be accomplished by coupling reaction between aryl iodide 4 and urea compounds 5 in the presence of a palladium or copper catalyst, a ligand and a base in solvents such as dioxane, DME, THF, toluene, DMF and DMSO at elevated temperatures. For example, using copper(I) iodide, KF/Al₂O₃ as base and N,N'-dibenzylethylenediamine, N,N'-bis(2-pyridyl-methyl)ethylenediamine or 1,10-phenanthroline as ligand according to the procedure of Hosseinzadeh et al. (*Tetrahedron Lett.* 2008, 49, 840-843). Preferred conditions are copper(I) iodide, KF/Al₂O₃ and N,N'-dibenzylethylenediamine in THF at 90° C. for 30 min in a sealed tube under microwave irradiation.

Step C: Reduction of the alkene 6 can be effected by hydrogenation with hydrogen under normal or elevated pressure or by transfer hydrogenation using ammonium formiate or cyclohexadiene as hydrogen source with a catalyst such as PtO₂, Pd—C or Raney nickel in solvents such as MeOH, EtOH, H₂O, dioxane, THF, HOAc, EtOAc, CH₂Cl₂, CHCl₃, DMF or mixtures thereof. Alternatively, the reduction of the alkene can be effected by Mg in MeOH or by LiAlH₄ in THF or diethylether.

Preferred conditions are hydrogenation in the presence of PtO₂ as catalyst with MeOH as solvent.

Step D: Simultaneous cleavage of the amino alcohol protecting groups can be effected with a mineral acid such as HCl, H₂SO₄ or H₃PO₄ or an organic acid such as CF₃COOH, CHCl₂COOH, HOAc or p-toluonesulfonic acid in a solvent such as CH₂Cl₂, CHCl₃, THF, MeOH, EtOH or H₂O at 0 to 80° C.

Preferred conditions are CF$_3$COOH in aqueous acetonitrile at 80° C. overnight or 4N HCl in dioxane at r.t. overnight.

Step E: Cyclisation of the amino alcohol 8 to the corresponding 2-aminooxazoline IA-1 can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

Scheme 2

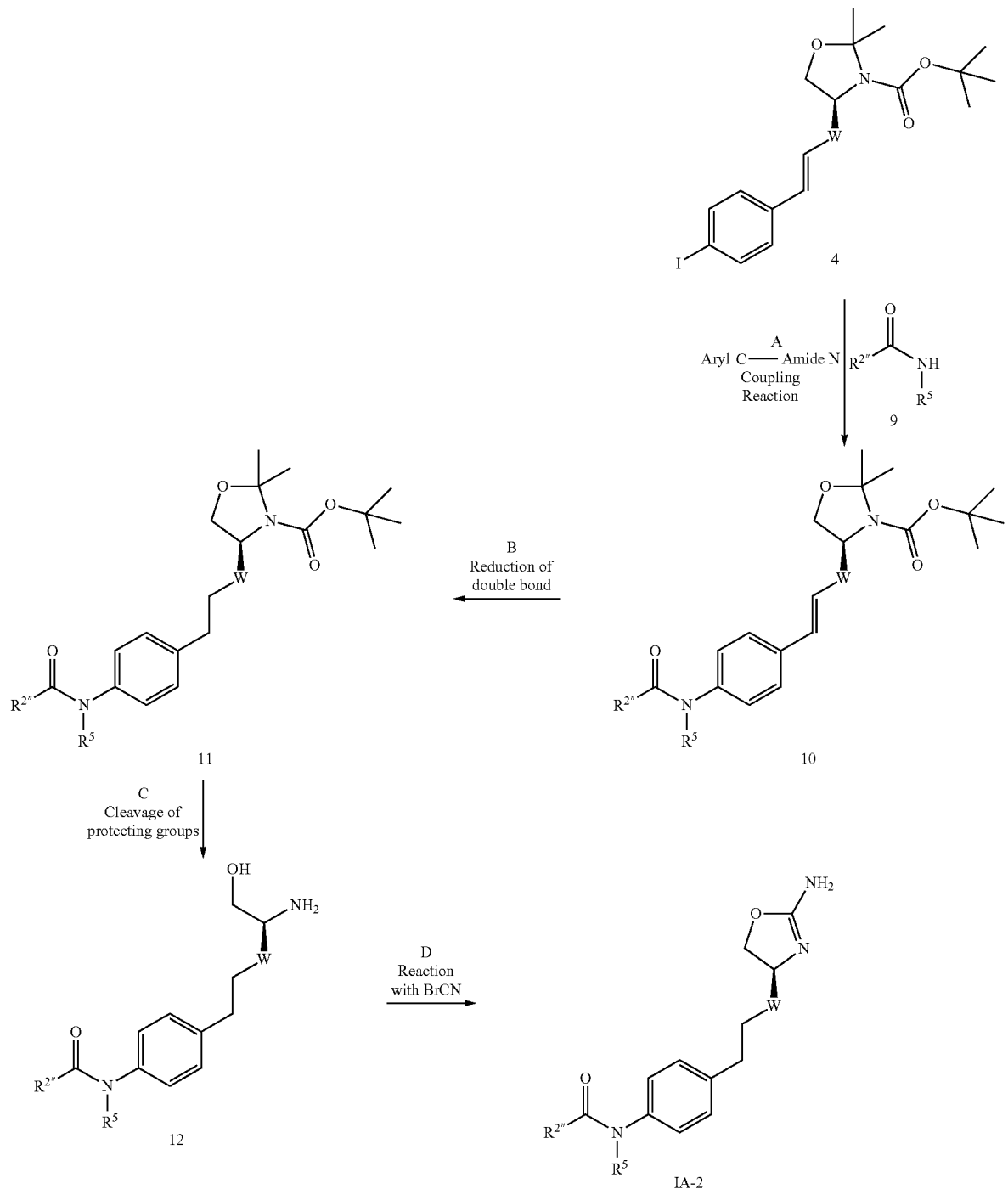

R[2'''] is (CR'R'')$_m$-cycloalkyl, optionally substituted by halogen, lower alkyl, lower alkyl substituted by halogen, halogen-substituted phenyl or heteroaryl; or is (CR'R'')$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or or heterocycloalkyl each of which is optionally substituted by halogen; or is (CR'R'')$_m$-aryl, optionally substituted by halogen, lower alkyl substituted by halogen, lower alkoxy substituted by halogen, lower alkyl, alkynyl, lower alkoxy, CH$_2$-lower alkoxy or cyano;

and R' and R'' are independently from each other hydrogen, lower alkoxy or lower alkyl, or together with the C-atom to which they are attached form a cycloalkyl group and W is a bond or —CH$_2$— and the other substituents are as described above.

Step A: C—N bond formation can be accomplished by coupling reaction between aryl iodide 4 and amide compounds 9 in the presence of a palladium or copper catalyst, a ligand and a base in solvents such as dioxane, DME, THF, toluene, DMF and DMSO at elevated temperatures. For example, using copper(I) iodide, potassium phosphate as base and N,N'-dimethylglycine, L-proline, glycine, N,N'-dimethylethylenediamine, 2-aminoethanol or 1,2-ethandiol as ligand.

Preferred conditions are copper(I) iodide, potassium phosphate and N,N'-dimethylglycine in DMSO in a sealed tube at 110° C. overnight according to the procedure of Chen et al. (*Org. Lett.* 2008, 10, 4565-4568).

Alternative preferred conditions are copper(I) iodide, potassium phosphate and N,N'-dimethylethylenediamine in toluene in a sealed tube at 120° C. overnight according to the procedure of Buchwald and co-workers (*J. Am. Chem. Soc.* 2009, 131, 78-88).

Step B: Reduction of the alkene can be effected by hydrogenation with hydrogen under normal or elevated pressure or by transfer hydrogenation using ammonium formiate or cyclohexadiene as hydrogen source with a catalyst such as PtO$_2$, Pt—C, Pd—C or Raney nickel in solvents such as MeOH, EtOH, H$_2$O, dioxane, THF, HOAc, EtOAc, CH$_2$Cl$_2$, CHCl$_3$, DMF or mixtures thereof. Alternatively, the reduction of the alkene can be effected by Mg in MeOH or by LiAlH$_4$ in THF or diethylether. Preferred conditions are hydrogenation in the presence of PtO$_2$ as catalyst with MeOH as solvent.

Step C: Simultaneous cleavage of the amino alcohol protecting groups can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 80° C. Preferred conditions are CF$_3$COOH in aqueous acetonitrile at 80° C. overnight or 4N HCl in dioxane at r.t. overnight.

Step D: Cyclisation of the amino alcohol to the corresponding 2-aminooxazoline can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

Scheme 3

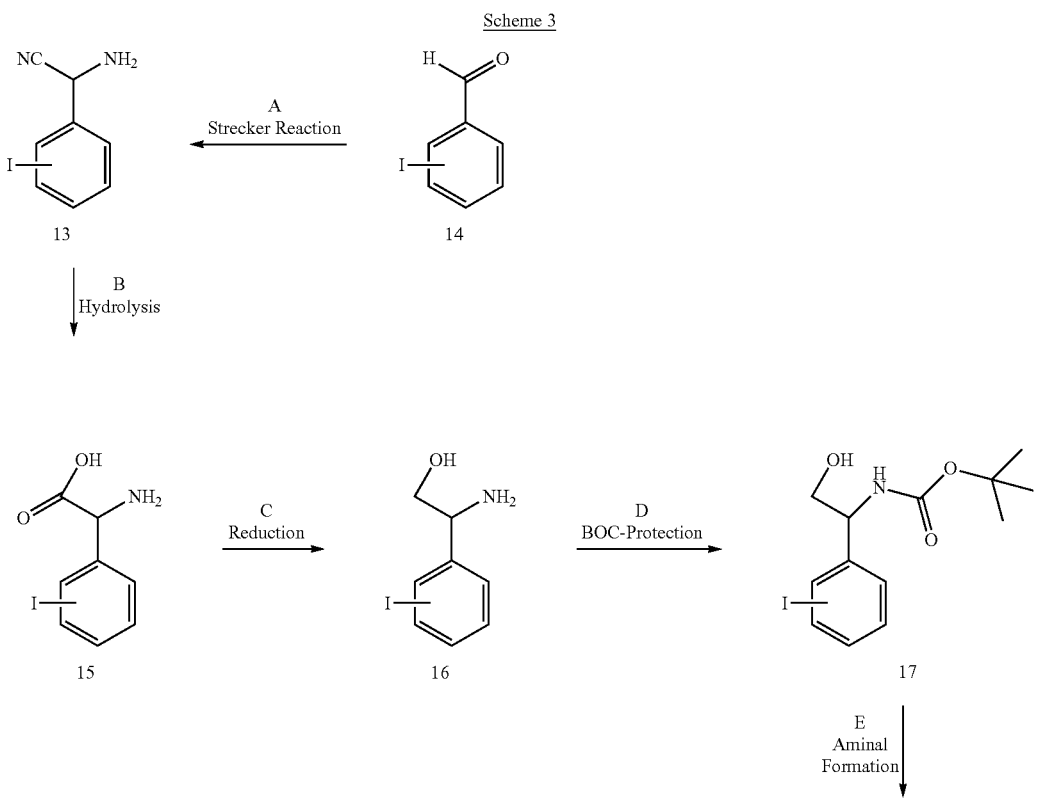

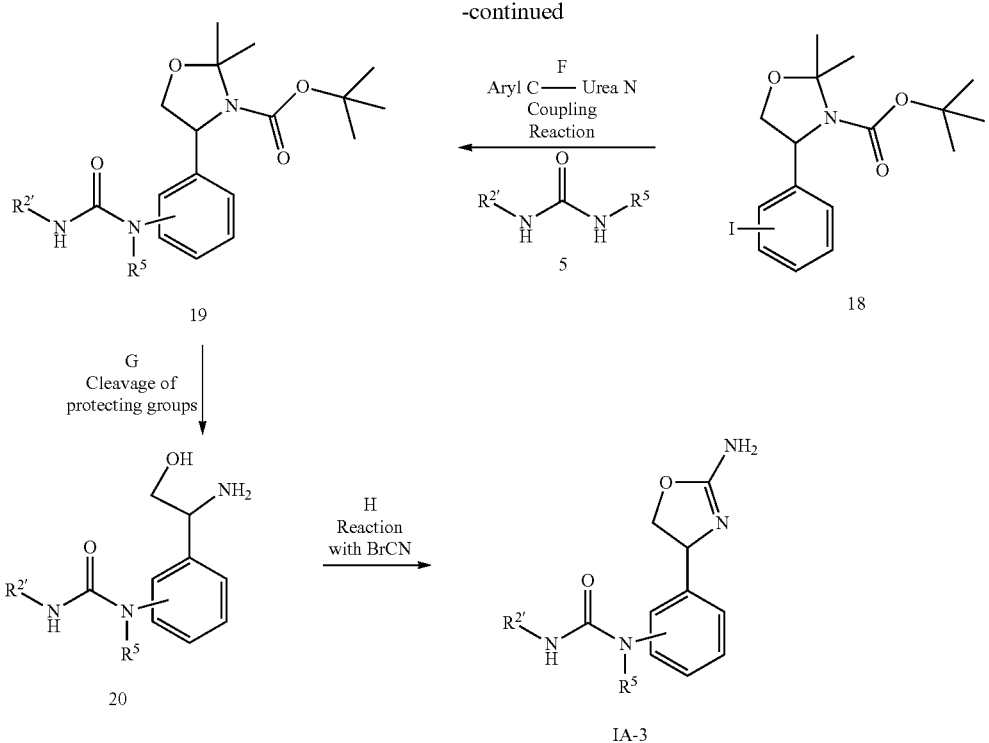

$R^2$ is aryl or heteroaryl, which are optionally substituted by one or more substituents selected from halogen and lower alkyl substituted by halogen and the other substituents are as described above.

Step A: Amino nitriles 13 can be prepared by Strecker reaction of 3-iodo-benzaldehyde or 4-iodo-benzaldehyde 14. Preferred conditions are imine formation by treatment with methanolic ammonia solution in the presence of tetraisopropylorthotitanate in methanol at room temperature, followed by treatment with trimethylsilyl cyanide.

Step B: Hydrolysis of the nitrile group to afford amino acid 15 can be effected by treatment with a mineral acid such as HCl, $H_2SO_4$ or $H_3PO_4$ in an aqueous solvent system at elevated temperature. Preferred conditions are 5N aqueous HCl at reflux overnight.

Step C: Reduction of an acid group can be effected by treatment with $LiAlH_4$, $BH_3$-THF, $BH_3$-$Me_2$S complex in the presence of $BF_3$-etherate or Red-Al in a solvent such as 1,2-dimethoxyethane, THF, diethylether or toluene at r.t.->reflux for 1-24 hrs. Alternatively, reduction of an acid group can be effected by treatment with $LiBH_4$ in the presence of $Me_3$SiCl in a solvent such as methanol at 0° C.->r.t. for 1-24 hrs. Preferred conditions are $LiBH_4$/$Me_3$SiCl in THF at r.t. for 4 hrs.

Step D: Introduction of a BOC protecting group can be accomplished by treatment with di-tert-butyl dicarbonate in the presence of an organic base such as N,N-diisopropylethylamine or triethylamine in non-protic solvents such as dichloromethane, dioxane, THF or DMF, or using inorganic bases such as sodium hydroxide or sodium carbonate in aqueous solvent systems such as water, aqueous ethanol or aqueous methanol. Preferred conditions are N,N-diisopropylethylamine in THF at room temperature for 5 hours.

Step E: Introduction of an aminal protecting group without effecting cleavage of the acid-labile BOC protecing group can be accomplished by treatment with dimethoxypropane in the presence of an organic acid such as p-toluenesulphonic acid or camphorsulphonic acid in non-protic solvents such as dichloromethane, 1,2-dichloroethane, diethyl ether or diisopropylether. Preferred conditions are p-toluenesulphonic acid in dichloromethane at room temperature overnight.

Step F: C—N bond formation can be accomplished by coupling reaction between aryl iodide 18 and urea compounds 5 in the presence of a palladium or copper catalyst, a ligand and a base in solvents such as dioxane, DME, THF, toluene, DMF and DMSO at elevated temperatures. For example, using copper(I) iodide, $KF/Al_2O_3$ as base and N,N'-dibenzylethylenediamine, N,N'-bis(2-pyridyl-methyl)ethylenediamine or 1,10-phenanthroline as ligand according to the procedure of Hosseinzadeh et al. (*Tetrahedron Lett.* 2008, 49, 840-843). Preferred conditions are copper(I) iodide, $KF/Al_2O_3$ and N,N'-dibenzylethylenediamine in THF at 90° C. for 30 min in a sealed tube under microwave irradiation.

Step G: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C. Preferred conditions are $CF_3COOH$ in aqueous acetonitrile at 80° C. overnight or 4N HCl in dioxane at r.t. overnight.

Step H: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

Scheme 4

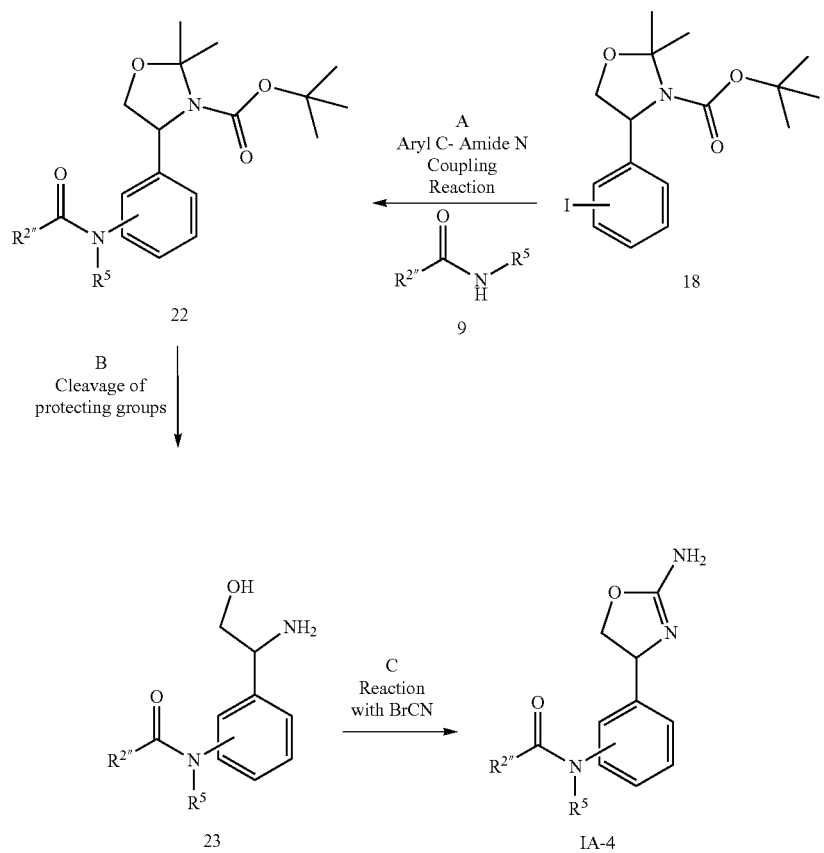

R²'' is (CR'R'')$_m$-cycloalkyl, optionally substituted by halogen, lower alkyl, lower alkyl substituted by halogen, halogen-substituted phenyl or heteroaryl; or is (CR'R'')$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen; or is (CR'R'')$_m$-aryl, optionally substituted by halogen, lower alkyl substituted by halogen, lower alkoxy substituted by halogen, lower alkyl, alkynyl, lower alkoxy, CH$_2$-lower alkoxy or cyano;

and R' and R'' are independently from each other hydrogen, lower alkoxy or lower alkyl, or together with the C-atom to which they are attached form a cycloalkyl group, m is 0 or 1 and the other substituents are as described above.

Step A: C—N bond formation can be accomplished by coupling reaction between aryl iodide 18 and amide compounds 9 in the presence of a palladium or copper catalyst, a ligand and a base in solvents such as dioxane, DME, THF, toluene, DMF and DMSO at elevated temperatures. For example, using copper(I) iodide, potassium phosphate as base and N,N'-dimethylglycine, L-proline, glycine, 2-aminoethanol or 1,2-ethandiol as ligand according to the procedure of Chen et al. (*Org. Lett.* 2008, 10, 4565-4568). Preferred conditions are copper(I) iodide, potassium phosphate and N,N'-dimethylglycine in DMSO in a sealed tube at 110° C. overnight.

Step B: Simultaneous cleavage of the amino alcohol protecting groups can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 80° C. Preferred conditions are CF$_3$COOH in aqueous acetonitrile at 80° C. overnight or 4N HCl in dioxane at r.t. overnight.

Step C: Cyclisation of the amino alcohol to the corresponding 2-aminooxazoline can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

Scheme 5

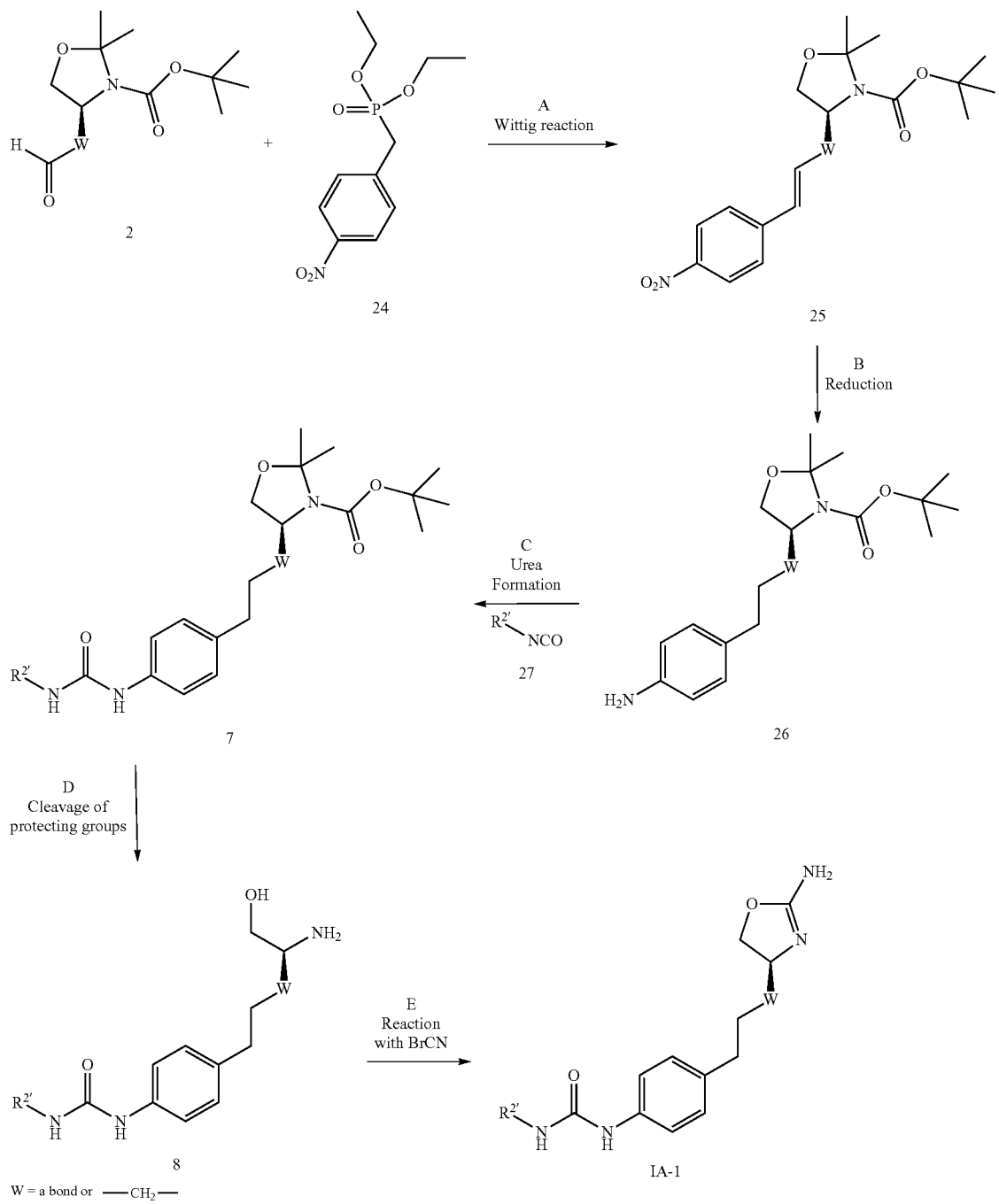

W = a bond or —CH₂—

R²' is aryl or heteroaryl, which are optionally substituted by one or more substituents selected from halogen and lower alkyl substituted by halogen, W is a bond or —CH₂— and the other substituents are as described above.

Step A: Wittig reaction between aldehyde 2 (W=a bond: CAS 95715-87-0 or W=—CH₂—: CAS 147959-19-1) and (4-nitro-benzyl)-phosphonic acid diethyl ester 24 (CAS 2609-49-6) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethane, DMF, benzene, toluene or mixtures thereof at temperatures from −78° C. to 80° C. for 15 min-8 hrs and if appropriate optional addition of a crown ether for ylide generation and then condensing the ylide with the carbonyl compound in the same solvent at a temperature between 0 and 80° C. for 1-24 hrs. Alternatively, the base, the carbonyl compound and the optional crown ether can be added to the reaction mixture at the same time without pre-formation of the ylide at temperatures from −78° C. to 80° C. Preferred conditions are ylide formation at −78° C. using LDA (prepared in situ from treatment of N,N-diisopropylamine with n-BuLi) as base and THF as solvent, reacting the phosphonic acid ester for 1 hour at −78° C., and then condensation with the carbonyl component warming to room temperature overnight.

Step B: Simultaneous reduction of the alkene and nitro group can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc, $CH_2Cl_2$, $CHCl_3$, DMF or mixtures thereof. Alternatively, the reduction of the alkene can be effected by Mg in MeOH or by $LiAlH_4$ in THF or diethylether. Preferred conditions are ammonium formate in the presence of palladium on charcoal in MeOH at 60° C. for 2 hours.

Step C: Urea formation can be accomplished by a coupling reaction between amine 26 and alkyl or aryl isocyanate compounds 27 in the presence of a base such as triethylamine or N,N-diisopropylethylamine in halogenated solvents such as dichloromethane. Preferred conditions are N,N-diisopropylethylamine in dichloromethane at room temperature overnight.

Step D: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C. Preferred conditions are $CF_3COOH$ in aqueous acetonitrile at 80° C. overnight or 4N HCl in dioxane at r.t. overnight.

Step E: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

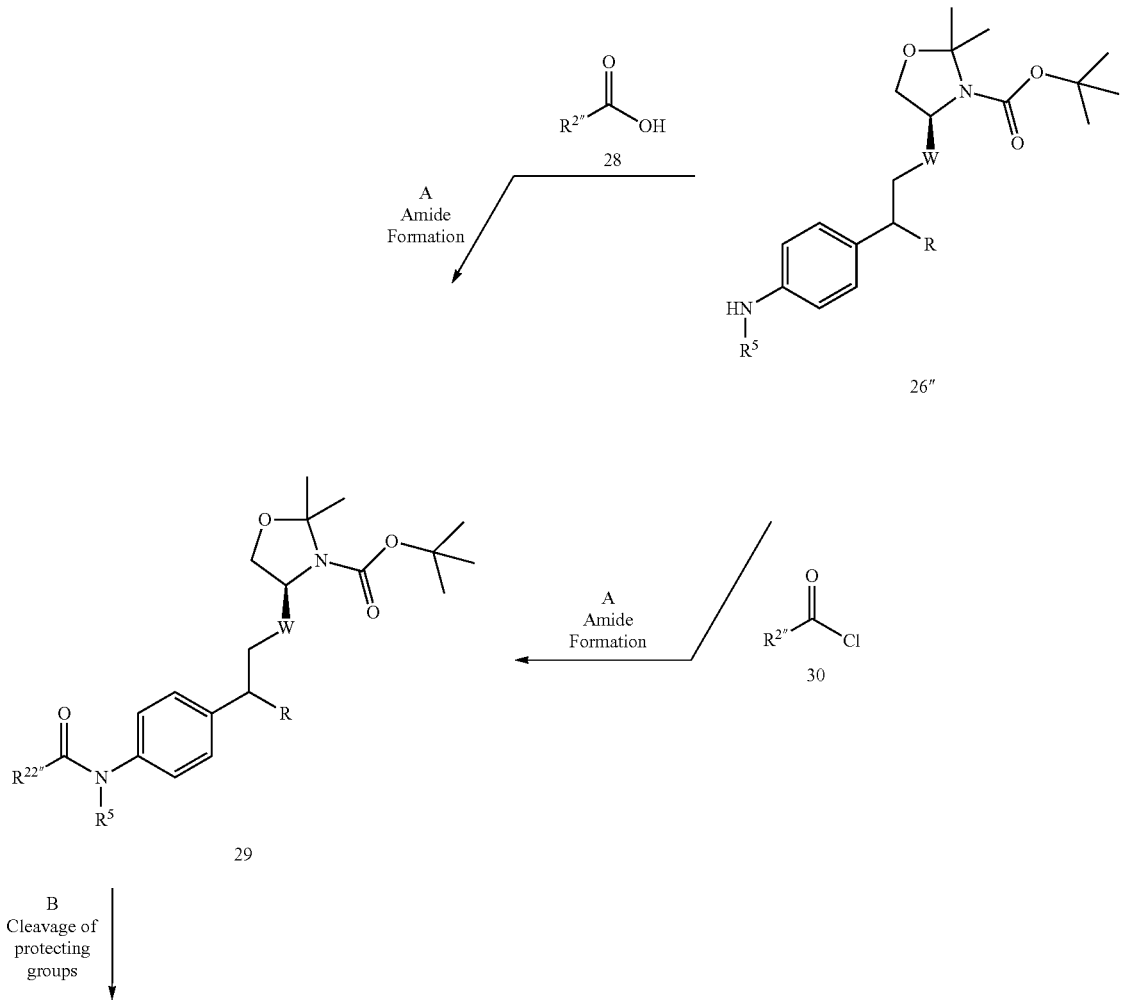

Scheme 6

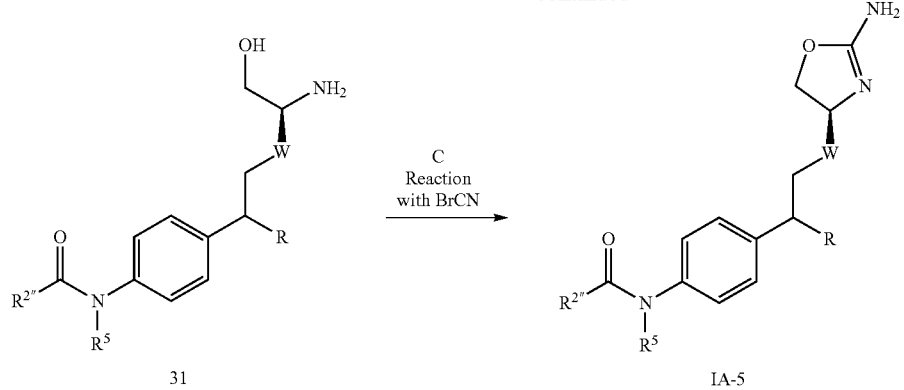

$R^{2\prime\prime}$ is $(CR'R'')_m$-cycloalkyl, optionally substituted by halogen, lower alkyl, lower alkyl substituted by halogen, halogen-substituted phenyl or heteroaryl; or is $(CR'R'')_m$-heteroaryl, optionally substituted by halogen, lower alkyl, lower alkyl substituted by halogen, lower alkoxy substituted by halogen, lower alkyl, cycloalkyl, NHC(O)-lower alkyl, cyano, $S(O)_2$-lower alkyl, $NR^6R^7$, or by heteroaryl or heterocycloalkyl each of which is optionally substituted by halogen; or is $(CR'R'')_m$-aryl, optionally substituted by halogen, lower alkyl substituted by halogen, lower alkoxy substituted by halogen, lower alkyl, alkynyl, lower alkoxy, $CH_2$-lower alkoxy or cyano;

and R' and R'' are independently from each other hydrogen, lower alkoxy or lower alkyl, or together with the C-atom to which they are attached form a cycloalkyl group, m is 0 or 1 and the other substituents are as described above.

W is a bond or —$CH_2$—, m is 0 or 1 and the other substituents are as described above.

Step A: Amide formation can be accomplished by a coupling reaction between amine 26" and carboxylic acids 28 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are TBTU with N-methylmorpholine in THF at 50° C. overnight. Alternatively, amide formation can be accomplished by a coupling reaction between amine 26" and acyl chlorides 30 in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are triethylamine in THF at 50° C. for 4 hours.

Step B: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C. Preferred conditions are $CF_3COOH$ in aqueous acetonitrile at 80° C. overnight or 4N HCl in dioxane at r.t. overnight.

Step C: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

Scheme 7

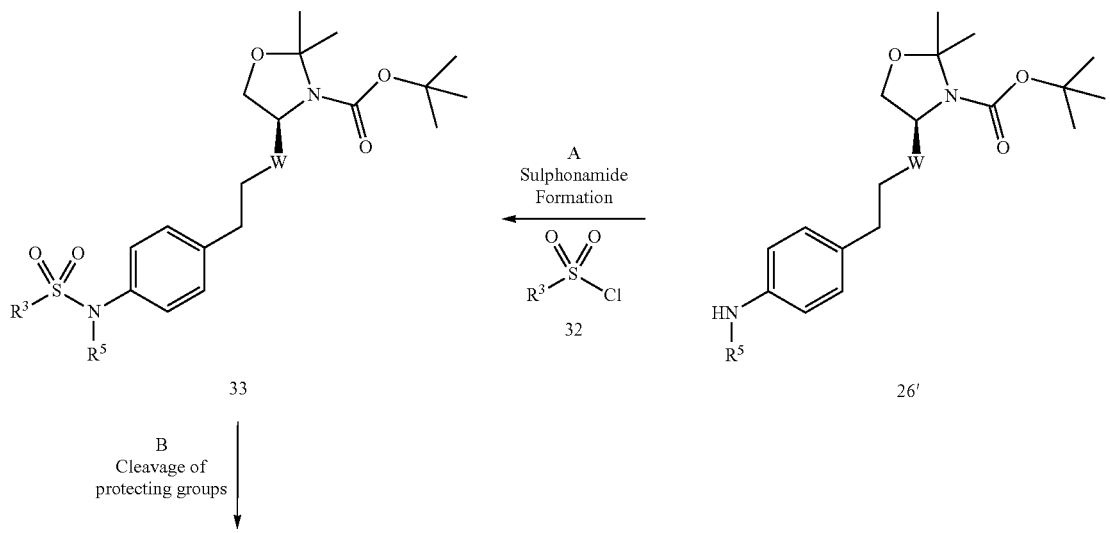

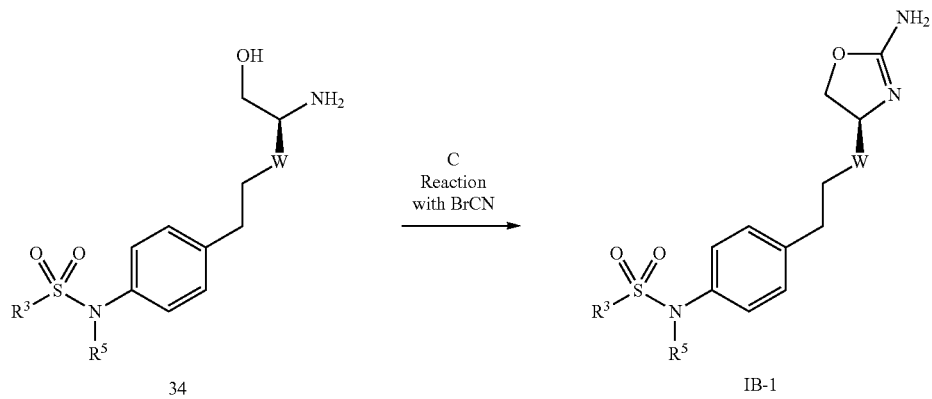

W is a bond or —CH$_2$—

The substituents are as described above and W is a bond or —CH$_2$—.

Step A: Sulphonamide formation can be accomplished by a coupling reaction between amine 26' and sulphonyl chlorides 32 in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are triethylamine in THF at 50° C. for 4 hours.

Step B: Simultaneous cleavage of the amino alcohol protecting groups can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 80° C. Preferred conditions are CF$_3$COOH in aqueous acetonitrile at 80° C. overnight or 4N HCl in dioxane at r.t. overnight.

Step C: Cyclisation of the amino alcohol to the corresponding 2-aminooxazoline can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

Scheme 8

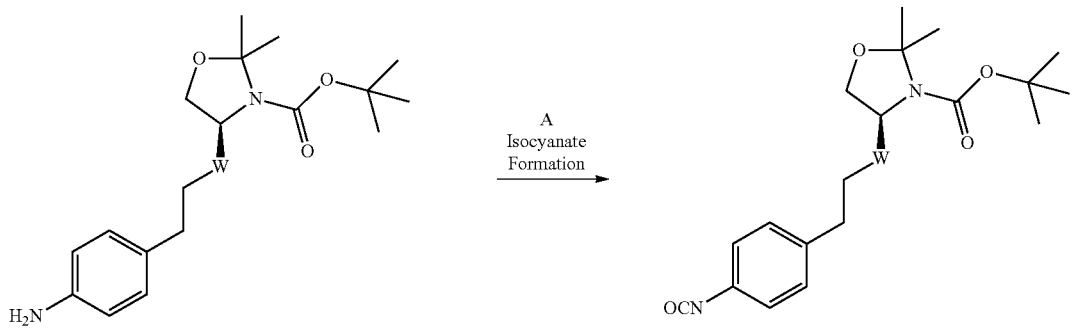

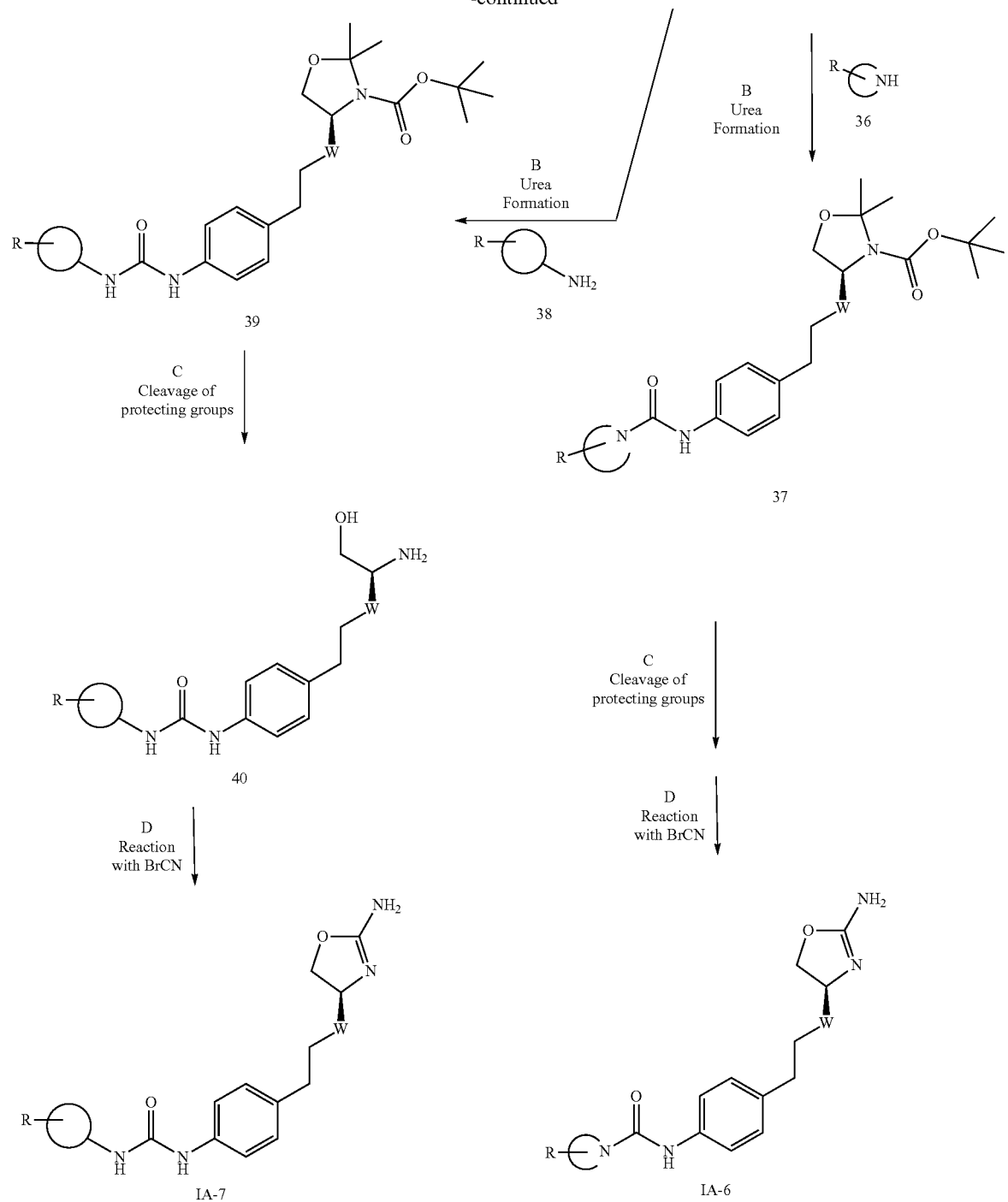
W = a bond or —CH₂—
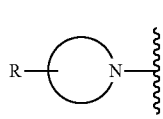
is a corresponding heterocycloalkyl, optionally substituted by halogen or lower alkyl substituted by halogen,
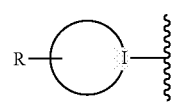
is cycloalkyl, optionally substituted by halogen, lower alkyl, lower alkyl substituted by halogen, halogen-substituted phenyl or heteroaryl, or is aryl, optionally substituted by halogen, lower alkyl substituted by halogen, lower alkoxy substituted by halogen, lower alkyl, alkynyl, lower alkoxy, $CH_2$-lower alkoxy or cyano, or is heteroaryl, optionally substituted by halogen, lower alkoxy, lower alkyl substituted by halogen, lower alkoxy substituted by halogen, lower alkyl, cycloalkyl, NHC(O)-lower alkyl, cyano, $S(O)_2$-lower alkyl, $NR^6R^7$, or by heteroaryl or heterocycloalkyl each of which is optionally substituted by halogen, and the other substituents are as described above and W is a bond or —$CH_2$—.

Step A: Isocyanate formation can be effected by treatment with triphosgene in the presence of an organic base such as triethylamine or N,N-diisopropylamine in a halogenated organic solvent such as dichloromethane or 1,2-dichloroethane at elevated temperature. Preferred conditions are triethylamine in dichloromethane at 50° C. overnight.

Step B: Urea formation can be accomplished by a coupling reaction between isocyanate 35 and primary amines 38 or secondary amines 36 in the presence of a base such as triethylamine or N,N-diisopropylethylamine in halogenated solvents such as dichloromethane. Preferred conditions are N,N-diisopropylethylamine in dichloromethane at room temperature overnight.

Step C: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C. Preferred conditions are $CF_3COOH$ in aqueous acetonitrile at 80° C. overnight or 4N HCl in dioxane at r.t. overnight.

Step D: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

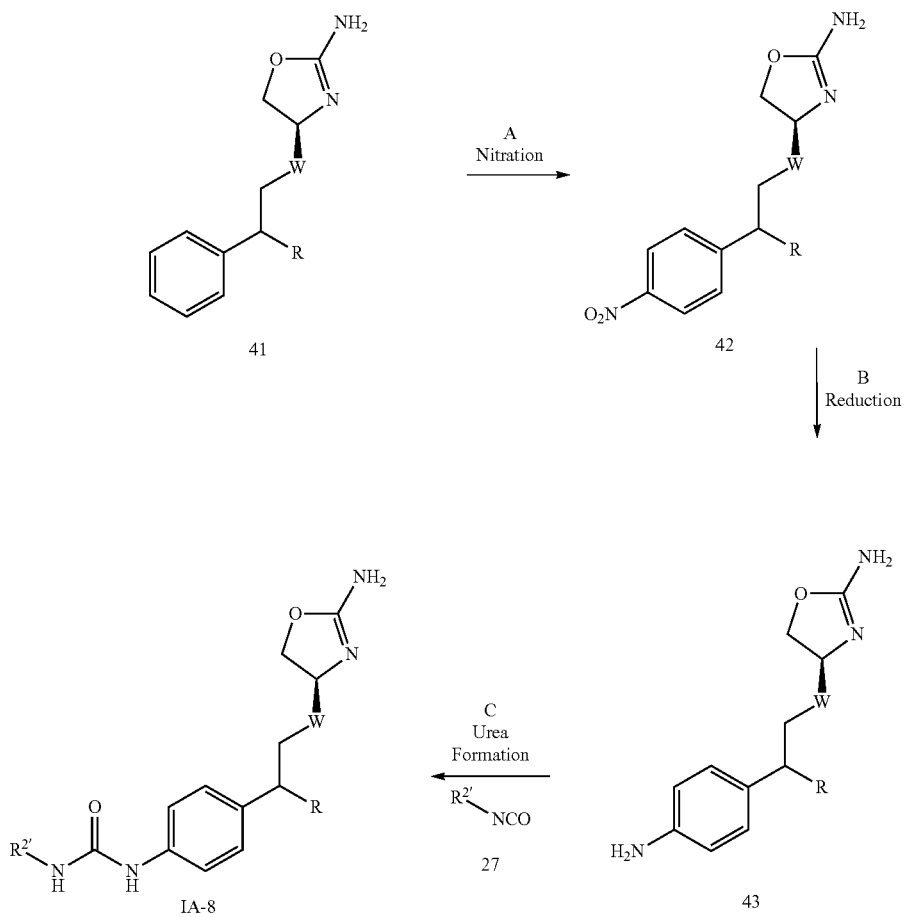

Scheme 9

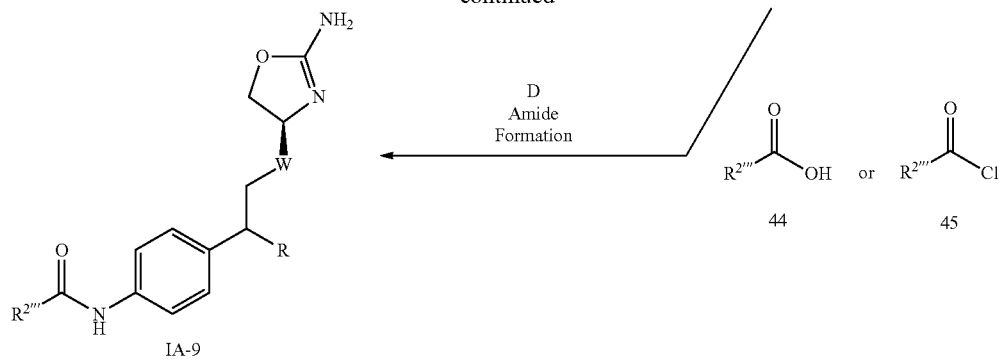

W is a bond or —CH$_2$—

R$^{2'}$ is aryl, optionally substituted by one or more substituents selected from halogen and lower alkyl substituted by halogen or heteroaryl, optionally substituted by one or more substituents selected from halogen and lower alkyl substituted by halogen, R$^{2''}$ is cycloalkyl, optionally substituted by halogen, lower alkyl, lower alkyl substituted by halogen, halogen-substituted phenyl or by heteroaryl, or is heterocycloalkyl, optionally substituted by halogen or lower alkyl substituted by halogen, or is (CR'R")$_m$-heteroaryl as described above, or is (CR'R")$_m$-aryl as described above, and the other substituents are as described above and W is a bond or —CH$_2$—.

Step A: Nitration can be accomplished by treatment of 41 with a nitrating reagent such as 65% conc. nitric acid at eleveated temperatures. Preferred conditions are 60° C. for 3 hours.

Step B: Reduction of the nitro group can be effected by hydrogenation with hydrogen under normal or elevated pressure or by transfer hydrogenation using ammonium formate or cyclohexadiene as hydrogen source with a catalyst such as PtO$_2$, Pd—C or Raney nickel in solvents such as MeOH, EtOH, H$_2$O, dioxane, THF, HOAc, EtOAc, CH$_2$Cl$_2$, CHCl$_3$, DMF or mixtures thereof. Alternatively, the reduction of the alkene can be effected by Mg in MeOH or by LiAlH$_4$ in THF or diethylether. Preferred conditions are ammonium formate in the presence of palladium on charcoal in MeOH at 60° C. for 2 hours.

Step C: Urea formation can be accomplished by a coupling reaction between amine 43 and alkyl or aryl isocyanate compounds 27 in the presence of a base such as triethylamine or N,N-diisopropylethylamine in halogenated solvents such as dichloromethane. Preferred conditions are N,N-diisopropylethylamine in dichloromethane at room temperature overnight.

Step D: Amide formation can be accomplished by a coupling reaction between amine 43 and carboxylic acids 44 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are TBTU with N-methylmorpholine in THF at 50° C. overnight.

Alternatively, amide formation can be accomplished by a coupling reaction between amine 43 and acyl chlorides 45 in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are triethylamine in THF at 50° C. for 4 hours.

Scheme 10

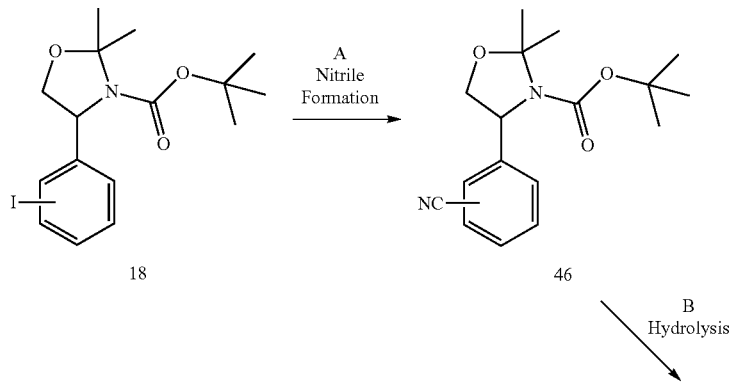

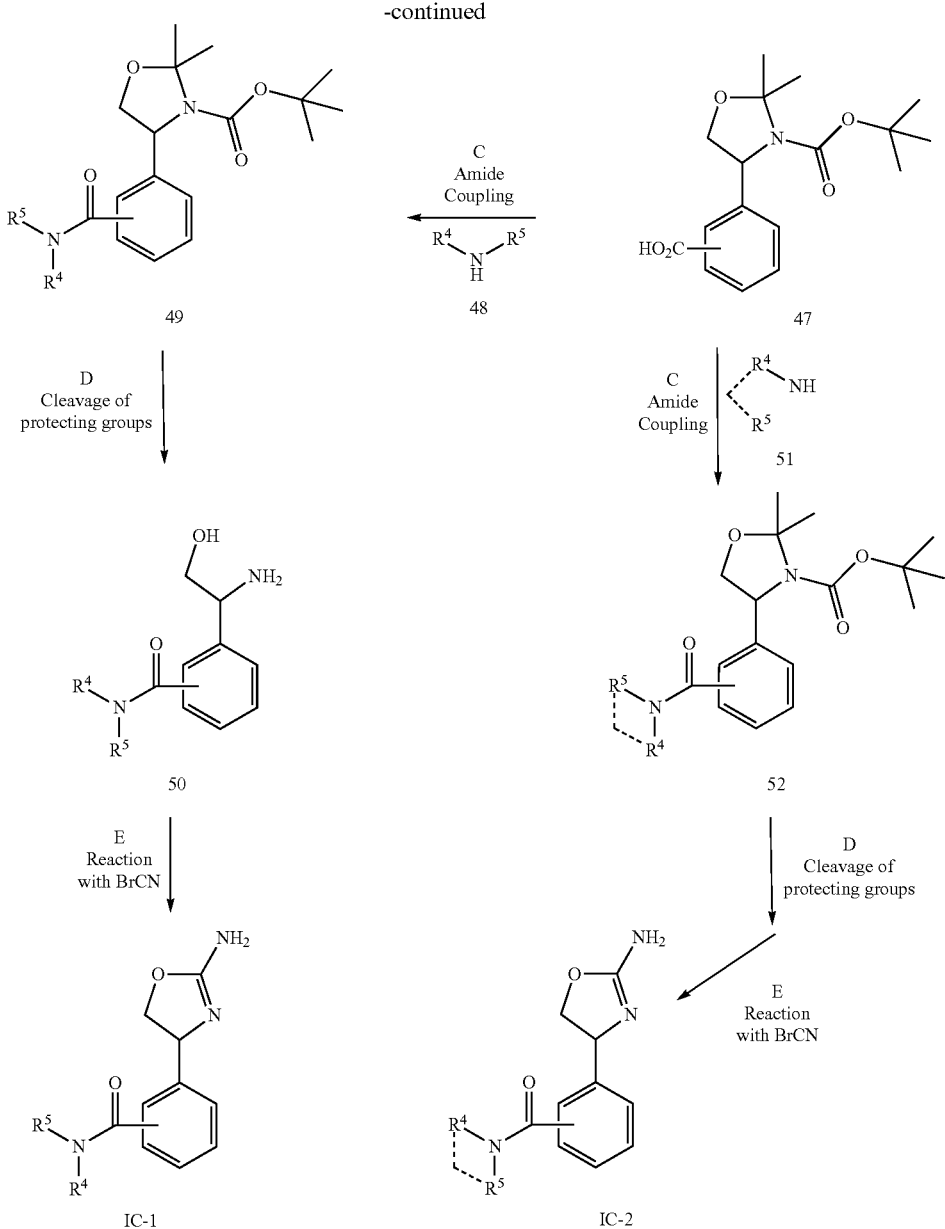

The dotted line means that $R^4$ and $R^5$ together with the N-atom to which they are attached optionally form a heterocyclic ring, and the other substituents are as described above.

Step A: Aryl nitrile 46 can be prepared from aryl iodide 18 by reaction with a metal cyanide salt in the presence of a palladium catalyst in an organic solvent such as DMF or DMSO at elevated temperature. Preferred conditions are zinc cyanide and tetrakis(triphenyl-phosphine)palladium in DMF at 160° C. for 15 min in a sealed tube under microwave irradiation.

Step B: Hydrolysis of the nitrile group to afford carboxylic acid 47 in the presence of the acid-labile BOC protecting group can be effected by treatment with an alkali such as KOH or NaOH in an aqueous solvent system at elevated temperature. Preferred conditions are 2N aqueous NaOH at 85° C. overnight.

Step C: Amide formation can be accomplished by a coupling reaction between carboxylic acid 47 and acyclic primary or secondary amines 48 or cyclic secondary amines 51 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are TBTU with N-methylmorpholine in THF at 50° C. overnight.

Step D: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C. Preferred conditions are $CF_3COOH$ in aqueous acetonitrile at 80° C. overnight or 4N HCl in dioxane at r.t. overnight.

Step E: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

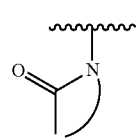 [SMILES: *NC(C)=O]

is a definition for

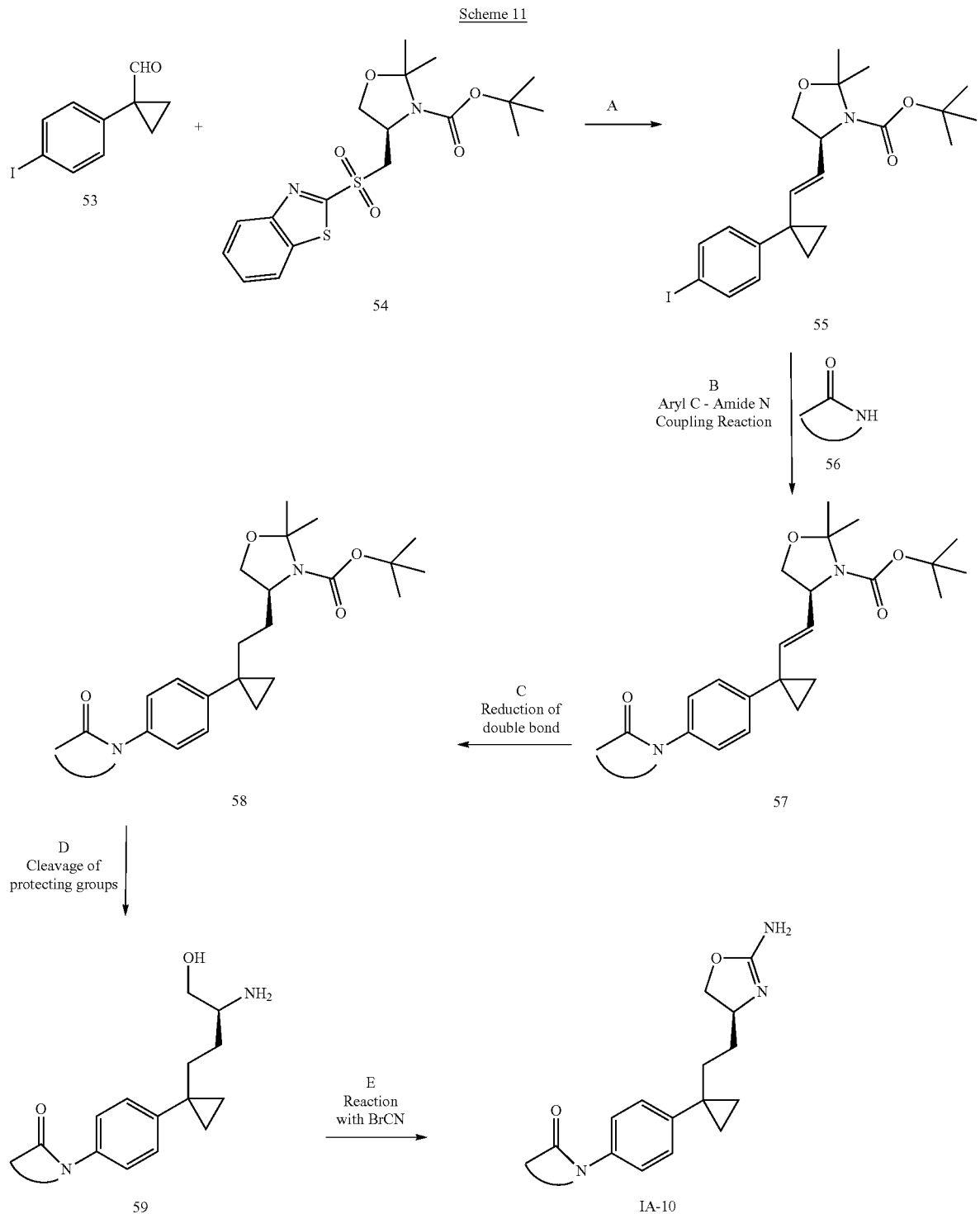

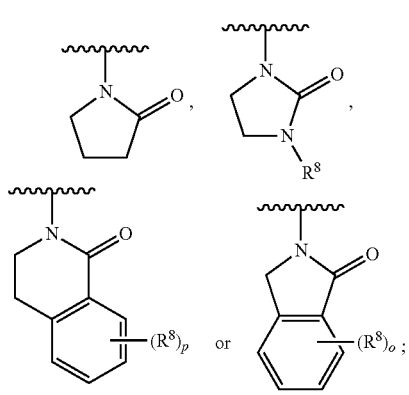

R[8] is hydrogen, halogen or aryl optionally substituted by halogen;

Step A: Julia reaction between the aldehyde 53 and the benzothiazole sulfonyl compound 54 can be accomplished by using a base such as LiHMDS, NaHMDS, KHMDS, LDA, KOtBu, DBU in a solvent such as THF, diethyl ether, 1,2-dimethoxyethane, dichloromethane, DMF or mixtures thereof at temperatures from −100° C.-r.t. for 15 min-8 hrs for anion generation and then condensing the glide with the carbonyl compound in the same solvent at temperatures between −100° C. and r.t. for 1-24 hrs. Preferred conditions are anion generation with LiHMDS at −78° C. in THF and subsequent condensation with the carbonyl component under the same conditions.

Step B: C—N bond formation can be accomplished by coupling reaction between aryl iodide 55 and amide compounds 56 in the presence of a palladium or copper catalyst, a ligand and a base in solvents such as dioxane, DME, THF, toluene, DMF and DMSO at elevated temperatures. For example, using copper(I) iodide, potassium phosphate as base and N,N'-dimethylglycine, L-proline, glycine, 2-aminoethanol or 1,2-ethandiol as ligand according to the procedure of Chen et al. (*Org. Lett.* 2008, 10, 4565-4568). Preferred conditions are copper(I) iodide, potassium phosphate and N,N'-dimethylglycine in DMSO in a sealed tube at 110° C. overnight.

Step C: Reduction of the alkene can be effected by hydrogenation with hydrogen under normal or elevated pressure or by transfer hydrogenation using ammonium formiate or cyclohexadiene as hydrogen source with a catalyst such as $PtO_2$, Pd—C or Raney nickel in solvents such as MeOH, EtOH, $H_2O$, dioxane, THF, HOAc, EtOAc, $CH_2Cl_2$, $CHCl_3$, DMF or mixtures thereof. Alternatively, the reduction of the alkene can be effected by Mg in MeOH or by $LiAlH_4$ in THF or diethylether. Preferred conditions are hydrogenation in the presence of $PtO_2$ as catalyst with MeOH as solvent.

Step D: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C. Preferred conditions are $CF_3COOH$ in aqueous acetonitrile at 80° C. overnight or 4N HCl in dioxane at r.t. overnight.

Step E: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour. Preferred conditions are methanol as solvent and sodium acetate as base at r.t. overnight followed by treatment with aqueous ammonia solution at room temperature for 1 hour.

Scheme 12

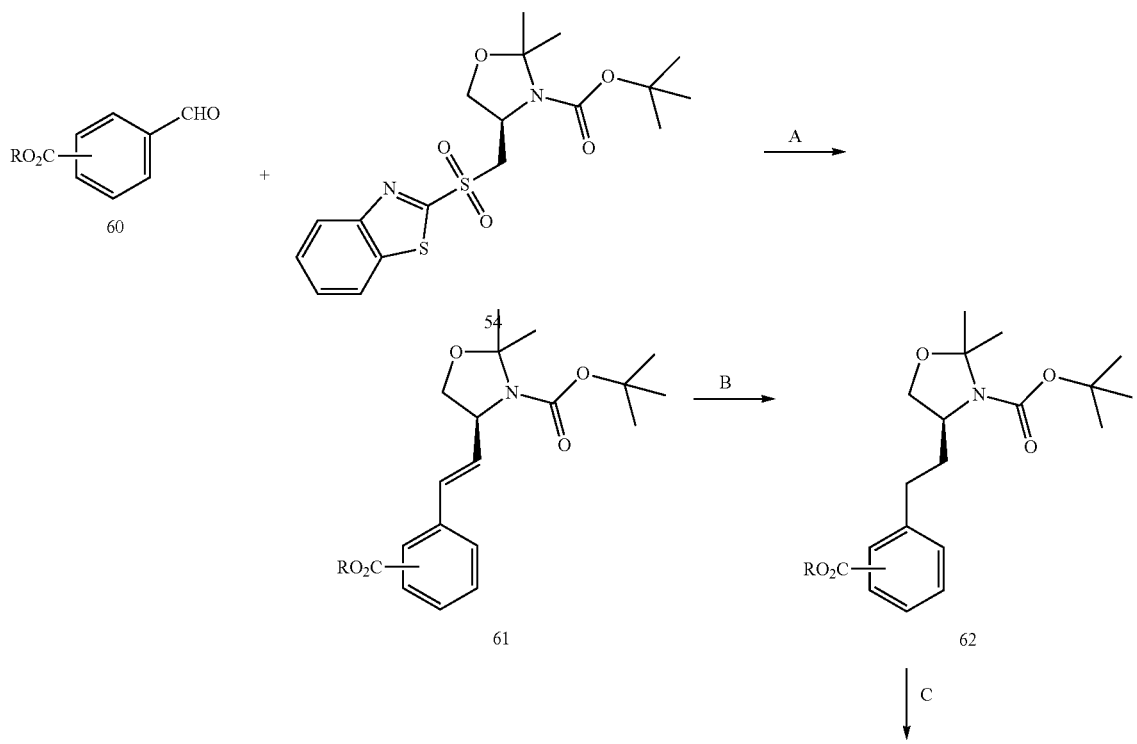

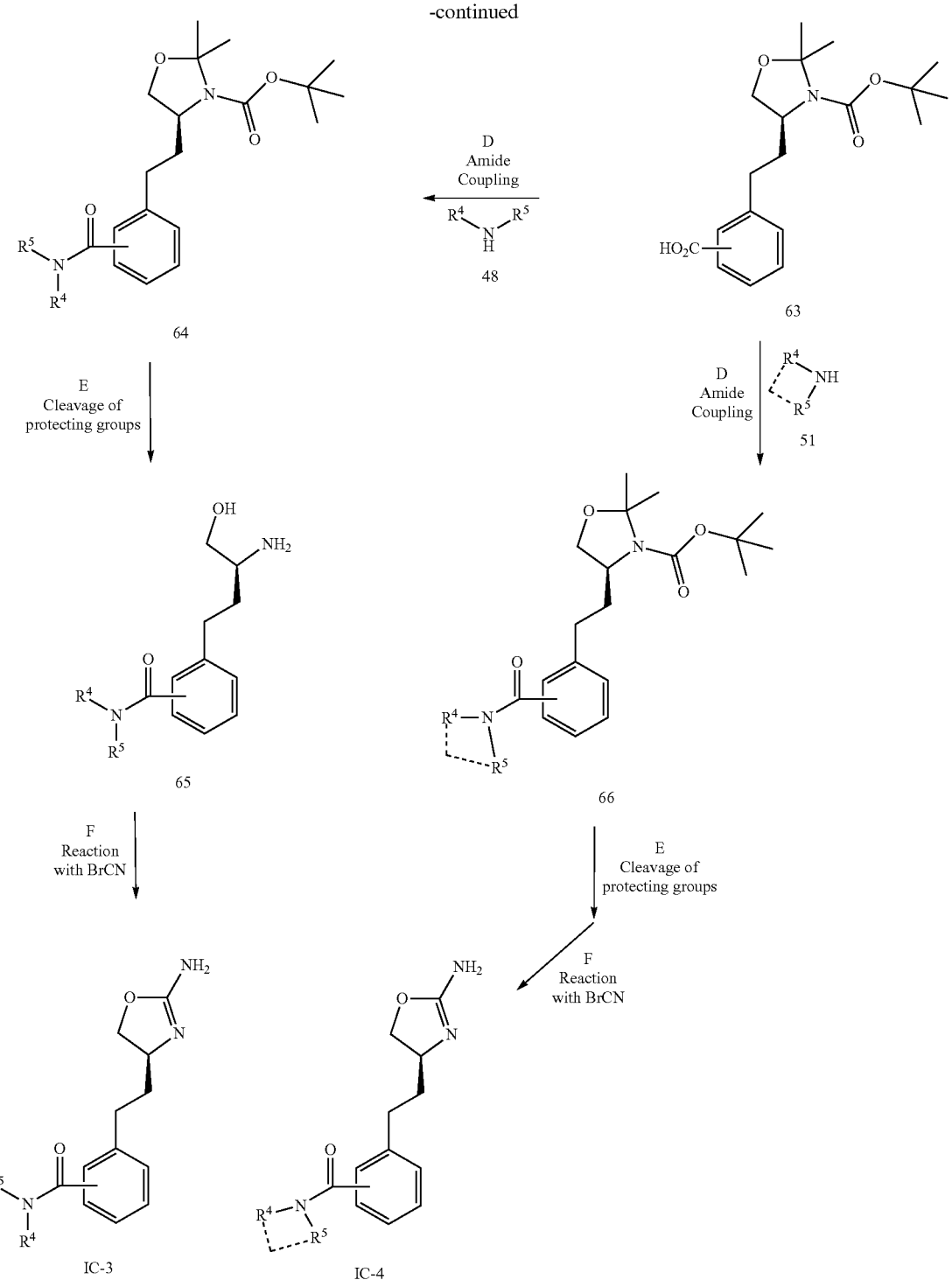

The dotted line means that R⁴ and R⁵ form together with the N-atom a heterocyclic ring, and the other substituents are as described above.

Step A: Julia reaction between formyl benzoic ester 60 and the benzothiazole sulfonyl compound 54 can be accomplished by using a base such as LiHMDS, NaHMDS, KHMDS, LDA, KOtBu, DBU in a solvent such as THF, diethyl ether, 1,2-dimethoxyethane, dichloromethane, DMF or mixtures thereof at temperatures from −100° C.-r.t. for 15 min-8 hrs for anion generation and then condensing the glide with the carbonyl compound in the same solvent at temperatures between −100° C. and r.t. for 1-24 hrs.

Preferred conditions are anion generation with LiHMDS at −78° C. in THF and subsequent condensation with the carbonyl component under the same conditions.

Step B: Reduction of the alkene can be effected by hydrogenation with hydrogen under normal or elevated pressure or by transfer hydrogenation using ammonium formiate or cyclohexadiene as hydrogen source with a catalyst such as PtO₂, Pd—C or Raney nickel in solvents such as MeOH, EtOH, H₂O, dioxane, THF, HOAc, EtOAc, CH₂Cl₂, CHCl₃, DMF or mixtures thereof.

Preferred conditions are hydrogenation in the presence of Pd on charcoal as catalyst with MeOH as solvent.

Step C: Saponification of the ester group to afford carboxylic acid can be effected by treatment with an alkali such as LiOH, KOH or NaOH in an aqueous or mixed aqueous-organic solvent system at room temperature.

Preferred conditions are LiOH in aqueous MeOH at room temperature for 2 hours.

Step D: Amide formation can be accomplished by a coupling reaction between carboxylic acid 63 and acyclic primary or secondary amines 48 or cyclic secondary amines 51 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME.

Preferred conditions are TBTU with N-methylmorpholine in THF at 50° C. overnight. Step E: Simultaneous cleavage of the amino alcohol protecting groups can be effected with a mineral acid such as HCl, H₂SO₄ or H₃PO₄ or an organic acid such as CF₃COOH, CHCl₂COOH, HOAc or p-toluonesulfonic acid in a solvent such as CH₂Cl₂, CHCl₃, THF, MeOH, EtOH or H₂O at 0 to 80° C.

Preferred conditions are CF₃COOH in aqueous acetonitrile at 80° C. overnight or 4N HCl in dioxane at r.t. overnight.

Step F: Cyclisation of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

Scheme 13

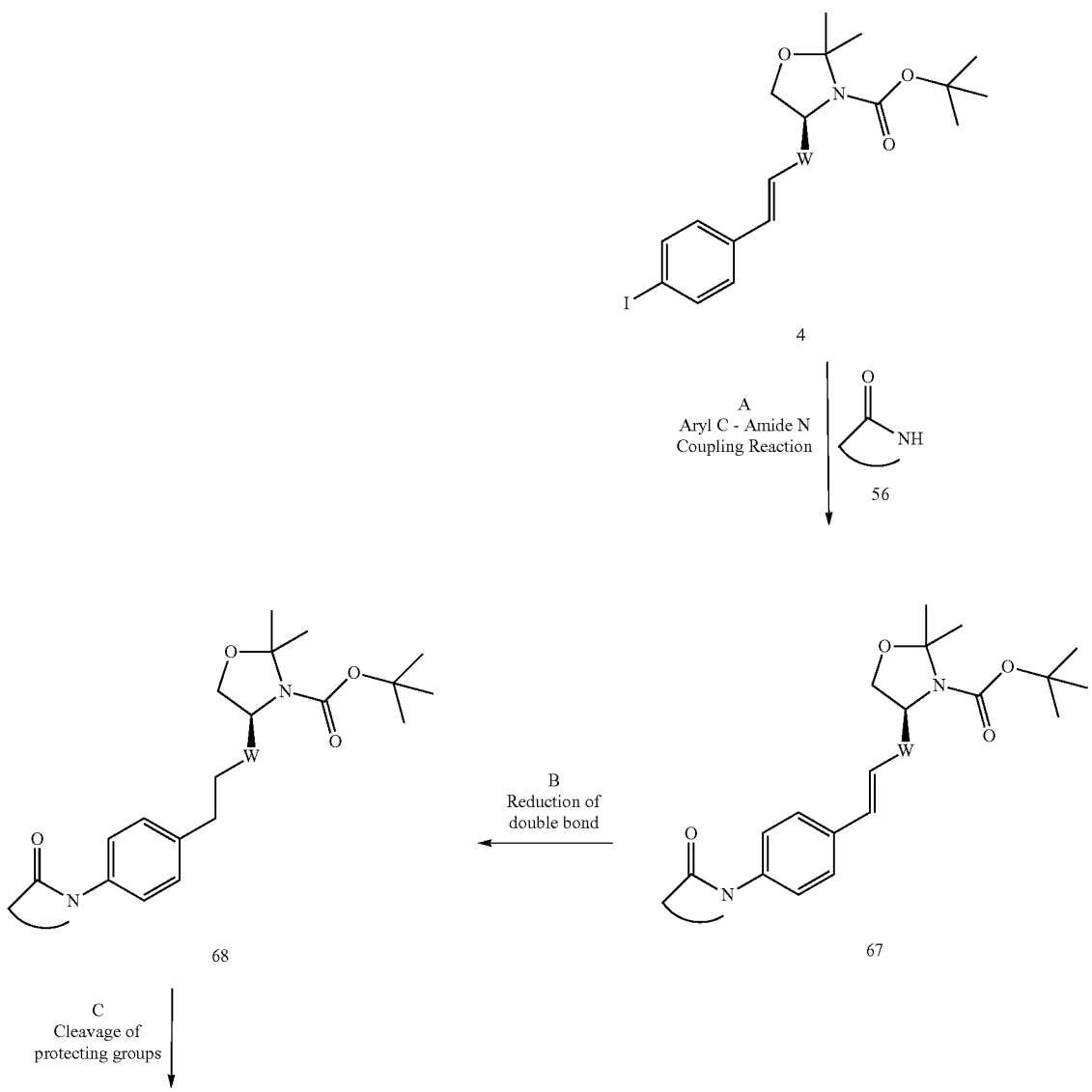

-continued

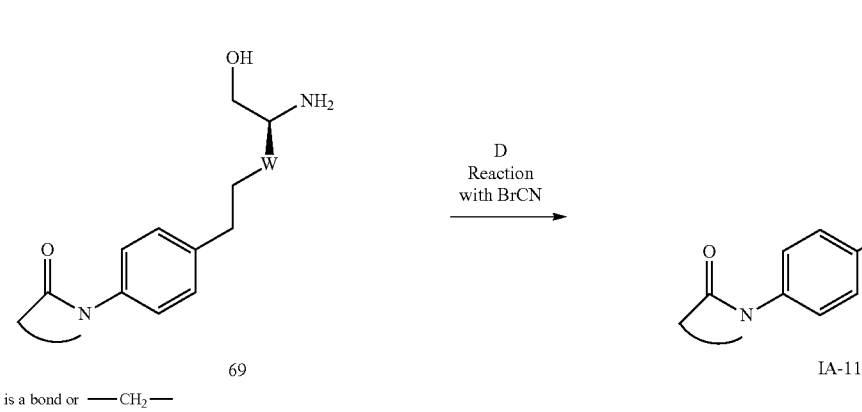

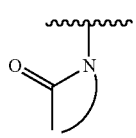

is a definition for

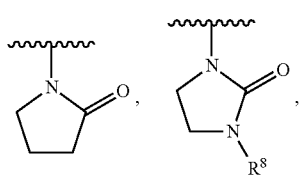

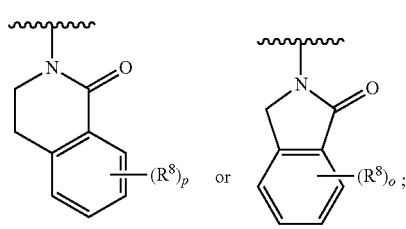

R⁸ is hydrogen, halogen or aryl optionally substituted by halogen;
and the other substituents are as described above and W is a bond or —CH₂—.

Step A: C—N bond formation can be accomplished by coupling reaction between aryl iodide 4 and amide compounds 56 in the presence of a palladium or copper catalyst, a ligand and a base in solvents such as dioxane, DME, THF, toluene, DMF and DMSO at elevated temperatures. For example, using copper(I) triflate benzene complex, caesium carbonate as base, and dibenzylideneacetone and trans-1,2-diaminocyclohexane as ligands according to the procedure of Hafner & Kunz. (*Synthesis.* 2007, 1403-1411).

Preferred conditions are copper(I) triflate benzene complex, caesium carbonate, dibenzylideneacetone and trans-1, 2-diaminocyclohexane in dioxane in a sealed tube at 180° C. for 40 min under microwave irradiation.

Step B: Reduction of the alkene can be effected by hydrogenation with hydrogen under normal or elevated pressure or by transfer hydrogenation using ammonium formiate or cyclohexadiene as hydrogen source with a catalyst such as PtO₂, Pd—C or Raney nickel in solvents such as MeOH, EtOH, H₂O, dioxane, THF, HOAc, EtOAc, CH₂Cl₂, CHCl₃, DMF or mixtures thereof. Alternatively, the reduction of the alkene can be effected by Mg in MeOH or by LiAlH₄ in THF or diethylether.

Preferred conditions are hydrogenation in the presence of PtO₂ as catalyst with MeOH as solvent.

Step C: Simultaneous cleavage of the amino alcohol protecting groups can be effected with a mineral acid such as HCl, H₂SO₄ or H₃PO₄ or an organic acid such as CF₃COOH, CHCl₂COOH, HOAc or p-toluonesulfonic acid in a solvent such as CH₂Cl₂, CHCl₃, THF, MeOH, EtOH or H₂O at 0 to 80° C.

Preferred conditions are CF₃COOH in aqueous acetonitrile at 80° C. overnight or 4N HCl in dioxane at r.t. overnight. Step D: Cyclisation of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

Scheme 14

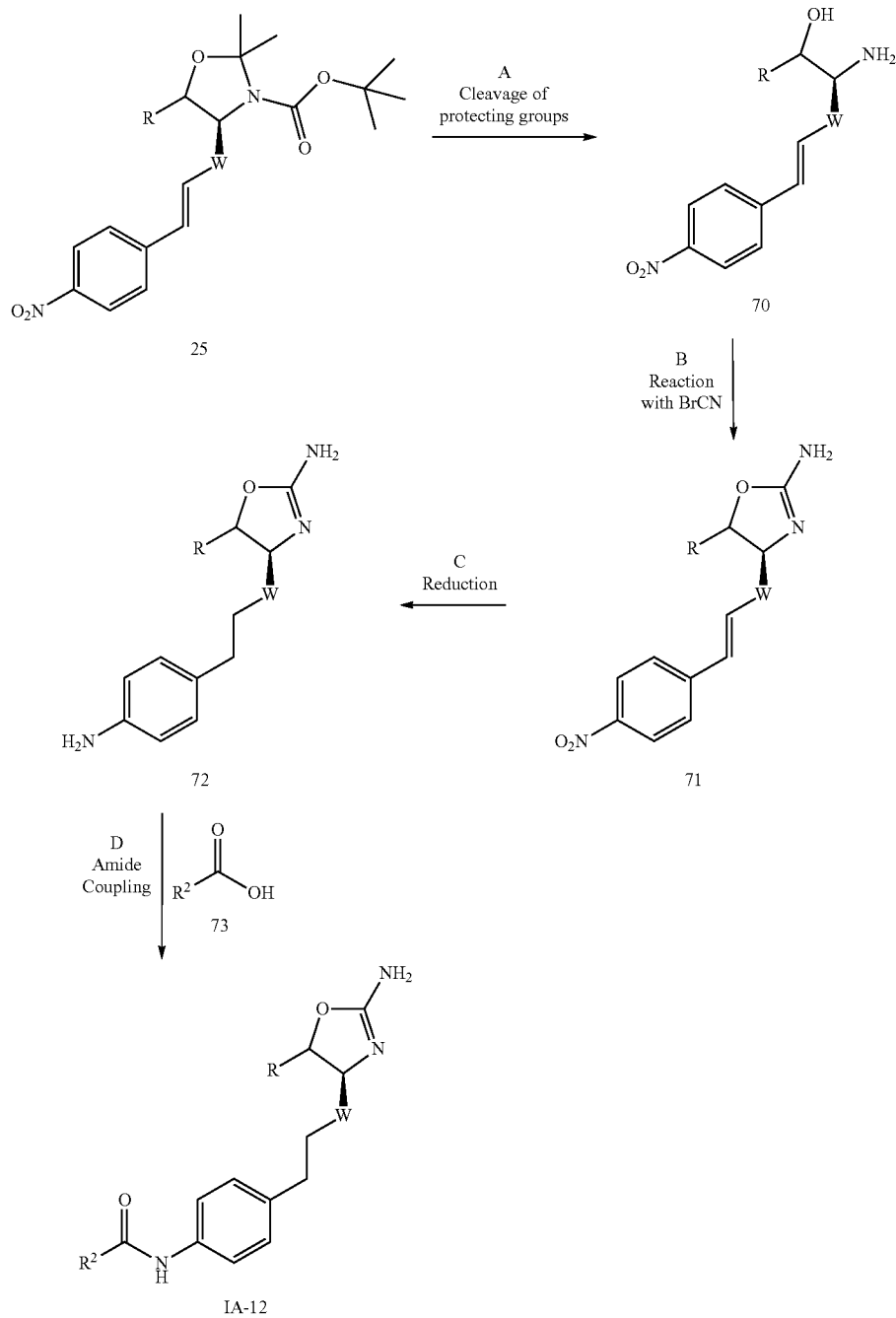

The substituents are as described above and W is a bond or —CH$_2$—.

Step A: Simultaneous cleavage of the amino alcohol protecting groups can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 80° C.

Preferred conditions are CF$_3$COOH in aqueous acetonitrile at 80° C. overnight or 4N HCl in dioxane at r.t. overnight.

Step B: Cyclisation of the amino alcohol to the corresponding 2-aminooxazoline can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

Step C: Simultaneous reduction of the alkene and nitro group can be effected by hydrogenation with hydrogen under normal or elevated pressure or by transfer hydrogenation using ammonium formate or cyclohexadiene as hydrogen source with a catalyst such as PtO$_2$, Pd—C or Raney nickel in solvents such as MeOH, EtOH, H$_2$O, dioxane, THF, HOAc, EtOAc, CH$_2$Cl$_2$, CHCl$_3$, DMF or mixtures thereof. Alternatively, the reduction of the alkene can be effected by Mg in MeOH or by LiAlH$_4$ in THF or diethylether.

Preferred conditions are ammonium formate in the presence of palladium on charcoal in MeOH at 60° C. for 2 hours.

Step D: C—N bond formation can be accomplished by coupling reaction between the aniline 72 and acid compounds 73 in the presence of 4-(4,6-dimethoxy[1.3.5]triazin-2-yl)-4-methylmorpholinium chloride hydrate (CAS 3945-69-5) or 4-(4,6-dimethoxy[1.3.5]triazin-2-yl)-4-methylmorpholinium tetrafluoroborate (CAS 293311-03-2) in solvents such as MeOH at 0-5° C. for 1 hour.

Preferred conditions are treatment of the acid compound with 4-(4,6-dimethoxy[1.3.5]triazin-2-yl)-4-methylmorpholinium chloride hydrate in methanol at 0° C. for 15 minutes, followed by addition of the aniline in methanol and stirring at 0° C. for 2 hours.

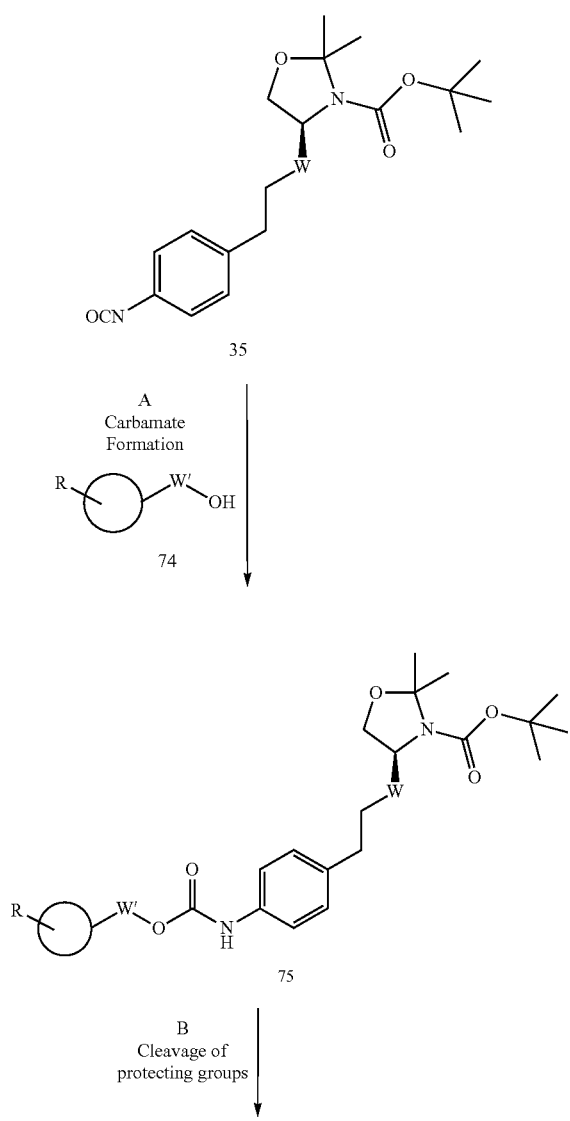

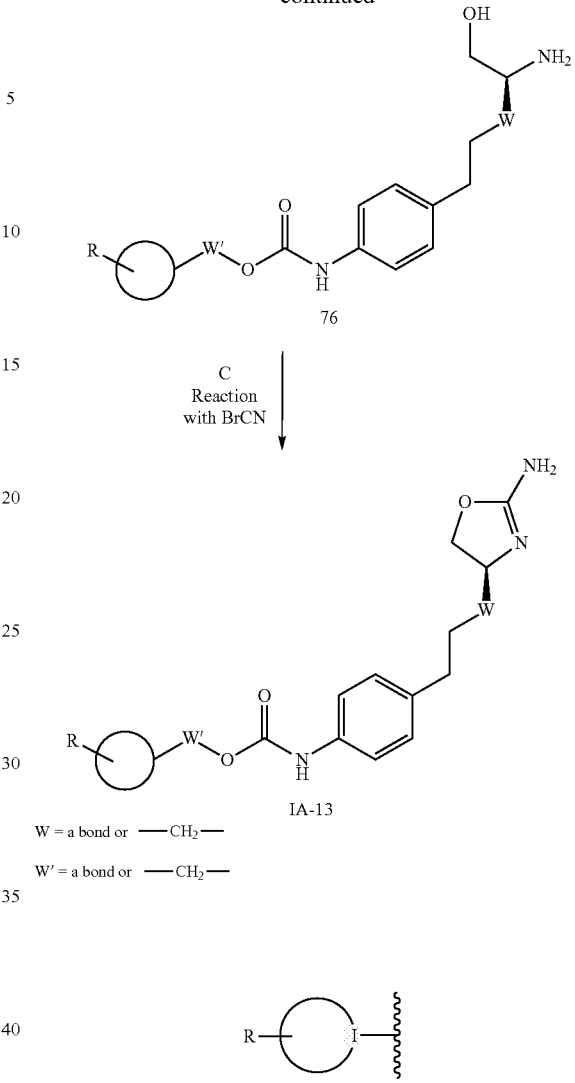

W = a bond or —CH$_2$—
W' = a bond or —CH$_2$— is cycloalkyl, optionally substituted by halogen, lower alkyl, lower alkyl substituted by halogen, halogen-substituted phenyl or heteroaryl, or is aryl optionally substituted by halogen, lower alkyl substituted by halogen, lower alkoxy substituted by halogen, lower alkyl, alkynyl, lower alkoxy, CH$_2$-lower alkoxy or cyano, or is heteroaryl optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen, and the other substituents are as described above and W and W' are, independently, a bond or —CH$_2$—.

Step A: Carbamate formation can be accomplished by a coupling reaction between isocyanate 35 and alcohols 74 in the presence of a base such as triethylamine or N,N-diisopropylethylamine in halogenated solvents such as dichloromethane or 1,2-dichloroethane, at room temperature or at elevated temperature.

Preferred conditions are N,N-diisopropylethylamine in 1,2-dichloroethane at 110° C. overnight.

Step B: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. overnight or 4N HCl in dioxane at r.t. overnight.

Step C: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

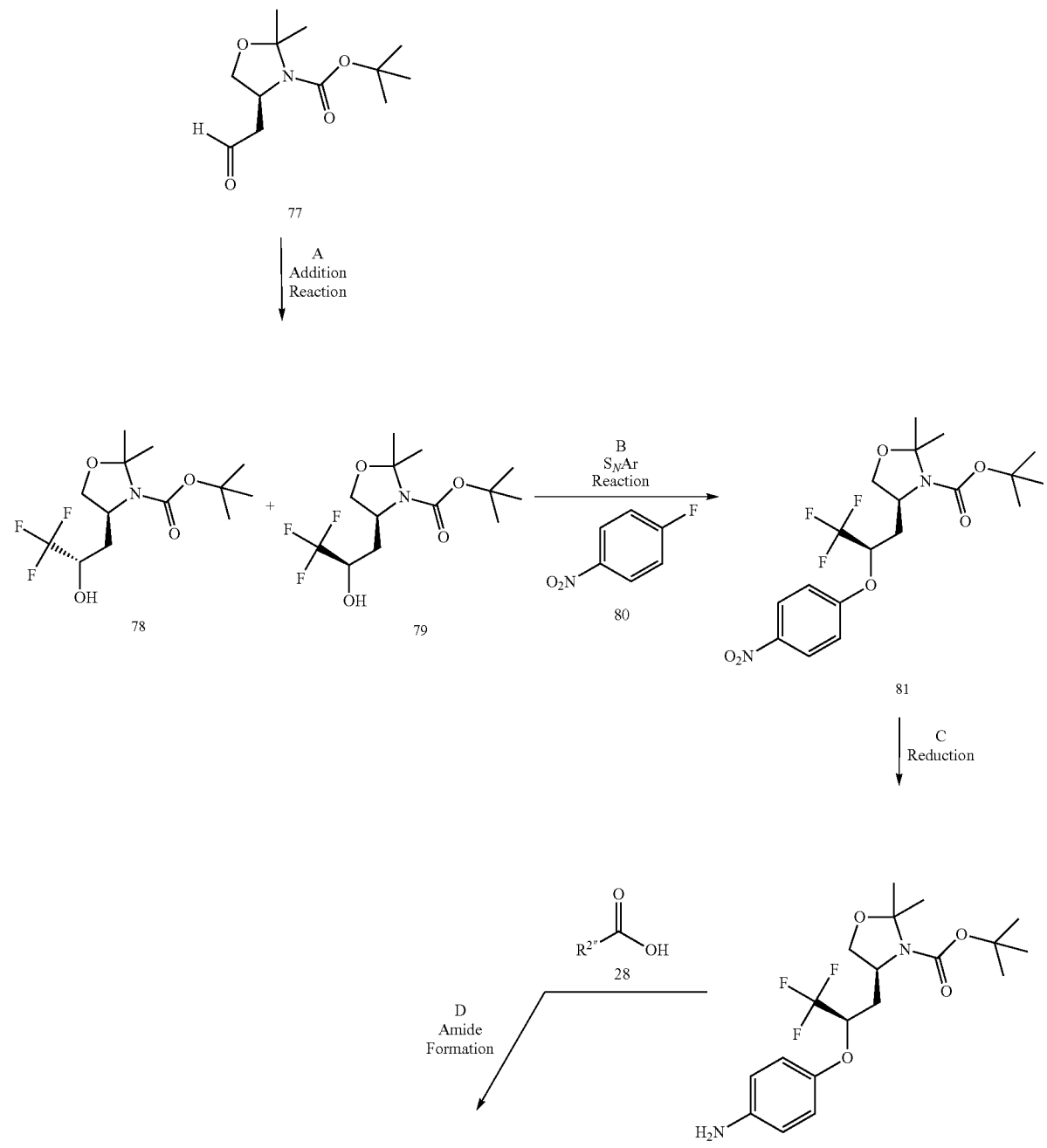

Scheme 16

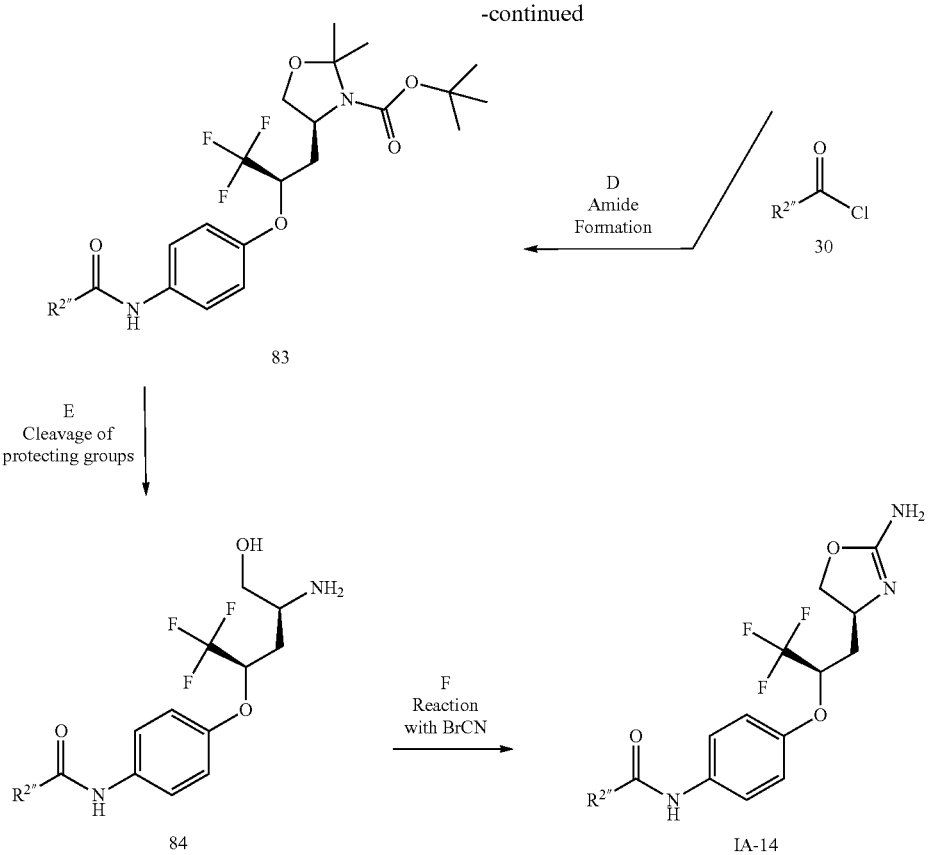

$R^{2''}$ is $(CR'R'')_m$-cycloalkyl, optionally substituted by halogen, lower alkyl, lower alkyl substituted by halogen, halogen-substituted phenyl or heteroaryl; or is
$(CR'R'')_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, $S(O)_2$-lower alkyl, $NR^6R^7$, or by heteroaryl or heterocycloalkyl, each of which is optionally substituted by halogen; or is
$(CR'R'')_m$-aryl, optionally substituted by halogen, lower alkyl substituted by halogen, lower alkoxy substituted by halogen, lower alkyl, alkynyl, lower alkoxy, $CH_2$-lower alkoxy or cyano;
and R' and R" are each independently hydrogen, lower alkoxy or lower alkyl, or together with the C-atom to which they are attached form a cycloalkyl group, m is 0 or 1 and the other substituents are as described above.

Step A: Addition of a $CF_3$ group to aldehyde 77 (CAS 147959-19-1) can be accomplished by treatment with (trifluoromethyl)trimethylsilane in the presence of a source of fluoride ion such as tetrabutylammonium fluoride in halogenated solvents such as dichloromethane or 1,2-dichloroethane or ethereal solvents such as diethyl ether, dioxane, THF or TBME, followed by treatment with aqueous acid. The reaction affords a mixture of epimeric products 78 & 79 which can be separated by chromatography.

Preferred conditions are THF at 0° C. to room temperature for 30 min, followed by treatment with 2 N aq. hydrochloric acid at room temperature for 30 min.

Step B: Ether formation can be accomplished by an aromatic nucleophilic substitution (SNAr) reaction between alcohol 79 and 1-fluoro-4-nitrobenzene 80 in the presence of a base such as NaH, KOtBu, n-BuLi, LiHMDS, NaHMDS, KHMDS, LDA in an ethereal solvent such as THF, dioxane, 1,2-dimethoxyethane, diethyl ether or TBME at a temperature at or below room temperature.

Preferred conditions are KHMDS in THF at 0° C. for 30 min and then at room temperature for 1 hour.

Step C: Reduction of the nitro group of 81 can be accomplished by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc, $CH_2Cl_2$, $CHCl_3$, DMF or mixtures thereof.

Preferred conditions are 10% palladium on charcoal in MeOH at room temperature for 3 hours.

Step D: Amide formation can be accomplished by a coupling reaction between amine 82 and carboxylic acids 28 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME.

Preferred conditions are TBTU with N-methylmorpholine in THF at 50° C. overnight. Alternatively, amide formation can be accomplished by a coupling reaction between amine 82 and acyl chlorides 30 in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are triethylamine in THF at 50° C. for 4 hours.

Step E: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. overnight or 4N HCl in dioxane at r.t. overnight.

Step F: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

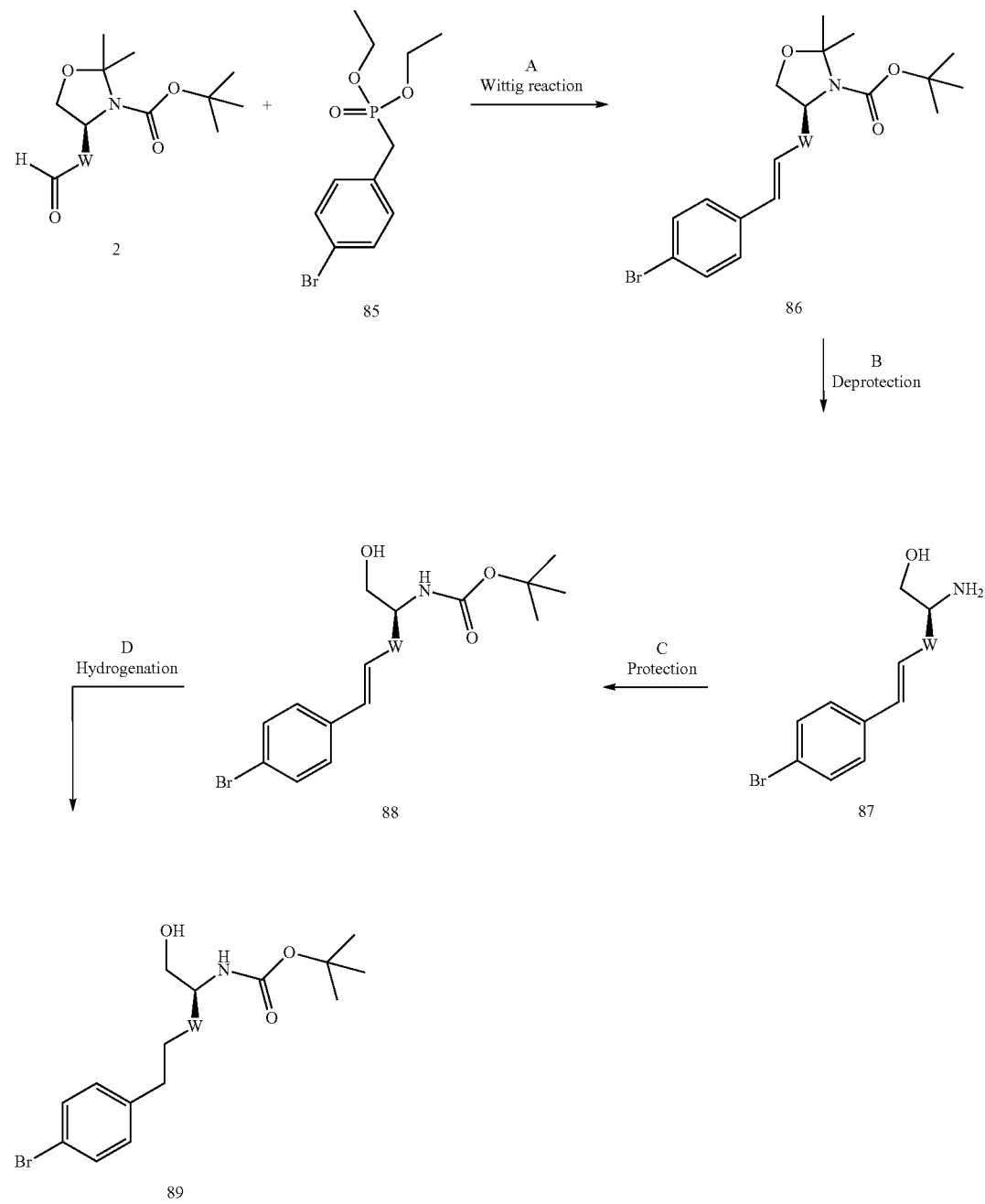

Scheme 17

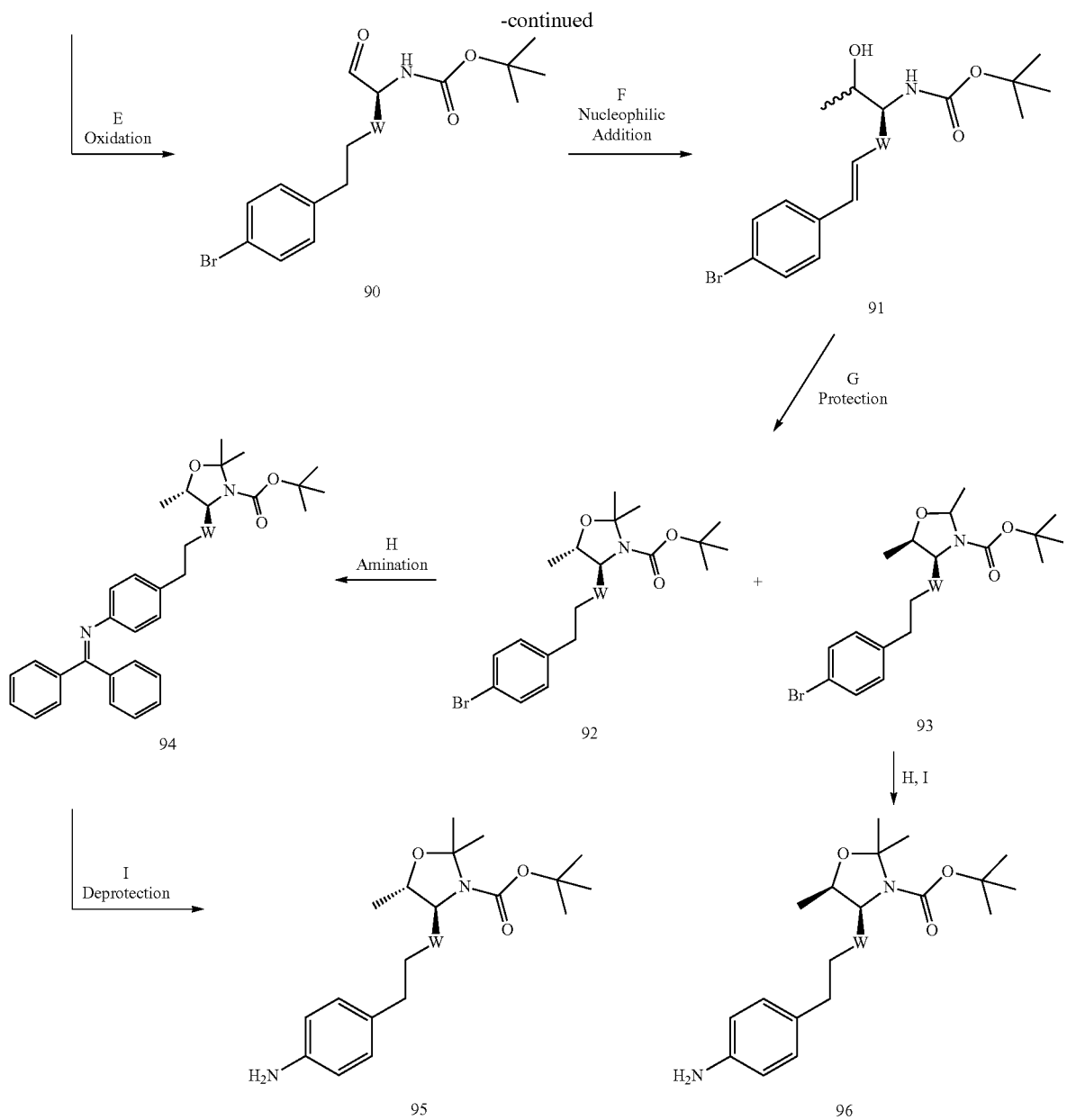

W = a bond or —CH$_2$—

W is a bond or —CH$_2$— and the other substituents are as described above.

Step A: Wittig reaction between aldehyde 2 (W=a bond: CAS 95715-87-0 or W=—CH$_2$—: CAS 147959-19-1) and (4-bromo-benzyl)-phosphonic acid diethyl ester 85 (38186-51-5) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethane, DMF, benzene, toluene or mixtures thereof at temperatures from −78° C. to 80° C. for 15 min-8 hrs and if appropriate optional addition of a crown ether for ylide generation and then condensing the ylide with the carbonyl compound in the same solvent at a temperature between 0 and 80° C. for 1-24 hrs. Alternatively, the base, the carbonyl compound and the optional crown ether can be added to the reaction mixture at the same time without preformation of the ylide at temperatures from −78° C. to 80° C.

Preferred conditions are ylide formation at −78° C. using LDA (prepared in situ from treatment of N,N-diisopropylamine with n-BuLi) as base and THF as solvent, reacting the phosphonic acid ester for 1 hour at −78° C., and then condensation with the carbonyl component warming to room temperature overnight.

Step B: Simultaneous cleavage of the protecting groups of 86 to afford amino alcohol 87 can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 80° C. Preferred conditions are CF$_3$COOH in aqueous acetonitrile at 80° C. for 3 hours.

Step C: Selective protection of the amino group of amino alcohol 87 can be effected by treatment with di-tert-butyl carbonate in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are N,N-diisopropylethylamine in THF at room temperature overnight.

Step D: Reduction of the olefinic bond of 88 without concomitant cleavage of the aryl-bromine bond can be accomplished by hydrogenation with hydrogen under normal or elevated pressure with a catalyst such as $PtO_2$ or Pt/C in solvents such as MeOH, EtOH, $H_2O$, dioxane, THF, HOAc, EtOAc, $CH_2Cl_2$, $CHCl_3$, DMF or mixtures thereof.

Preferred conditions are 10% platinum on charcoal in MeOH at room temperature for 3 hours. Step E: Oxidation of the alcohol 89 to the corresponding aldehyde 90 can be accomplished using DMSO-derived oxidation reagents, e.g. DMSO activated by the use of oxalyl chloride with subsequent treatment with triethylamine according to the method of Swern, or DMSO activated by use of sulphur trioxide-pyridine complex in the presence of triethylamine according to the method of Doering. Preferred conditions are sulphur trioxide-pyridine complex and triethylamine in DMSO at a temperature between 0° C. and room temperature for 30 min.

Step F: Nucleophilic addition of a methyl group to aldehyde 90 can be accomplished by reaction with an organometallic reagent such as methylmagnesium chloride, methylmagnesium bromide, methylmagnesium iodide or methyllithium. The reaction is performed in ethereal solvents such as diethyl ether, dioxane, THF or TBME. Preferred conditions are methylmagnesium bromide in a mixture of THF and diethyl ether at 0° C. and then at room temperature for 4 hours. The reaction affords alcohol 91 as a mixture of epimers which need not be separated at this stage.

Step G: Protection of alcohol 91 as a cyclic aminal can be accomplished by treatment with 2,2-dimethoxypropane in the presence of a catalytic amount of an organic acid such as p-toluenesulphonic acid or camphorsulphonic acid. The reaction can be performed using excess 2,2-dimethoxypropane as solvent, or in the presence of additional non-protic co-solvents such as halogenated solvents such as dichloromethane or 1,2-dichloroethane or ethereal solvents such as diethyl ether, dioxane, THF or TBME. The reaction can be performed at room temperature or at an elevated temperature such as the reflux temperature of the solvent.

Preferred conditions are p-toluenesulphonic acid in dichloromethane at room temperature overnight.

The reaction affords epimeric products 92 & 93 which can be readily separated by chromatography at this stage.

Step H: C—N bond formation to afford imine 94 can be accomplished by coupling reaction between aryl bromide 92 and diphenylmethanimine in the presence of a palladium or copper catalyst, a ligand and a base in solvents such as dioxane, DME, THF, toluene, and DMF at elevated temperatures.

Preferred conditions are $Pd_2(dba)_3$, BINAP and sodium tert-butoxide in toluene at 100° C. overnight.

Step I: Deprotection of imine 94 to afford aniline 95 can be accomplished by hydrogenation with hydrogen under normal or elevated pressure or by transfer hydrogenation using ammonium formiate or cyclohexadiene as hydrogen source with a catalyst such as $PtO_2$, Pt/C or Pd/C in solvents such as MeOH, EtOH, $H_2O$, dioxane, THF, HOAc, EtOAc, $CH_2Cl_2$, $CHCl_3$, DMF or mixtures thereof.

Preferred conditions are 10% palladium on charcoal and ammonium formiate in MeOH at 60° C. for 1 hour.

Aryl bromide 93 can be converted to aniline 96 following a similar sequence of reaction steps H and I.

Scheme 18

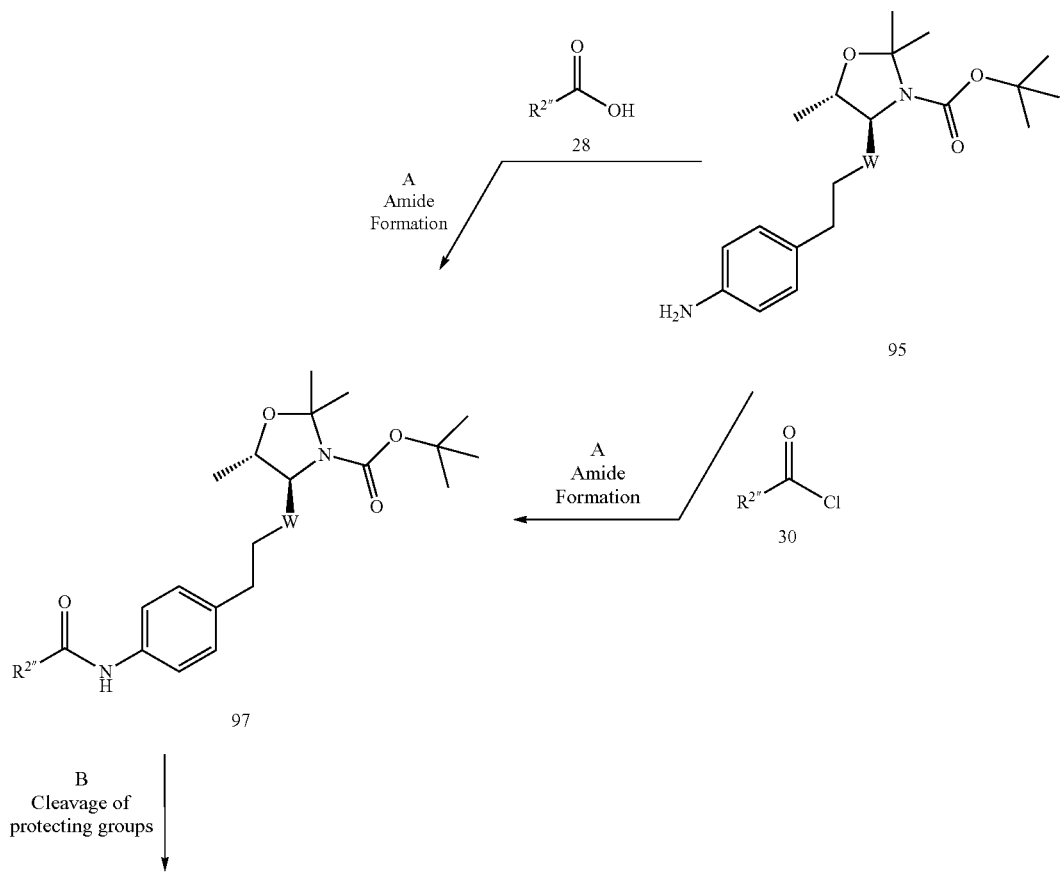

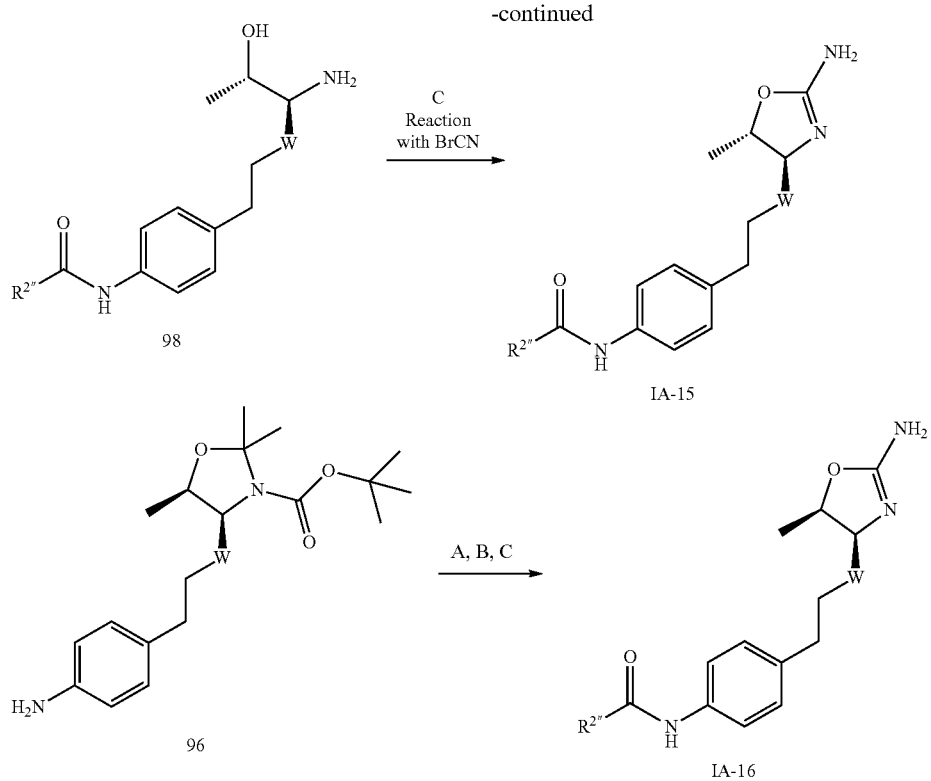

R[2″] is (CR'R″)$_m$-cycloalkyl, optionally substituted by halogen, lower alkyl, lower alkyl substituted by halogen, halogen-substituted phenyl or heteroaryl; or is
(CR'R″)$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR[6]R[7], or by heteroaryl or heterocycloalkyl each of which is optionally substituted by halogen; or is
(CR'R″)$_m$-aryl, optionally substituted by halogen, lower alkyl substituted by halogen, lower alkoxy substituted by halogen, lower alkyl, alkynyl, lower alkoxy, CH$_2$-lower alkoxy or cyano;
and R' and R″ are each independently f hydrogen, lower alkoxy or lower alkyl, or together with the C-atom to which they are attached form a cycloalkyl group, m is 0 or 1 and the other substituents are as described above.

Step A: Amide formation can be accomplished by a coupling reaction between amine 95 and carboxylic acids 28 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME.

Preferred conditions are TBTU with N-methylmorpholine in THF at 50° C. overnight. Alternatively, amide formation can be accomplished by a coupling reaction between amine 95 and acyl chlorides 30 in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME. Preferred conditions are triethylamine in THF at 50° C. for 4 hours.

Step B: Simultaneous cleavage of the protecting groups of 97 to afford amino alcohol 98 can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 80° C.

Preferred conditions are CF$_3$COOH in aqueous acetonitrile at 80° C. overnight or 4N HCl in dioxane at r.t. overnight.

Step C: Cyclisation of the amino alcohol 98 to the corresponding 2-aminooxazoline 1A-15 can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour. Amine 96 can be converted to 2-aminooxazoline 1A-16 following a similar sequence of reaction steps A, B and C.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of Taar Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and the cell pellet was frozen immediately by immersion in liquid nitrogen and stored until use at −80° C. The cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

The binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 μM). Competing ligands were tested in a wide range of concentrations (10 pM-30 μM). The final dimethylsulphoxide concentration in the assay was 2%, and it did not affect radioligand binding. Each experiment was performed in duplicate. All incubations were terminated by rapid filtration through Uni-Filter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse or rat on TAAR1 in the range of <0.01 μM. Values for representative compounds are shown in the table below.

| Example | Ki (μM) mouse/rat |
|---|---|
| 1 | 0.0026/0.0005 |
| 3 | 0.0002/0.0003 |
| 8 | 0.0034/0.0001 |
| 9 | 0.0002/0.0004 |
| 12 | 0.0012/0.002 |
| 13 | 0.0007/0.0023 |
| 14 | 0.0001/0.0001 |
| 15 | 0.0001/0.0001 |
| 16 | 0.0008/0.0003 |
| 17 | 0.0002/0.0004 |
| 18 | 0.0002/0.0002 |
| 31 | 0.0025/0.0035 |
| 33 | 0.0006/0.001 |
| 34 | 0.0067/0.0035 |
| 35 | 0.0001/0.0003 |
| 38 | 0.0017/0.0004 |
| 40 | 0.0036/0.0187 |
| 41 | 0.0091/0.0094 |
| 43 | 0.0029/0.002 |
| 44 | 0.0035/0.0014 |
| 45 | 0.0026/0.0017 |
| 46 | 0.0042/0.0018 |

-continued

| Example | Ki (µM) mouse/rat |
|---------|-------------------|
| 48 | 0.001/0.0003 |
| 49 | 0.0024/0.0036 |
| 52 | 0.0073/0.006 |
| 53 | 0.0009/0.0016 |
| 54 | 0.0008/0.0019 |
| 55 | 0.0025/0.003 |
| 56 | 0.0094/0.0009 |
| 58 | 0.0014/0.0007 |
| 59 | 0.0022/0.0022 |
| 60 | 0.001/0.0006 |
| 61 | 0.0002/0.0007 |
| 62 | 0.0003/0.0005 |
| 63 | 0.0026/0.0013 |
| 66 | 0.0026/0.0017 |
| 68 | 0.0043/0.0019 |
| 69 | 0.003/0.0009 |
| 70 | 0.001/0.001 |
| 71 | 0.0009/0.0005 |
| 72 | 0.0008/0.001 |
| 73 | 0.0026/0.0049 |
| 74 | 0.009/0.0073 |
| 76 | 0.009/0.0009 |
| 78 | 0.0048/0.0031 |
| 79 | 0.0057/0.0051 |
| 80 | 0.0014/0.0011 |
| 81 | 0.001/0.0022 |
| 82 | 0.0005/0.0017 |
| 83 | 0.0074/0.0052 |
| 85 | 0.0012/0.0015 |
| 86 | 0.0022/0.0006 |
| 87 | 0.0057/0.0018 |
| 88 | 0.0097/0.0014 |
| 89 | 0.0044/0.0007 |
| 90 | 0.0007/0.0003 |
| 91 | 0.0005/0.0002 |
| 92 | 0.0002/0.0004 |
| 93 | 0.0016/0.0003 |
| 94 | 0.0003/0.0003 |
| 95 | 0.0001/0.0001 |
| 96 | 0.001/0.0006 |
| 97 | 0.0018/0.0015 |
| 98 | 0.0068/0.0019 |
| 99 | 0.0081/0.0018 |
| 100 | 0.004/0.0018 |
| 101 | 0.0007/0.0021 |
| 104 | 0.0034/0.0014 |
| 105 | 0.0051/0.0011 |
| 106 | 0.0012/0.0009 |
| 107 | 0.0014/0.0012 |
| 109 | 0.0006/0.0016 |
| 110 | 0.0054/0.0048 |
| 111 | 0.004/0.0057 |
| 112 | 0.0013/0.0005 |
| 113 | 0.0006/0.001 |
| 115 | 0.0029/0.0024 |
| 117 | 0.002/0.0008 |
| 119 | 0.0015/0.0044 |
| 121 | 0.0032/0.0046 |
| 122 | 0.0043/0.0043 |
| 123 | 0.0007/0.0017 |
| 124 | 0.004/0.0061 |
| 125 | 0.0006/0.0011 |
| 126 | 0.0007/0.002 |
| 127 | 0.0063/0.0022 |
| 128 | 0.0079/0.0054 |
| 129 | 0.0039/0.0033 |
| 131 | 0.004/0.0008 |
| 136 | 0.0003/0.0006 |
| 137 | 0.0003/0.0006 |
| 138 | 0.0002/0.0002 |
| 142 | 0.0044/0.0011 |
| 145 | 0.0018/0.0001 |
| 146 | 0.0001/0.0003 |
| 147 | 0.0006/0.0003 |
| 148 | 0.0005/0.0006 |
| 149 | 0.0097/0.0092 |
| 150 | 0.0004/0.0005 |
| 151 | 0.0071/0.0028 |
| 152 | 0.008/0.0002 |
| 153 | 0.0009/0.001 |
| 155 | 0.0004/0.0006 |
| 156 | 0.0006/0.0063 |
| 157 | 0.0019/0.0006 |
| 158 | 0.0006/0.0006 |
| 159 | 0.001/0.0024 |
| 160 | 0.0047/0.0018 |
| 161 | 0.001/0.0012 |
| 164 | 0.0018/0.0027 |
| 168 | 0.0014/0.0009 |
| 169 | 0.0005/0.0001 |
| 170 | 0.0074/0.0018 |
| 171 | 0.0008/0.0011 |
| 172 | 0.0084/0.0019 |
| 173 | 0.0014/0.0014 |
| 174 | 0.0035/0.0016 |
| 175 | 0.0008/0.0009 |
| 178 | 0.0004/0.0004 |
| 179 | 0.0059/0.0023 |
| 186 | 0.0029/0.001 |
| 189 | 0.0008/0.0018 |
| 190 | 0.0041/0.004 |
| 191 | 0.0042/0.0021 |
| 194 | 0.0091/0.0035 |
| 195 | 0.0037/0.0023 |
| 197 | 0.003/0.0049 |
| 198 | 0.0036/0.0029 |
| 199 | 0.0027/0.0037 |
| 201 | 0.0005/0.0007 |
| 202 | 0.0007/0.0004 |
| 203 | 0.0008/0.0014 |
| 205 | 0.0007/0.0005 |
| 206 | 0.0076/0.0013 |
| 207 | 0.0007/0.0011 |
| 208 | 0.0028/0.0023 |
| 209 | 0.0013/0.0035 |
| 211 | 0.0023/0.0024 |
| 213 | 0.0015/0.0022 |
| 214 | 0.0011/0.0028 |
| 215 | 0.0012/0.0038 |
| 216 | 0.0027/0.0061 |
| 217 | 0.0051/0.0025 |
| 218 | 0.0014/0.0035 |
| 219 | 0.0048/0.0037 |
| 222 | 0.0071/0.004 |
| 226 | 0.0011/0.0021 |
| 227 | 0.007/0.0059 |
| 230 | 0.0009/0.0016 |
| 231 | 0.0009/0.0013 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers, gelatin Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD).

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL

Example 1

(RS)-1-[4-(2-Amino-4,5-dihydro-oxazol-4-yl)-phenyl]-3-(4-chloro-phenyl)-urea

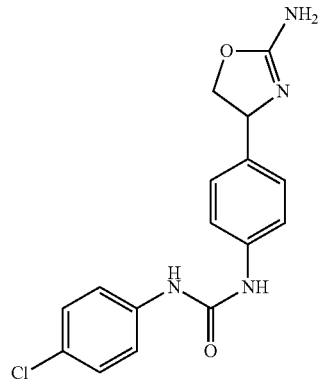 [SMILES: NC1=NC(c2ccc(NC(=O)Nc3ccc(Cl)cc3)cc2)CO1]

(RS)-Amino-(4-iodo-phenyl)-acetonitrile

To a stirred solution of 4-iodo-benzaldehyde (7.10 g) in methanol (25 ml) were added sequentially ammonia solution (35 ml, 7 M solution in methanol) and tetraisopropyl orthotitanate (10.9 ml) and the resulting mixture was stirred at r.t. for 2 h. Trimethylsilylcyanide (3.84 ml) was then added dropwise and stirring continued at r.t. for 22 hours. The reaction mixture was poured onto ice-water (100 ml) and after stirring the resulting mixture was filtered through celite, washing with ethyl acetate. The filtrate was concentrated in vacuo and the residue was taken up in ethyl acetate and washed sequentially with distilled water and with saturated brine. The organic phase was then dried over sodium sulphate and concentrated in vacuo to afford (RS)-amino-(4-iodo-phenyl)-acetonitrile (6.41 g, 81%) as a yellow solid. $^1$H NMR δ (CDCl$_3$, 300 MHz): 7.76 (2H, d, J=7.8 Hz), 7.30 (2H, d, J=7.8 Hz), 4.87 (1H, brs), 1.94 (2H, brs).

b) (RS)-Amino-(4-iodo-phenyl)-acetic acid hydrochloride (RS)-Amino-(4-iodo-phenyl)-acetonitrile (6.40 g) was suspended in 5 N aq hydrochloric acid (100 ml) and the mixture was heated at reflux overnight. The mixture was then cooled first to room temperature and then to 0° C. whereby crystals formed. The crystals were collected by filtration, washing with heptane, and were dried in vacuo at 60° C. to afford (RS)-amino-(4-iodo-phenyl)-acetic acid hydrochloride (6.34 g, 82%) as a light brown crystalline solid. MS (ISP): 275.9 ([M−H]$^-$).

c) (RS)-2-Amino-2-(4-iodo-phenyl)-ethanol

To a stirred solution of lithium borohydride in THF (25.1 ml, 2 M solution) under an argon atmosphere was added dropwise chlorotrimethylsilane (12.7 ml). To the resulting suspension was added portionwise (RS)-amino-(4-iodo-phenyl)-acetic acid hydrochloride (6.30 g). Stirring was continued for 4 h and then the mixture was cooled to 0° C. and quenched by dropwise addition of methanol (4.5 ml). After stirring for 15 min at room temperature, water was added and the mixture was then diluted with ethyl acetate. Saturated brine was then added and the aqueous phase made alkaline (pH 14) by addition of 5 N aq NaOH. The phases were separated and the organic phase was washed with saturated brine and then dried over sodium sulphate and concentrated in vacuo to afford (RS)-2-amino-2-(4-iodo-phenyl)-ethanol (5.27 g, quant.) as a yellow solid. MS (ISP): 264.1 ([M+H]$^+$).

d) (RS)-[2-Hydroxy-1-(4-iodo-phenyl)-ethyl]-carbamic acid tert-butyl ester

To a stirred solution of (RS)-2-amino-2-(4-iodo-phenyl)-ethanol (5.20 g) in THF (150 ml) were added sequentially N,N-diisopropylethylamine (4.03 ml) and di-tert-butyl dicarbonate (5.18 g) and the resulting yellow solution was stirred at room temperature for 5 hours. The mixture was partitioned between water and ethyl acetate and the phases were separated. The organic layer was washed sequentially with dilute aq. hydrochloric acid, saturated aq. sodium bicarbonate solution and saturated brine. The organic phase was then dried over sodium sulphate, filtered and concentrated in vacuo to afford (RS)-[2-hydroxy-1-(4-iodo-phenyl)-ethyl]-carbamic acid tert-butyl ester (7.97 g, quant.) as a yellow solid. MS (ISP): 386.0 ([M+Na]$^+$), 364.0 ([M+H]$^+$), 308.1 ([M+H—$C_4H_8$]$^+$).

e) (RS)-4-(4-Iodo-phenyl)-2,2-dimethyl-oxazolidine-3-carboxylic acid tert-butyl ester To a stirred solution of (RS)-[2-hydroxy-1-(4-iodo-phenyl)-ethyl]-carbamic acid tert-butyl ester (7.97 g) in dichloromethane (400 ml) were added sequentially 2,2-dimethoxypropane (36 ml) and p-toluenesulphonic acid monohydrate (0.75 g) and the mixture was stirred at room temperature for 18 hours. The mixture was then washed with 0.5 N aq NaOH, the phases were separated and the organic phase was dried over sodium sulphate, filtered and concentrated in vacuo to afford (RS)-4-(4-iodo-phenyl)-2,2-dimethyl-oxazolidine-3-carboxylic acid tert-butyl ester (7.05 g, 89%) as a yellow solid. MS (EI): 403 (M$^+$), 388 ([M-$CH_3$]$^+$), 332 ([M-$CH_3$—$C_4H_8$]$^+$), 288 ([M-$CH_3$—$C_4H_8$—$CO_2$]$^+$), 57 ([$C_4H_9$]$^+$).

f) (RS)-4-{4-[3-(4-Chloro-phenyl)-ureido]-phenyl}-2,2-dimethyl-oxazolidine-3-carboxylic acid tert-butyl ester A stirred suspension of (RS)-4-(4-iodo-phenyl)-2,2-dimethyl-oxazolidine-3-carboxylic acid tert-butyl ester (1.60 g), 4-chlorophenylurea (0.81 g), potassium fluoride (2.88 g, 40 wt % on alumina), N,N'-dibenzylethylenediamine (0.14 ml) and copper(I) iodide (0.11 g) in THF (16 ml) in a sealed tube was heated at 90° C. for 30 minutes under microwave irradiation. The mixture was then cooled to room temperature and filtered through celite. The filtrate was concentrated in vacuo and the residue was purified by column chromatography (SiO$_2$; gradient: heptane/EtOAc) to give (RS)-4-{4-[3-(4-chloro-phenyl)-ureido]-phenyl}-2,2-dimethyl-oxazolidine-3-carboxylic acid tert-butyl ester (0.24 g, 14%) as a light yellow solid. MS (ISP): 392.1 ([{$^{37}$Cl}M+H—$C_4H_8$]$^+$), 390.1 ([{$^{35}$Cl}M+H—$C_4H_8$]$^+$).

g) (RS)-1-[4-(1-Amino-2-hydroxy-ethyl)-phenyl]-3-(4-chloro-phenyl)-urea

To a solution of (RS)-4-{4-[3-(4-chloro-phenyl)-ureido]-phenyl}-2,2-dimethyl-oxazolidine-3-carboxylic acid tert-butyl ester (0.24 g) in acetonitrile (3 ml) were added water (9 ml) and trifluoroacetic acid (0.33 ml). The mixture was heated overnight at 80° C. The mixture was then cooled to room temperature and diluted with ethyl acetate/THF (1:1). The resulting mixture was washed sequentially with 1 N aq. sodium hydroxide solution and saturated brine, the phases were then separated and the organic phase was dried over sodium sulphate and concentrated in vacuo to afford (RS)-1-[4-(1-amino-2-hydroxy-ethyl)-phenyl]-3-(4-chloro-phenyl)-urea (0.22 g, quant.) an off-white solid. MS (ISP): 291.1 ([{$^{37}$Cl}M+H—OH]$^+$), 289.1 ([{$^{35}$Cl}M+H—OH]$^+$).

h) (RS)-1-[4-(2-Amino-4,5-dihydro-oxazol-4-yl)-phenyl]-3-(4-chloro-phenyl)-urea To a stirred suspension of 1-[4-(1-amino-2-hydroxy-ethyl)-phenyl]-3-(4-chloro-phenyl)-urea (160 mg) and sodium acetate (129 mg) in methanol (8 ml) was added dropwise a solution of cyanogen bromide (72 mg) in methanol (0.5 ml). The resulting pale yellow solution was then stirred at room temperature for 16 h. Aqueous ammonia solution (0.4 ml, 25%) was added dropwise and stirring was continued for a further hour. The mixture was then concentrated in vacuo and the residue was purified by column chromatography (Isolute® Flash-NH$_2$ from Separtis; gradient: heptane/dichloromethane/methanol) to give (RS)-1-[4-(2-amino-4,5-dihydro-oxazol-4-yl)-phenyl]-3-(4-chloro-phenyl)-urea (91 mg, 53%) as a white solid. MS (ISP): 333.2 ([{$^{37}$Cl}M+H]$^+$), 331.1 ([{$^{35}$Cl}M+H]$^+$).

Example 2

1-[4-((S)-2-Amino-4,5-dihydro-oxazol-4-ylmethyl)-phenyl]-3-(4-chloro-phenyl)-urea

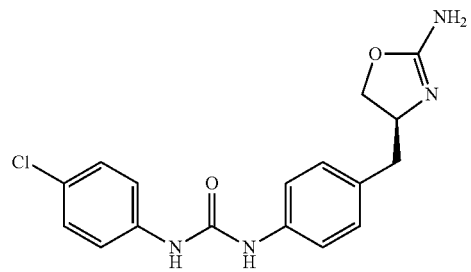 [SMILES: NC1=N[C@@H](Cc2ccc(NC(=O)Nc3ccc(Cl)cc3)cc2)CO1]

The title compound was obtained in analogy to example 1(c)-1(h) starting from 4-iodo-L-phenylalanine (CAS 24250-85-9) instead of (RS)-amino-(4-iodo-phenyl)-acetic acid hydrochloride. White solid. MS (ISP): 347.1 ([{$^{37}$Cl}M+H]$^+$), 345.1 ([{$^{35}$Cl}M+H]$^+$).

Example 3

1-{4-[2-((S)-2-Amino-4,5-dihydro-oxazol-4-yl)-ethyl]-phenyl}-3-(4-chloro-phenyl)-urea

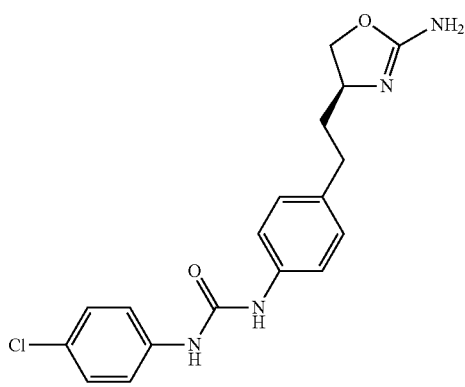 [SMILES: NC1=N[C@@H](CCc2ccc(NC(=O)Nc3ccc(Cl)cc3)cc2)CO1]

a) (S)-4-[(E)-2-(4-Iodo-phenyl)-vinyl]-2,2-dimethyl-oxazolidine-3-carboxylic acid tert-butyl ester To a stirred solution of diisopropylamine (1.55 ml) in THF (12 ml) cooled to −78° C. was added dropwise a solution of n-butyllithium in hexane (6.88 ml, 1.6 M). The cooling bath was removed and the reaction mixture was allowed to warm up to 10° C. before being re-cooled to −78° C. A solution of (4-iodo-benzyl)-phosphonic acid diethyl ester (3.45 g, CAS 173443-43-1) in THF (8 ml) was then added dropwise and the reaction mixture stirred at −78° C. for 1 hour. A solution of (R)-4-formyl-2,2-dimethyl-oxazolidine-3-carboxylic acid tert-butyl ester (2.14 g, CAS 95715-87-0) in THF (8 ml) was then added dropwise over 15 min and the mixture was then allowed to warm to room temperature overnight. The mixture was then diluted with ethyl acetate and acidified by addition of 1 N aq. hydrochloric acid. The mixture was then washed sequentially with water and saturated brine. The organic phase was separated and dried over sodium sulphate and concentrated in vacuo. The reside was purified by column chromatography (SiO$_2$; gradient: heptane/EtOAc) to give (S)-4-[(E)-2-(4-iodo-phenyl)-vinyl]-2,2-dimethyl-oxazolidine-3-carboxylic acid tert-butyl ester (2.49 g, 68%) as a white solid. MS (EI): 429 (M$^+$), 373 ([M-C$_4$H$_8$]$^+$), 358 ([M-CH$_3$—C$_4$H$_8$]$^+$), 315 ([M-C$_4$H$_8$—(CH$_3$)$_2$C=O]$^+$), 57 ([C$_4$H$_9$]$^+$).

b) (S)-4-((E)-2-{4-[3-(4-Chloro-phenyl)-ureido]-phenyl}-vinyl)-2,2-dimethyl-oxazolidine-3-carboxylic acid tert-butyl ester The title compound was obtained in analogy to example 1(f) starting from (S)-4-[(E)-2-(4-iodo-phenyl)-vinyl]-2,2-dimethyl-oxazolidine-3-carboxylic acid tert-butyl ester instead of (RS)-4-(4-iodo-phenyl)-2,2-dimethyl-oxazolidine-3-carboxylic acid tert-butyl ester. Brown solid. MS (ISP): 496.2 ([{$^{37}$Cl}M+Na]$^+$), 494.2 ([{$^{35}$Cl}M+Na]$^+$).

c) (S)-4-(2-{4-[3-(4-Chloro-phenyl)-ureido]-phenyl}-ethyl)-2,2-dimethyl-oxazolidine-3-carboxylic acid tert-butyl ester To a stirred suspension of (S)-4-((E)-2-{4-[3-(4-chloro-phenyl)-ureido]-phenyl}-vinyl)-2,2-dimethyl-oxazolidine-3-carboxylic acid tert-butyl ester (57 mg) in methanol (8 ml) was added platinum(IV) oxide (14 mg) and the mixture was then stirred under an atmosphere of hydrogen at room temperature for 1 hour. The mixture was then filtered through celite and the filtrate was concentrated in vacuo to afford (S)-4-(2-{4-[3-(4-chloro-phenyl)-ureido]-phenyl}-ethyl)-2,2-dimethyl-oxazolidine-3-carboxylic acid tert-butyl ester (60 mg, quant) as an off-white solid. MS (ISP): 476.2 ([{$^{37}$Cl}M−H]$^+$), 474.3 ([{$^{35}$Cl}M−H]$^+$), 420.2 ([{$^{37}$Cl}M+H—C$_4$H$_8$]$^+$), 418.3 ([{$^{35}$Cl}M+H—C$_4$H$_8$]$^+$).

d) 1-{4-[2-((S)-2-Amino-4,5-dihydro-oxazol-4-yl)-ethyl]-phenyl}-3-(4-chloro-phenyl)-urea The title compound was obtained in analogy to example 1(g)-1(h) starting from (S)-4-(2-{4-[3-(4-chloro-phenyl)-ureido]-phenyl}-ethyl)-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 361.1 ([{$^{37}$Cl}M+H]$^+$), 359.1 ([{$^{35}$Cl}M+H]$^+$).

Example 4

(RS)—N-[4-(2-Amino-4,5-dihydro-oxazol-4-yl)-phenyl]-4-chloro-benzamide

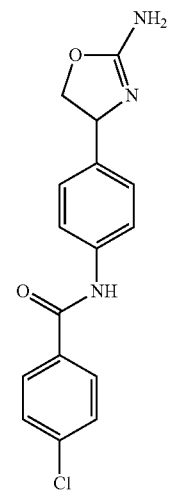

a) (RS)-4-[4-(4-Chloro-benzoylamino)-phenyl]-2,2-dimethyl-oxazolidine-3-carboxylic acid tert-butyl ester A stirred suspension of (RS)-4-(4-iodo-phenyl)-2,2-dimethyl-oxazolidine-3-carboxylic acid tert-butyl ester (400 mg, Example 1e), 4-chlorobenzamide (185 mg), copper(I) iodide (20 mg), N,N'-dimethylglycine (20 mg) and potassium phosphate (1.05 g) in DMSO (2 ml) in a sealed tube was heated at 110° C. overnight. The mixture was then cooled to room temperature and was purified by column chromatography (SiO$_2$; gradient: heptane/EtOAc) to give (RS)-4-[4-(4-chloro-benzoylamino)-phenyl]-2,2-dimethyl-oxazolidine-3-carboxylic acid tert-butyl ester (297 mg, 69%) as a white solid. MS (ISP): 450.2 ([{$^{37}$Cl}M+NH$_4$]$^+$), 448.2 ([{$^{35}$Cl}M+NH$_4$]$^+$), 433.2 ([{$^{37}$Cl}M+H]$^+$), 431.2 ([{$^{35}$Cl}M+H]$^+$), 377.2 ([{$^{37}$Cl}M+H—C$_4$H$_8$]$^+$), 375.2 ([{$^{35}$Cl}M+H—C$_4$H$_8$]$^+$).

b) (RS)—N-[4-(2-Amino-4,5-dihydro-oxazol-4-yl)-phenyl]-4-chloro-benzamide

The title compound was obtained in analogy to example 1(g)-1(h) starting from (RS)-4-[4-(4-chloro-benzoylamino)-phenyl]-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 316.1 ([{$^{37}$Cl}M–H]$^-$), 314.1 ([{$^{35}$Cl}M–H]$^-$).

Example 5

(RS)—N-[4-(2-Amino-4,5-dihydro-oxazol-4-yl)-phenyl]-benzamide

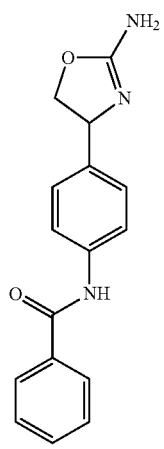 [SMILES: NC1=NC(c2ccc(NC(=O)c3ccccc3)cc2)CO1]

To a stirred suspension of (RS)—N-[4-(2-amino-4,5-dihydro-oxazol-4-yl)-phenyl]-4-chloro-benzamide (50 mg) in methanol (3 ml) were added ammonium formate (100 mg) and palladium on charcoal (13 mg, 10 wt %) and the mixture was heated at 60° C. for 2 hours. The mixture was then cooled to room temperature, filtered through celite and the filtrate was concentrated in vacuo. The residue was taken up in ethyl acetate/THF (1:1) and this solution was washed sequentially with saturated aq. sodium bicarbonate solution and saturated brine. The organic phase was then separated, dried over sodium sulphate and concentrated in vacuo. The residue was purified by column chromatography (Isolute® Flash-NH$_2$ from Separtis; gradient: heptane/dichloromethane/methanol) to give (RS)—N-[4-(2-amino-4,5-dihydro-oxazol-4-yl)-phenyl]-benzamide (20 mg, 45%) as a white solid. MS (ISP): 282.1 ([M+H]$^+$).

Example 6

(RS)—N-[3-(2-Amino-4,5-dihydro-oxazol-4-yl)-phenyl]-4-chloro-benzamide

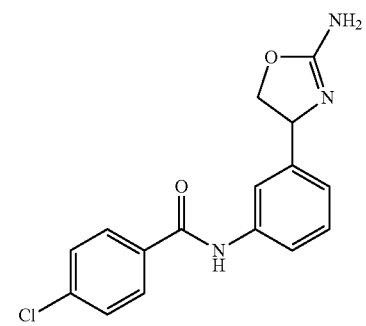 [SMILES: NC1=NC(c2cccc(NC(=O)c3ccc(Cl)cc3)c2)CO1]

The title compound was obtained in analogy to example 1(a)-1(e) & then example 4 starting from 3-iodo-benzaldehyde instead of 4-iodo-benzaldehyde. White solid. MS (ISP): 318.1 ([{$^{37}$Cl}M+H]$^+$), 316.1 ([{$^{35}$Cl}M+H]$^+$).

Example 7

(RS)-1-[3-(2-Amino-4,5-dihydro-oxazol-4-yl)-phenyl]-3-(4-chloro-phenyl)-urea

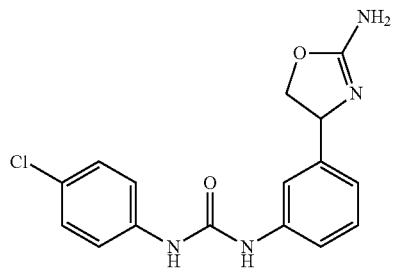 [SMILES: NC1=NC(c2cccc(NC(=O)Nc3ccc(Cl)cc3)c2)CO1]

The title compound was obtained in analogy to example 1 starting from 3-iodo-benzaldehyde instead of 4-iodo-benzaldehyde. White solid. MS (ISP): 333.2 ([{$^{37}$Cl}M+H]$^+$), 331.2 ([{35Cl}M+H]$^+$).

Example 8

N-{4-[3-((S)-2-Amino-4,5-dihydro-oxazol-4-yl)-propyl]-phenyl}-4-chloro-benzamide

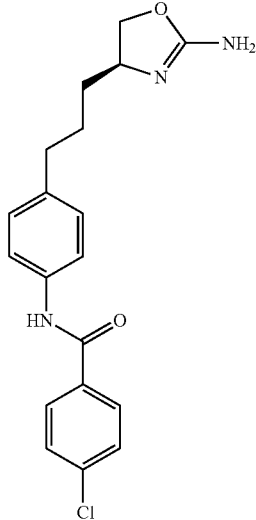 [SMILES: NC1=N[C@@H](CCCc2ccc(NC(=O)c3ccc(Cl)cc3)cc2)CO1]

a) (S)-4-[(E)-3-(4-Iodo-phenyl)-allyl]-2,2-dimethyl-oxazolidine-3-carboxylic acid tert-butyl ester The title compound was obtained in analogy to example 3(a) starting from (S)-2,2-dimethyl-4-(2-oxo-ethyl)-oxazolidine-3-carboxylic acid tert-butyl ester (CAS 147959-19-1) instead of (R)-4-formyl-2,2-dimethyl-oxazolidine-3-carboxylic acid tert-butyl ester. Light yellow solid. MS (ISP): 344 ([M+H—$C_4H_8$—$CO_2$]$^+$).

b) N-{4-[3-((S)-2-Amino-4,5-dihydro-oxazol-4-yl)-propyl]-phenyl}-4-chloro-benzamide The title compound was obtained in analogy to example 9 starting from (S)-4-[(E)-3-(4-iodo-phenyl)-allyl]-2,2-dimethyl-oxazolidine-3-carboxylic acid tert-butyl ester instead of (S)-4-[(E)-2-(4-iodo-phenyl)-vinyl]-2,2-dimethyl-oxazolidine-3-carboxylic acid tert-butyl ester. Light yellow solid. MS (ISP): 360.1 ([$\{^{37}Cl\}$M+H]$^+$), 358.2 ([$\{^{35}Cl\}$M+H]$^+$).

Example 9

N-{4-[2-((S)-2-Amino-4,5-dihydro-oxazol-4-yl)-ethyl]-phenyl}-4-chloro-benzamide

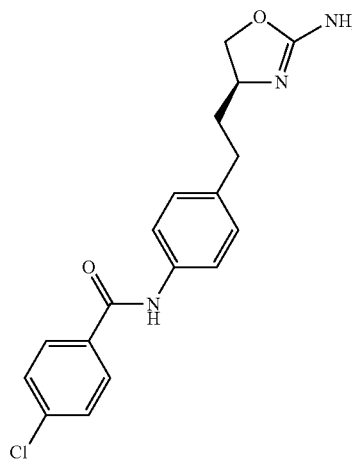

a) (S)-4-{(E)-2-[4-(4-Chloro-benzoylamino)-phenyl]-vinyl}-2,2-dimethyl-oxazolidine-3-carboxylic acid tert-butyl ester The title compound was obtained in analogy to example 4(a) starting from (S)-4-[(E)-2-(4-iodo-phenyl)-vinyl]-2,2-dimethyl-oxazolidine-3-carboxylic acid tert-butyl ester (example 3(a)) instead of (RS)-4-(4-iodo-phenyl)-2,2-dimethyl-oxazolidine-3-carboxylic acid tert-butyl ester. Yellow solid. MS (ISP): 457.2 ([$\{^{37}Cl\}$M−H]$^−$), 455.2 ([$\{^{35}Cl\}$M−H]$^−$).

b) (S)-4-{2-[4-(4-Chloro-benzoylamino)-phenyl]-ethyl}-2,2-dimethyl-oxazolidine-3-carboxylic acid tert-butyl ester The title compound was obtained in analogy to example 3(c) starting from (S)-4-{(E)-2-[4-(4-chloro-benzoylamino)-phenyl]-vinyl}-2,2-dimethyl-oxazolidine-3-carboxylic acid tert-butyl ester instead of (S)-4-((E)-2-{4-[3-(4-chloro-phenyl)-ureido]-phenyl}-vinyl)-2,2-dimethyl-oxazolidine-3-carboxylic acid tert-butyl ester. White solid. MS (ISP): 478.3 ([$\{^{37}Cl\}$M+NH$_4$]$^+$), 476.3 ([$\{^{35}Cl\}$M+NH$_4$]$^+$), 405.4 ([$\{^{37}Cl\}$M+H—$C_4H_8$]$^+$), 403.2 ([$\{^{35}Cl\}$M+H—$C_4H_8$]$^+$).

c) N-{4-[2-((S)-2-Amino-4,5-dihydro-oxazol-4-yl)-ethyl]-phenyl}-4-chloro-benzamide The title compound was obtained in analogy to example 1(g)-1(h) starting from (S)-4-{2-[4-(4-chloro-benzoylamino)-phenyl]-ethyl}-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 346.1 ([$\{^{37}Cl\}$M+H]$^+$), 344.2 ([$\{^{35}Cl\}$M+H]$^+$).

Example 10

N-{3-[2-((S)-2-Amino-4,5-dihydro-oxazol-4-yl)-ethyl]-phenyl}-4-chloro-benzamide

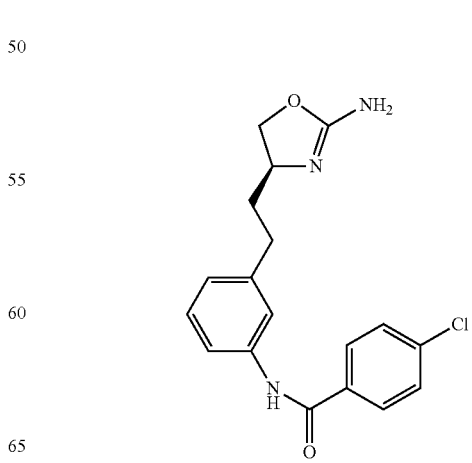

The title compound was obtained in analogy to example 3(a) & then example 9 starting from (3-iodo-benzyl)-phosphonic acid diethyl ester (CAS 261966-88-5) instead of (4-iodo-benzyl)-phosphonic acid diethyl ester. Yellow oil. MS (ISP): 346.1 ([{$^{37}$Cl}M+H]$^+$), 344.2 ([{$^{35}$Cl}M+H]$^+$).

Example 11

1-{4-[(S)-1-((S)-2-Amino-4,5-dihydro-oxazol-4-ylmethyl)-propyl]-phenyl}-3-(4-chloro-phenyl)-urea

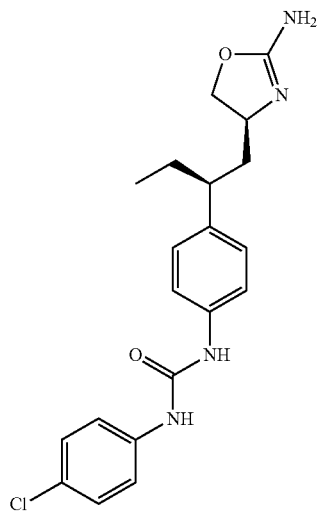 [SMILES: CC[C@@H](C[C@H]1COC(N)=N1)c1ccc(NC(=O)Nc2ccc(Cl)cc2)cc1]

a) (S)-4-[(S)-2-(4-Nitro-phenyl)-butyl]-4,5-dihydro-oxazol-2-ylamine

To stirred nitric acid (9.5 ml, 65% conc.) at room temperature was added (S)-4-((S)-2-phenyl-butyl)-4,5-dihydro-oxazol-2-ylamine (1.5 g, CAS 1043495-96-0) and the mixture was then heated at 60° C. for 3 hours. The mixture was then cooled in an ice-bath before being made basic by careful addition of 30% aq. sodium hydroxide solution. The resulting mixture was diluted with ethyl acetate/THF (1:1) and the phases were separated. The organic phase was washed with saturated brine, dried over sodium sulphate and concentrated in vacuo to give (S)-4-[(S)-2-(4-nitro-phenyl)-butyl]-4,5-dihydro-oxazol-2-ylamine (1.89 g, quant.) as a yellow solid. MS (ISP): 264.2 ([M+H]$^+$).

b) 1-{4-[(S)-1-((S)-2-Amino-4,5-dihydro-oxazol-4-ylmethyl)-propyl]-phenyl}-3-(4-chloro-phenyl)-urea The title compound was obtained in analogy to example 14(b)-(c) starting from (S)-4-[(S)-2-(4-nitro-phenyl)-butyl]-4,5-dihydro-oxazol-2-ylamine instead of (S)-2,2-dimethyl-4-[(E)-2-(4-nitro-phenyl)-vinyl]-oxazolidine-3-carboxylic acid tert-butyl ester and using 4-chlorophenyl isocyanate (CAS 104-12-1) instead of 3,4-dichlorophenyl isocyanate. White solid. MS (ISP): 389.1 ([{$^{37}$Cl}M+H]$^+$), 387.2 ([{$^{35}$Cl}M+H]$^+$).

Example 12

1-{4-[(S)-1-((S)-2-Amino-4,5-dihydro-oxazol-4-ylmethyl)-propyl]-phenyl}-3-(4-fluoro-phenyl)-urea

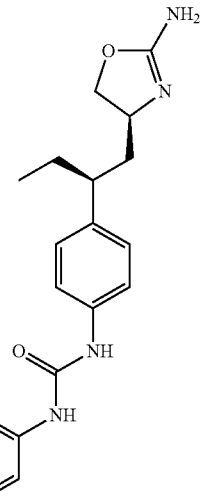

The title compound was obtained in analogy to example 11 using 4-fluorophenyl isocyanate (CAS 1195-45-5) instead of 4-chlorophenyl isocyanate. White solid. MS (ISP): 371.1 ([M+H]$^+$).

Example 13

1-{4-[(S)-1-((S)-2-Amino-4,5-dihydro-oxazol-4-ylmethyl)-propyl]-phenyl}-3-(4-trifluoromethyl-phenyl)-urea

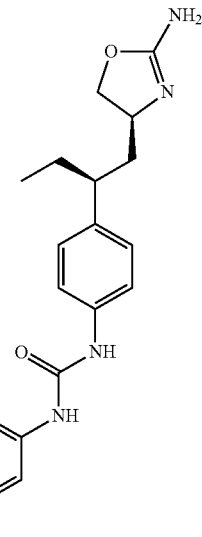

The title compound was obtained in analogy to example 11 using 4-(trifluoromethyl)phenyl isocyanate (CAS 1548-13-6) instead of 4-chlorophenyl isocyanate. White solid. MS (ISP): 421.1 ([M+H]$^+$).

Example 14

1-{4-[2-((S)-2-Amino-4,5-dihydro-oxazol-4-yl)-ethyl]-phenyl}-3-(3,4-dichloro-phenyl)-urea

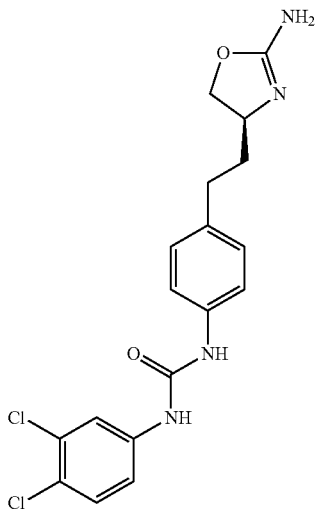 [SMILES: NC1=N[C@@H](CCc2ccc(NC(=O)Nc3ccc(Cl)c(Cl)c3)cc2)CO1]

a) (S)-2,2-Dimethyl-4-[(E)-2-(4-nitro-phenyl)-vinyl]-oxazolidine-3-carboxylic acid tert-butyl ester The title compound was obtained in analogy to example 3(a) starting from (4-nitro-benzyl)-phosphonic acid diethyl ester (CAS 2609-49-6) instead of (4-iodo-benzyl)-phosphonic acid diethyl ester. Yellow oil. MS (EI): 333 ([M–CH$_3$]$^+$), 292 ([M–C$_4$H$_8$]$^+$), 277 ([M–CH$_3$—C$_4$H$_8$]$^+$), 57 ([C$_4$H$_9$]$^+$).

(S)-4-[2-4-Amino-phenyl)-ethyl]-2,2-dimethyl-oxazolidine-3-carboxylic acid tert-butyl ester To a stirred suspension of (S)-2,2-dimethyl-4-[(E)-2-(4-nitro-phenyl)-vinyl]-oxazolidine-3-carboxylic acid tert-butyl ester (2.08 g) in methanol (140 ml) were added ammonium formate (5.66 g) and palladium on charcoal (0.51 g, 10 wt %) and the mixture was heated at 60° C. for 2 hours. The mixture was then cooled to room temperature, filtered through celite and the filtrate was concentrated in vacuo. The residue was purified by column chromatography (SiO$_2$; gradient: heptane/EtOAc) to give (S)-4-[2-(4-amino-phenyl)-ethyl]-2,2-dimethyl-oxazolidine-3-carboxylic acid tert-butyl ester (1.58 g, 82%) as a yellow oil. MS (ISP): 321.4 ([M+H]$^+$).

c) (S)-4-(2-{4-[3-(3,4-Dichloro-phenyl)-ureido]-phenyl}-ethyl)-2,2-dimethyl-oxazolidine-3-carboxylic acid tert-butyl ester To a stirred suspension of (S)-4-[2-(4-amino-phenyl)-ethyl]-2,2-dimethyl-oxazolidine-3-carboxylic acid tert-butyl ester (180 mg) in dichloromethane (3 ml) were added sequentially N,N-diisopropylethylamine (0.19 ml) and 3,4-dichlorophenyl isocyanate (137 mg, CAS 102-36-3) and stirring was continued at room temperature for 18 h. The mixture was then concentrated in vacuo and the residue was purified by column chromatography (SiO$_2$; gradient: heptane/EtOAc) to give (S)-4-(2-{4-[3-(3,4-dichloro-phenyl)-ureido]-phenyl}-ethyl)-2,2-dimethyl-oxazolidine-3-carboxylic acid tert-butyl ester (267 mg, 93%) as a colourless amorphous solid. MS (ISP): 529.4 ([{$^{37}$Cl}M+NH$_4$]$^+$), 527.4 ([{$^{37}$Cl$^{35}$Cl}M+NH$_4$]$^+$), 525.4 ([{$^{35}$Cl}M+NH$_4$]$^+$), 512.2 ([{$^{37}$Cl}M+H]$^+$), 510.2 ([{$^{37}$Cl$^{35}$Cl}M+H]$^+$), 508.2 ([{$^{35}$Cl}M+H]$^+$), 456.2 ([{$^{37}$Cl}M+H—C$_4$H$_8$]$^+$), 454.2 ([{$^{37}$Cl$^{35}$Cl}M+H—C$_4$H$_8$]$^+$), 452.2 ([{$^{35}$Cl}M+H—C$_4$H$_8$]$^+$).

d) 1-{4-[2-((S)-2-Amino-4,5-dihydro-oxazol-4-yl)-ethyl]-phenyl}-3-(3,4-dichloro-phenyl)-urea The title compound was obtained in analogy to example 1(g)-1(h) starting from (S)-4-(2-{4-[3-(3,4-dichloro-phenyl)-ureido]-phenyl}-ethyl)-2,2-dimethyl-oxazolidine-3-carboxylic acid tert-butyl ester instead of (RS)-4-{3-[4-(4-chloro-phenyl)-ureido]-phenyl}-2,2-dimethyl-oxazolidine-3-carboxylic acid tert-butyl ester. White solid. MS (ISP): 397.1 ([{$^{37}$Cl}M+H]$^+$), 395.0 ([{$^{37}$Cl$^{35}$Cl}M+H]$^+$), 393.2 ([{$^{35}$Cl}M+H]$^+$).

Example 15

1-{4-[2-((S)-2-Amino-4,5-dihydro-oxazol-4-yl)-ethyl]-phenyl}-3-(4-trifluoromethyl-phenyl)-urea

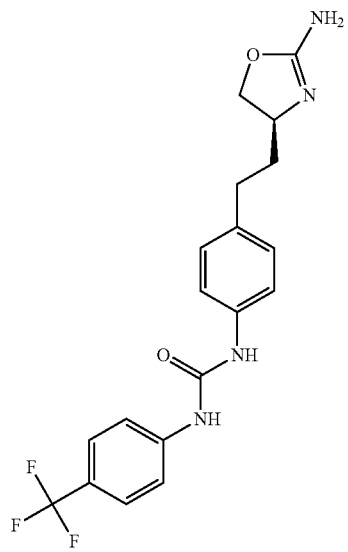 [SMILES: NC1=N[C@@H](CCc2ccc(NC(=O)Nc3ccc(C(F)(F)F)cc3)cc2)CO1]

The title compound was obtained in analogy to example 14(c)-(d) starting from (S)-4-[2-(4-amino-phenyl)-ethyl]-2,2-dimethyl-oxazolidine-3-carboxylic acid tert-butyl ester and using 4-(trifluoromethyl)phenyl isocyanate (CAS 1548-13-6) instead of 3,4-dichlorophenyl isocyanate. White solid. MS (ISP): 393.2 ([M+H]$^+$).

Example 16

N-{4-[2-((S)-2-Amino-4,5-dihydro-oxazol-4-yl)-ethyl]-phenyl}-4-fluoro-benzamide

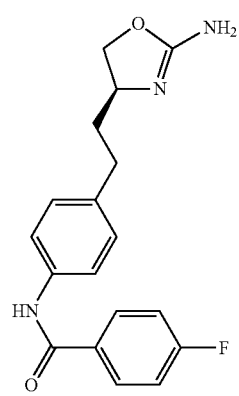 [SMILES: NC1=N[C@@H](CCc2ccc(NC(=O)c3ccc(F)cc3)cc2)CO1]

The title compound was obtained in analogy to example 9 starting from (S)-4-[(E)-2-(4-iodo-phenyl)-vinyl]-2,2-dimethyl-oxazolidine-3-carboxylic acid tert-butyl ester and using 4-fluorobenzamide instead of 4-chlorobenzamide. White solid. MS (ISP): 328.3 ([M+H]$^+$).

Example 17

N-{4-[2-((S)-2-Amino-4,5-dihydro-oxazol-4-yl)-ethyl]-phenyl}-4-trifluoromethyl-benzamide

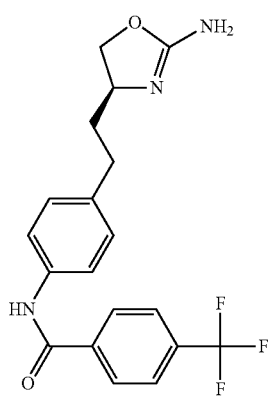 [SMILES: NC1=N[C@@H](CCc2ccc(NC(=O)c3ccc(C(F)(F)F)cc3)cc2)CO1]

The title compound was obtained in analogy to example 9 starting from (S)-4-[(E)-2-(4-iodo-phenyl)-vinyl]-2,2-dimethyl-oxazolidine-3-carboxylic acid tert-butyl ester and using 4-(trifluoromethyl)benzamide instead of 4-chlorobenzamide. White solid. MS (ISP): 378.3 ([M+H]$^+$).

Example 18

N-{4-[2-((S)-2-Amino-4,5-dihydro-oxazol-4-yl)-ethyl]-phenyl}-3-chloro-benzamide

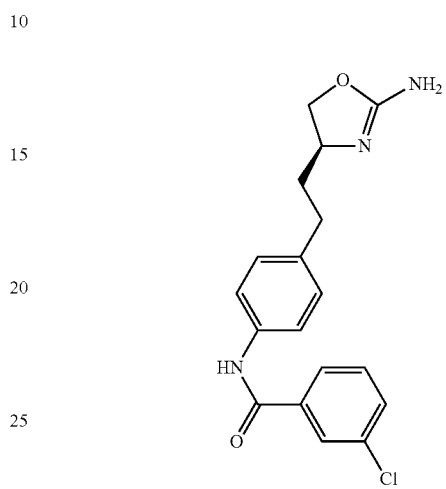

The title compound was obtained in analogy to example 9 starting from (S)-4-[(E)-2-(4-iodo-phenyl)-vinyl]-2,2-dimethyl-oxazolidine-3-carboxylic acid tert-butyl ester and using 3-chlorobenzamide instead of 4-chlorobenzamide. White solid. MS (ISP): 346.1 ([{$^{37}$Cl}M+H]$^+$), 344.2 ([{$^{35}$Cl}M+H]$^+$).

Example 19

1-(4-{1-[2-((S)-2-Amino-4,5-dihydro-oxazol-4-yl)-ethyl]-cyclopropyl}-phenyl)-pyrrolidin-2-one

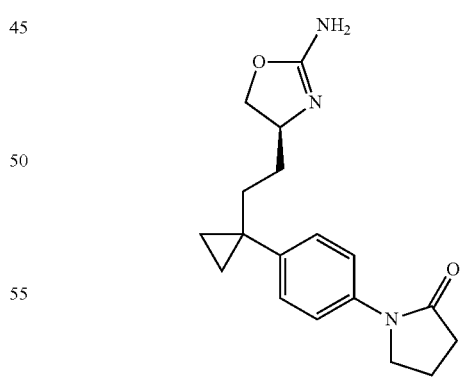

a) (S)-4-{(Z)-2-[1-(4-Iodo-phenyl)-cyclopropyl]-vinyl}-2,2-dimethyl-oxazolidine-3-carboxylic acid tert-butyl ester To a stirred, cooled (0° C.) solution of 1-(4-iodo-phenyl)-cyclopropanecarbaldehyde (1.6 g) in tetrahydrofurane (40 ml) was added under an argon atmosphere (R)-4-(benzothiazole-2-sulfonylmethyl)-2,2-dimethyl-oxazolidine-3-carboxylic acid tert-butyl ester (2.9 g) [CAS 1043499-96-2] followed by a 1 M solution of LiHMDS in THF (11.8 ml). After 1 h at 0° C. the cooling bath was removed and stirring was continued overnight. The mixture was quenched by the addition of sat. aqueous NH$_4$Cl (50 ml) and H$_2$O (50 ml) and extracted with EtOAc. The aqueous phase was back extracted with EtOAc. The combined organics were washed with brine, dried over MgSO$_4$, filtered and concentrated. The crude product was purified by column chromatography (SiO$_2$; gradient: heptane->heptane/EtOAc 2:1) to give (S)-4-{(Z)-2-[1-(4-iodo-phenyl)-cyclopropyl]-vinyl}-2,2-dimethyl-oxazolidine-3-carboxylic acid tert-butyl ester (2.0 g) as light yellow solid. MS (ISP): 470.3 ([M+H]$^+$).

b) 1-(4-{1-[2-((S)-2-Amino-4,5-dihydro-oxazol-4-yl)-ethyl]-cyclopropyl}-phenyl)-pyrrolidin-2-one The title compound was obtained in analogy to example 9 starting from (S)-4-{(Z)-2-[1-(4-iodo-phenyl)-cyclopropyl]-vinyl}-2,2-dimethyl-oxazolidine-3-carboxylic acid tert-butyl ester instead of (S)-4-[(E)-2-(4-iodo-phenyl)-vinyl]-2,2-dimethyl-oxazolidine-3-carboxylic acid tert-butyl ester and using pyrrolidin-2-one instead of 4-chlorobenzamide. White foam. MS (ISP): 314.3 ([M+H]$^+$).

Example 20

(RS)-Cyclohexanecarboxylic acid [4-(2-amino-4,5-dihydro-oxazol-4-yl)-phenyl]amide

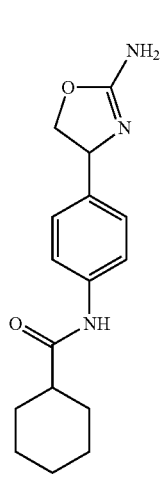 [SMILES: NC1=NC(c2ccc(NC(=O)C3CCCCC3)cc2)CO1]

The title compound was obtained in analogy to example 4 starting from (RS)-4-(4-iodo-phenyl)-2,2-dimethyl-oxazolidine-3-carboxylic acid tert-butyl ester and using cyclohexanecarboxamide instead of 4-chlorobenzamide. White solid. MS (ISP): 288.2 ([M+H]$^+$).

Example 21

(RS)-Cyclopropanecarboxylic acid [4-(2-amino-4,5-dihydro-oxazol-4-yl)-phenyl]amide

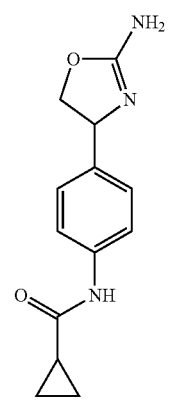 [SMILES: NC1=NC(c2ccc(NC(=O)C3CC3)cc2)CO1]

The title compound was obtained in analogy to example 4 starting from (RS)-4-(4-iodo-phenyl)-2,2-dimethyl-oxazolidine-3-carboxylic acid tert-butyl ester and using cyclopropanecarboxamide instead of 4-chlorobenzamide. White solid. MS (ISP): 246.3 ([M+H]$^+$).

Example 22

(RS)—N-[4-(2-Amino-4,5-dihydro-oxazol-4-yl)-phenyl]-4-fluoro-benzamide

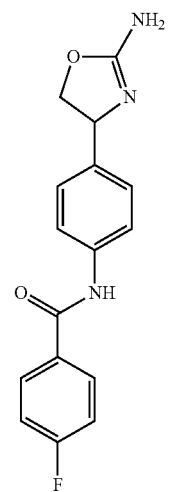 [SMILES: NC1=NC(c2ccc(NC(=O)c3ccc(F)cc3)cc2)CO1]

The title compound was obtained in analogy to example 4 starting from (RS)-4-(4-iodo-phenyl)-2,2-dimethyl-oxazolidine-3-carboxylic acid tert-butyl ester and using 4-fluorobenzamide instead of 4-chlorobenzamide. White solid. MS (ISP): 300.4 ([M+H]$^+$).

Example 23

(RS)—N-[4-(2-Amino-4,5-dihydro-oxazol-4-yl)-phenyl]-4-trifluoromethyl-benzamide

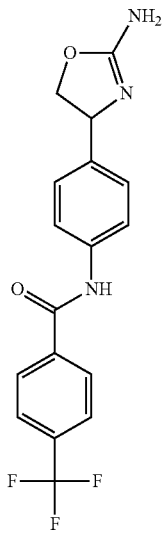 [SMILES: NC1=NC(c2ccc(NC(=O)c3ccc(C(F)(F)F)cc3)cc2)CO1]

The title compound was obtained in analogy to example 4 starting from (RS)-4-(4-iodo-phenyl)-2,2-dimethyl-oxazolidine-3-carboxylic acid tert-butyl ester and using 4-(trifluoromethyl)benzamide instead of 4-chlorobenzamide. White solid. MS (ISP): 350.2 ([M+H]$^+$).

Example 24

(RS)—N-[4-(2-Amino-4,5-dihydro-oxazol-4-yl)-phenyl]-2-(4-chloro-phenyl)-acetamide

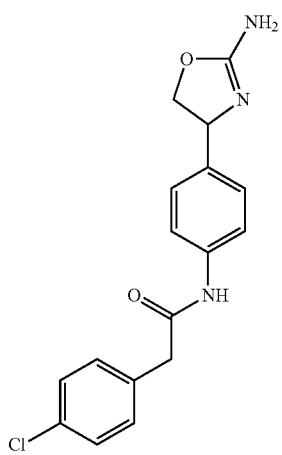 [SMILES: NC1=NC(c2ccc(NC(=O)Cc3ccc(Cl)cc3)cc2)CO1]

The title compound was obtained in analogy to example 4 starting from (RS)-4-(4-iodo-phenyl)-2,2-dimethyl-oxazolidine-3-carboxylic acid tert-butyl ester and using 2-(4-chlorophenyl)-acetamide instead of 4-chlorobenzamide. White solid. MS (ISP): 332.2 ([{$^{37}$Cl}M+H]$^+$), 330.2 ([{35Cl}M+H]$^+$).

Example 25

N-{4-[3-((S)-2-Amino-4,5-dihydro-oxazol-4-yl)-1-methyl-propyl]-phenyl}-acetamide

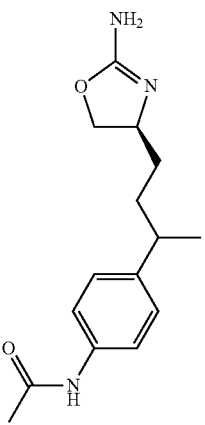 [SMILES: CC(=O)Nc1ccc(C(C)CC[C@H]2COC(N)=N2)cc1]

a) (S)-4-[3-(4-Amino-phenyl)-butyl]-2,2-dimethyl-oxazolidine-3-carboxylic acid tert-butyl ester (S)-4-[3-(4-Amino-phenyl)-butyl]-2,2-dimethyl-oxazolidine-3-carboxylic acid tert-butyl ester was obtained in analogy to example 14 (a, b) starting from [1-(4-nitro-phenyl)-ethyl]-phosphonic acid diethyl ester instead of (4-nitrobenzyl)-phosphonic acid diethyl ester and (S)-2,2-dimethyl-4-(2-oxo-ethyl)-oxazolidine-3-carboxylic acid tert-butyl ester (CAS 147959-19-1) instead of (R)-4-formyl-2,2-dimethyl-oxazolidine-3-carboxylic acid tert-butyl ester. Colourless oil. MS (ISP): 249.4 (M-BOC+H]$^+$).

b) N-{4-[3-((S)-2-Amino-4,5-dihydro-oxazol-4-yl)-1-methyl-propyl]-phenyl}-acetamide The title compound was obtained in analogy to example 31 starting from (S)-4-[3-(4-amino-phenyl)-butyl]-2,2-dimethyl-oxazolidine-3-carboxylic acid tert-butyl ester instead of (S)-4-[2-(4-amino-phenyl)-ethyl]-2,2-dimethyl-oxazolidine-3-carboxylic acid tert-butyl ester and using acetylchloride instead of 6-chloronicotinoyl chloride. Colourless oil. MS (ISP): 276.4 (M+H]$^+$).

Example 26

N-{4-[3-((S)-2-Amino-4,5-dihydro-oxazol-4-yl)-1-methyl-propyl]-phenyl}-benzamide

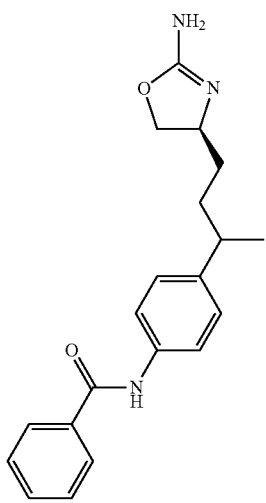 [SMILES: CC(CC[C@H]1COC(N)=N1)c1ccc(NC(=O)c2ccccc2)cc1]

The title compound was obtained in analogy to example 25 using benzoylchloride instead of acetylchloride in step b). Colourless oil. MS (ISP): 338.4 (M+H)$^+$.

Example 27

N-{4-[3-((S)-2-Amino-4,5-dihydro-oxazol-4-yl)-propyl]-phenyl}-N-methyl-acetamide

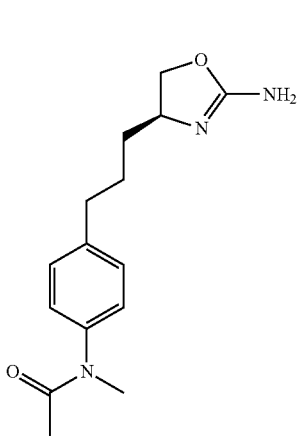 [SMILES: CC(=O)N(C)c1ccc(CCC[C@H]2COC(N)=N2)cc1]

The title compound was obtained in analogy to example 9 using N-methyl-acetamide instead of 4-chlorobenzamide. White gummy solid. MS (ISP): 276.4 ([M+H]$^+$).

Example 28

N-{4-[3-((S)-2-Amino-4,5-dihydro-oxazol-4-yl)-propyl]-phenyl}-acetamide

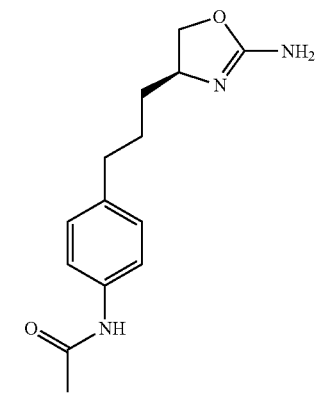 [SMILES: CC(=O)Nc1ccc(CCC[C@H]2COC(N)=N2)cc1]

The title compound was obtained in analogy to example 9 using acetamide instead of 4-chlorobenzamide. Light yellow oil. MS (ISP): 262.2 ([M+H]$^+$).

Example 29

N-{4-[3-((S)-2-Amino-4,5-dihydro-oxazol-4-yl)-propyl]-phenyl}-N-(4-fluoro-phenyl)-acetamide

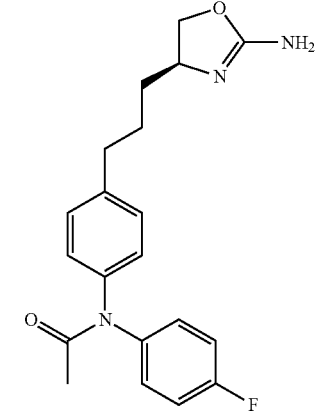 [SMILES: CC(=O)N(c1ccc(F)cc1)c1ccc(CCC[C@H]2COC(N)=N2)cc1]

The title compound was obtained in analogy to example 9 using N-methyl-acetamide instead of 4-chlorobenzamide. Yellow gum. MS (ISP): 356.4 ([M+H]$^+$).

Example 30

4-[2-((S)-2-Amino-4,5-dihydro-oxazol-4-yl)-ethyl]-N-isopropyl-benzamide

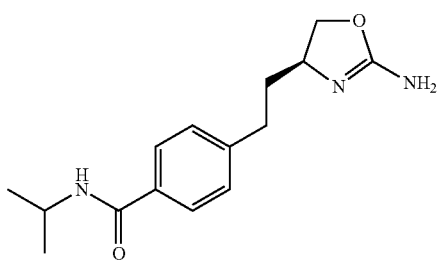 [SMILES: CC(C)NC(=O)c1ccc(CC[C@H]2COC(N)=N2)cc1]

The title compound was obtained in analogy to example 48 using isopropylamine instead of 4-chloroaniline in step b). Light brown gum. MS (ISP): 276.2 ([M+H]$^+$).

Example 31

N-{4-[2-((S)-2-Amino-4,5-dihydro-oxazol-4-yl)-ethyl]-phenyl}-6-chloro-nicotinamide

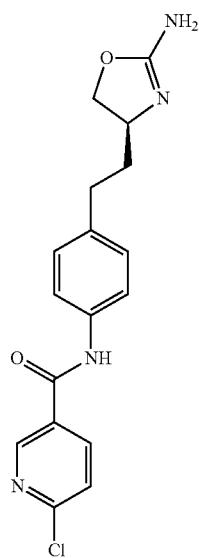

a) (S)-4-(2-{4-[(6-Chloro-pyridine-3-carbonyl)-amino]-phenyl}-ethyl)-2,2-dimethyl-oxazolidine-3-carboxylic acid tert-butyl ester To a stirred suspension of (S)-4-[2-(4-amino-phenyl)-ethyl]-2,2-dimethyl-oxazolidine-3-carboxylic acid tert-butyl ester (150 mg, example 14 (b)) in THF (4 ml) were added sequentially triethylamine (0.13 ml) and 6-chloronicotinoyl chloride (107 mg, CAS 58757-38-3) and the mixture was heated at 50° C. for 4 h. The mixture was then concentrated in vacuo and the residue was purified by column chromatography (SiO$_2$; gradient: heptane/EtOAc) to give (S)-4-(2-{4-[(6-chloro-pyridine-3-carbonyl)-amino]-phenyl}-ethyl)-2,2-dimethyl-oxazolidine-3-carboxylic acid tert-butyl ester (177 mg, 82%) as a white solid. MS (ISP): 484.3 ([{$^{37}$Cl}M+Na]$^+$), 482.3 ([{$^{35}$Cl}M+Na]$^+$), 462.4 ([{$^{37}$Cl}M+H]$^+$), 460.5 ([{$^{35}$Cl}M+H]$^+$), 406.4 ([{$^{37}$Cl}M+H—C$_4$H$_8$]$^+$), 404.3 ([{$^{35}$Cl}M+H—C$_4$H$_8$]$^+$).

b) N-{4-[2-((S)-2-Amino-4,5-dihydro-oxazol-4-yl)-ethyl]-phenyl}-6-chloro-nicotinamide The title compound was obtained in analogy to example 1(g)-1(h) starting from (S)-4-(2-{4-[(6-chloro-pyridine-3-carbonyl)-amino]-phenyl}-ethyl)-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 347.1 ([{$^{37}$Cl}M+H]$^+$), 345.2 ([{$^{35}$Cl}M+H]$^+$).

Example 32

N-{4-[2-((S)-2-Amino-4,5-dihydro-oxazol-4-yl)-ethyl]-phenyl}-4-chloro-benzenesulfonamide

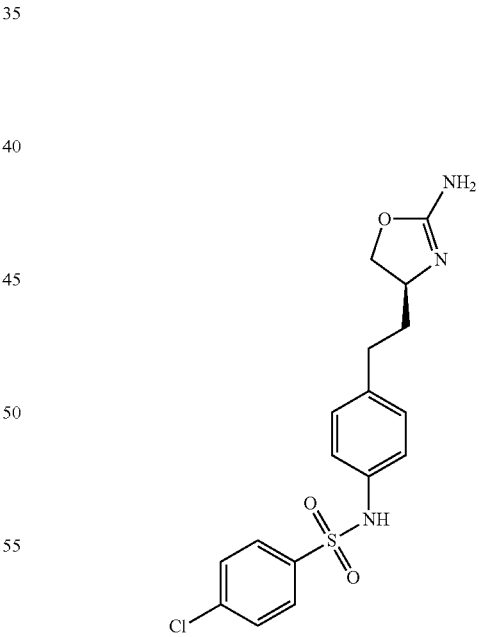

The title compound was obtained in analogy to example 31 starting from (S)-4-[2-(4-amino-phenyl)-ethyl]-2,2-dimethyl-oxazolidine-3-carboxylic acid tert-butyl ester and using 4-chlorobenzenesulphonyl chloride (CAS 98-60-2) instead of 6-chloronicotinoyl chloride. White solid. MS (ISP): 382.2 ([{$^{37}$Cl}M+H]$^+$), 380.3 ([{$^{35}$Cl}M+H]$^+$).

Example 33

5-Chloro-pyridine-2-carboxylic acid {4-[2-((S)-2-amino-4,5-dihydro-oxazol-4-yl)-ethyl]-phenyl}-amide

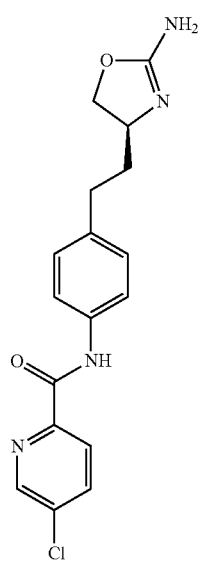 [SMILES: NC1=N[C@@H](CCc2ccc(NC(=O)c3ccc(Cl)cn3)cc2)CO1]

a) (S)-4-(2-{4-[(5-Chloro-pyridine-2-carbonyl)-amino]-phenyl}-ethyl)-2,2-dimethyl-oxazolidine-3-carboxylic acid tert-butyl ester To a stirred suspension of (S)-4-[2-(4-amino-phenyl)-ethyl]-2,2-dimethyl-oxazolidine-3-carboxylic acid tert-butyl ester (150 mg, example 14 (b)) in THF (4 ml) were added sequentially N-methylmorpholine (0.21 ml), TBTU (301 mg) and 5-chloro-2-pyridinecarboxylic acid (111 mg, CAS 86873-60-1) and the mixture was heated at 50° C. for 18 h. The mixture was then concentrated in vacuo and the residue was purified by column chromatography (SiO$_2$; gradient: heptane/EtOAc) to give (S)-4-(2-{4-[(5-chloro-pyridine-2-carbonyl)-amino]-phenyl}-ethyl)-2,2-dimethyl-oxazolidine-3-carboxylic acid tert-butyl ester (197 mg, 91%) as a white solid. MS (ISP): 484.3 ([{$^{37}$Cl}M+Na]$^+$), 482.3 ([{$^{35}$Cl}M+Na]$^+$), 462.4 ([{$^{37}$Cl}M+H]$^+$), 460.5 ([{$^{35}$Cl}M+H]$^+$), 406.4 ([{$^{37}$Cl}M+H—C$_4$H$_8$]$^+$), 404.3 ([{$^{35}$Cl}M+H—C$_4$H$_8$]$^+$).

b) 5-Chloro-pyridine-2-carboxylic acid {4-[2-((S)-2-amino-4,5-dihydro-oxazol-4-yl)-ethyl]-phenyl}-amide The title compound was obtained in analogy to example 1(g)-1(h) starting from (S)-4-(2-{4-[(5-chloro-pyridine-2-carbonyl)-amino]-phenyl}-ethyl)-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 347.1 ([{$^{37}$Cl}M+H]$^+$), 345.2 ([{$^{35}$Cl}M+H]$^+$).

Example 34

5-Chloro-pyrimidine-2-carboxylic acid {4-[2-((S)-2-amino-4,5-dihydro-oxazol-4-yl)-ethyl]-phenyl}-amide

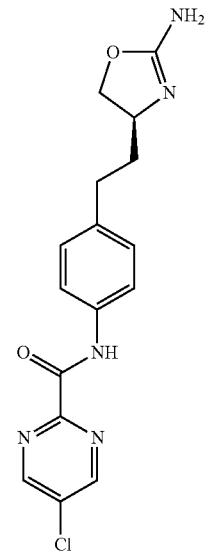

The title compound was obtained in analogy to example 33 starting from (S)-4-[2-(4-amino-phenyl)-ethyl]-2,2-dimethyl-oxazolidine-3-carboxylic acid tert-butyl ester and using 5-chloro-2-pyrimidinecarboxylic acid (CAS 38275-61-5) instead of 5-chloro-2-pyridinecarboxylic acid. White solid. MS (ISP): 348.2 ([{$^{37}$Cl}M+H]$^+$), 346.1 ([{$^{35}$Cl}M+H]$^+$).

Example 35

1-{4-[2-((S)-2-Amino-4,5-dihydro-oxazol-4-yl)-ethyl]-phenyl}-3-(5-chloro-pyridin-2-yl)-urea

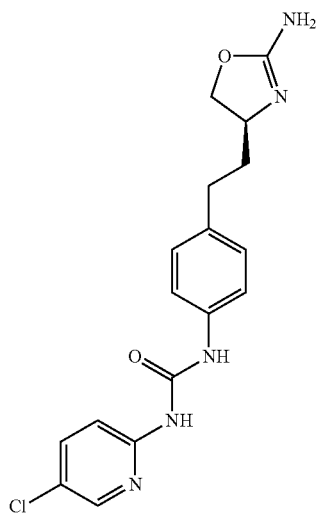 [SMILES: NC1=N[C@@H](CCc2ccc(NC(=O)Nc3ccc(Cl)cn3)cc2)CO1]

(S)-4-[2-4-Isocyanato-phenyl)-ethyl]-2,2-dimethyl-oxazolidine-3-carboxylic acid tert-butyl ester To a stirred suspension of (S)-4-[2-(4-amino-phenyl)-ethyl]-2,2-dimethyl-oxazolidine-3-carboxylic acid tert-butyl ester (600 mg, example 14 (b)) in dichloromethane (10 ml) were added sequentially triethylamine (0.52 ml) and triphosgene (206 mg) and the mixture was heated at 50° C. for 18 h. The mixture was then concentrated in vacuo and to the residue was added diethyl ether. After stirring for 10 min at room temperature the resulting crystals were removed by filtration. The filtrate was concentrated in vacuo to give (S)-4-[2-(4-isocyanato-phenyl)-ethyl]-2,2-dimethyl-oxazolidine-3-carboxylic acid tert-butyl ester (610 mg, 94%) as a yellow oil which was used immediately in the next step without further purification.

b) (S)-4-(2-{4-[3-(5-Chloro-pyridin-2-yl)-ureido]-phenyl}-ethyl)-2,2-dimethyl-oxazolidine-3-carboxylic acid tert-butyl ester The title compound was obtained in analogy to example 14(c) using (S)-4-[2-(4-isocyanato-phenyl)-ethyl]-2,2-dimethyl-oxazolidine-3-carboxylic acid tert-butyl ester in place of 3,4-dichlorophenyl isocyanate and 2-amino-5-chloropyridine (CAS 1072-98-6) instead of (S)-4-[2-(4-amino-phenyl)-ethyl]-2,2-dimethyl-oxazolidine-3-carboxylic acid tert-butyl ester. Yellow solid. MS (ISP): 499.3 ([$^{37}$Cl]M+Na]$^+$), 497.3 ([$^{35}$Cl]M+Na]$^+$), 477.3 ([$^{37}$Cl]M+H]$^+$), 475.3 ([$^{35}$Cl]M+H]$^+$), 421.1 ([$^{37}$Cl]M+H—C$_4$H$_8$]$^+$), 419.3 ([$^{35}$Cl]M+H—C$_4$H$_8$]$^+$).

c) 1-{4-[2-((S)-2-Amino-4,5-dihydro-oxazol-4-yl)-ethyl]-phenyl}-3-(5-chloro-pyridin-2-yl)-urea The title compound was obtained in analogy to example 1(g)-1(h) starting from (S)-4-(2-{4-[3-(5-chloro-pyridin-2-yl)-ureido]-phenyl}-ethyl)-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 362.1 ([$^{37}$Cl]M+H]$^+$), 360.2 ([$^{35}$Cl]M+H]$^+$).

Example 36

4,4-Difluoro-piperidine-1-carboxylic acid {4-[2-((S)-2-amino-4,5-dihydro-oxazol-4-yl)-ethyl]-phenyl}-amide

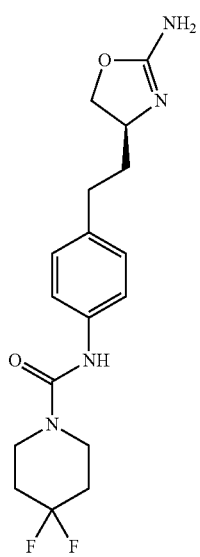 [SMILES: NC1=N[C@@H](CCc2ccc(NC(=O)N3CCC(F)(F)CC3)cc2)CO1]

The title compound was obtained in analogy to example 35(b)-(c) starting from (S)-4-[2-(4-isocyanato-phenyl)-ethyl]-2,2-dimethyl-oxazolidine-3-carboxylic acid tert-butyl ester and using 4,4-difluoro-piperidine hydrochloride (CAS 144230-52-4) instead of 2-amino-5-chloropyridine. White solid. MS (ISP): 353.4 ([M+H]$^+$).

Example 37

Morpholine-4-carboxylic acid {4-[2-((S)-2-amino-4,5-dihydro-oxazol-4-yl)-ethyl]-phenyl}-amide

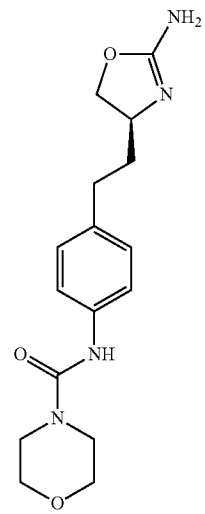 [SMILES: NC1=N[C@@H](CCc2ccc(NC(=O)N3CCOCC3)cc2)CO1]

The title compound was obtained in analogy to example 35(b)-(c) starting from (S)-4-[2-(4-isocyanato-phenyl)-ethyl]-2,2-dimethyl-oxazolidine-3-carboxylic acid tert-butyl ester and using morpholine instead of 2-amino-5-chloropyridine. White solid. MS (ISP): 319.2 ([M+H]$^+$).

Example 38

1-{4-[2-((S)-2-Amino-4,5-dihydro-oxazol-4-yl)-ethyl]-phenyl}-3-(6-chloro-pyridin-3-yl)-urea

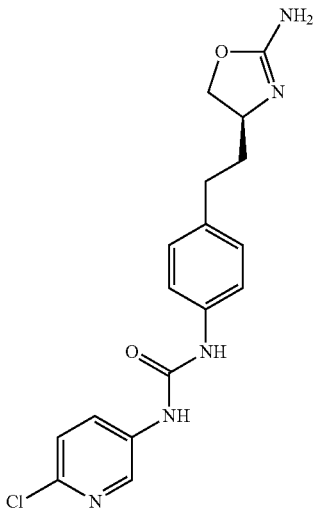 [SMILES: NC1=N[C@@H](CCc2ccc(NC(=O)Nc3ccc(Cl)nc3)cc2)CO1]

The title compound was obtained in analogy to example 35(b)-(c) starting from (S)-4-[2-(4-isocyanato-phenyl)-ethyl]-2,2-dimethyl-oxazolidine-3-carboxylic acid tert-butyl ester and using 5-amino-2-chloropyridine (CAS 5350-93-6)

instead of 2-amino-5-chloropyridine. White solid. MS (ISP): 362.1 ([{$^{37}$Cl}M+H]$^+$), 360.2 ([{$^{35}$Cl}M+H]$^+$).

Example 39

4-Trifluoromethyl-piperidine-1-carboxylic acid {4-[2-((S)-2-amino-4,5-dihydro-oxazol-4-yl)-ethyl]-phenyl}-amide

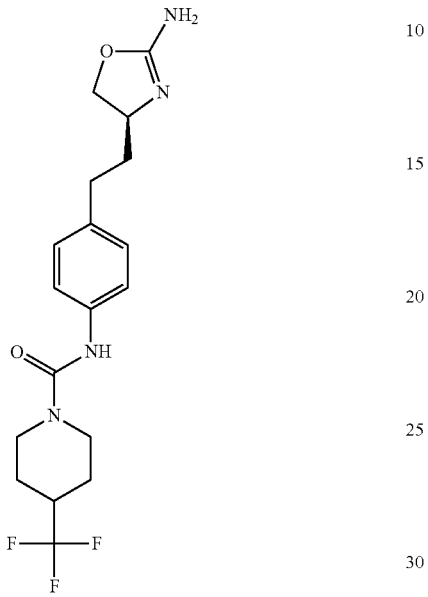

The title compound was obtained in analogy to example 35(b)-(c) starting from (S)-4-[2-(4-isocyanato-phenyl)-ethyl]-2,2-dimethyl-oxazolidine-3-carboxylic acid tert-butyl ester and using 4-(trifluoromethyl)piperidine hydrochloride (CAS 155849-49-3) instead of 2-amino-5-chloropyridine. White solid. MS (ISP): 385.2 ([M+H]$^+$).

Example 40

4,4-Difluoro-cyclohexanecarboxylic acid {4-[2-((S)-2-amino-4,5-dihydro-oxazol-4-yl)-ethyl]-phenyl}-amide

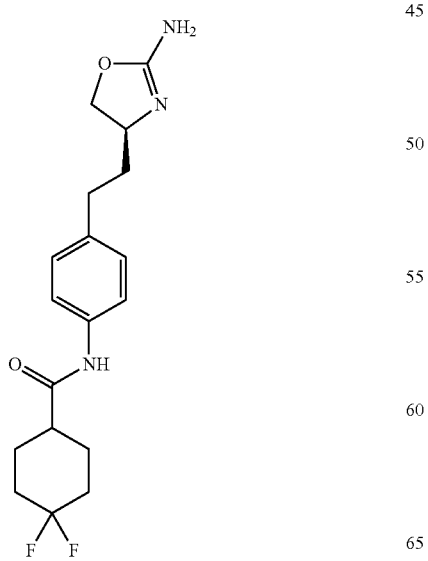

The title compound was obtained in analogy to example 83 starting from 4,4-difluorocyclohexanecarboxylic acid and (S)-4-[2-(4-amino-phenyl)-ethyl]-4,5-dihydro-oxazol-2-ylamine. Colourless foam. MS (ISP): 352.3 ([M+H]$^+$).

Example 41

1-Methyl-cyclopropanecarboxylic acid {4-[2-((S)-2-amino-4,5-dihydro-oxazol-4-yl)-ethyl]-phenyl}-amide

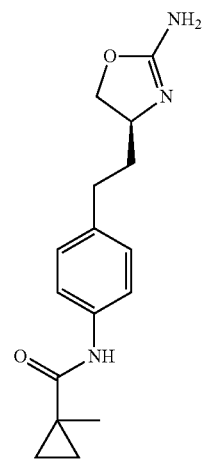 [SMILES: CC1(C(=O)Nc2ccc(CC[C@H]3COC(N)=N3)cc2)CC1]

The title compound was obtained in analogy to example 83 starting from 1-methylcyclopropane-1-carboxylic acid and (S)-4-[2-(4-amino-phenyl)-ethyl]-4,5-dihydro-oxazol-2-ylamine. Colourless foam. MS (ISP): 288.1 ([M+H]$^+$).

Example 42

Tetrahydro-pyran-4-carboxylic acid {4-[2-((S)-2-amino-4,5-dihydro-oxazol-4-yl)-ethyl]-phenyl}-amide

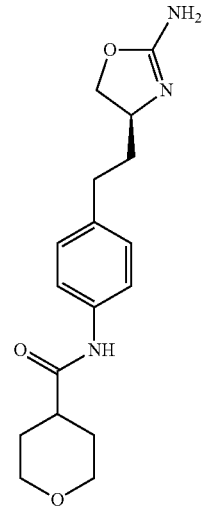 [SMILES: NC1=N[C@@H](CCc2ccc(NC(=O)C3CCOCC3)cc2)CO1]

The title compound was obtained in analogy to example 83 starting from tetrahydropyran-4-yl carboxylic acid and (S)-

4-[2-(4-amino-phenyl)-ethyl]-4,5-dihydro-oxazol-2-ylamine. White solid. MS (ISP): 318.1 ([M+H]$^+$).

Example 43

Cyclopentanecarboxylic acid {4-[2-((S)-2-amino-4,5-dihydro-oxazol-4-yl)-ethyl]-phenyl}-amide

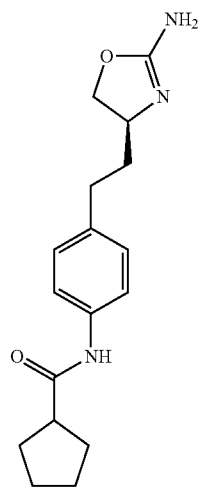 [SMILES: NC1=N[C@@H](CCc2ccc(NC(=O)C3CCCC3)cc2)CO1]

The title compound was obtained in analogy to example 83 starting from cyclopentanecarboxylic acid and (S)-4-[2-(4-amino-phenyl)-ethyl]-4,5-dihydro-oxazol-2-ylamine. Colourless foam. MS (ISP): 302.2 ([M+H]$^+$).

Example 44

3,3-Difluoro-cyclobutanecarboxylic acid {4-[2-((S)-2-amino-4,5-dihydro-oxazol-4-yl)-ethyl]-phenyl}-amide

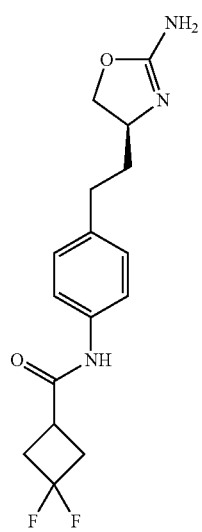 [SMILES: NC1=N[C@@H](CCc2ccc(NC(=O)C3CC(F)(F)C3)cc2)CO1]

The title compound was obtained in analogy to example 83 starting from 3,3-difluorocyclobutanecarboxylic acid and (S)-4-[2-(4-amino-phenyl)-ethyl]-4,5-dihydro-oxazol-2-ylamine. Colourless foam. MS (ISP): 324.3 ([M+H]$^+$).

Example 45

Cyclobutanecarboxylic acid {4-[2-((S)-2-amino-4,5-dihydro-oxazol-4-yl)-ethyl]-phenyl}-amide

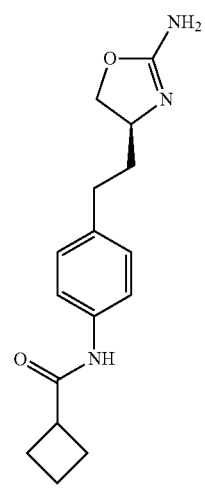 [SMILES: NC1=N[C@@H](CCc2ccc(NC(=O)C3CCC3)cc2)CO1]

The title compound was obtained in analogy to example 83 starting from cyclobutanecarboxylic acid and (S)-4-[2-(4-amino-phenyl)-ethyl]-4,5-dihydro-oxazol-2-ylamine. Colourless foam. MS (ISP): 288.1 ([M+H]$^+$).

Example 46

Cyclopropanecarboxylic acid {4-[2-((S)-2-amino-4,5-dihydro-oxazol-4-yl)-ethyl]-phenyl}-amide

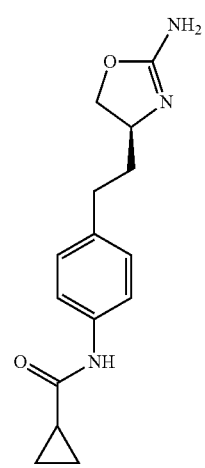 [SMILES: NC1=N[C@@H](CCc2ccc(NC(=O)C3CC3)cc2)CO1]

The title compound was obtained in analogy to example 83 starting from cyclopropanecarboxylic acid and (S)-4-[2-(4-amino-phenyl)-ethyl]-4,5-dihydro-oxazol-2-ylamine. Colourless foam. MS (ISP): 274.2 ([M+H]$^+$).

Example 47

N-{4-[2-((S)-2-Amino-4,5-dihydro-oxazol-4-yl)-ethyl]-phenyl}-4-chloro-N-methyl-benzamide

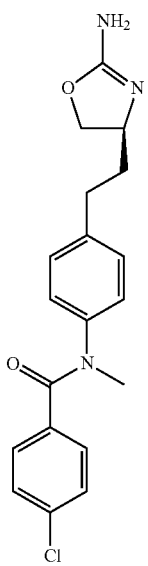 [SMILES: CN(C(=O)c1ccc(Cl)cc1)c1ccc(CC[C@H]2COC(N)=N2)cc1]

a) (S)-4-(2-{4-[(4-Chloro-benzoyl)-methyl-amino]-phenyl}-ethyl)-2,2-dimethyl-oxazolidine-3-carboxylic acid tert-butyl ester (S)-4-{2-[4-(4-Chloro-benzoylamino)-phenyl]-ethyl}-2,2-dimethyl-oxazolidine-3-carboxylic acid tert-butyl ester (109 mg) was azeotroped with toluene prior dissolution in dimethylformamide (2 ml) under argon and cooling to 0° C. NaH 55% in oil (12.2 mg) was added in portions and the resulting mixture stirred for 30 minutes before addition of methyl iodide (29.7 µl). The reaction mixture was then stirred for 1 hour at 0° C. and then quenched by dropwise addition of NaHCO$_3$, the mixture was extracted three times with ethyl acetate, the combined organic layers were dried over Na$_2$SO$_4$, filtered and concentrated in vacuo to afford title compound (S)-4-(2-{4-[(4-Chloro-benzoyl)-methyl-amino]-phenyl}-ethyl)-2,2-dimethyl-oxazolidine-3-carboxylic acid tert-butyl ester (110 mg) as a yellow solid. MS (ISP): 317.3 ([M-tBu+H]$^+$).

b) N-[4-((S)-3-Amino-4-hydroxy-butyl)-phenyl]-4-chloro-N-methyl-benzamide (S)-4-(2-{4-[(4-Chloro-benzoyl)-methyl-amino]-phenyl}-ethyl)-2,2-dimethyl-oxazolidine-3-carboxylic acid tert-butyl ester (110 mg) was dissolved in acetonitrile (1 ml) and water (2 ml) at room temperature before addition of trifluoroacetic acid (140 µl). The reaction mixture was heated to 80° C. and then stirred for 3 hours. After cooling to room temperature, ethyl acetate (4 ml) was added and the solution basified to pH 14 by addition of 2M aqueous sodium hydroxide. The mixture was stirred for 5 minutes and then extracted four times with ethyl acetate, dried over Na$_2$SO$_4$, filtered and concentrated in vacuo to afford N-[4-((S)-3-amino-4-hydroxy-butyl)-phenyl]-4-chloro-N-methyl-benzamide (95 mg) as a light yellow viscous oil. MS (ISP): 333.4 ([M+H]$^+$).

c) N-{4-[2-((S)-2-Amino-4,5-dihydro-oxazol-4-yl)-ethyl]-phenyl}-4-chloro-N-methyl-benzamide N-[4-((S)-3-amino-4-hydroxy-butyl)-phenyl]-4-chloro-N-methyl-benzamide [4-((S)-3-amino-4-hydroxy-butyl)-phenyl]-amide (95 mg) was dissolved in methanol (3 ml) at room temperature before addition of sodium acetate (69.9 mg) and a solution of cyanogen bromide (39.1 mg) in methanol (1 ml) dropwise. The reaction mixture was stirred at room temperature for 36 hours, then aqueous ammonia 25% was added (214.5 µl) and stirring was continued for an another hour. The solvent was evaporated in vacuo and the residue purified by preparative HPLC to give N-{4-[2-((S)-2-amino-4,5-dihydro-oxazol-4-yl)-ethyl]-phenyl}-4-chloro-N-methyl-benzamide (10 mg) as a light yellow foam. Description. MS (ISP): 316.2 ([M+H]$^+$).

Example 48

4-[2-((S)-2-Amino-4,5-dihydro-oxazol-4-yl)-ethyl]-N-(4-chloro-phenyl)-benzamide

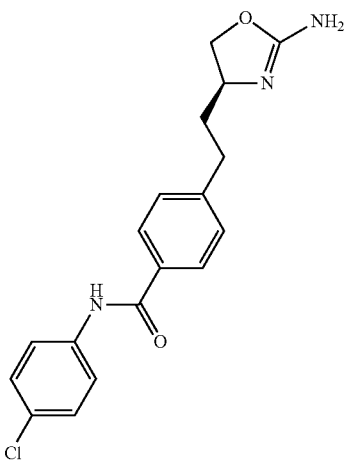

a) (S)-4-[2-4-Carboxy-phenyl)-ethyl]-2,2-dimethyl-oxazolidine-3-carboxylic acid tert-butyl ester To a stirred, cooled (0° C.) solution of methyl 4-formyl-benzoate (2.0 g) in tetrahydrofurane (60 ml) was added under an argon atmosphere (R)-4-(benzothiazole-2-sulfonylmethyl)-2,2-dimethyl-oxazolidine-3-carboxylic acid tert-butyl ester (6.0 g) [CAS 1043499-96-2] followed by a 1 M solution of LiHMDS in THF (29.2 ml). After 1 h at 0° C. the cooling bath was removed and stirring was continued overnight. The mixture was quenched by the addition of sat. aqueous NH₄Cl (100 ml) and H₂O (100 ml) and extracted with EtOAc. The aqueous phase was back extracted with EtOAc. The combined organics were washed with brine, dried over MgSO₄, filtered and concentrated. The crude product was purified by column chromatography (SiO₂; gradient: heptane->heptane/EtOAc 2:1) to give 2.56 g of a yellow oil. This was dissolved in methanol (10 ml), palladium on charcoal (10%, 0.2 g) was added and the mixture was stirred vigorously overnight at room temperature under hydrogen atmosphere using a balloon. The catalyst was filtered off and washed with methanol (10 ml). A solution of lithiumhydroxide (0.9 g) in water (15 ml) was added and the mixture was stirred for 2 hours at room temperature. The mixture was then neutralised by careful addition of 0.1 M aq. hydrochloric acid and extracted with ethyl acetate. The organic extracts were dried over sodium sulphate and concentrated in vacuo to give (S)-4-[2-(4-carboxy-phenyl)-ethyl]-2,2-dimethyl-oxazolidine-3-carboxylic acid tert-butyl ester as a white solid. MS (ISP): 348.3 ([M−H]⁻).

b) 4-[2-((S)-2-Amino-4,5-dihydro-oxazol-4-yl)-ethyl]-N-(4-chloro-phenyl)-benzamide The title compound was obtained in analogy to example 84 starting from (S)-4-[2-(4-carboxy-phenyl)-ethyl]-2,2-dimethyl-oxazolidine-3-carboxylic acid tert-butyl ester instead of (RS)-4-(4-carboxy-phenyl)-2,2-dimethyl-oxazolidine-3-carboxylic acid tert-butyl ester in step c). White solid. MS (ISP): 344.1 ([{³⁷Cl}M+H]⁺), 346.2 ([{³⁵Cl}M+H]⁺).

Example 49

Cyclohexanecarboxylic acid {4-[2-((S)-2-amino-4,5-dihydro-oxazol-4-yl)-ethyl]-phenyl}-amide

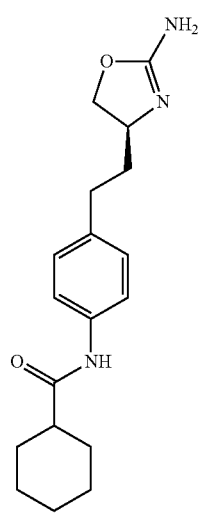 [SMILES: NC1=N[C@@H](CCc2ccc(NC(=O)C3CCCCC3)cc2)CO1]

The title compound was obtained in analogy to example 83 starting from cyclohexanecarboxylic acid and (S)-4-[2-(4-amino-phenyl)-ethyl]-4,5-dihydro-oxazol-2-ylamine. Light yellow foam. MS (ISP): 316.2 ([M+H]⁺).

Example 50

N-{4-[2-((S)-2-Amino-4,5-dihydro-oxazol-4-yl)-ethyl]-phenyl}-acetamide

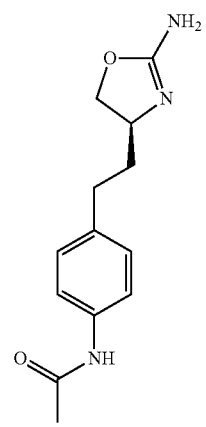 [SMILES: CC(=O)Nc1ccc(CC[C@H]2COC(N)=N2)cc1]

The title compound was obtained in analogy to example 83 starting from acetic acid and (S)-4-[2-(4-amino-phenyl)-ethyl]-4,5-dihydro-oxazol-2-ylamine. Colourless foam. MS (ISP): 248.2 ([M+H]⁺).

Example 51

N-{4-[2-((S)-2-Amino-4,5-dihydro-oxazol-4-yl)-ethyl]-phenyl}-2,2-dimethyl-propionamide

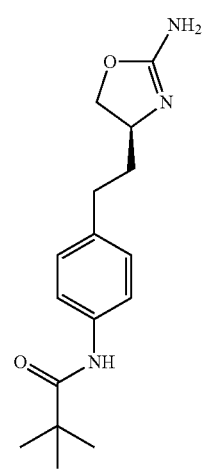 [SMILES: CC(C)(C)C(=O)Nc1ccc(CC[C@H]2COC(N)=N2)cc1]

The title compound was obtained in analogy to example 83 starting from pivalic acid and (S)-4-[2-(4-amino-phenyl)-ethyl]-4,5-dihydro-oxazol-2-ylamine. Colourless foam. MS (ISP): 290.2 ([M+H]$^+$).

Example 52

1-Trifluoromethyl-cyclopropanecarboxylic acid {4-[2-((S)-2-amino-4,5-dihydro-oxazol-4-yl)-ethyl]-phenyl}-amide

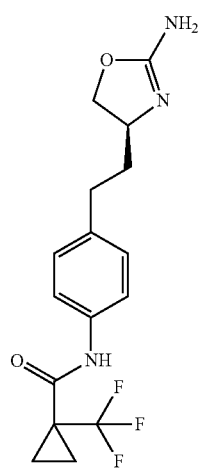 [SMILES: NC1=N[C@@H](CCc2ccc(NC(=O)C3(C(F)(F)F)CC3)cc2)CO1]

The title compound was obtained in analogy to example 83 starting from 1-(trifluoromethyl)-cyclopropane-1-carboxylic acid and (S)-4-[2-(4-amino-phenyl)-ethyl]-4,5-dihydro-oxazol-2-ylamine. Colourless foam. MS (ISP): 342.2 ([M+H]$^+$).

Example 53

1-(4-Chloro-phenyl)-cyclopropanecarboxylic acid {4-[2-((S)-2-amino-4,5-dihydro-oxazol-4-yl)-ethyl]-phenyl}-amide

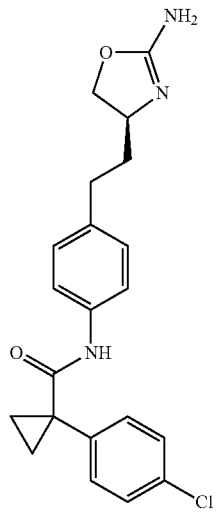 [SMILES: NC1=N[C@@H](CCc2ccc(NC(=O)C3(c4ccc(Cl)cc4)CC3)cc2)CO1]

The title compound was obtained in analogy to example 83 starting from 1-(4-chlorophenyl)-1-cyclopropane carboxylic acid and (S)-4-[2-(4-amino-phenyl)-ethyl]-4,5-dihydro-oxazol-2-ylamine. Colourless foam. MS (ISP): 384.2 ([M+H]$^+$).

Example 54

5-Trifluoromethyl-pyridine-2-carboxylic acid {4-[2-((S)-2-amino-4,5-dihydro-oxazol-4-yl)-ethyl]-phenyl}-amide

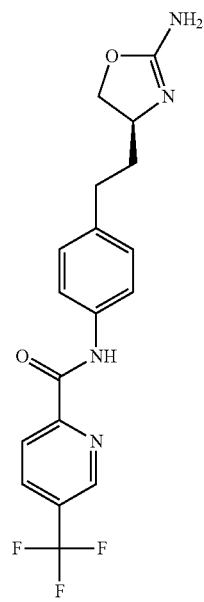 [SMILES: NC1=N[C@@H](CCc2ccc(NC(=O)c3ccc(C(F)(F)F)cn3)cc2)CO1]

The title compound was obtained in analogy to example 33 starting from (S)-4-[2-(4-amino-phenyl)-ethyl]-2,2-dimethyl-oxazolidine-3-carboxylic acid tert-butyl ester and using 5-trifluoromethyl-pyridine-2-carboxylic acid (CAS 80194-69-0) instead of 5-chloro-2-pyridinecarboxylic acid. White solid. MS (ISP): 379.2 ([M+H]$^+$).

Example 55

N-{4-[2-((S)-2-Amino-4,5-dihydro-oxazol-4-yl)-ethyl]-phenyl}-6-trifluoromethyl-nicotinamide

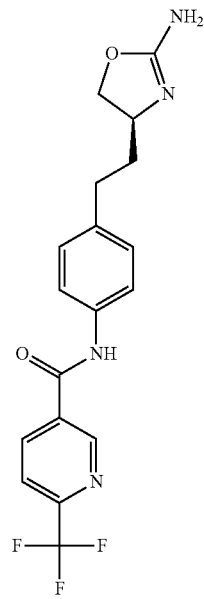

The title compound was obtained in analogy to example 33 starting from (S)-4-[2-(4-amino-phenyl)-ethyl]-2,2-dimethyl-oxazolidine-3-carboxylic acid tert-butyl ester and using 6-trifluoromethyl-nicotinic acid (CAS 231291-22-8) instead of 5-chloro-2-pyridinecarboxylic acid. White solid. MS (ISP): 379.3 ([M+H]$^+$).

Example 56

1-{4-[2-((S)-2-Amino-4,5-dihydro-oxazol-4-yl)-ethyl]-phenyl}-3-(4-fluoro-phenyl)-imidazolidin-2-one

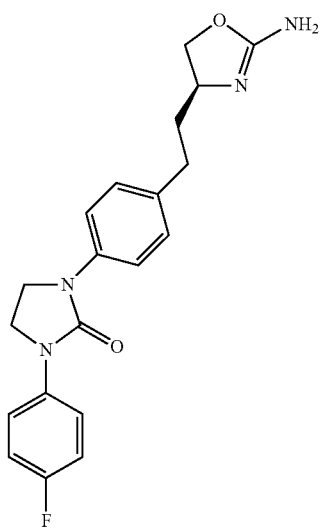 [SMILES: NC1=N[C@@H](CCc2ccc(N3CCN(c4ccc(F)cc4)C3=O)cc2)CO1]

(S)-4-((E)-2-{4-[3-(4-Fluoro-phenyl)-2-oxo-imidazolidin-1-yl]-phenyl}-vinyl)-2,2-dimethyl-oxazolidine-3-carboxylic acid tert-butyl ester A stirred suspension of (S)-4-[(E)-2-(4-iodo-phenyl)-vinyl]-2,2-dimethyl-oxazolidine-3-carboxylic acid tert-butyl ester (250 mg, example 3(a)), 1-(4-fluorophenyl)imidazoline-2-one (320 mg, CAS 53159-75-4), caesium carbonate (418 mg), trans-1,2-diaminocyclohexane (0.14 ml), dibenzylideneacetone (54 mg) and copper(I) triflate benzene complex (58 mg) in dioxane (3 ml) under an atmosphere of argon in a sealed tube was heated at 180° C. for 40 min under microwave irradiation. The mixture was then cooled to room temperature and was purified by column chromatography (SiO$_2$; gradient: heptane/EtOAc) to give (S)-4-((E)-2-{4-[3-(4-fluoro-phenyl)-2-oxo-imidazolidin-1-yl]-phenyl}-vinyl)-2,2-dimethyl-oxazolidine-3-carboxylic acid tert-butyl ester (187 mg, 67%) as an off-white solid. MS (ISP): 504.2 ([M+Na]$^+$), 426.2 ([M+H—C$_4$H$_8$]$^+$).

b) 1-{4-[2-((S)-2-Amino-4,5-dihydro-oxazol-4-yl)-ethyl]-phenyl}-3-(4-fluoro-phenyl)-imidazolidin-2-one The title compound was obtained in analogy to example 9(c)-(d) starting from (S)-4-((E)-2-{4-[3-(4-fluoro-phenyl)-2-oxo-imidazolidin-1-yl]-phenyl}-vinyl)-2,2-dimethyl-oxazolidine-3-carboxylic acid tert-butyl ester instead of (S)-4-{(E)-2-[4-(4-chloro-benzoylamino)-phenyl]-vinyl}-2,2-dimethyl-oxazolidine-3-carboxylic acid tert-butyl ester. White solid. MS (ISP): 369.1 ([M+H]$^+$).

Example 57

1-Pyridin-4-yl-cyclopropanecarboxylic acid {4-[2-((S)-2-amino-4,5-dihydro-oxazol-4-yl)-ethyl]-phenyl}-amide

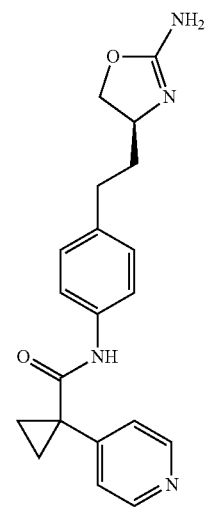 [SMILES: NC1=N[C@@H](CCc2ccc(NC(=O)C3(c4ccncc4)CC3)cc2)CO1]

The title compound was obtained in analogy to example 83 starting from 1-(pyridin-4-yl)-cyclopropane carboxylic acid and (S)-4-[2-(4-amino-phenyl)-ethyl]-4,5-dihydro-oxazol-2-ylamine. Colourless foam. MS (ISP): 349.2 ([M+H]$^+$).

Example 58

N-{4-[2-((S)-2-Amino-4,5-dihydro-oxazol-4-yl)-ethyl]-phenyl}-2-(4-chloro-phenyl)-propionamide

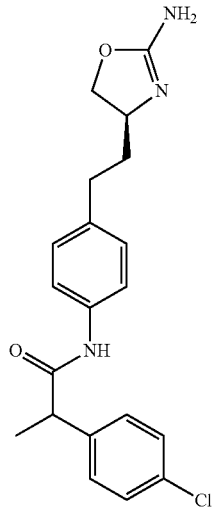 [SMILES: CC(C(=O)Nc1ccc(CC[C@H]2COC(N)=N2)cc1)c1ccc(Cl)cc1]

The title compound was obtained in analogy to example 83 starting from 4-chloro-1-methyl benzeneacetic acid and (S)-4-[2-(4-amino-phenyl)-ethyl]-4,5-dihydro-oxazol-2-ylamine. Colourless foam. MS (ISP): 372.2 ([M+H]$^+$).

Example 59

N-{4-[2-((S)-2-Amino-4,5-dihydro-oxazol-4-yl)-ethyl]-phenyl}-4-cyano-benzamide

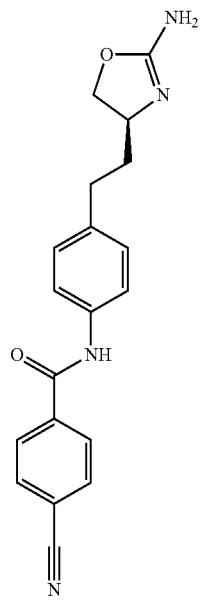 [SMILES: N#Cc1ccc(C(=O)Nc2ccc(CC[C@H]3COC(N)=N3)cc2)cc1]

The title compound was obtained in analogy to example 83 starting from 4-cyanobenzoic acid and (S)-4-[2-(4-aminophenyl)-ethyl]-4,5-dihydro-oxazol-2-ylamine. White solid. MS (ISP): 335.3 ([M+H]$^+$).

Example 60

N-{4-[2-((S)-2-Amino-4,5-dihydro-oxazol-4-yl)-ethyl]-phenyl}-4-ethoxy-benzamide

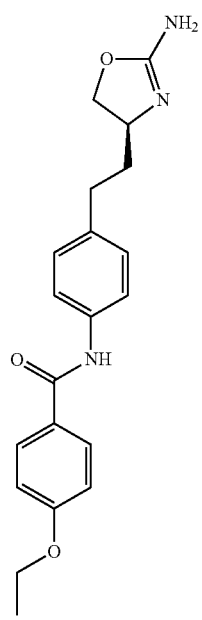 [SMILES: CCOc1ccc(C(=O)Nc2ccc(CC[C@H]3COC(N)=N3)cc2)cc1]

The title compound was obtained in analogy to example 83 starting from 4-ethoxybenzoic acid and (S)-4-[2-(4-aminophenyl)-ethyl]-4,5-dihydro-oxazol-2-ylamine. White solid. MS (ISP): 354.3 ([M+H]$^+$).

Example 61

N-{4-[2-((S)-2-Amino-4,5-dihydro-oxazol-4-yl)-ethyl]-phenyl}-4-propyl-benzamide

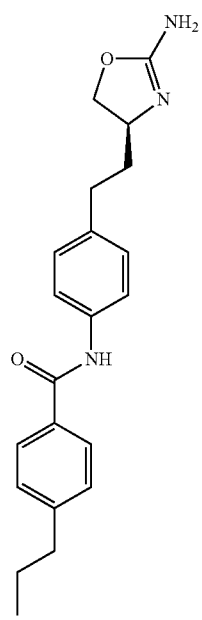 [SMILES: CCCc1ccc(C(=O)Nc2ccc(CC[C@H]3COC(N)=N3)cc2)cc1]

The title compound was obtained in analogy to example 83 starting from 4-n-propylbenzoic acid and (S)-4-[2-(4-aminophenyl)-ethyl]-4,5-dihydro-oxazol-2-ylamine. White solid. MS (ISP): 352.3 ([M+H]$^+$).

Example 62

N-{4-[2-((S)-2-Amino-4,5-dihydro-oxazol-4-yl)-ethyl]-phenyl}-4-ethynyl-benzamide

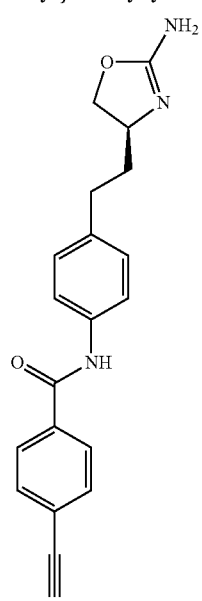

The title compound was obtained in analogy to example 83 starting from 4-ethynylbenzoic acid and (S)-4-[2-(4-amino-phenyl)-ethyl]-4,5-dihydro-oxazol-2-ylamine. White solid. MS (ISP): 334.3 ([M+H]$^+$).

Example 63

N-{4-[2-((S)-2-Amino-4,5-dihydro-oxazol-4-yl)-ethyl]-phenyl}-4-methoxymethyl-benzamide

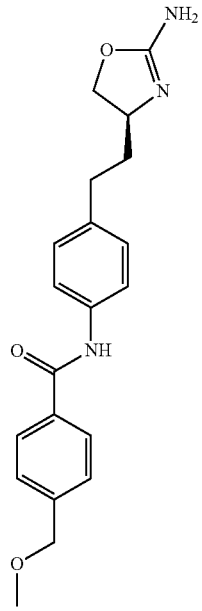 [SMILES: COCc1ccc(C(=O)Nc2ccc(CC[C@H]3COC(N)=N3)cc2)cc1]

The title compound was obtained in analogy to example 83 starting from 4-methoxymethyl-benzoic acid (CAS 67003-50-3) and (S)-4-[2-(4-amino-phenyl)-ethyl]-4,5-dihydro-oxazol-2-ylamine. White solid. MS (ISP): 354.4 ([M+H]$^+$).

Example 64

N-{4-[2-((S)-2-Amino-4,5-dihydro-oxazol-4-yl)-ethyl]-phenyl}-3,5-dichloro-benzenesulfonamide

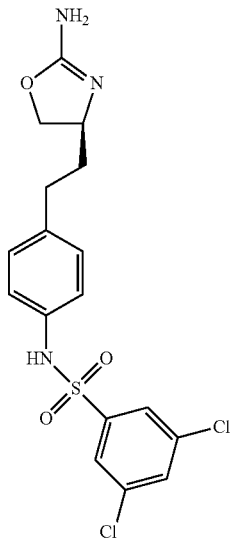 [SMILES: NC1=N[C@@H](CCc2ccc(NS(=O)(=O)c3cc(Cl)cc(Cl)c3)cc2)CO1]

The title compound was obtained in analogy to example 77 starting from 3,5-dichlorobenzene-sulfonyl chloride and (S)-4-[2-(4-amino-phenyl)-ethyl]-2,2-dimethyl-oxazolidine-3-carboxylic acid tert-butyl ester. Colourless waxy solid. MS (ISP): 414.2 ([M+H]$^+$).

Example 65

N-{4-[2-((S)-2-Amino-4,5-dihydro-oxazol-4-yl)-ethyl]-phenyl}-4-methoxy-benzenesulfonamide

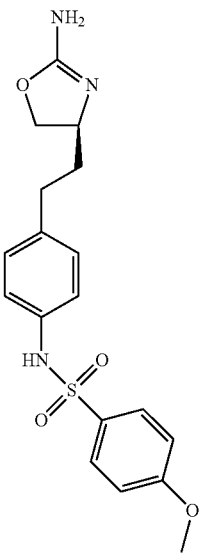 [SMILES: COc1ccc(S(=O)(=O)Nc2ccc(CC[C@H]3COC(N)=N3)cc2)cc1]

The title compound was obtained in analogy to example 77 starting from 4-methoxy-benzene sulfonyl chloride and (S)-4-[2-(4-amino-phenyl)-ethyl]-2,2-dimethyl-oxazolidine-3-carboxylic acid tert-butyl ester. Colourless waxy solid. MS (ISP): 376.3 ([M+H]$^+$).

Example 66

N-{4-[2-((S)-2-Amino-4,5-dihydro-oxazol-4-yl)-ethyl]-phenyl}-2-(4-ethoxy-phenyl)-acetamide

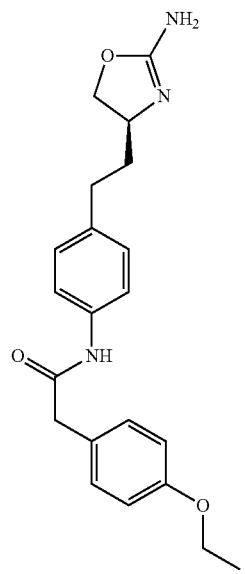 [SMILES: CCOc1ccc(CC(=O)Nc2ccc(CC[C@H]3COC(N)=N3)cc2)cc1]

The title compound was obtained in analogy to example 83 starting from 4-ethoxyphenylacetic acid and (S)-4-[2-(4- amino-phenyl)-ethyl]-4,5-dihydro-oxazol-2-ylamine. Light yellow solid. MS (ISP): 368.2 ([M+H]+).

Example 67

N-{4-[2-((S)-2-Amino-4,5-dihydro-oxazol-4-yl)-ethyl]-phenyl}-2-(4-cyano-phenyl)-acetamide

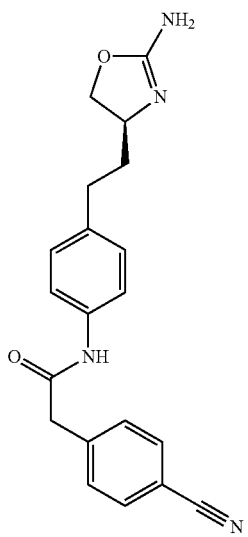 [SMILES: N#Cc1ccc(CC(=O)Nc2ccc(CC[C@H]3COC(N)=N3)cc2)cc1]

The title compound was obtained in analogy to example 83 starting from 4-cyanophenylacetic acid and (S)-4-[2-(4-amino-phenyl)-ethyl]-4,5-dihydro-oxazol-2-ylamine. White solid. MS (ISP): 349.3 ([M+H]+).

Example 68

N-{4-[2-((S)-2-Amino-4,5-dihydro-oxazol-4-yl)-ethyl]-phenyl}-2-(4-methoxy-phenyl)-acetamide

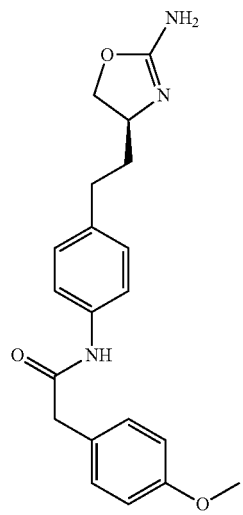 [SMILES: COc1ccc(CC(=O)Nc2ccc(CC[C@H]3COC(N)=N3)cc2)cc1]

The title compound was obtained in analogy to example 83 starting from 4-methoxyphenylacetic acid and (S)-4-[2-(4- amino-phenyl)-ethyl]-4,5-dihydro-oxazol-2-ylamine. White solid. MS (ISP): 354.3 ([M+H]+).

Example 69

N-{4-[2-((S)-2-Amino-4,5-dihydro-oxazol-4-yl)-ethyl]-phenyl}-2-(4-fluoro-phenyl)-acetamide

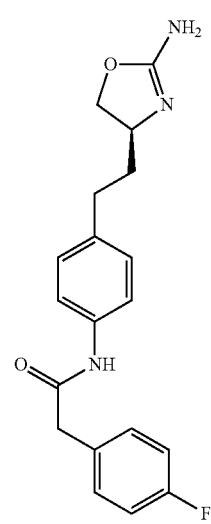 [SMILES: NC1=N[C@@H](CCc2ccc(NC(=O)Cc3ccc(F)cc3)cc2)CO1]

The title compound was obtained in analogy to example 83 starting from 4-fluorophenylacetic acid and (S)-4-[2-(4-amino-phenyl)-ethyl]-4,5-dihydro-oxazol-2-ylamine. White solid. MS (ISP): 342.2 ([M+H]+).

Example 70

N-{4-[2-((S)-2-Amino-4,5-dihydro-oxazol-4-yl)-ethyl]-phenyl}-2-(4-chloro-phenyl)-acetamide

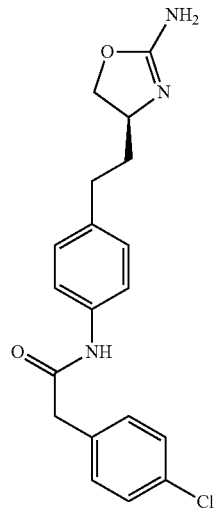 [SMILES: NC1=N[C@@H](CCc2ccc(NC(=O)Cc3ccc(Cl)cc3)cc2)CO1]

The title compound was obtained in analogy to example 83 starting from 4-chloro-benzeneacetic acid (CAS 1878-66-6)

and (S)-4-[2-(4-amino-phenyl)-ethyl]-4,5-dihydro-oxazol-2-ylamine. White solid. MS (ISP): 358.3 ([M+H]+).

Example 71

N-{4-[2-((S)-2-Amino-4,5-dihydro-oxazol-4-yl)-ethyl]-phenyl}-4-methoxy-benzamide

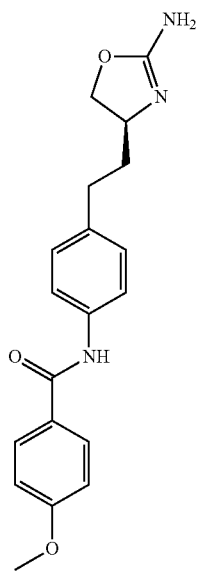 [SMILES: COc1ccc(C(=O)Nc2ccc(CC[C@H]3COC(N)=N3)cc2)cc1]

The title compound was obtained in analogy to example 83 starting from p-anisic acid and (S)-4-[2-(4-amino-phenyl)-ethyl]-4,5-dihydro-oxazol-2-ylamine. White solid. MS (ISP): 340.1 ([M+H]+).

Example 72

N-{4-[2-((S)-2-Amino-4,5-dihydro-oxazol-4-yl)-ethyl]-phenyl}-2-(4-chloro-phenyl)-isobutyramide

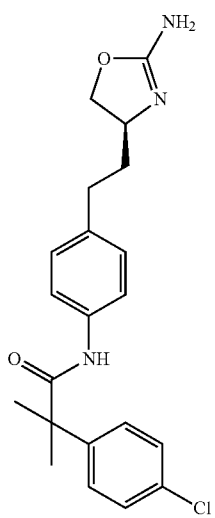 [SMILES: CC(C)(C(=O)Nc1ccc(CC[C@H]2COC(N)=N2)cc1)c1ccc(Cl)cc1]

The title compound was obtained in analogy to example 83 starting from 4-chloro-,-dimethyl-benzeneacetic acid (CAS 57225-90-8) and (S)-4-[2-(4-amino-phenyl)-ethyl]-4,5-dihydro-oxazol-2-ylamine. White foam. MS (ISP): 386.3 ([M+H]+).

Example 73

N-{4-[2-((S)-2-Amino-4,5-dihydro-oxazol-4-yl)-ethyl]-phenyl}-2-(4-bromo-phenyl)-2-methoxy-acetamide

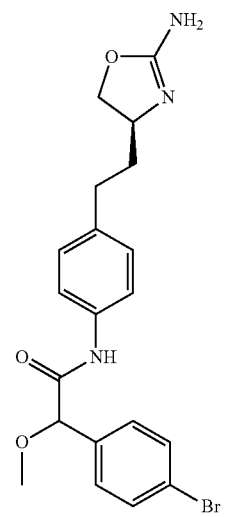 [SMILES: COC(C(=O)Nc1ccc(CC[C@H]2COC(N)=N2)cc1)c1ccc(Br)cc1]

The title compound was obtained in analogy to example 83 starting from (4-bromo-phenyl)-methoxy-acetic acid and (S)-4-[2-(4-amino-phenyl)-ethyl]-4,5-dihydro-oxazol-2-ylamine. Light yellow solid. MS (ISP): 434.3 ([M+H]+).

Example 74

(S)-N-{4-[2-((S)-2-Amino-4,5-dihydro-oxazol-4-yl)-ethyl]-phenyl}-2-methoxy-2-phenyl-acetamide

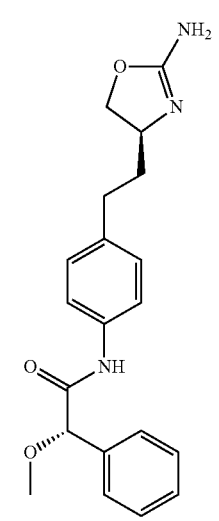 [SMILES: CO[C@H](C(=O)Nc1ccc(CC[C@H]2COC(N)=N2)cc1)c1ccccc1]

The title compound was obtained in analogy to example 83 starting from (S)-(+)-α-methoxyphenylacetic acid and (S)-4-

[2-(4-amino-phenyl)-ethyl]-4,5-dihydro-oxazol-2-ylamine. Colourless oil. MS (ISP): 354.3 ([M+H]⁺).

Example 75

(R)—N-{4-[2-((S)-2-Amino-4,5-dihydro-oxazol-4-yl)-ethyl]-phenyl}-2-methoxy-2-phenyl-acetamide

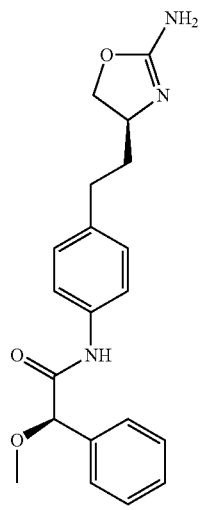 [SMILES: CO[C@@H](C(=O)Nc1ccc(CC[C@H]2COC(N)=N2)cc1)c1ccccc1]

The title compound was obtained in analogy to example 83 starting from (R)-(−)α-methoxyphenylacetic acid and (S)-4-[2-(4-amino-phenyl)-ethyl]-4,5-dihydro-oxazol-2-ylamine. Light yellow oil. MS (ISP): 354.3 ([M+H]⁺).

Example 76

N-{4-[2-((S)-2-Amino-4,5-dihydro-oxazol-4-yl)-ethyl]-phenyl}-3,4-dichloro-benzenesulfonamide

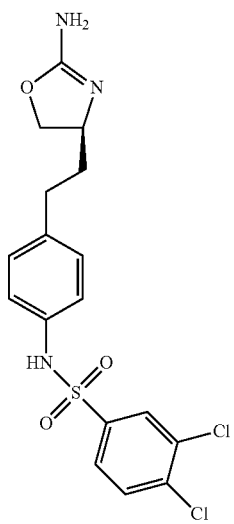 [SMILES: NC1=N[C@@H](CCc2ccc(NS(=O)(=O)c3ccc(Cl)c(Cl)c3)cc2)CO1]

The title compound was obtained in analogy to example 77 starting from 3,4-dichlorobenzene-sulfonyl chloride and (S)-4-[2-(4-amino-phenyl)-ethyl]-2,2-dimethyl-oxazolidine-3-carboxylic acid tent-butyl ester. White solid. MS (ISP): 414.2 ([M+H]⁺).

Example 77

Isoquinoline-5-sulfonic acid {4-[2-((S)-2-amino-4,5-dihydro-oxazol-4-yl)-ethyl]-phenyl}-amide

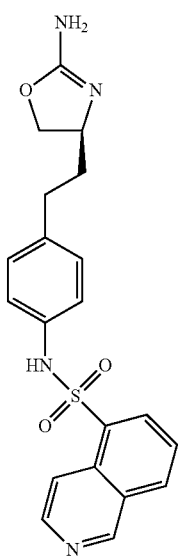 [SMILES: NC1=N[C@@H](CCc2ccc(NS(=O)(=O)c3cccc4cnccc34)cc2)CO1]

a) (S)-4-{2-[4-(Isoquinoline-5-sulfonylamino)-phenyl]-ethyl}-2,2-dimethyl-oxazolidine-3-carboxylic acid tert-butyl ester (S)-4-[2-(4-Amino-phenyl)-ethyl]-2,2-dimethyl-oxazolidine-3-carboxylic acid tert-butyl ester (150 mg) was dissolved in tetrahydrofuran at room temperature before treatment with triethylamine (129.8 µl) and isoquinoline-5-sulfonyl chloride (141.4 mg), the reaction mixture was then warmed to 50° C. and stirred for 6 hours. Upon evaporation of the solvent in vacuo the residue was purified by flash column chromatography (SiO₂; hexane/EtOAc 3:1) to afford title compound (S)-4-{2-[4-(isoquinoline-5-sulfonylamino)-phenyl]-ethyl}-2,2-dimethyl-oxazolidine-3-carboxylic acid tert-butyl ester (155 mg) as a white solid. MS (ISP): 512.3 ([M+H]⁺).

b) Isoquinoline-5-sulfonic acid [4-((S)-3-amino-4-hydroxy-butyl)-phenyl]-amide (S)-4-{2-[4-(isoquinoline-5-sulfonylamino)-phenyl]-ethyl}-2,2-dimethyl-oxazolidine-3-carboxylic acid tert-butyl ester (155 mg) was dissolved in acetonitrile (1.5 ml) and water (3 ml) before addition of trifluoroacetic acid (68.6 µl) at room temperature. The reaction mixture was then warmed to 50° C. and stirred for 5 hours and then cooled at room temperature and stirred for 12 hours. Ethyl acetate (4 ml) was added and then the solution basified by addition of 1N aqueous solution of sodium hydroxide until pH 14 followed by stirring for 15 minutes. The two layers were then separated and the aqueous was extracted twice with ethyl acetate, the combined organic layers were dried over Mg2SO4, filtered and concentrated in vacuo to give isoquinoline-5-sulfonic acid [4-((S)-3-amino-4-hydroxy-butyl)-phenyl]-amide (109 mg) as a yellow solid. MS (ISP): 372.2 ([M+H]⁺).

c) Isoquinoline-5-sulfonic acid {4-[2-((S)-2-amino-4,5-dihydro-oxazol-4-yl)-ethyl]-phenyl}-amide Isoquinoline-5-sulfonic acid [4-((S)-3-amino-4-hydroxy-butyl)-phenyl]-amide (109 mg) was dissolved in methanol (3 ml) at room temperature before addition of sodium acetate (72.2 mg) and a solution of cyanogen bromide (40.4 mg) in methanol (1 ml) dropwise. The reaction mixture was stirred at room temperature for 36 hours, then aqueous ammonia 25% was added (55 μl) and stirring was continued for an another hour. The solvent was evaporated in vacuo and the residue purified by Isco chromatography (column: Silicycle Si-Amine, AcOEt) to give isoquinoline-5-sulfonic acid {4-[2-((S)-2-amino-4,5-dihydro-oxazol-4-yl)-ethyl]-phenyl}-amide (7.8 mg) as a yellow solid. Description. MS (ISP): 397.2 ([M+H]⁺).

Example 78

N-{4-[2-((S)-2-Amino-4,5-dihydro-oxazol-4-yl)-ethyl]-phenyl}-2-(4-chloro-phenyl)-2-methoxy-acetamide

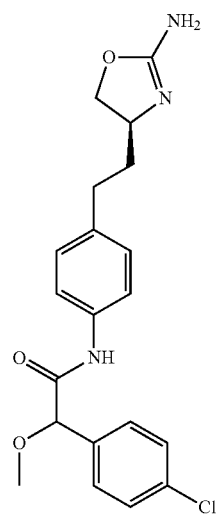 [SMILES: COC(C(=O)Nc1ccc(CC[C@H]2COC(N)=N2)cc1)c1ccc(Cl)cc1]

The title compound was obtained in analogy to example 83 starting from (4-chloro-phenyl)-methoxy-acetic acid and (S)-4-[2-(4-amino-phenyl)-ethyl]-4,5-dihydro-oxazol-2-ylamine. White solid. MS (ISP): 388.2 ([M+H]⁺)

Example 79

4-Trifluoromethyl-cyclohexanecarboxylic acid {4-[2-((S)-2-amino-4,5-dihydro-oxazol-4-yl)-ethyl]-phenyl}-amide

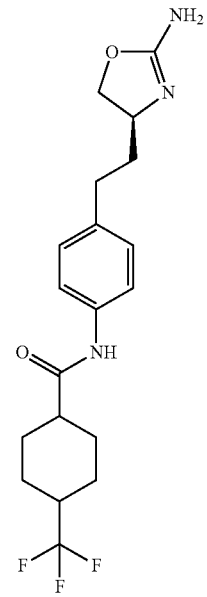 [SMILES: NC1=N[C@@H](CCc2ccc(NC(=O)C3CCC(C(F)(F)F)CC3)cc2)CO1]

The title compound was obtained in analogy to example 83 starting from 4-(trifluoromethyl)-cyclohexanecarboxylic acid and (S)-4-[2-(4-amino-phenyl)-ethyl]-4,5-dihydro-oxazol-2-ylamine. White solid. MS (ISP): 384.3 ([M+H]⁺)

Example 80

N-{4-[2-((S)-2-Amino-4,5-dihydro-oxazol-4-yl)-ethyl]-phenyl}-3-(2-chloro-phenyl)-propionamide

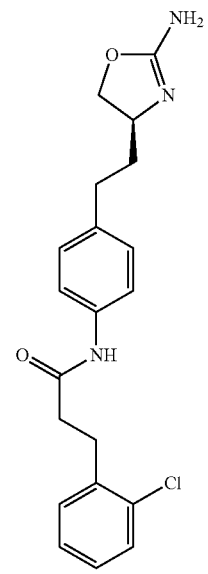 [SMILES: NC1=N[C@@H](CCc2ccc(NC(=O)CCc3ccccc3Cl)cc2)CO1]

The title compound was obtained in analogy to example 83 starting from 3-(2-chlorophenyl)propionic acid and (S)-4-[2-(4-amino-phenyl)-ethyl]-4,5-dihydro-oxazol-2-ylamine. Light yellow solid. MS (ISP): 372.2 ([M+H]⁺)

Example 81

N-{4-[2-((S)-2-Amino-4,5-dihydro-oxazol-4-yl)-ethyl]-phenyl}-2-(3-trifluoromethyl-phenyl)-propionamide

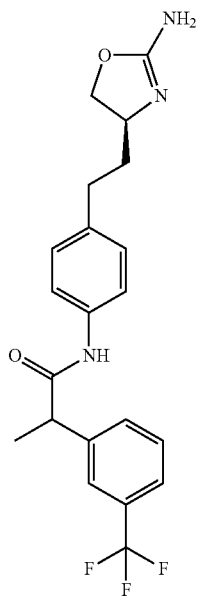 [SMILES: CC(C(=O)Nc1ccc(CC[C@H]2COC(N)=N2)cc1)c1cccc(C(F)(F)F)c1]

The title compound was obtained in analogy to example 83 starting from 2-(3-trifluoromethyl-phenyl)-propionic acid and (S)-4-[2-(4-amino-phenyl)-ethyl]-4,5-dihydro-oxazol-2-ylamine. Colourless foam. MS (ISP): 406.3 ([M+H]$^+$)

Example 82

N-{4-[2-((S)-2-Amino-4,5-dihydro-oxazol-4-yl)-ethyl]-phenyl}-2-(3-trifluoromethoxy-phenyl)-propionamide

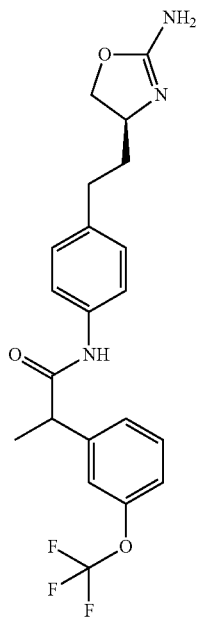 [SMILES: CC(C(=O)Nc1ccc(CC[C@H]2COC(N)=N2)cc1)c1cccc(OC(F)(F)F)c1]

a) 2-(3-Trifluoromethoxy-phenyl)-propionic acid

A solution of diisopropylamine (3.1 ml) in tetrahydrofuran (30 ml) was cooled to 0° C. before dropwise addition of 1.6M nBuLi in hexane (13.5 ml) and then stirred for 15 minutes and cooled to −70° C. 3-(trifluoromethoxy)-phenylacetic acid (2 g) was dissolved in tetrahydrofuran (20 ml) and added dropwise to the reaction mixture which was then allowed to warm to 0° C., stirred for 30 minutes and then cooled back to −70° C. Methyl iodide (0.9 ml) was then added slowly and the solution stirred for further 1.5 hours at −70° C. Water was added the solution washed with diethyl ether, the aqueous phase was acidified by addition of 25% aqueous HCl and then extracted twice with diethyl ether, dried over $Mg_2SO_4$, filtered and concentrated. The residue was purified by flash column chromatography ($SiO_2$; hexane/EtOAc 3:1) to afford 2-(3-trifluoromethoxy-phenyl)-propionic acid (1.5 g) as a light yellow oil. MS (ISP): 232.9 ([M−H]$^+$)).

b) N-{4-[2-((S)-2-Amino-4,5-dihydro-oxazol-4-yl)-ethyl]-phenyl}-2-(3-trifluoromethoxy-phenyl)-propionamide The title compound was obtained in analogy to example 83 starting from 2-(3-trifluoromethoxy-phenyl)-propionic acid and (S)-4-[2-(4-amino-phenyl)-ethyl]-4,5-dihydro-oxazol-2-ylamine. Colourless foam. MS (ISP): 422.2 ([M+H]$^+$).

Example 83

2-Methoxy-pyrimidine-5-carboxylic acid {4-[2-((S)-2-amino-4,5-dihydro-oxazol-4-yl)-ethyl]-phenyl}-amide

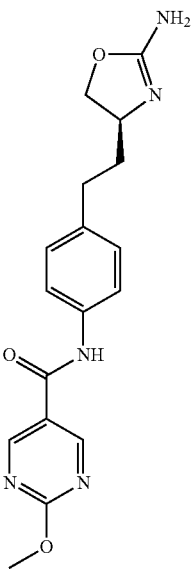 [SMILES: COc1ncc(C(=O)Nc2ccc(CC[C@H]3COC(N)=N3)cc2)cn1]

a) (E)-(S)-2-Amino-4-(4-nitro-phenyl)-but-3-en-1-ol

To a stirred solution of trifluoroacetic acid (4.9 ml) in water (24 ml) was added (S)-2,2-dimethyl-4-[(E)-2-(4-nitro-phenyl)-vinyl]-oxazolidine-3-carboxylic acid tent-butyl ester (Example 14(a)) (5.0 g) in acetonitrile (4.0 ml). After stirring at 80° C. for 4 hours, the reaction mixture was cooled to room temperature and the solution basified to pH>11 by dropwise addition of a 1N solution of sodium hydroxide The mixture was extracted three times with ethyl acetate, the combined organic layers were dried (MgSO₄) and concentrated in vacuo to yield (E)-(S)-2-Amino-4-(4-nitro-phenyl)-but-3-en-1-ol as a brown oil (2.5 g). $^1$H-NMR (300 MHz, CDCl₃, δ); 8.23-8.11 (m, 2H), 8.54-8.47 (m, 2H), 7.67 (d, J=16 Hz, 1H), 6.7 (dd, J=16 and 8 Hz, 1H). 3.78-3.69 (m, 2H), 3.58-3.42 (m, 1H).

b) (S)-4-[(E)-2-(4-Nitro-phenyl)-vinyl]-4,5-dihydro-oxazol-2-ylamine

To a solution of (E)-(S)-2-amino-4-(4-nitro-phenyl)-but-3-en-1-ol (2.5 g) in methanol (90 ml) at room temperature was added sodium acetate (3.0 g) followed by a solution of cyanogen bromide (1.65 g) in methanol (10 ml) dropwise over 15 minutes. The reaction mixture was stirred for 2 days, then 25% aqueous ammonia (8.2 ml) was added and the solution stirred for 1 hour at room temperature. The solvent was evaporated in vacuo and the residue purified by Isco chromatography (column: Silicycle Si-Amine, AcOEt) to give (S)-4-[(E)-2-(4-nitro-phenyl)-vinyl]-4,5-dihydro-oxazol-2-ylamine (950 mg) as a yellow oil. MS (ISP): 234.1 ([M+H]⁺).

c) (S)-4-[2-(4-Amino-phenyl)-ethyl]-4,5-dihydro-oxazol-2-ylamine (S)-4-[(E)-2-(4-Nitro-phenyl)-vinyl]-4,5-dihydro-oxazol-2-ylamine (0.95 g) was dissolved in methanol (40 ml) before addition of Pd/C 10% (95 mg). The reaction mixture was hydrogenated for 1 hour at room temperature and then the catalyst was filtered off and washed with methanol. The residue was concentrated in vacuo and purified by Isco chromatography (column: Silicycle Si-Amine, AcOEt) to afford (S)-4-[2-(4-amino-phenyl)-ethyl]-4,5-dihydro-oxazol-2-ylamine (800 mg) as an off-white solid. MS (ISP): 206.2 ([M+H]⁺).

d) 2-Methoxy-pyrimidine-5-carboxylic acid {4-[2-((S)-2-amino-4,5-dihydro-oxazol-4-yl)-ethyl]-phenyl}-amide 2-Chloro-pyrimidine-5-carboxylic acid (23 mg) was dissolved in methanol (1 ml) and the solution cooled to 0° C. before addition of 4-(4,6-dimethoxy[1.3.5]triazin-2-yl)-4-methylmorpholinium chloride hydrate (45 mg). The reaction mixture was stirred for 5 minutes at 0° C. before dropwise addition of a solution of (S)-4-[2-(4-Amino-phenyl)-ethyl]-4,5-dihydro-oxazol-2-ylamine (30 mg) in methanol (1 ml). Stirring at 0° C. was continued for 1 hour before quenching by addition of a 1N solution of sodium hydroxide. The reaction mixture was then extracted three times with ethyl acetate and the combined organic layers washed with brine, dried over Na₂SO₄, filtered and concentrated in vacuo. The residue was purified by preparative HPLC to give 2-methoxy-pyrimidine-5-carboxylic acid {4-[2-((S)-2-amino-4,5-dihydro-oxazol-4-yl)-ethyl]-phenyl}-amide (9 mg) as a yellow solid. MS (ISP): 342.2 ([M+H]⁺).

Example 84

(RS)-4-(2-Amino-4,5-dihydro-oxazol-4-yl)-N-(4-chloro-phenyl)-benzamide

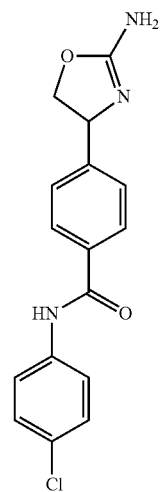 [SMILES: NC1=NC(c2ccc(C(=O)Nc3ccc(Cl)cc3)cc2)CO1]

(RS)-4-(4-Cyano-phenyl)-2,2-dimethyl-oxazolidine-3-carboxylic acid tert-butyl ester A stirred solution of (RS)-4-(4-iodo-phenyl)-2,2-dimethyl-oxazolidine-3-carboxylic acid tert-butyl ester (200 mg, example 1(e)), zinc cyanide (66 mg) and tetrakis(triphenylphosphine)palladium (57 mg) in DMF (4 ml) under an argon atmosphere in a sealed tube was heated at 160° C. for 15 minutes under microwave irradiation. The mixture was then poured onto ice-water and the mixture extracted twice with ethyl acetate. The combined organic extracts were washed with water, dried over sodium sulphate and concentrated in vacuo. The residue was purified by column chromatography (SiO₂; gradient: heptane/EtOAc) to give (RS)-4-(4-cyano-phenyl)-2,2-dimethyl-oxazolidine-3-carboxylic acid tert-butyl ester (82 mg, 55%) as a colourless viscous oil. MS (ISP): 325.4 ([M+Na]⁺), 303.4 ([M+H]⁺), 247.3 ([M+H—C₄H₈]⁺).

b) (RS)-4-(4-Carboxy-phenyl)-2,2-dimethyl-oxazolidine-3-carboxylic acid tert-butyl ester To a stirred solution of (RS)-4-(4-cyano-phenyl)-2,2-dimethyl-oxazolidine-3-carboxylic acid tert-butyl ester (80 mg) in ethanol (2 ml) was added 2 M aq. sodium hydroxide solution (2 ml) and the mixture was heated at 85° C. for 18 h. The mixture was then cooled to room temperature and acidified by addition of 1 M aq. hydrochloric acid. The mixture was then extracted with ethyl acetate. The organic extracts were dried over sodium sulphate and concentrated in vacuo to give (RS)-4-(4-carboxy-phenyl)-2,2-dimethyl-oxazolidine-3-carboxylic acid tert-butyl ester (81 mg, 95%) as a white solid. MS (ISP): 320.2 ([M−H]⁻).

c) (RS)-4-[4-(4-Chloro-phenylcarbamoyl)-phenyl]-2,2-dimethyl-oxazolidine-3-carboxylic acid tert-butyl ester To a stirred suspension of (RS)-4-(4-carboxy-phenyl)-2,2-dimethyl-oxazolidine-3-carboxylic acid tert-butyl ester (80 mg) in THF (4 ml) were added sequentially N-methylmorpholine (0.11 ml), TBTU (160 mg) and 4-chloro-aniline (48 mg) and the mixture was heated at 50° C. for 18 h. The mixture was then concentrated in vacuo and the residue was purified by column chromatography (SiO$_2$; gradient: heptane/EtOAc) to give (RS)-4-[4-(4-chloro-phenylcarbamoyl)-phenyl]-2,2-dimethyl-oxazolidine-3-carboxylic acid tert-butyl ester (110 mg, quant.) as a light yellow solid. MS (ISP): 455.2 ([{$^{37}$Cl}M+Na]$^+$), 453.2 ([{$^{35}$Cl}M+Na]$^+$), 433.3 ([{$^{37}$Cl}M+H]$^+$), 431.4 ([{$^{35}$Cl}M+H]$^+$), 377.3 ([{$^{37}$Cl}M+H—C$_4$H$_8$]$^+$), 375.3 ([{$^{35}$Cl}M+H—C$_4$H$_8$]$^+$).

d) (RS)-4-(2-Amino-4,5-dihydro-oxazol-4-yl)-N-(4-chloro-phenyl)-benzamide

The title compound was obtained in analogy to example 1(g)-1(h) starting from (RS)-4-[4-(4-chloro-phenylcarbamoyl)-phenyl]-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 318.3 ([{$^{37}$Cl}M+H]$^+$), 316.2 ([{35Cl}M+H]$^+$).

Example 85

N-{4-[2-((S)-2-Amino-4,5-dihydro-oxazol-4-yl)-ethyl]-phenyl}-6-pyrazol-1-yl-nicotinamide

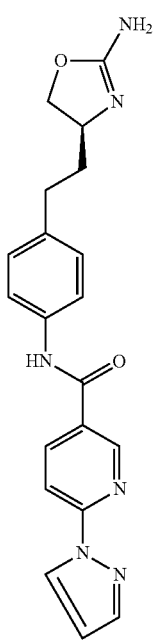 [SMILES: NC1=N[C@@H](CCc2ccc(NC(=O)c3ccc(-n4cccn4)nc3)cc2)CO1]

The title compound was obtained in analogy to example 83 starting from 6-(1H-pyrazol-1yl)nicotinic acid and (S)-4-[2-(4-amino-phenyl)-ethyl]-4,5-dihydro-oxazol-2-ylamine. Off-white solid. MS (ISP): 377.3 ([M+H]$^+$)

Example 86

1H-Benzoimidazole-2-carboxylic acid {4-[2-((S)-2-amino-4,5-dihydro-oxazol-4-yl)-ethyl]-phenyl}-amide

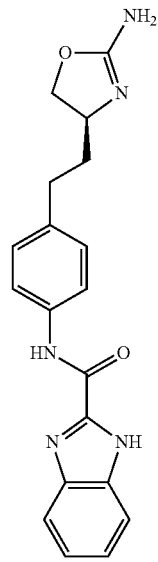 [SMILES: NC1=N[C@@H](CCc2ccc(NC(=O)c3nc4ccccc4[nH]3)cc2)CO1]

The title compound was obtained in analogy to example 83 starting from 1H-benzimidazole-2-carboxylic acid and (S)-4-[2-(4-amino-phenyl)-ethyl]-4,5-dihydro-oxazol-2-ylamine. Off-white solid MS (ISP): 350.3 ([M+H]$^+$)

Example 87

3,5-Difluoro-pyridine-2-carboxylic acid {4-[2-((S)-2-amino-4,5-dihydro-oxazol-4-yl)-ethyl]-phenyl}-amide

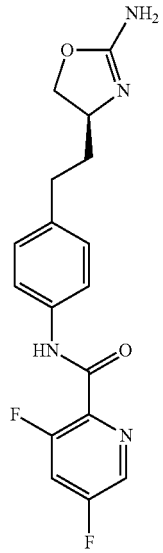 [SMILES: NC1=N[C@@H](CCc2ccc(NC(=O)c3ncc(F)cc3F)cc2)CO1]

The title compound was obtained in analogy to example 83 starting from 3,5-difluoropyridine-carboxylic acid and (S)-4-

[2-(4-amino-phenyl)-ethyl]-4,5-dihydro-oxazol-2-ylamine. Off-white solid MS (ISP): 347.2 ([M+H]⁺)

Example 88

6-Fluoro-pyridine-2-carboxylic acid {4-[2-((S)-2-amino-4,5-dihydro-oxazol-4-yl)-ethyl]-phenyl}-amide

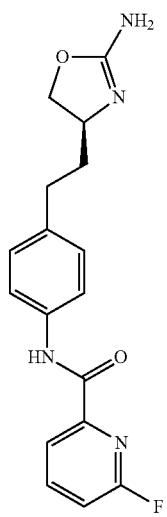 [SMILES: NC1=N[C@@H](CCc2ccc(NC(=O)c3cccc(F)n3)cc2)CO1]

The title compound was obtained in analogy to example 83 starting from 6-fluoropyridine-2-carboxylic acid and (S)-4-[2-(4-amino-phenyl)-ethyl]-4,5-dihydro-oxazol-2-ylamine. Off-white solid MS (ISP): 329.2 ([M+H]⁺)

Example 89

6-Chloro-3-fluoro-pyridine-2-carboxylic acid {4-[2-((S)-2-amino-4,5-dihydro-oxazol-4-yl)-ethyl]-phenyl}-amide

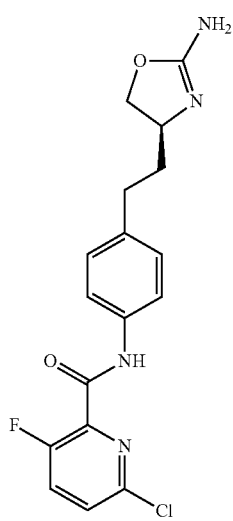 [SMILES: NC1=N[C@@H](CCc2ccc(NC(=O)c3nc(Cl)ccc3F)cc2)CO1]

The title compound was obtained in analogy to example 83 starting from 2-Chloro-5-fluoropyridine-6-carboxylic acid and (S)-4-[2-(4-amino-phenyl)-ethyl]-4,5-dihydro-oxazol-2-ylamine. White solid MS (ISP): 363.2 ([M+H]⁺)

Example 90

4-Chloro-pyridine-2-carboxylic acid {4-[2-((S)-2-amino-4,5-dihydro-oxazol-4-yl)-ethyl]-phenyl}-amide

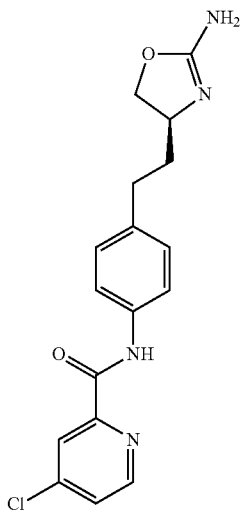 [SMILES: NC1=N[C@@H](CCc2ccc(NC(=O)c3cc(Cl)ccn3)cc2)CO1]

The title compound was obtained in analogy to example 83 starting from 4-chloropicolinic acid and (S)-4-[2-(4-amino-phenyl)-ethyl]-4,5-dihydro-oxazol-2-ylamine. White solid MS (ISP): 345.1 ([M+H]⁺)

Example 91

Quinoline-2-carboxylic acid {4-[2-((S)-2-amino-4,5-dihydro-oxazol-4-yl)-ethyl]-phenyl}-amide

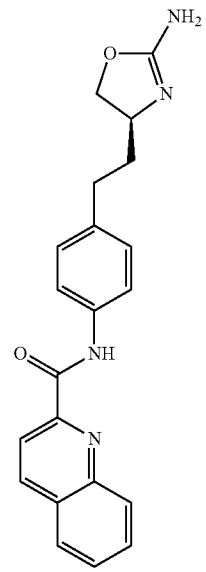 [SMILES: NC1=N[C@@H](CCc2ccc(NC(=O)c3ccc4ccccc4n3)cc2)CO1]

The title compound was obtained in analogy to example 83 starting from quinaldic acid and (S)-4-[2-(4-amino-phenyl)-ethyl]-4,5-dihydro-oxazol-2-ylamine. White solid MS (ISP): 361.1 ([M+H]⁺)

Example 92

5-Bromo-pyridine-2-carboxylic acid {4-[2-((S)-2-amino-4,5-dihydro-oxazol-4-yl)-ethyl]-phenyl}-amide

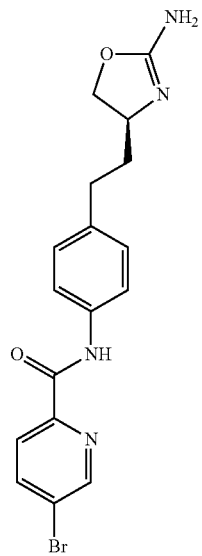 [SMILES: NC1=N[C@@H](CCc2ccc(NC(=O)c3ccc(Br)cn3)cc2)CO1]

The title compound was obtained in analogy to example 83 starting from 5-bromo-pyridine-2-carboxylic acid and (S)-4-[2-(4-amino-phenyl)-ethyl]-4,5-dihydro-oxazol-2-ylamine. White solid MS (ISP): 389.2 ([M+H]⁺)

Example 93

Isoquinoline-1-carboxylic acid {4-[2-((S)-2-amino-4,5-dihydro-oxazol-4-yl)-ethyl]-phenyl}-amide

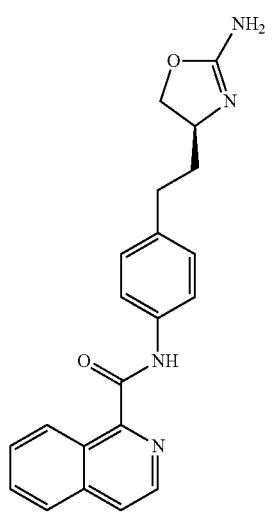 [SMILES: NC1=N[C@@H](CCc2ccc(NC(=O)c3nccc4ccccc34)cc2)CO1]

The title compound was obtained in analogy to example 83 starting from 1-isoquinolinecarboxylic acid and (S)-4-[2-(4-amino-phenyl)-ethyl]-4,5-dihydro-oxazol-2-ylamine. Light-yellow foam: MS (ISP): 361.2 ([M+H]⁺)

Example 94

1-{4-[2-((S)-2-Amino-4,5-dihydro-oxazol-4-yl)-ethyl]-phenyl}-3-(4-fluoro-phenyl)-urea

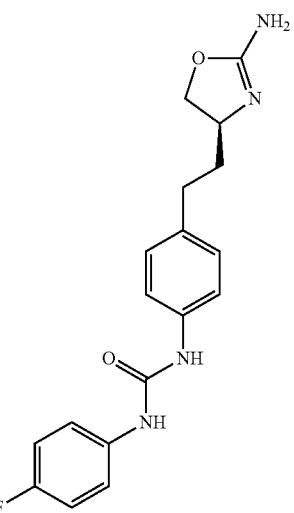

The title compound was obtained in analogy to example 35(b)-(c) starting from (S)-4-[2-(4-isocyanato-phenyl)-ethyl]-2,2-dimethyl-oxazolidine-3-carboxylic acid tert-butyl ester and using 4-fluoroaniline instead of 2-amino-5-chloro-pyridine. White solid. MS (ISP): 343.3 ([M+H]⁺)

Example 95

1-{4-[2-((S)-2-Amino-4,5-dihydro-oxazol-4-yl)-ethyl]-phenyl}-3-(3-chloro-phenyl)-urea

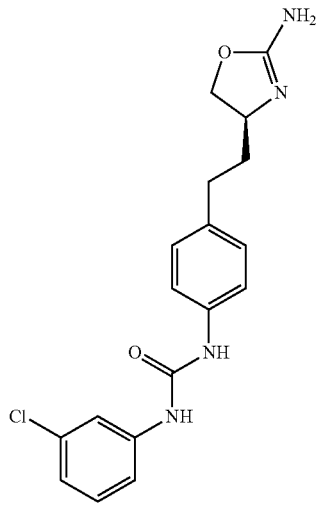 [SMILES: NC1=N[C@@H](CCc2ccc(NC(=O)Nc3cccc(Cl)c3)cc2)CO1]

The title compound was obtained in analogy to example 35(b)-(c) starting from (S)-4-[2-(4-isocyanato-phenyl)-ethyl]-2,2-dimethyl-oxazolidine-3-carboxylic acid tert-butyl

Example 96

(S)-N-(4-(2-(2-amino-4,5-dihydrooxazol-4-yl)ethyl)phenyl)-5-fluoropicolinamide

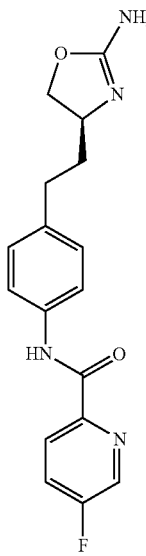

The title compound was obtained in analogy to example 83 starting from 5-fluoropyridine-2-carboxylic acid and (S)-4-[2-(4-amino-phenyl)-ethyl]-4,5-dihydro-oxazol-2-ylamine. White solid. MS (ISP): 329.1 ([M+H]$^+$)

Example 97

N-{4-[2-((S)-2-Amino-4,5-dihydro-oxazol-4-yl)-ethyl]-phenyl}-6-methoxy-nicotinamide

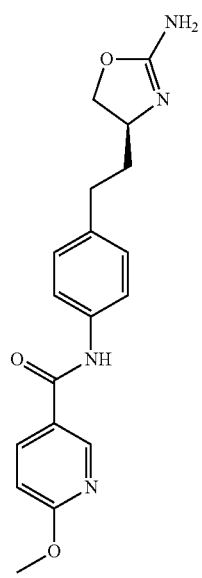 [SMILES: COc1ccc(C(=O)Nc2ccc(CC[C@H]3COC(N)=N3)cc2)cn1]

The title compound was obtained in analogy to example 83 starting from 6-methoxynicotinic acid and (S)-4-[2-(4-amino-phenyl)-ethyl]-4,5-dihydro-oxazol-2-ylamine. White solid. MS (ISP): 341.1 ([M+H]$^+$)

Example 98

N-{4-[2-((S)-2-Amino-4,5-dihydro-oxazol-4-yl)-ethyl]-phenyl}-6-methyl-nicotinamide

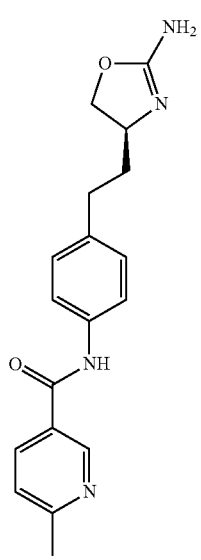 [SMILES: Cc1ccc(C(=O)Nc2ccc(CC[C@H]3COC(N)=N3)cc2)cn1]

The title compound was obtained in analogy to example 83 starting from 6-methylnicotinic acid and (S)-4-[2-(4-amino-phenyl)-ethyl]-4,5-dihydro-oxazol-2-ylamine. White solid. MS (ISP): 325.3 ([M+H]$^+$)

Example 99

(S)-N-(4-(2-(2-amino-4,5-dihydrooxazol-4-yl)ethyl)phenyl)-2-fluoronicotinamide

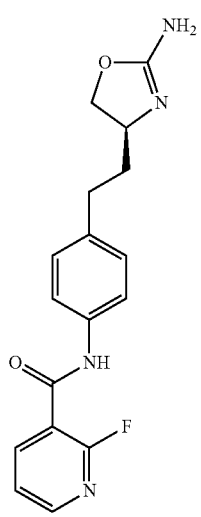

The title compound was obtained in analogy to example 83 starting from 2-fluoronicotinic acid and (S)-4-[2-(4-amino-phenyl)-ethyl]-4,5-dihydro-oxazol-2-ylamine. White solid. MS (ISP): 329.2 ([M+H]+)

Example 100

N-{4-[2-((S)-2-Amino-4,5-dihydro-oxazol-4-yl)-ethyl]-phenyl}-5-fluoro-nicotinamide

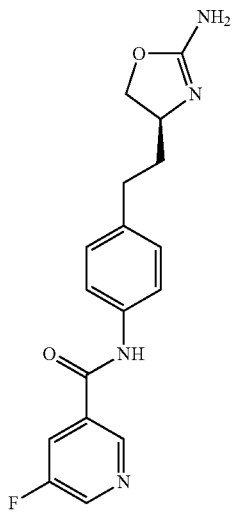 [SMILES: NC1=N[C@@H](CCc2ccc(NC(=O)c3cncc(F)c3)cc2)CO1]

The title compound was obtained in analogy to example 83 starting from 5-fluoro-3-pyridinecarboxylic acid and (S)-4-[2-(4-amino-phenyl)-ethyl]-4,5-dihydro-oxazol-2-ylamine. White solid. MS (ISP): 329.2 ([M+H]+)

Example 101

3-Chloro-5-trifluoromethyl-pyridine-2-carboxylic acid {4-[2-((S)-2-amino-4,5-dihydro-oxazol-4-yl)-ethyl]-phenyl}-amide

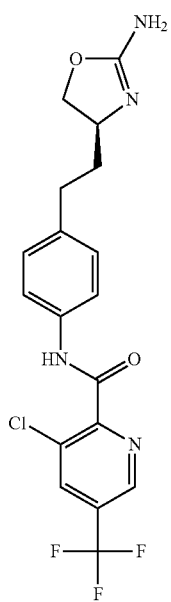 [SMILES: NC1=N[C@@H](CCc2ccc(NC(=O)c3ncc(C(F)(F)F)cc3Cl)cc2)CO1]

The title compound was obtained in analogy to example 83 starting from 3-chloro-5-trifluoromethyl-2-pyridinecarboxylic acid and (S)-4-[2-(4-amino-phenyl)-ethyl]-4,5-dihydro-oxazol-2-ylamine. White solid. MS (ISP): 413.2 ([M+H]+)

Example 102

6-Acetylamino-N-{4-[2-((S)-2-amino-4,5-dihydro-oxazol-4-yl)-ethyl]-phenyl}-nicotinamide

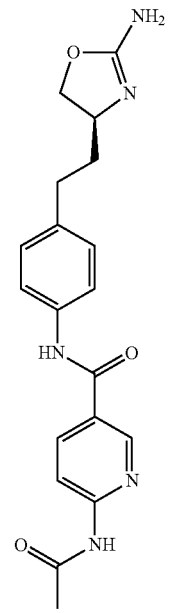 [SMILES: CC(=O)Nc1ccc(C(=O)Nc2ccc(CC[C@H]3COC(N)=N3)cc2)cn1]

The title compound was obtained in analogy to example 83 starting from 6-acetamidonicotinic acid and (S)-4-[2-(4-amino-phenyl)-ethyl]-4,5-dihydro-oxazol-2-ylamine. Off-white solid. MS (ISP): 368.2 ([M+H]+)

Example 103

3H-Imidazo[4,5-b]pyridine-6-carboxylic acid {4-[2-((S)-2-amino-4,5-dihydro-oxazol-4-yl)-ethyl]-phenyl}-amide

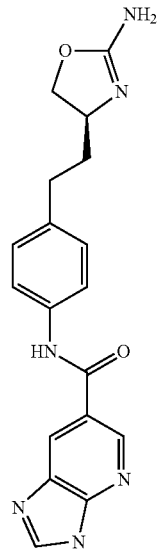 [SMILES: NC1=N[C@@H](CCc2ccc(NC(=O)c3cnc4[nH]cnc4c3)cc2)CO1]

The title compound was obtained in analogy to example 83 starting from 3H-imidazo[4,5b]pyridine-6-carboxylic acid and (S)-4-[2-(4-amino-phenyl)-ethyl]-4,5-dihydro-oxazol-2-ylamine. Off-white solid. MS (ISP): 345.1 ([M+H]+)

Example 104

[1,6]Naphthyridine-2-carboxylic acid {4-[2-((S)-2-amino-4,5-dihydro-oxazol-4-yl)-ethyl]-phenyl}-amide

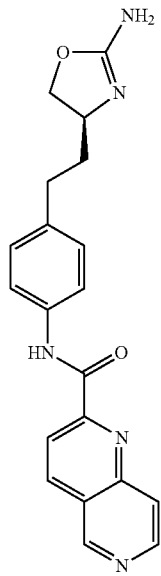 [SMILES: NC1=N[C@@H](CCc2ccc(NC(=O)c3ccc4cnccc4n3)cc2)CO1]

The title compound was obtained in analogy to example 83 starting from [1,6]naphthyridine-2-carboxylic acid and (S)-4-[2-(4-amino-phenyl)-ethyl]-4,5-dihydro-oxazol-2-ylamine. Off-white solid. MS (ISP): 362.2 ([M+H]$^+$)

Example 105 [1,8]Naphthyridine-2-carboxylic acid {4-[2-((S)-2-amino-4,5-dihydro-oxazol-4-yl)-ethyl]-phenyl}-amide

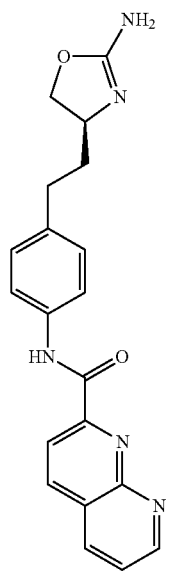 [SMILES: NC1=N[C@@H](CCc2ccc(NC(=O)c3ccc4cccnc4n3)cc2)CO1]

The title compound was obtained in analogy to example 83 starting from [1,8]naphthyridine-2-carboxylic acid and (S)-4-[2-(4-amino-phenyl)-ethyl]-4,5-dihydro-oxazol-2-ylamine. Off-white solid. MS (ISP): 362.2 ([M+H]$^+$)

Example 106

N-{4-[2-((S)-2-Amino-4,5-dihydro-oxazol-4-yl)-ethyl]-phenyl}-6-bromo-nicotinamide

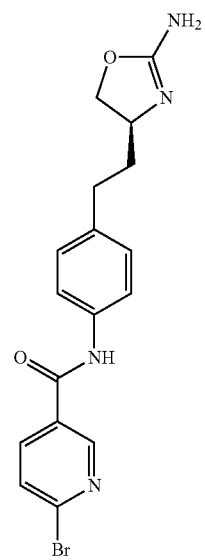 [SMILES: NC1=N[C@@H](CCc2ccc(NC(=O)c3ccc(Br)nc3)cc2)CO1]

The title compound was obtained in analogy to example 83 starting from 6-bromo-3-pyridinecarboxylic acid and (S)-4-[2-(4-amino-phenyl)-ethyl]-4,5-dihydro-oxazol-2-ylamine. White solid. MS (ISP): 389.2 ([M+H]$^+$)

Example 107

N-{4-[2-((S)-2-Amino-4,5-dihydro-oxazol-4-yl)-ethyl]-phenyl}-2,5-difluoro-nicotinamide

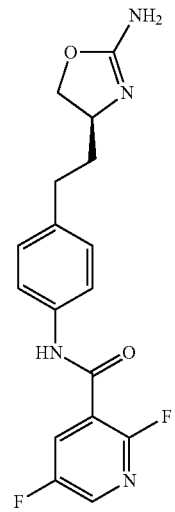 [SMILES: NC1=N[C@@H](CCc2ccc(NC(=O)c3cc(F)cnc3F)cc2)CO1]

The title compound was obtained in analogy to example 83 starting from 2,5-difluoro-3-pyridinecarboxylic acid and (S)-

4-[2-(4-amino-phenyl)-ethyl]-4,5-dihydro-oxazol-2-ylamine. White solid. MS (ISP): 347.2 ([M+H]+)

Example 108

1H-Imidazole-4-carboxylic acid {4-[2-((S)-2-amino-4,5-dihydro-oxazol-4-yl)-ethyl]-phenyl}-amide

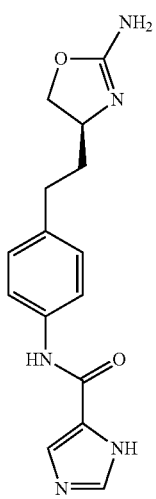 [SMILES: NC1=N[C@@H](CCc2ccc(NC(=O)c3cnc[nH]3)cc2)CO1]

The title compound was obtained in analogy to example 83 starting from 4-imidazole-carboxylic acid monohydrate and (S)-4-[2-(4-amino-phenyl)-ethyl]-4,5-dihydro-oxazol-2-ylamine. White solid. MS (ISP): 345.1 ([M+H]+)

Example 109

N-{4-[2-((S)-2-Amino-4,5-dihydro-oxazol-4-yl)-ethyl]-phenyl}-5,6-dichloro-nicotinamide

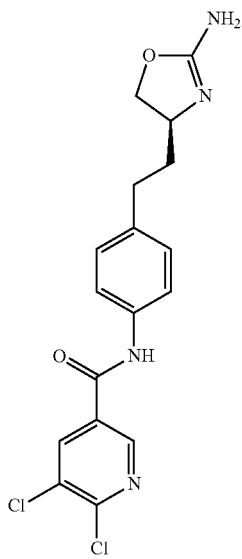 [SMILES: NC1=N[C@@H](CCc2ccc(NC(=O)c3cnc(Cl)c(Cl)c3)cc2)CO1]

The title compound was obtained in analogy to example 83 starting from 5,6-dichloronicotinic acid and (S)-4-[2-(4-amino-phenyl)-ethyl]-4,5-dihydro-oxazol-2-ylamine. White solid. MS (ISP): 379.2 ([M+H]+)

Example 110

N-{4-[2-((S)-2-Amino-4,5-dihydro-oxazol-4-yl)-ethyl]-phenyl}-2,6-difluoro-nicotinamide

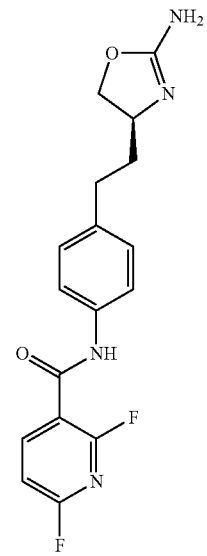 [SMILES: NC1=N[C@@H](CCc2ccc(NC(=O)c3ccc(F)nc3F)cc2)CO1]

The title compound was obtained in analogy to example 83 starting from 2,6-difluoronicotinic acid and (S)-4-[2-(4-amino-phenyl)-ethyl]-4,5-dihydro-oxazol-2-ylamine. White solid. MS (ISP): 347.2 ([M+H]+)

Example 111

N-{4-[2-((S)-2-Amino-4,5-dihydro-oxazol-4-yl)-ethyl]-phenyl}-6-cyano-nicotinamide

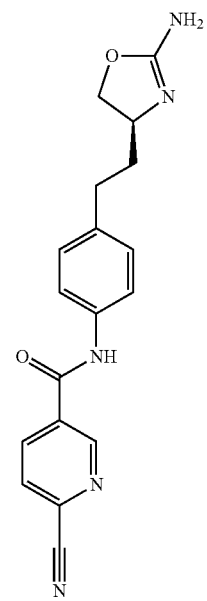 [SMILES: N#Cc1ccc(C(=O)Nc2ccc(CC[C@H]3COC(N)=N3)cc2)cn1]

The title compound was obtained in analogy to example 83 starting from 6-cyanonicotinic acid and (S)-4-[2-(4-amino-phenyl)-ethyl]-4,5-dihydro-oxazol-2-ylamine. White solid. MS (ISP): 336.3 ([M+H]⁺)

Example 112

6-Bromo-pyridine-2-carboxylic acid {4-[2-((S)-2-amino-4,5-dihydro-oxazol-4-yl)-ethyl]-phenyl}-amide

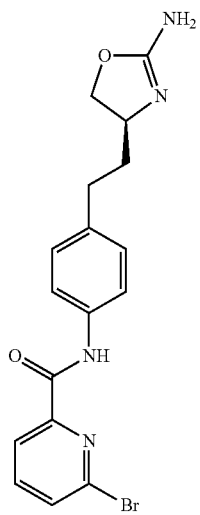 [SMILES: NC1=N[C@@H](CCc2ccc(NC(=O)c3cccc(Br)n3)cc2)CO1]

The title compound was obtained in analogy to example 83 starting from 6-bromo-pyridine-2-carboxylic acid and (S)-4-[2-(4-amino-phenyl)-ethyl]-4,5-dihydro-oxazol-2-ylamine. White solid. MS (ISP): 389.2 ([M+H]⁺)

Example 113

N-{4-[2-((S)-2-Amino-4,5-dihydro-oxazol-4-yl)-ethyl]-phenyl}-6-(2,2,2-trifluoro-ethoxy)-nicotinamide

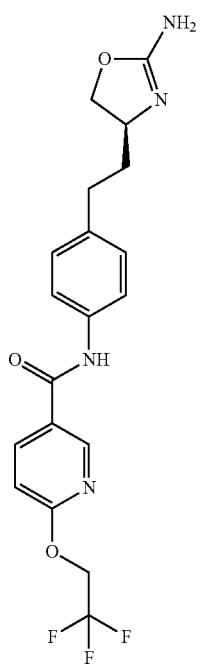 [SMILES: NC1=N[C@@H](CCc2ccc(NC(=O)c3ccc(OCC(F)(F)F)nc3)cc2)CO1]

The title compound was obtained in analogy to example 83 starting from 6-(2,2,2-trifluoroethoxy)-nicotinic acid and (S)-4-[2-(4-amino-phenyl)-ethyl]-4,5-dihydro-oxazol-2-ylamine. White solid. MS (ISP): 409.3 ([M+H]⁺)

Example 114

N-{4-[2-((S)-2-Amino-4,5-dihydro-oxazol-4-yl)-ethyl]-phenyl}-4-chloro-nicotinamide

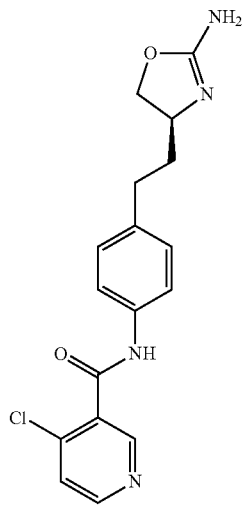 [SMILES: NC1=N[C@@H](CCc2ccc(NC(=O)c3cnccc3Cl)cc2)CO1]

The title compound was obtained in analogy to example 83 starting from 4-chloronicotinic acid and (S)-4-[2-(4-amino-phenyl)-ethyl]-4,5-dihydro-oxazol-2-ylamine. White solid. MS (ISP): 345.1 ([M+H]⁺)

Example 115

N-{4-[2-((S)-2-Amino-4,5-dihydro-oxazol-4-yl)-ethyl]-phenyl}-2-methoxy-nicotinamide

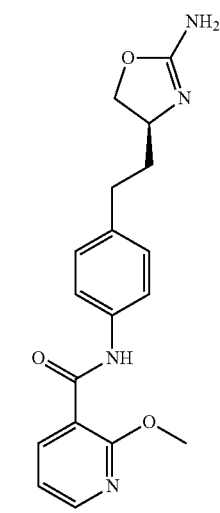 [SMILES: COc1ncccc1C(=O)Nc1ccc(CC[C@H]2COC(N)=N2)cc1]

The title compound was obtained in analogy to example 83 starting from 2-methoxynicotinic acid and (S)-4-[2-(4-amino-phenyl)-ethyl]-4,5-dihydro-oxazol-2-ylamine. White solid. MS (ISP): 341.1 ([M+H]+)

Example 116

(S)-N-(4-(2-(2-Amino-4,5-dihydrooxazol-4-yl)ethyl)phenyl)-2-methylpyrimidine-5-carboxamide

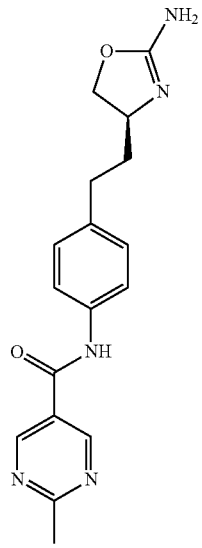 [SMILES: Cc1ncc(C(=O)Nc2ccc(CC[C@H]3COC(N)=N3)cc2)cn1]

The title compound was obtained in analogy to example 83 starting from 2-methyl-pyrimidine-5-carboxylic acid and (S)-4-[2-(4-amino-phenyl)-ethyl]-4,5-dihydro-oxazol-2-ylamine. White solid. MS (ISP): 326.2 ([M+H]+)

Example 117

(S)-N-(4-(2-(2-Amino-4,5-dihydrooxazol-4-yl)ethyl)phenyl)-5-methoxypicolinamide

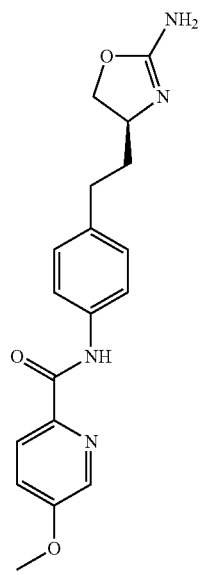 [SMILES: COc1ccc(C(=O)Nc2ccc(CC[C@H]3COC(N)=N3)cc2)nc1]

The title compound was obtained in analogy to example 83 starting from 5-methoxy-pyridine-2-carboxylic acid and (S)-4-[2-(4-amino-phenyl)-ethyl]-4,5-dihydro-oxazol-2-ylamine. White solid. MS (ISP): 341.1 ([M+H]+)

Example 118

(S)-N-(4-(2-(2-Amino-4,5-dihydrooxazol-4-yl)ethyl)phenyl)-3-fluoropicolinamide

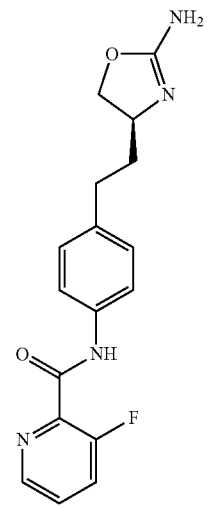 [SMILES: NC1=N[C@@H](CCc2ccc(NC(=O)c3ncccc3F)cc2)CO1]

The title compound was obtained in analogy to example 83 starting from 2-fluoropyridine-2-carboxylic acid and (S)-4-[2-(4-amino-phenyl)-ethyl]-4,5-dihydro-oxazol-2-ylamine. White solid. MS (ISP): 329.1 ([M+H]+)

Example 119

(S)-N-(4-(2-(2-Amino-4,5-dihydrooxazol-4-yl)ethyl)phenyl)-5-cyanopicolinamide

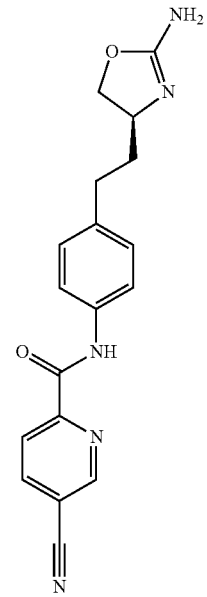 [SMILES: N#Cc1ccc(C(=O)Nc2ccc(CC[C@H]3COC(N)=N3)cc2)nc1]

The title compound was obtained in analogy to example 83 starting from 5-cyano-2-pyridine carboxylic acid and (S)-4-[2-(4-amino-phenyl)-ethyl]-4,5-dihydro-oxazol-2-ylamine. White solid. MS (ISP): 336.3 ([M+H]+)

Example 120

(S)-N-(4-(2-(2-Amino-4,5-dihydrooxazol-4-yl)ethyl)phenyl)-1-(6-chloropyridin-3-yl)cyclopropanecarboxamide

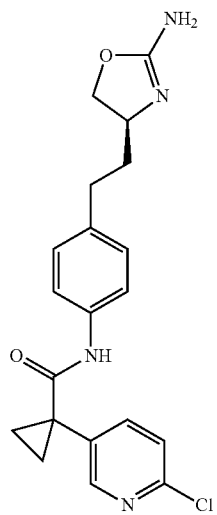 [SMILES: NC1=N[C@@H](CCc2ccc(NC(=O)C3(c4ccc(Cl)nc4)CC3)cc2)CO1]

The title compound was obtained in analogy to example 83 starting from 1-(6-chloropyridin-3-yl)cyclopropanecarboxylic acid (CAS 854267-90-6) and (S)-4-[2-(4-amino-phenyl)-ethyl]-4,5-dihydro-oxazol-2-ylamine. White solid. MS (ISP): 385.2 ([M+H]$^+$)

Example 121

(S)-N-(4-(2-(2-Amino-4,5-dihydrooxazol-4-yl)ethyl)phenyl)-6-fluoronicotinamide

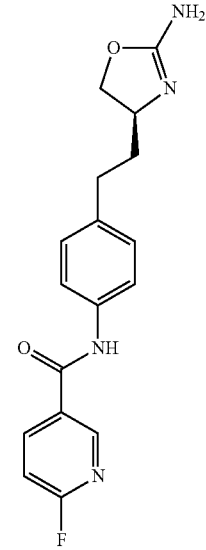 [SMILES: NC1=N[C@@H](CCc2ccc(NC(=O)c3ccc(F)nc3)cc2)CO1]

The title compound was obtained in analogy to example 83 starting from 6-fluoronicotinic acid and (S)-4-[2-(4-amino-phenyl)-ethyl]-4,5-dihydro-oxazol-2-ylamine. White solid. MS (ISP): 329.1 ([M+H]$^+$)

Example 122

(S)-N-(4-(2-(2-Amino-4,5-dihydrooxazol-4-yl)ethyl)phenyl)-6-chloropyridazine-3-carboxamide

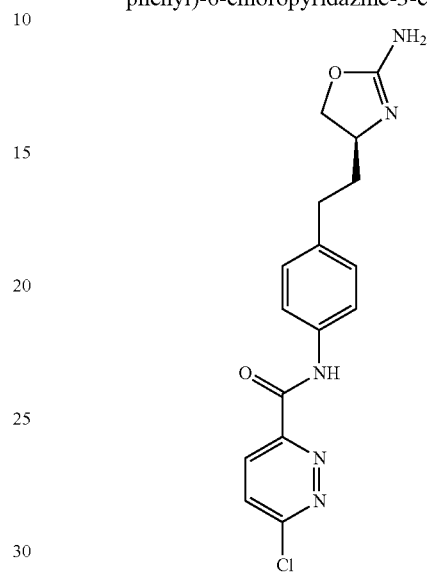

The title compound was obtained in analogy to example 83 starting from 6-chloropyridazine-3-carboxylic acid and (S)-4-[2-(4-amino-phenyl)-ethyl]-4,5-dihydro-oxazol-2-ylamine. White solid. MS (ISP): 346.1 ([M+H]$^+$)

Example 123

(S)-N-(4-(2-(2-Amino-4,5-dihydrooxazol-4-yl)ethyl)phenyl)-2-(piperidin-1-yl)pyrimidine-5-carboxamide

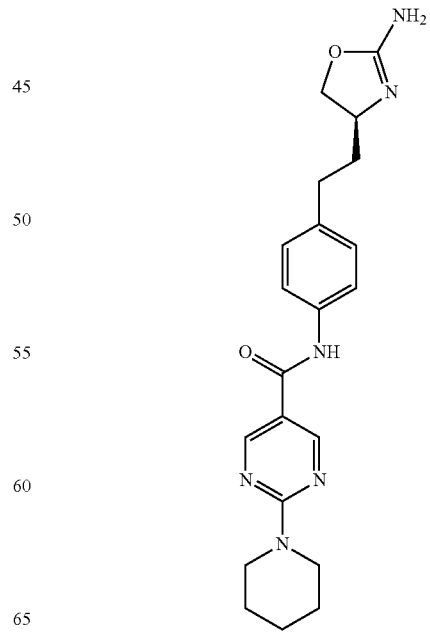

The title compound was obtained in analogy to example 83 starting from 2-piperidin-1-yl-pyrimidine-5-carboxylic acid and (S)-4-[2-(4-amino-phenyl)-ethyl]-4,5-dihydro-oxazol-2-ylamine. White solid. MS (ISP): 395.2 ([M+H]⁺)

Example 124

(S)-N-(4-(2-(2-Amino-4,5-dihydrooxazol-4-yl)ethyl) phenyl)-5-chloronicotinamide

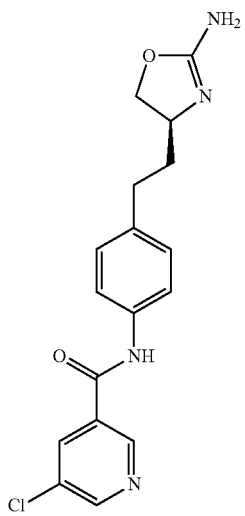 [SMILES: NC1=N[C@@H](CCc2ccc(NC(=O)c3cncc(Cl)c3)cc2)CO1]

The title compound was obtained in analogy to example 83 starting from 5-chloronicotinic acid and (S)-4-[2-(4-amino-phenyl)-ethyl]-4,5-dihydro-oxazol-2-ylamine. White solid. MS (ISP): 345.2 ([M+H]⁺)

Example 125

(S)-N-(4-(2-(2-Amino-4,5-dihydrooxazol-4-yl)ethyl) phenyl)-2-(3,4-dichlorophenyl)-2,2-difluoroacetamide

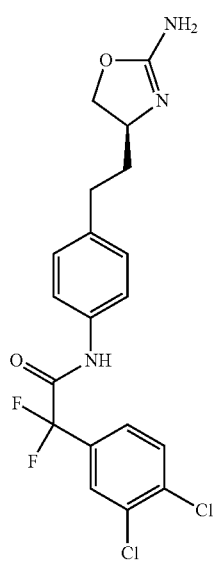 [SMILES: NC1=N[C@@H](CCc2ccc(NC(=O)C(F)(F)c3ccc(Cl)c(Cl)c3)cc2)CO1]

The title compound was obtained in analogy to example 83 starting from, 3,4-dichloro-α,α-difluoro-benzeneacetic acid (CAS 56072-00-5) and (S)-4-[2-(4-amino-phenyl)-ethyl]-4, 5-dihydro-oxazol-2-ylamine. Light brown solid. MS (ISP): 428.2 ([M+H]⁺)

Example 126

(S)-N-(4-(2-(2-Amino-4,5-dihydrooxazol-4-yl)ethyl) phenyl)-5-chloropyrazine-2-carboxamide

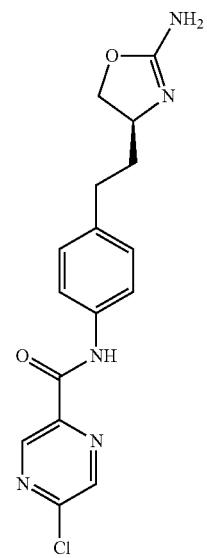 [SMILES: NC1=N[C@@H](CCc2ccc(NC(=O)c3cnc(Cl)cn3)cc2)CO1]

The title compound was obtained in analogy to example 83 starting from 5-chloropyrazine-2-carboxylic acid and (S)-4-[2-(4-amino-phenyl)-ethyl]-4,5-dihydro-oxazol-2-ylamine. Off-white solid. MS (ISP): 346.1 ([M+H]⁺)

Example 127

(S)-N-(4-(2-(2-Amino-4,5-dihydrooxazol-4-yl)ethyl) phenyl)-5-methoxypyrazine-2-carboxamide

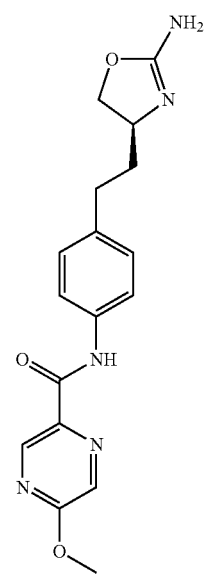 [SMILES: COc1cnc(C(=O)Nc2ccc(CC[C@H]3COC(N)=N3)cc2)cn1]

The title compound was obtained in analogy to example 83 starting from 5-methoxypyrazine-2-carboxylic acid and (S)-4-[2-(4-amino-phenyl)-ethyl]-4,5-dihydro-oxazol-2-ylamine. Light yellow solid. MS (ISP): 342.1 ([M+H]⁺)

Example 128

(S)-N-(4-(2-(2-Amino-4,5-dihydrooxazol-4-yl)ethyl)
phenyl)-6-methoxypyrazine-2-carboxamide

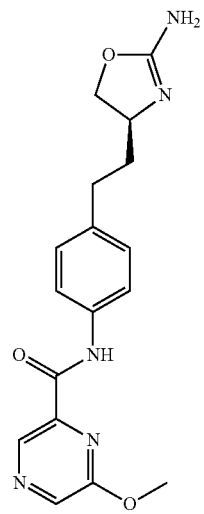 [SMILES: COc1cncc(C(=O)Nc2ccc(CC[C@H]3COC(N)=N3)cc2)n1]

The title compound was obtained in analogy to example 83 starting from 6-methoxypyrazine-2-carboxylic acid and (S)-4-[2-(4-amino-phenyl)-ethyl]-4,5-dihydro-oxazol-2-ylamine. Light yellow solid. MS (ISP): 342.1 ([M+H]$^+$)

Example 129

(S)-N-(4-(2-(2-Amino-4,5-dihydrooxazol-4-yl)ethyl)
phenyl)-5-methylpyrazine-2-carboxamide

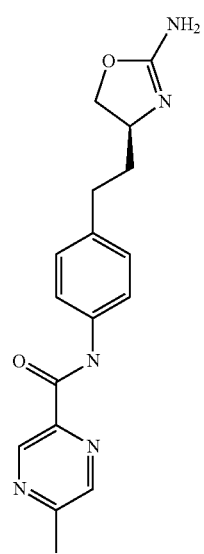 [SMILES: Cc1cnc(C(=O)Nc2ccc(CC[C@H]3COC(N)=N3)cc2)cn1]

The title compound was obtained in analogy to example 83 starting from 5-methylpyrazine-2-carboxylic acid and (S)-4-[2-(4-amino-phenyl)-ethyl]-4,5-dihydro-oxazol-2-ylamine. Off-white solid. MS (ISP): 362.2 ([M+H]$^+$)

Example 130

(S)-N-(4-(2-(2-Amino-4,5-dihydrooxazol-4-yl)ethyl)
phenyl)-6-methylpyrazine-2-carboxamide

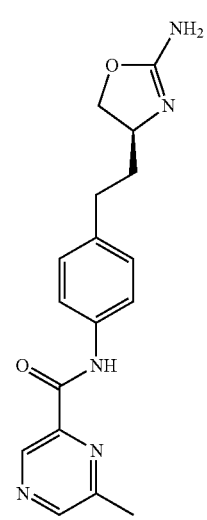 [SMILES: Cc1cncc(C(=O)Nc2ccc(CC[C@H]3COC(N)=N3)cc2)n1]

The title compound was obtained in analogy to example 83 starting from 6-methylpyrazine-2-carboxylic acid and (S)-4-[2-(4-amino-phenyl)-ethyl]-4,5-dihydro-oxazol-2-ylamine. Light yellow solid. MS (ISP): 326.2 ([M+H]$^+$)

Example 131

(S)-4-(2-(2-Amino-4,5-dihydrooxazol-4-yl)ethyl)-N-
(5-chloropyridin-2-yl)benzamide

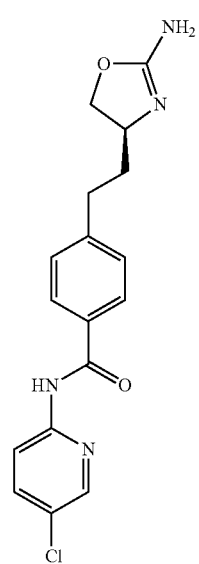 [SMILES: NC1=N[C@@H](CCc2ccc(C(=O)Nc3ccc(Cl)cn3)cc2)CO1]

The title compound was obtained in analogy to example 84 starting from (S)-4-[2-(4-carboxy-phenyl)-ethyl]-2,2-dimethyl-oxazolidine-3-carboxylic acid tert-butyl ester (this acid is described in example 48) instead of (RS)-4-(4-carboxy-phenyl)-2,2-dimethyl-oxazolidine-3-carboxylic acid tert-butyl ester and 2-amino-5-chloro-pyridine instead of 4-chloroaniline in step c). White solid. MS (ISP): 345.1 ([M+H]$^+$)

Example 132

(S)-4-(2-(2-Amino-4,5-dihydrooxazol-4-yl)ethyl)-N-(5-fluoropyridin-2-yl)benzamide

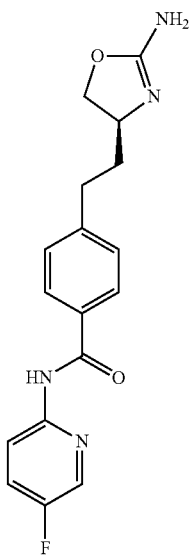 [SMILES: NC1=N[C@@H](CCc2ccc(C(=O)Nc3ccc(F)cn3)cc2)CO1]

The title compound was obtained in analogy to example 84 starting from (S)-4-[2-(4-carboxy-phenyl)-ethyl]-2,2-dimethyl-oxazolidine-3-carboxylic acid tert-butyl ester (this acid is described in example 48) instead of (RS)-4-(4-carboxy-phenyl)-2,2-dimethyl-oxazolidine-3-carboxylic acid tert-butyl ester and 2-amino-5-fluoro-pyridine instead of 4-chloroaniline in step c). White solid. MS 329.1 (ISP): ([M+H]$^+$)

Example 133

4-[2-((S)-2-Amino-4,5-dihydro-oxazol-4-yl)-ethyl]-N-(4-methoxy-phenyl)-benzamide

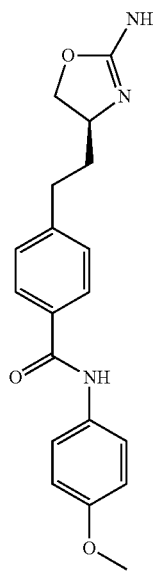

The title compound was obtained in analogy to example 84 starting from (S)-4-[2-(4-carboxy-phenyl)-ethyl]-2,2-dimethyl-oxazolidine-3-carboxylic acid tert-butyl ester (this acid is described in example 48) instead of (RS)-4-(4-carboxy-phenyl)-2,2-dimethyl-oxazolidine-3-carboxylic acid tert-butyl ester and 2-amino-5-fluoro-pyridine instead of 4-chloroaniline in step c). The residue was purified by preparative HPLC to give title compound as a white solid. MS (ISP): 340.2 ([M+H]$^+$)

Example 134

4-[2-(2-Amino-4,5-dihydro-oxazol-4-yl)-ethyl]-N-(6-methoxy-pyridin-3-yl)-benzamide

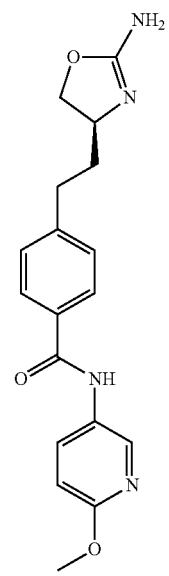 [SMILES: COc1ccc(NC(=O)c2ccc(CC[C@H]3COC(N)=N3)cc2)cn1]

The title compound was obtained in analogy to example 84 starting from (S)-4-[2-(4-carboxy-phenyl)-ethyl]-2,2-dimethyl-oxazolidine-3-carboxylic acid tert-butyl ester (this acid is described in example 48) instead of (RS)-4-(4-carboxy-phenyl)-2,2-dimethyl-oxazolidine-3-carboxylic acid tert-butyl ester and 5-amino-2-methoxy-pyridine instead of 4-chloroaniline in step c). The residue was purified by preparative HPLC to give title compound as a pink gum. MS (ISP): 341.1 ([M+H]$^+$)

Example 135

(S)-N-(4-(2-(2-Amino-4,5-dihydrooxazol-4-yl)ethyl)phenyl)-2-(6-bromopyridin-2-yl)-2,2-difluoroacetamide

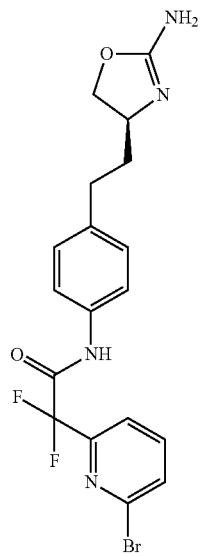 [SMILES: NC1=N[C@@H](CCc2ccc(NC(=O)C(F)(F)c3cccc(Br)n3)cc2)CO1]

a) 6-Bromo-α,α-difluoro-2-pyridineacetic acid

To a stirred solution of 2-pyridineacetic acid, 6-bromo-α,α-difluoro ethyl ester (CAS 503627-77-8) (200 g) in THF:water 1:1 (3 ml) was added LiOH.H$_2$O (45 mg) and the reaction mixture was stirred for 4 hours at room temperature. The reaction was then concentrated, taken up in ethyl acetate and water, acidified to pH 1 by addition of HC12N. The reaction mixture was then extracted three times with ethyl acetate and the combined organic layers washed with brine, dried over Na$_2$SO$_4$, filtered and concentrated in vacuo to afford 6-bromo-α,α-difluoro-2-pyridineacetic acid (175 mg). MS (ISP): ([M+H]$^+$)

b) (S)-N-(4-(2-(2-Amino-4,5-dihydrooxazol-4-yl)ethyl)phenyl)-2-(6-bromopyridin-2-yl)-2,2-difluoroacetamide The title compound was obtained in analogy to example 83 starting from 6-bromo-α,α-difluoro-2-pyridineacetic acid and (S)-4-[2-(4-amino-phenyl)-ethyl]-4,5-dihydro-oxazol-2-ylamine. Light yellow solid. MS (ISP): 441.2 ([M+H]$^+$)

Example 136

(S)-N-(4-(2-(2-Amino-4,5-dihydrooxazol-4-yl)ethyl)phenyl)-4-chloro-2-fluorobenzamide

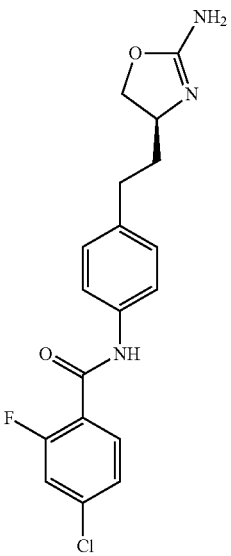 [SMILES: NC1=N[C@@H](CCc2ccc(NC(=O)c3ccc(Cl)cc3F)cc2)CO1]

The title compound was obtained in analogy to example 83 starting from 4-chloro-2-fluorobenzoic acid and (S)-4-[2-(4-amino-phenyl)-ethyl]-4,5-dihydro-oxazol-2-ylamine. Off-white solid. MS (ISP): 362.2 ([M+H]$^+$)

Example 137

(S)-N-(4-(2-(2-Amino-4,5-dihydrooxazol-4-yl)ethyl)phenyl)-2,4-dichlorobenzamide

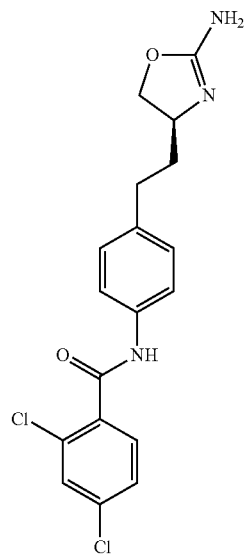 [SMILES: NC1=N[C@@H](CCc2ccc(NC(=O)c3ccc(Cl)cc3Cl)cc2)CO1]

The title compound was obtained in analogy to example 83 starting from 2,4-dichlorobenzoic acid and (S)-4-[2-(4- amino-phenyl)-ethyl]-4,5-dihydro-oxazol-2-ylamine. Light yellow solid. MS (ISP): 378.2 ([M+H]+)

Example 138

(S)-N-(4-(2-(2-Amino-4,5-dihydrooxazol-4-yl)ethyl) phenyl)-4-chloro-2-methoxybenzamide

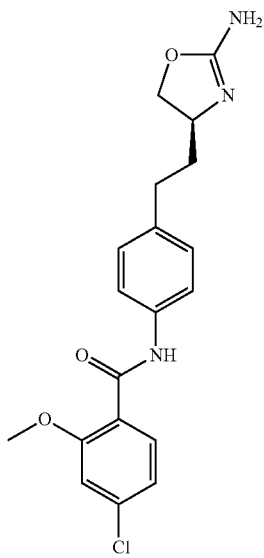 [SMILES: COc1cc(Cl)ccc1C(=O)Nc1ccc(CC[C@H]2COC(N)=N2)cc1]

The title compound was obtained in analogy to example 83 starting from 4-chloro-2-methoxybenzoic acid and (S)-4-[2-(4-amino-phenyl)-ethyl]-4,5-dihydro-oxazol-2-ylamine. Light yellow solid. MS (ISP): 374.2 ([M+H]+)

Example 139

(S)-N-(4-(2-(2-Amino-4,5-dihydrooxazol-4-yl)ethyl) phenyl)-6-morpholinonicotinamide

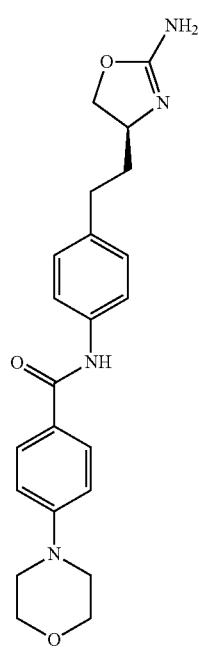 [SMILES: NC1=N[C@@H](CCc2ccc(NC(=O)c3ccc(N4CCOCC4)cc3)cc2)CO1]

The title compound was obtained in analogy to example 83 starting from 6-morpholinonicotinic acid and (S)-4-[2-(4-amino-phenyl)-ethyl]-4,5-dihydro-oxazol-2-ylamine. White solid. MS (ISP): 396.2 ([M+H]+)

Example 140

N-{4-[2-((S)-2-Amino-4,5-dihydro-oxazol-4-yl)-ethyl]-phenyl}-2,2-difluoro-2-pyridin-2-yl-acetamide

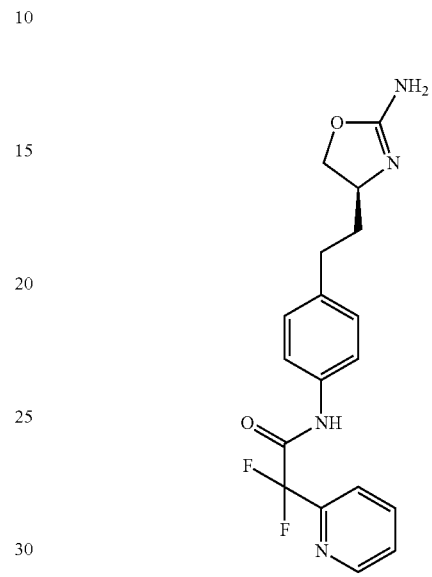

The title compound was obtained in analogy to example 83 starting from α,α-difluoro-2-pyridineacetic acid and (S)-4-[2-(4-amino-phenyl)-ethyl]-4,5-dihydro-oxazol-2-ylamine. Off-white solid. MS (ISP): 361.2 ([M+H]+)

Example 141

4-((S)-2-Amino-4,5-dihydro-oxazol-4-ylmethyl)-N-phenyl-benzamide

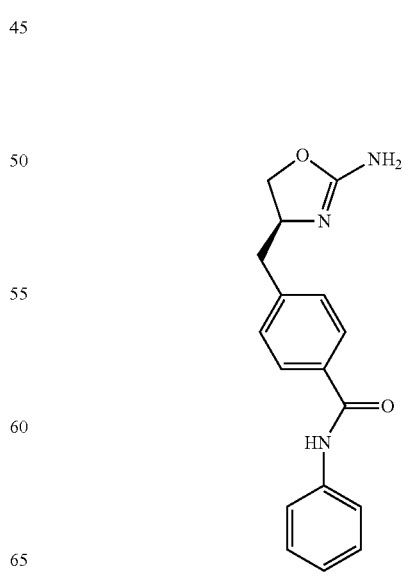

a) 4-((S)-2-tert-Butoxycarbonylamino-3-hydroxy-propyl)-benzoic acid 4-((S)-2-tert-Butoxycarbonylamino-3-hydroxy-propyl)-benzoic acid was obtained from 4-((S)-2-tert-butoxycarbonylamino-3-hydroxy-propyl)-benzoic acid ethyl ester (CAS 885022-30-0) and lithium hydroxide in analogy to example 48 step a) and was used directly for the next step.

4-((S)-2-Amino-4,5-dihydro-oxazol-4-ylmethyl)-N-phenyl-benzamide

The title compound was obtained in analogy to example 84 starting from 4-((S)-2-tert-butoxycarbonylamino-3-hydroxy-propyl)-benzoic acid instead of (RS)-4-(4-carboxy-phenyl)-2,2-dimethyl-oxazolidine-3-carboxylic acid tert-butyl ester and aniline instead of 4-chloroaniline in step c). Light yellow solid. MS (ISP): 296.2 ([M+H]$^+$)

Example 142

(S)-4-(2-(2-Amino-4,5-dihydrooxazol-4-yl)ethyl)-N-(4-cyanophenyl)benzamide

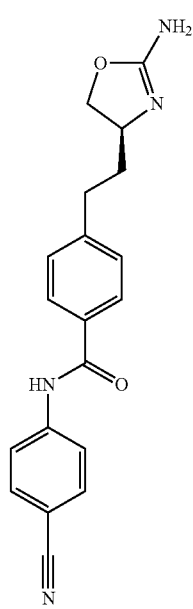 [SMILES: N#Cc1ccc(NC(=O)c2ccc(CC[C@H]3COC(N)=N3)cc2)cc1]

The title compound was obtained in analogy to example 84 starting from (S)-4-[2-(4-carboxy-phenyl)-ethyl]-2,2-dimethyl-oxazolidine-3-carboxylic acid tert-butyl ester (example 48) instead of (RS)-4-(4-carboxy-phenyl)-2,2-dimethyl-oxazolidine-3-carboxylic acid tert-butyl ester and 4-cyanoaniline instead of 4-chloroaniline in step c). Colourless foam. MS (ISP): 353.3 ([M+H]$^+$)

Example 143

(S)-4-(2-(2-Amino-4,5-dihydrooxazol-4-yl)ethyl)-N-cyclobutylbenzamide

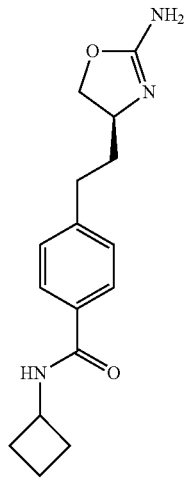 [SMILES: NC1=N[C@@H](CCc2ccc(C(=O)NC3CCC3)cc2)CO1]

The title compound was obtained in analogy to example 84 starting from (S)-4-[2-(4-carboxy-phenyl)-ethyl]-2,2-dimethyl-oxazolidine-3-carboxylic acid tert-butyl ester (example 48) instead of (RS)-4-(4-carboxy-phenyl)-2,2-dimethyl-oxazolidine-3-carboxylic acid tert-butyl ester and aminocyclobutane instead of 4-chloroaniline in step c). White solid. MS (ISP): 288.1 ([M+H]$^+$)

Example 144

(S)-4-(2-(2-amino-4,5-dihydrooxazol-4-yl)ethyl)-N-(5-cyanopyridin-2-yl)benzamide

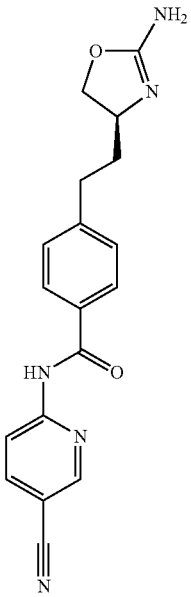

The title compound was obtained in analogy to example 84 starting from (S)-4-[2-(4-carboxy-phenyl)-ethyl]-2,2-dimethyl-oxazolidine-3-carboxylic acid tert-butyl ester (example 48) instead of (RS)-4-(4-carboxy-phenyl)-2,2-dimethyl-oxazolidine-3-carboxylic acid tert-butyl ester and 2-amino-5-cyano-pyridine instead of 4-chloroaniline in step c). White solid. MS (ISP): 336.3 ([M+H]$^+$)

Example 145

(S)-4-(2-(2-amino-4,5-dihydrooxazol-4-yl)ethyl)-N-(4-ethynylphenyl)benzamide

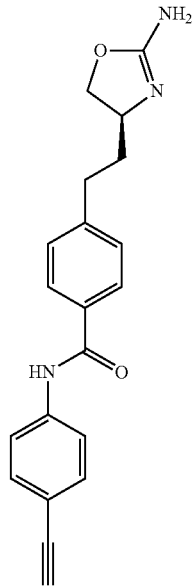 [SMILES: C#Cc1ccc(NC(=O)c2ccc(CC[C@H]3COC(N)=N3)cc2)cc1]

The title compound was obtained in analogy to example 84 starting from (S)-4-[2-(4-carboxy-phenyl)-ethyl]-2,2-dimethyl-oxazolidine-3-carboxylic acid tert-butyl ester (example 48) instead of (RS)-4-(4-carboxy-phenyl)-2,2-dimethyl-oxazolidine-3-carboxylic acid tert-butyl ester and 4-ethynyl-aniline instead of 4-chloroaniline in step c). White solid. MS (ISP): 334.2 ([M+H]$^+$).

Example 146

{4-[2-((S)-2-Amino-4,5-dihydro-oxazol-4-yl)-ethyl]-phenyl}-carbamic acid 4-chloro-benzyl ester

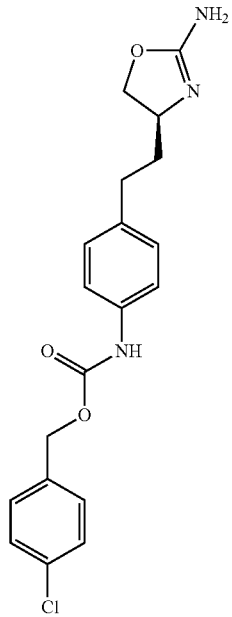 [SMILES: NC1=N[C@@H](CCc2ccc(NC(=O)OCc3ccc(Cl)cc3)cc2)CO1]

a) (S)-4-{2-[4-(4-Chloro-benzyloxycarbonylamino)-phenyl]-ethyl}-2,2-dimethyl-oxazolidine-3-carboxylic acid tert-butyl ester To a stirred suspension of (S)-4-[2-(4-isocyanato-phenyl)-ethyl]-2,2-dimethyl-oxazolidine-3-carboxylic acid tert-butyl ester (240 mg) in 1,2-dichloroethane (2 ml) in a pressure tube were added sequentially N,N-diisopropylethylamine (0.24 ml) and 4-chloro-benzyl alcohol (148 mg). The tube was capped and stirring was continued while the reaction mixture was heated at 110° C. for 18 h. The mixture was then cooled to room temperature and concentrated in vacuo. The residue was purified by column chromatography (SiO$_2$; gradient: heptane/EtOAc) to give (S)-4-{2-[4-(4-chloro-benzyloxycarbonylamino)-phenyl]-ethyl}-2,2-dimethyl-oxazolidine-3-carboxylic acid tert-butyl ester (174 mg, 51%) as a colourless amorphous solid. MS (ISP): 508.2 ([{$^{37}$Cl}M+NH$_4$]$^+$), 506.2 ([{$^{35}$Cl}M+NH$_4$]$^+$), 491.2 ([{$^{37}$Cl}M+H]$^+$), 489.2 ([{$^{35}$Cl}M+H]$^+$), 435.2 ([{$^{37}$Cl}M+H—C$_4$H$_8$]$^+$), 433.2 ([{$^{35}$Cl}M+H—C$_4$H$_8$]$^+$).

b) {4-[2-((S)-2-Amino-4,5-dihydro-oxazol-4-yl)-ethyl]-phenyl}-carbamic acid 4-chloro-benzyl ester The title compound was obtained in analogy to example 1(g)-1(h) starting from (S)-4-{2-[4-(4-chloro-benzyloxycarbonylamino)-phenyl]-ethyl}-2,2-dimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 376.3 ([{$^{37}$Cl}M+H]$^+$), 374.2 ([{35Cl}M+H]$^+$).

Example 147

{4-[2-((S)-2-Amino-4,5-dihydro-oxazol-4-yl)-ethyl]-phenyl}-carbamic acid 4-methoxy-phenyl ester

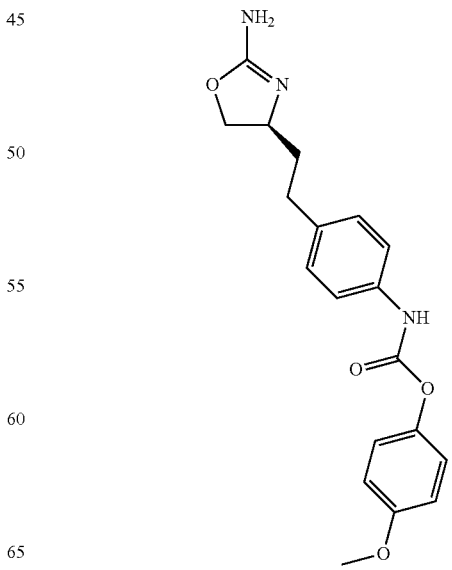

The title compound was obtained in analogy to example 146 starting from 4-methoxyphenol instead of 4-chloro-benzyl alcohol. White solid. MS (ISP): 356.1 ([M+H]$^+$)

Example 148

{4-[2-((S)-2-Amino-4,5-dihydro-oxazol-4-yl)-ethyl]-phenyl}-carbamic acid 4-fluoro-phenyl ester

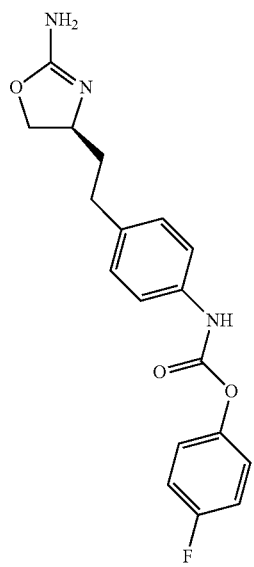 [SMILES: NC1=N[C@@H](CCc2ccc(NC(=O)Oc3ccc(F)cc3)cc2)CO1]

The title compound was obtained in analogy to example 146 starting from 4-fluorophenol instead of 4-chloro-benzyl alcohol. White solid. MS (ISP): 344.1 ([M+H]$^+$)

Example 149

{4-[2-((S)-2-Amino-4,5-dihydro-oxazol-4-yl)-ethyl]-phenyl}-carbamic acid 3-trifluoromethyl-phenyl ester

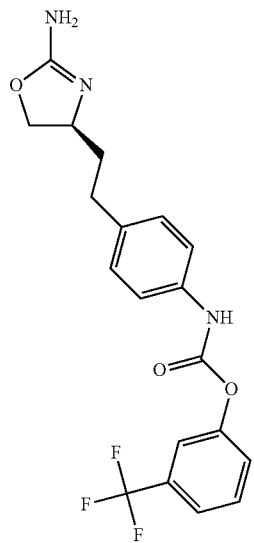 [SMILES: NC1=N[C@@H](CCc2ccc(NC(=O)Oc3cccc(C(F)(F)F)c3)cc2)CO1]

The title compound was obtained in analogy to example 146 starting from 3-trifluoromethylphenol instead of 4-chloro-benzyl alcohol. White solid. MS (ISP): 394.1 ([M+H]$^+$)

Example 150

N-{4-[(R)-1-((S)-2-Amino-4,5-dihydro-oxazol-4-ylmethyl)-2,2,2-trifluoro-ethoxy]-phenyl}-4-chloro-benzamide

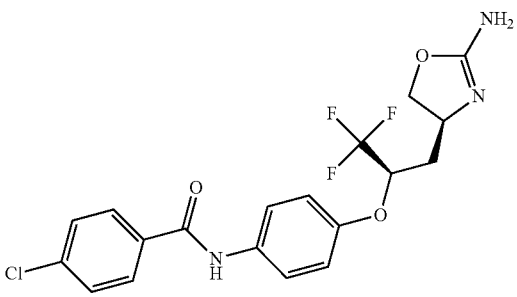 [SMILES: NC1=N[C@@H](C[C@@H](Oc2ccc(NC(=O)c3ccc(Cl)cc3)cc2)C(F)(F)F)CO1]

a) (S)-2,2-Dimethyl-4-((R)-3,3,3-trifluoro-2-hydroxy-propyl)-oxazolidine-3-carboxylic acid tert-butyl ester and (S)-2,2-Dimethyl-4-((S)-3,3,3-trifluoro-2-hydroxy-propyl)-oxazolidine-3-carboxylic acid tert-butyl ester To a cooled, stirred solution of (S)-2,2-Dimethyl-4-(2-oxo-ethyl)-oxazolidine-3-carboxylic acid tert-butyl ester (4.35 g, CAS 147959-19-1) and (trifluoromethyl)trimethylsilane (2.7 ml) in THF (50 ml) at 0° C. was added dropwise tetrabutylammonium fluoride solution (1.8 ml, 1 M solution in THF). The reaction mixture was allowed to warm to room temperature and then stirred for a further 30 min. The mixture was then diluted with 2 N aq. HCl (50 ml) and stirring was continued for a further 30 min. The mixture was extracted twice with ethyl acetate and the combined organic phases were dried over sodium sulfate and concentrated in vacuo. The residue was purified by column chromatography (SiO$_2$; gradient: heptane/EtOAc) to give (S)-2,2-dimethyl-4-((S)-3,3,3-trifluoro-2-hydroxy-propyl)-oxazolidine-3-carboxylic acid tert-butyl ester as a colourless viscous oil (1.6 g, 28%, fractions eluting first) and (S)-2,2-dimethyl-4-((R)-3,3,3-trifluoro-2-hydroxy-propyl)-oxazolidine-3-carboxylic acid tert-butyl ester as a colourless viscous oil (2.0 g, 36%, fractions eluting last).

b) (S)-2,2-Dimethyl-4-[(R)-3,3,3-trifluoro-2-(4-nitro-phenoxy)-propyl]-oxazolidine-3-carboxylic acid tert-butyl ester To a cooled, stirred solution of (S)-2,2-dimethyl-4-((R)-3,3,3-trifluoro-2-hydroxy-propyl)-oxazolidine-3-carboxylic acid tert-butyl ester (1.99 g) and 1-fluoro-4-nitrobenzene (0.69 ml) in THF (20 ml) at 0° C. was added dropwise potassium bis(trimethylsilyl)amide solution (7.7 ml, 1 M solution in THF). The reaction mixture was stirred for 30 min at 0° C., then allowed to warm to room temperature and stirred for a further 1 h. The mixture was then diluted with dichloromethane and washed with sat. aq. ammonium chloride solution. The phases were separated and the aqueous phase was extracted with dichloromethane. The combined organic phases were dried over sodium sulfate and concentrated in vacuo. The residue was purified by column chromatography (SiO$_2$; gradient: heptane/EtOAc) to give (S)-2,2-dimethyl-4-[(R)-3,3,3-trifluoro-2-(4-nitro-phenoxy)-propyl]-oxazolidine-3-carboxylic acid tert-butyl ester as a yellow viscous oil (2.7 g, 97%). MS (ISP): 435.3 ([M+H]$^+$), 379.3 ([M+H—C$_4$H$_8$]$^+$), 335.4 ([M+H—C$_4$H$_8$—CO$_2$]$^+$).

c) (S)-4-[(R)-2-(4-Amino-phenoxy)-3,3,3-trifluoro-propyl]-2,2-dimethyl-oxazolidine-3-carboxylic acid tert-butyl ester To a stirred suspension of (S)-2,2-dimethyl-4-[(R)-3,3,3-trifluoro-2-(4-nitro-phenoxy)-propyl]-oxazolidine-3-carboxylic acid tert-butyl ester (2.66 g) in methanol (20 ml) was added 10% palladium on charcoal (326 mg) and the mixture was then stirred under an atmosphere of hydrogen at room temperature for 3 hours. The mixture was then filtered through celite and the filtrate was concentrated in vacuo to afford (S)-4-[(R)-2-(4-amino-phenoxy)-3,3,3-trifluoro-propyl]-2,2-dimethyl-oxazolidine-3-carboxylic acid tert-butyl ester (1.80 g, 73%) as a yellow viscous oil. MS (ISP): 405.4 ([M+H]$^+$), 349.3 ([M+H—C$_4$H$_8$]$^+$), 305.3 ([M+H—C$_4$H$_8$—CO$_2$]$^+$).

d) N-{4-[(R)-1-((S)-2-Amino-4,5-dihydro-oxazol-4-ylmethyl)-2,2,2-trifluoro-ethoxy]-phenyl}-4-chloro-benzamide The title compound was obtained in analogy to example 33 starting from (S)-4-[(R)-2-(4-amino-phenoxy)-3,3,3-trifluoro-propyl]-2,2-dimethyl-oxazolidine-3-carboxylic acid tert-butyl ester in place of (S)-4-[2-(4-amino-phenyl)-ethyl]-2,2-dimethyl-oxazolidine-3-carboxylic acid tert-butyl ester and using 4-chloro-benzoic acid instead of 5-chloro-2-pyridinecarboxylic acid. White solid. MS (ISP): 430.1 ([{$^{37}$Cl}M+H]$^+$), 428.1 ([{$^{35}$Cl}M+H]$^+$).

Example 151

1-{4-[2-((S)-2-Amino-4,5-dihydro-oxazol-4-yl)-ethyl]-phenyl}-3-(5-chloro-pyrimidin-2-yl)-urea

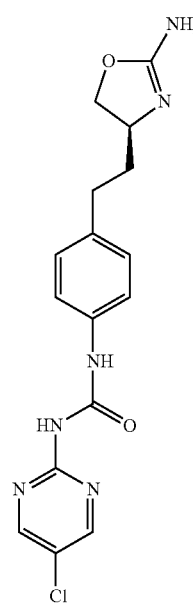

The title compound was obtained in analogy to example 35(b)-(c) starting from (S)-4-[2-(4-isocyanato-phenyl)-ethyl]-2,2-dimethyl-oxazolidine-3-carboxylic acid tert-butyl ester and using 2-amino-5-chloropyrimidine instead of 2-amino-5-chloropyridine. Off-white solid. MS (ISP): 363.1 ([{$^{37}$Cl}M+H]$^+$), 361.1 ([{$^{35}$Cl}M+H]$^+$).

Example 152

(S)-4-(2-(2-Amino-4,5-dihydrooxazol-4-yl)ethyl)-N-(5-ethynylpyridine-2-yl)benzamide

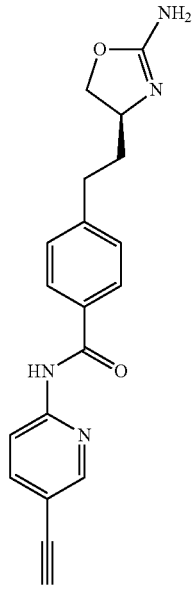 [SMILES: C#Cc1ccc(NC(=O)c2ccc(CC[C@H]3COC(N)=N3)cc2)nc1]

The title compound was obtained in analogy to example 84 starting from (S)-4-[2-(4-carboxy-phenyl)-ethyl]-2,2-dimethyl-oxazolidine-3-carboxylic acid tert-butyl ester (example 48) instead of (RS)-4-(4-carboxy-phenyl)-2,2-dimethyl-oxazolidine-3-carboxylic acid tert-butyl ester and 2-amino-5-ethynyl-pyridine instead of 4-chloroaniline in step c). White solid. MS (ISP): 335.2 ([M+H]$^+$)

Example 153

(S)-N-(4-(2-(2-Amino-4,5-dihydrooxazol-4-yl)ethyl)phenyl)-5-ethoxypicolinamide

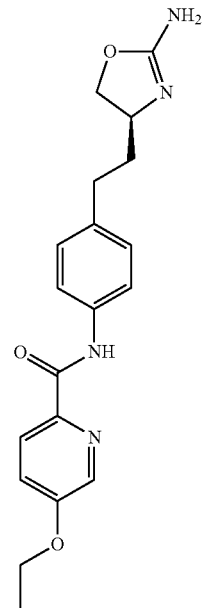 [SMILES: CCOc1ccc(C(=O)Nc2ccc(CC[C@H]3COC(N)=N3)cc2)nc1]

The title compound was obtained in analogy to example 83 starting from 5-ethoxy-pyridine-2-carboxylic acid and (S)-4-[2-(4-amino-phenyl)-ethyl]-4,5-dihydro-oxazol-2-ylamine. White solid. MS (ISP): 355.2 ([M+H]⁺)

Example 154

(S)-N-(4-(2-(2-Amino-4,5-dihydrooxazol-4-yl)ethyl)phenyl)-2-(5-fluoropyridin-2-yl)-2-methylpropanamide

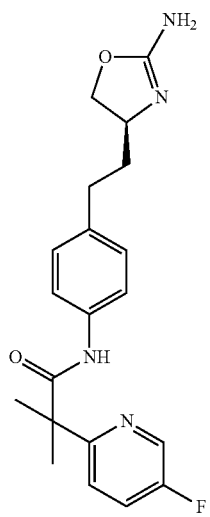 [SMILES: CC(C)(C(=O)Nc1ccc(CC[C@H]2COC(N)=N2)cc1)c1ccc(F)cn1]

The title compound was obtained in analogy to example 83 starting from 5-fluoro-α,α-dimethyl-2-pyridineacetic acid (CAS 1057395-84-2) and (S)-4-[2-(4-amino-phenyl)-ethyl]-4,5-dihydro-oxazol-2-ylamine. White solid. MS (ISP): 371.2 ([M+H]⁺)

Example 155

(S)-N-(4-(2-(2-Amino-4,5-dihydrooxazol-4-yl)ethyl)phenyl)-5-chloro-4-methylpicolinamide

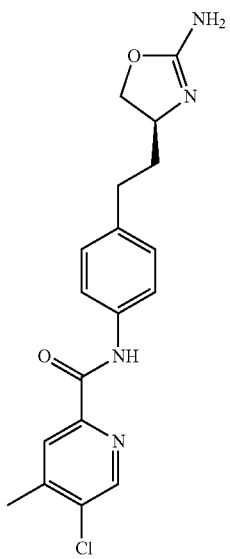 [SMILES: Cc1cc(C(=O)Nc2ccc(CC[C@H]3COC(N)=N3)cc2)ncc1Cl]

The title compound was obtained in analogy to example 83 starting from 5-chloro-4-methyl-pyridine-2-carboxylic acid and (S)-4-[2-(4-amino-phenyl)-ethyl]-4,5-dihydro-oxazol-2-ylamine. White solid. MS (ISP): 359.1 ([M+H]⁺)

Example 156

(S)-N-(4-(2-(2-Amino-4,5-dihydrooxazol-4-yl)ethyl)phenyl)-4-chloro-6-methylpicolinamide

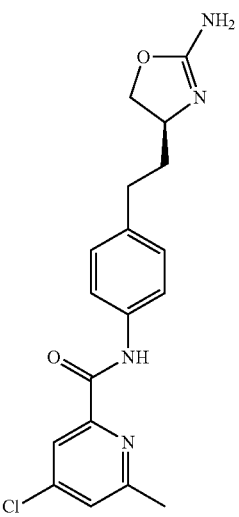 [SMILES: Cc1cc(Cl)cc(C(=O)Nc2ccc(CC[C@H]3COC(N)=N3)cc2)n1]

The title compound was obtained in analogy to example 83 starting from 4-chloro-6-methyl-pyridine-2-carboxylic acid and (S)-4-[2-(4-amino-phenyl)-ethyl]-4,5-dihydro-oxazol-2-ylamine. Off-white solid. MS (ISP): 359.1 ([M+H]⁺)

Example 157

(S)-N-(4-(2-(2-Amino-4,5-dihydrooxazol-4-yl)ethyl)phenyl)-4,6-dimethylpicolinamide

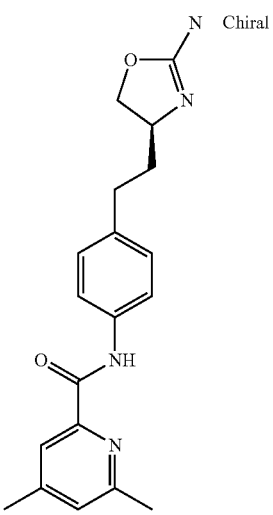 [SMILES: Cc1cc(C)nc(C(=O)Nc2ccc(CC[C@H]3COC(N)=N3)cc2)c1]

The title compound was obtained in analogy to example 83 starting from 4,6-dimethyl-pyridine-2-carboxylic acid and (S)-4-[2-(4-amino-phenyl)-ethyl]-4,5-dihydro-oxazol-2-ylamine. White solid. MS (ISP): 339.2 ([M+H]⁺)

Example 158

(S)-N-(4-(2-(2-Amino-4,5-dihydrooxazol-4-yl)ethyl)phenyl)-4,6-dichloropicolinamide

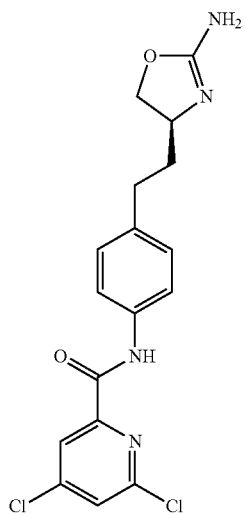 [SMILES: NC1=N[C@@H](CCc2ccc(NC(=O)c3cc(Cl)cc(Cl)n3)cc2)CO1]

The title compound was obtained in analogy to example 83 starting from 4,6-dichloro-pyridine-2-carboxylic acid and (S)-4-[2-(4-amino-phenyl)-ethyl]-4,5-dihydro-oxazol-2-ylamine. White solid. MS (ISP): 379.2 ([M+H]⁺)

Example 159

(S)-N-(4-(2-(2-Amino-4,5-dihydrooxazol-4-yl)ethyl)phenyl)-5-(trifluoromethyl)pyrazine-2-carboxamide

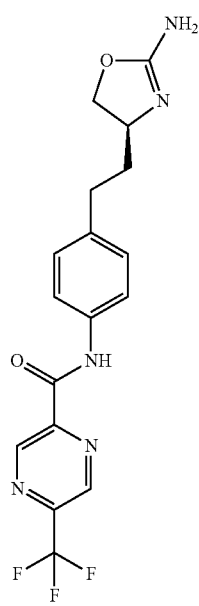 [SMILES: NC1=N[C@@H](CCc2ccc(NC(=O)c3cnc(C(F)(F)F)cn3)cc2)CO1]

The title compound was obtained in analogy to example 83 starting from 5-trifluoromethyl-pyrazine-2-carboxylic acid and (S)-4-[2-(4-amino-phenyl)-ethyl]-4,5-dihydro-oxazol-2-ylamine. Off-white solid. MS (ISP): 380.2 ([M+H]⁺)

Example 160

(S)-N-(4-(2-(2-Amino-4,5-dihydrooxazol-4-yl)ethyl)phenyl)-6-chloropyrazine-2-carboxamide

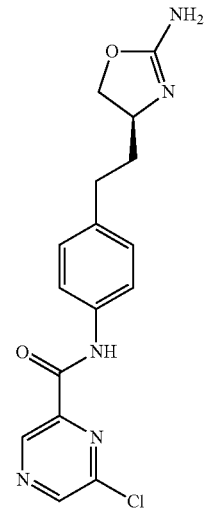 [SMILES: NC1=N[C@@H](CCc2ccc(NC(=O)c3cncc(Cl)n3)cc2)CO1]

The title compound was obtained in analogy to example 83 starting from 6-chloro-pyrazine-2-carboxylic acid and (S)-4-[2-(4-amino-phenyl)-ethyl]-4,5-dihydro-oxazol-2-ylamine. Light yellow solid. MS (ISP): 346.2 ([M+H]⁺)

Example 161

(S)-N-(4-(2-(2-Amino-4,5-dihydrooxazol-4-yl)ethyl)phenyl)-5-ethoxypyrazine-2-carboxamide

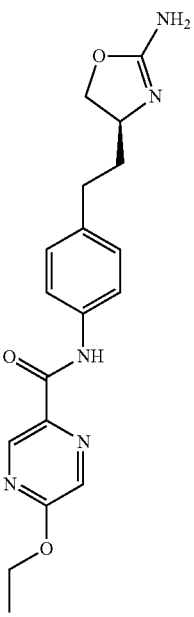 [SMILES: CCOc1cnc(C(=O)Nc2ccc(CC[C@H]3COC(N)=N3)cc2)cn1]

The title compound was obtained in analogy to example 83 starting from 5-ethoxy-pyrazine-2-carboxylic acid and (S)-4-[2-(4-amino-phenyl)-ethyl]-4,5-dihydro-oxazol-2-ylamine. White solid. MS (ISP): 356.1 ([M+H]+)

Example 162

(S)-N-(4-(2-(2-Amino-4,5-dihydrooxazol-4-yl)ethyl)phenyl)-1-(5-fluoropyridin-2-yl)cyclopropanecarboxamide

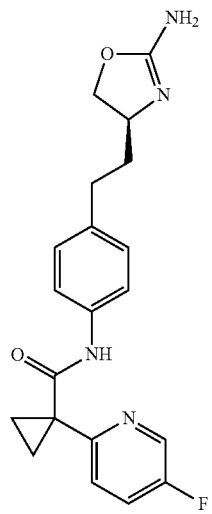 [SMILES: NC1=N[C@@H](CCc2ccc(NC(=O)C3(c4ccc(F)cn4)CC3)cc2)CO1]

a) 1-(5-fluoropyridin-2-yl)cyclopropanecarbonitrile

Cyclopropanecarbonitrile (815 mg) was dissolved in THF (15 ml) and the solution cooled to 0° C. before dropwise addition of 0.9 M KHMDS (14.0 ml). The reaction mixture was allowed to warm to room temperature and stirred for further 15 min. The resulting solution was then added dropwise to a solution of 2,5-difluoropyridine (1.52 g) in THF (15 ml) and the reaction mixture stirred for 1 hour. Reaction was quenched by addition of aqueous NH4Cl, stirred for 5 min and then the organics washed with NaHCO3 and brine and dried over Na2SO4. The mixture was then concentrated in vacuo and the residue was purified by flash column chromatography (SiO2; gradient: heptane/EtOAc) to give title compound as a white solid (880 mg). MS (ISP): 163.2 ([M+H]+)

b) 1-(5-fluoro-pyridin-2-yl)-cyclopropanecarboxylic acid 1-(5-fluoropyridin-2-yl)cyclopropanecarbonitrile (880 mg) was dissolved in ethanol (10 ml) before slow, dropwise addition of 96% sulfuric acid (10 ml). The reaction mixture was allowed to stir at 60° C. for 24 hr. Upon cooling, NaHCO3 was added until pH 8 and then the solution extracted three times with ethyl acetate, the organics were washed with brine and dried over Na2SO4 before concentration in vacuo.

c) (S)-N-(4-(2-(2-Amino-4,5-dihydrooxazol-4-yl)ethyl)phenyl)-1-(5-fluoropyridin-2-yl)cyclopropanecarboxamide The title compound was obtained in analogy to example 83 starting from 1-(5-fluoro-pyridin-2-yl)-cyclopropanecarboxylic acid and (S)-4-[2-(4-amino-phenyl)-ethyl]-4,5-dihydro-oxazol-2-ylamine. White solid. MS (ISP): 369.2 ([M+H]+)

Example 163

(S)-N-(4-(2-(2-Amino-4,5-dihydrooxazol-4-yl)ethyl)phenyl)-5-morpholinopyrazine-2-carboxamide

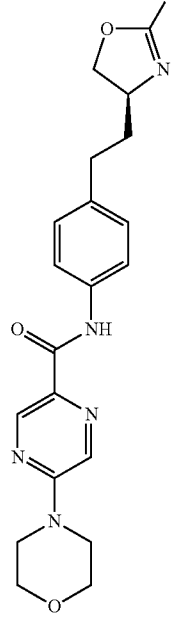

The title compound was obtained in analogy to example 83 starting from 5-(morpholinyl)-2-pyrazinecarboxylic acid (CAS 946598-39-6) and (S)-4-[2-(4-amino-phenyl)-ethyl]-4,5-dihydro-oxazol-2-ylamine. White solid. MS (ISP): 397.2 ([M+H]+)

Example 164

(S)-N-(4-(2-(2-Amino-4,5-dihydrooxazol-4-yl)ethyl)phenyl)-5-morpholinopyrazine-2-carboxamide

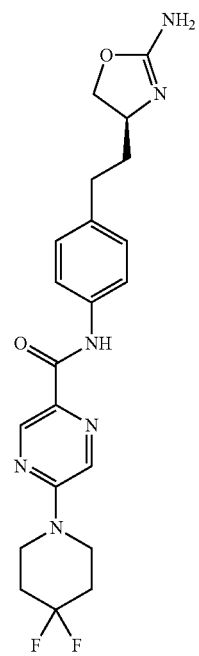 [SMILES: NC1=N[C@@H](CCc2ccc(NC(=O)c3cnc(N4CCC(F)(F)CC4)cn3)cc2)CO1]

a) 5-(4,4-difluoro-1-piperidinyl)-2-pyrazinecarboxylic acid 5-(4,4-difluoro-1-piperidinyl)-2-pyrazinecarboxylic acid was obtained from 5-(4,4-difluoro-1-piperidinyl)-2pyrazinecarboxylic acid methyl ester (CAS 1017604-27-1) and lithium hydroxide in analogy to example 48 step a) and was used directly for the next step.

b) (S)-N-(4-(2-(2-Amino-4,5-dihydrooxazol-4-yl)ethyl)phenyl)-5-morpholinopyrazine-2-carboxamide The title compound was obtained in analogy to example 83 starting from 5-(4,4-difluoro-1-piperidinyl)-2-pyrazinecarboxylic acid and (S)-4-[2-(4-amino-phenyl)-ethyl]-4,5-dihydro-oxazol-2-ylamine. White solid. MS (ISP): 431.1 ([M+H]$^+$)

Example 165

5-(1,1-Dioxo-1$\lambda^6$-thiomorpholin-4-yl)-pyrazine-2-carboxylic acid {4-[2-((S)-2-amino-4,5-dihydro-oxazol-4-yl)-ethyl]-phenyl}-amide

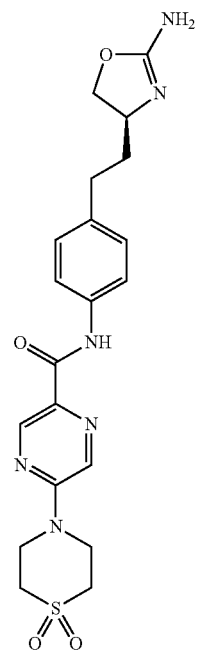 [SMILES: NC1=N[C@@H](CCc2ccc(NC(=O)c3cnc(N4CCS(=O)(=O)CC4)cn3)cc2)CO1]

a) 5-(1,1-Dioxo-1$\lambda^6$-thiomorpholin-4-yl)-pyrazine-2-carboxylic acid methyl ester Title compound was obtained by coupling of methyl 5-chloropyrazine-2-carboxylate and thiomorpholine 1,1'-dioxide with TEA in dioxane at 45° C. for 16 hours according to patent WO 2008040649.

b) 5-(1,1-Dioxo-1$\lambda^6$-thiomorpholin-4-yl)-pyrazine-2-carboxylic acid 5-(1,1-Dioxo-1$\lambda^6$-thiomorpholin-4-yl)-pyrazine-2-carboxylic acid was obtained from 5-(1,1-dioxo-1$\lambda^6$-thiomorpholin-4-yl)-pyrazine-2-carboxylic acid methyl ester and lithium hydroxide in analogy to example 48 step a) and was used directly for the next step.

c) 5-(1,15-(1,1-Dioxo-1$\lambda^6$-thiomorpholin-4-yl)-pyrazine-2-carboxylic acid {4-[2-((S)-2-amino-4,5-dihydro-oxazol-4-yl)-ethyl]-phenyl}-amide The title compound was obtained in analogy to example 83 starting from 5-(1,1-Dioxo-1$\lambda^6$-thiomorpholin-4-yl)-pyrazine-2-carboxylic acid and (S)-4-[2-(4-amino-phenyl)-ethyl]-4,5-dihydro-oxazol-2-ylamine. White solid. MS (ISP): 445.2 ([M+H]$^+$)

Example 166

(S)-N-(4-(2-(2-Amino-4,5-dihydrooxazol-4-yl)ethyl)phenyl)-6-((2-methoxyethyl)(methyl)amino)pyrazine-2-carboxamide

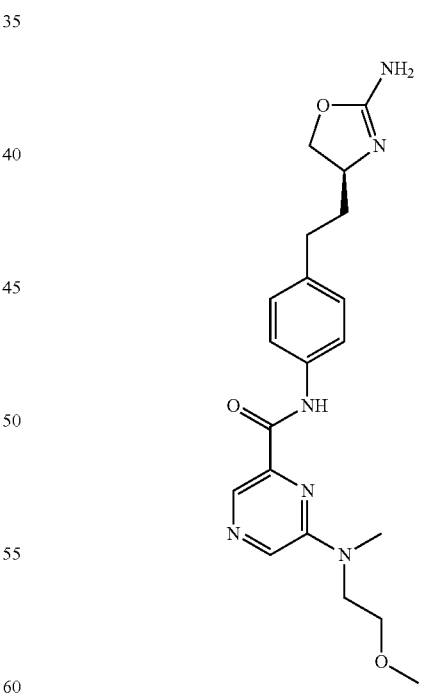

The title compound was obtained in analogy to example 83 starting from 6-[(2-methoxy-ethyl)-methyl-amino]-pyrazine-2-carboxylic acid and (S)-4-[2-(4-amino-phenyl)-ethyl]-4,5-dihydro-oxazol-2-ylamine. Light yellow solid. MS (ISP): 399.2 ([M+H]$^+$)

Example 167

(S)-N-(4-(2-(2-Amino-4,5-dihydrooxazol-4-yl)ethyl)phenyl)-5-(dimethylamino)pyrazine-2-carboxamide

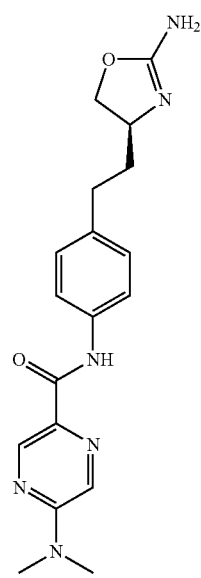

The title compound was obtained in analogy to example 83 starting from 5-(dimethylamino)-pyrazine-2-carboxylic acid and (S)-4-[2-(4-amino-phenyl)-ethyl]-4,5-dihydro-oxazol-2-ylamine. White solid. MS (ISP): 355.2 ([M+H]+)

Example 168

(S)-N-(4-(2-(2-Amino-4,5-dihydrooxazol-4-yl)ethyl)phenyl)-6-chloro-5-methoxypicolinamide

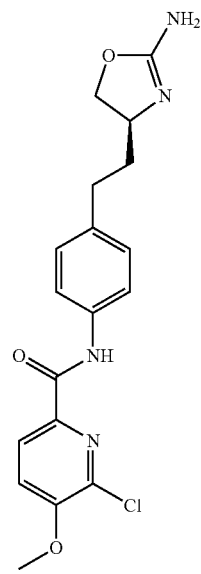

The title compound was obtained in analogy to example 83 starting from 6-chloro-5-methoxy-pyridine-2-carboxylic acid and (S)-4-[2-(4-amino-phenyl)-ethyl]-4,5-dihydro-oxazol-2-ylamine. White solid. MS (ISP): 375.2 ([M+H]+)

Example 169

(S)-N-(4-(2-(2-Amino-4,5-dihydrooxazol-4-yl)ethyl)phenyl)-5-chlorothiophene-2-carboxamide

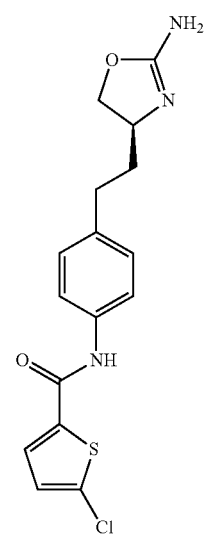 [SMILES: NC1=N[C@@H](CCc2ccc(NC(=O)c3ccc(Cl)s3)cc2)CO1]

The title compound was obtained in analogy to example 83 starting from 5-chloro-thiophene-2-carboxylic acid and (S)-4-[2-(4-amino-phenyl)-ethyl]-4,5-dihydro-oxazol-2-ylamine. White solid. MS (ISP): 350.2 ([M+H]+)

Example 170

(S)-N-(4-(2-(2-Amino-4,5-dihydrooxazol-4-yl)ethyl)phenyl)-3-cyclopropylpropanamide

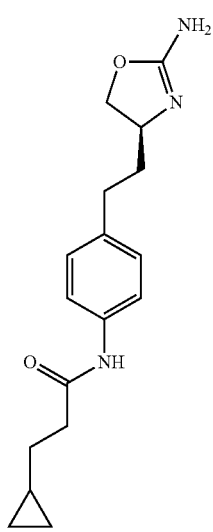 [SMILES: NC1=N[C@@H](CCc2ccc(NC(=O)CCC3CC3)cc2)CO1]

The title compound was obtained in analogy to example 83 starting from 3-cyclopropyl-propionic acid and (S)-4-[2-(4- amino-phenyl)-ethyl]-4,5-dihydro-oxazol-2-ylamine. White solid. MS (ISP): 302.2 ([M+H]⁺)

Example 171

(S)-N-(4-(2-(2-Amino-4,5-dihydrooxazol-4-yl)ethyl)phenyl)-5-methylpicolinamide

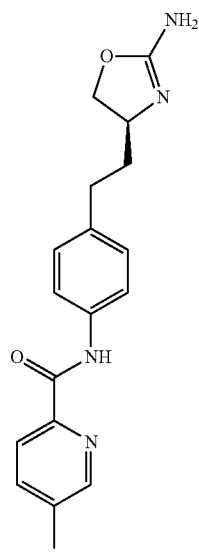

The title compound was obtained in analogy to example 83 starting from 5-methylpyridine-2-carboxylic acid and (S)-4-[2-(4-amino-phenyl)-ethyl]-4,5-dihydro-oxazol-2-ylamine. White solid. MS (ISP): 325.2 ([M+H]⁺)

Example 172

(S)-N-(4-(2-(2-Amino-4,5-dihydrooxazol-4-yl)ethyl)phenyl)-2-methylisonicotinamide

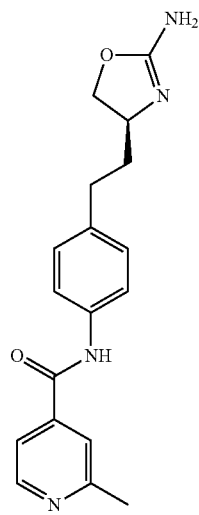 [SMILES: Cc1cc(C(=O)Nc2ccc(CC[C@H]3COC(N)=N3)cc2)ccn1]

The title compound was obtained in analogy to example 83 starting from 5-methylisonicotinic acid and (S)-4-[2-(4-amino-phenyl)-ethyl]-4,5-dihydro-oxazol-2-ylamine. White solid. MS (ISP): 325.2 ([M+H]⁺)

Example 173

(S)-N-(4-(2-(2-Amino-4,5-dihydrooxazol-4-yl)ethyl)phenyl)-2-chloroisonicotinamide

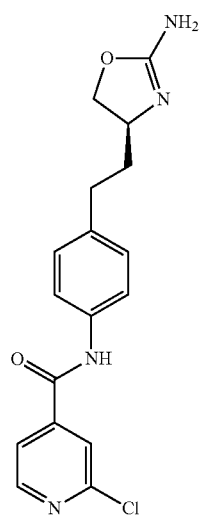 [SMILES: NC1=N[C@@H](CCc2ccc(NC(=O)c3ccnc(Cl)c3)cc2)CO1]

The title compound was obtained in analogy to example 83 starting from 2-chloroisonicotinic acid and (S)-4-[2-(4-amino-phenyl)-ethyl]-4,5-dihydro-oxazol-2-ylamine. White solid. MS (ISP): 345.1 ([M+H]⁺)

Example 174

(S)-N-(4-(2-(2-Amino-4,5-dihydrooxazol-4-yl)ethyl)phenyl)-2-chloro-3-fluoroisonicotinamide

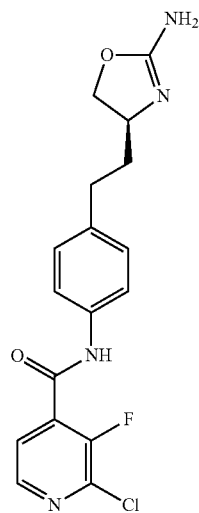 [SMILES: NC1=N[C@@H](CCc2ccc(NC(=O)c3ccnc(Cl)c3F)cc2)CO1]

The title compound was obtained in analogy to example 83 starting from 2-chloro-3-fluoroisonicotinic acid and (S)-4-[2-(4-amino-phenyl)-ethyl]-4,5-dihydro-oxazol-2-ylamine. White solid. MS (ISP): 363.2 ([M+H]⁺)

Example 175

(S)-N-(4-(2-(2-Amino-4,5-dihydrooxazol-4-yl)ethyl)phenyl)-2,6-dichloroisonicotinamide

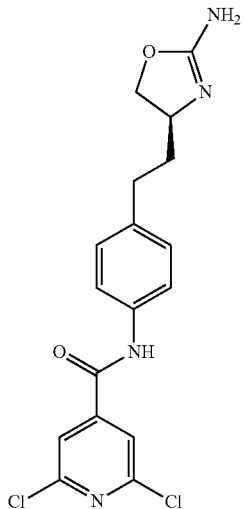 [SMILES: NC1=N[C@@H](CCc2ccc(NC(=O)c3cc(Cl)nc(Cl)c3)cc2)CO1]

The title compound was obtained in analogy to example 83 starting from 2,6-dichloropyridine-4-carboxylic acid and (S)-4-[2-(4-amino-phenyl)-ethyl]-4,5-dihydro-oxazol-2-ylamine. White solid. MS (ISP): 379.2 ([M+H]⁺)

Example 176

(S)-N-(4-(2-(2-Amino-4,5-dihydrooxazol-4-yl)ethyl)phenyl)-3-chloroisonicotinamide

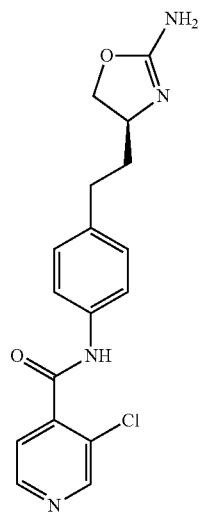 [SMILES: NC1=N[C@@H](CCc2ccc(NC(=O)c3ccncc3Cl)cc2)CO1]

The title compound was obtained in analogy to example 83 starting from 3-chloropyridine-4-carboxylic acid and (S)-4-[2-(4-amino-phenyl)-ethyl]-4,5-dihydro-oxazol-2-ylamine. White solid. MS (ISP): 345.1 ([M+H]⁺)

Example 177

(S)-2-(4-(2-(2-Amino-4,5-dihydrooxazol-4-yl)ethyl)phenyl)-5,6-dichloro-3,4-dihydroisoquinolin-1(2H)-one

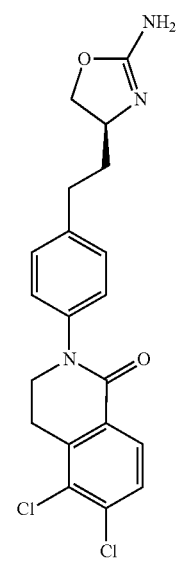 [SMILES: NC1=N[C@@H](CCc2ccc(N3CCc4c(ccc(Cl)c4Cl)C3=O)cc2)CO1]

a) (S,E)-tert-Butyl 4-(4-(5,6-dichloro-1-oxo-3,4-dihydroisoquinolin-2(1H)-yl)styryl)-2,2-dimethyloxazolidine-3-carboxylate A stirred suspension of (S)-4-[(E)-2-(4-iodo-phenyl)-vinyl]-2,2-dimethyl-oxazolidine-3-carboxylic acid tert-butyl ester (300 mg, Example 3a), 5,6-dichloro-3,4-dihydro-2H-isoquinolin-1-one (204 mg), copper(I) iodide (13 mg), N,N'-dimethylethylenediamine (15 µl) and potassium phosphate (356 mg) in toluene (3 ml) in a sealed tube was heated at 120° C. overnight. The mixture was then cooled to room temperature and was purified by column chromatography (SiO₂; gradient: heptane/EtOAc) to give (S,E)-tert-butyl 4-(4-(5,6-dichloro-1-oxo-3,4-dihydroisoquinolin-2(1H)-yl)styryl)-2,2-dimethyloxazolidine-3-carboxylate (221 mg, 61%) as a yellow amorphous solid. MS (ISP): 541.2 ([{³⁷Cl³⁵Cl}M+Na]⁺), 539.2 ([{³⁵Cl}M+Na]⁺), 519.3 ([{³⁷Cl³⁵Cl}M+H]⁺), 517.2 ([{³⁵Cl}M+H]⁺), 463.2 ([{³⁷Cl³⁵Cl}M+H—C₄H₈]⁺), 461.2 ([{³⁵Cl}M+H—C₄H₈]⁺), 419.2 ([{³⁷Cl³⁵Cl}M+H—C₄H₈—CO₂]⁺), 417.2 ([{³⁵Cl}M+H—C₄H₈—CO₂]⁺).

b) (S)-tert-Butyl 4-(4-(5,6-dichloro-1-oxo-3,4-dihydroisoquinolin-2(1H)-yl)phenethyl)-2,2-dimethyloxazolidine-3-carboxylate To a stirred suspension of (S,E)-tert-butyl 4-(4-(5,6-dichloro-1-oxo-3,4-dihydroisoquinolin-2(1H)-yl)styryl)-2,2-dimethyloxazolidine-3-carboxylate (220 mg) in methanol (8 ml) was added 10% platinum on charcoal (42 mg) and the mixture was then stirred under an atmosphere of hydrogen at room temperature for 2 hours. The mixture was then filtered through celite and the filtrate was concentrated in vacuo to afford (S)-tert-butyl 4-(4-(5,6-dichloro-1-oxo-3,4-dihydroisoquinolin-2(1H)-yl)phenethyl)-2,2-dimethyloxazolidine-3-carboxylate (166 mg, 75%) as a white amorphous solid. MS (ISP): 538.3 ([{$^{37}$Cl$^{35}$Cl}M+NH$_4$]$^+$), 536.2 ([{$^{35}$Cl}M+NH$_4$]$^+$), 521.3 ([{$^{37}$Cl$^{35}$Cl}M+H]$^+$), 519.2 ([{$^{35}$Cl}M+H]$^+$), 465.3 ([{$^{37}$Cl$^{35}$Cl}M+H—C$_4$H$_8$]$^+$), 463.1 ([{$^{35}$Cl}M+H—C$_4$H$_8$]$^+$).

c) N-{4-[2-((S)-2-Amino-4,5-dihydro-oxazol-4-yl)-ethyl]-phenyl}-4-chloro-benzamide The title compound was obtained in analogy to example 1(g)-1(h) starting from (S)-tert-butyl 4-(4-(5,6-dichloro-1-oxo-3,4-dihydroisoquinolin-2(1H)-yl)phenethyl)-2,2-dimethyloxazolidine-3-carboxylate instead of (RS)-4-{4-[3-(4-chloro-phenyl)-ureido]-phenyl}-2,2-dimethyl-oxazolidine-3-carboxylic acid tert-butyl ester. White solid. MS (ISP): 408.3 ([{$^{37}$Cl}M+H]$^+$), 406.3 ([{$^{37}$Cl$^{35}$Cl}M+H]$^+$), 404.2 ([{35Cl}M+H]$^+$).

Example 178

(S)-N-(4-(2-(2-Amino-4,5-dihydrooxazol-4-yl)ethyl)phenyl)-5-ethylpicolinamide

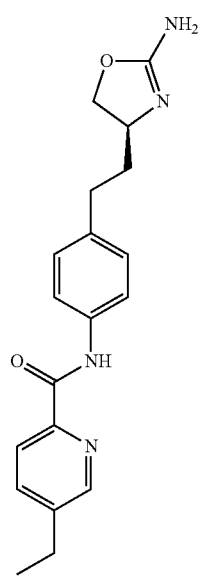

The title compound was obtained in analogy to example 83 starting from 5-ethylpyridine-2-carboxylic acid and (S)-4-[2-(4-amino-phenyl)-ethyl]-4,5-dihydro-oxazol-2-ylamine. White solid. MS (ISP): 339.1 ([M+H]$^+$)

Example 179

(S)-N-(4-(2-(2-Amino-4,5-dihydrooxazol-4-yl)ethyl)phenyl)-2,5-dimethyloxazole-4-carboxamide

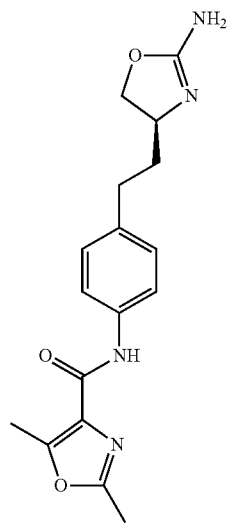 [SMILES: Cc1nc(C(=O)Nc2ccc(CC[C@H]3COC(N)=N3)cc2)c(C)o1]

The title compound was obtained in analogy to example 83 starting from 2,5-dimethyl-1,3-oxazole-4-carboxylic acid and (S)-4-[2-(4-amino-phenyl)-ethyl]-4,5-dihydro-oxazol-2-ylamine. White solid. MS (ISP): 329.2 ([M+H]$^+$)

Example 180

(S)-N-(4-(2-(2-Amino-4,5-dihydrooxazol-4-yl)ethyl)phenyl)-2,4-dimethyloxazole-5-carboxamide

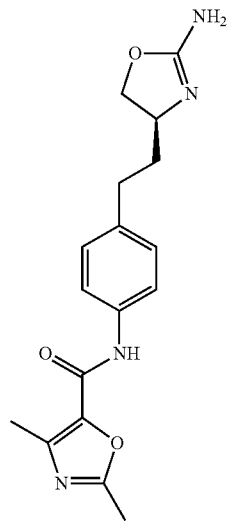 [SMILES: Cc1nc(C)c(C(=O)Nc2ccc(CC[C@H]3COC(N)=N3)cc2)o1]

The title compound was obtained in analogy to example 83 starting from 2,4-dimethyloxazole-5-carboxylic acid and (S)-4-[2-(4-amino-phenyl)-ethyl]-4,5-dihydro-oxazol-2-ylamine. White solid. MS (ISP): 329.1 ([M+H]⁺)

Example 181

(S)-N-(4-(2-(2-Amino-4,5-dihydrooxazol-4-yl)ethyl)phenyl)-2-methyloxazole-4-carboxamide

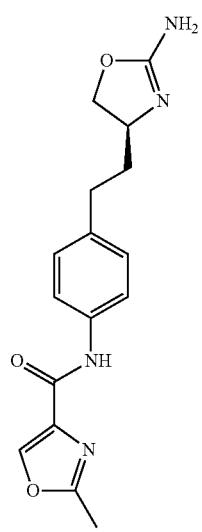 [SMILES: Cc1nc(C(=O)Nc2ccc(CC[C@H]3COC(N)=N3)cc2)co1]

The title compound was obtained in analogy to example 83 starting from 2-methyl-1,3-oxazole-4-carboxylic acid and (S)-4-[2-(4-amino-phenyl)-ethyl]-4,5-dihydro-oxazol-2-ylamine. White solid. MS (ISP): 315.1 ([M+H]⁺)

Example 182

(S)-N-(4-(2-(2-Amino-4,5-dihydrooxazol-4-yl)ethyl)phenyl)-4-methyloxazole-5-carboxamide

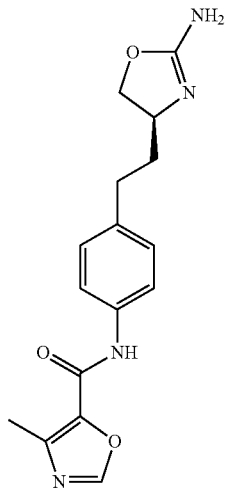 [SMILES: Cc1ncoc1C(=O)Nc1ccc(CC[C@H]2COC(N)=N2)cc1]

The title compound was obtained in analogy to example 83 starting from 4-methyloxazole-5-carboxylic acid and (S)-4-[2-(4-amino-phenyl)-ethyl]-4,5-dihydro-oxazol-2-ylamine. White solid. MS (ISP): 315.1 ([M+H]⁺)

Example 183

(S)-N-(4-(2-(2-Amino-4,5-dihydrooxazol-4-yl)ethyl)phenyl)-2-ethyl-4-methyloxazole-5-carboxamide

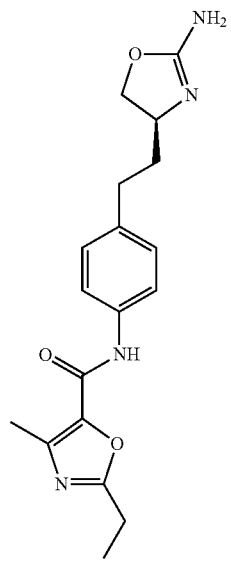 [SMILES: CCc1nc(C)c(C(=O)Nc2ccc(CC[C@H]3COC(N)=N3)cc2)o1]

The title compound was obtained in analogy to example 83 starting from 2-ethyl-4-methyl-1,3-oxazole-5-carboxylic acid and (S)-4-[2-(4-amino-phenyl)-ethyl]-4,5-dihydro-oxazol-2-ylamine. White solid. MS (ISP): 343.2 ([M+H]⁺)

Example 184

(S)-N-(4-(2-(2-Amino-4,5-dihydrooxazol-4-yl)ethyl)phenyl)-2-methylthiazole-4-carboxamide

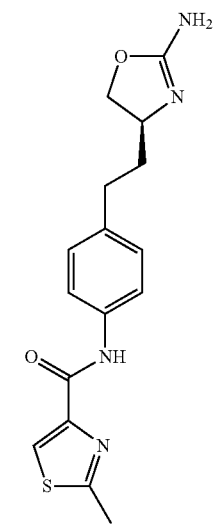 [SMILES: Cc1nc(C(=O)Nc2ccc(CC[C@H]3COC(N)=N3)cc2)cs1]

The title compound was obtained in analogy to example 83 starting from 2-methylthiazole-4-carboxylic acid and (S)-4-[2-(4-amino-phenyl)-ethyl]-4,5-dihydro-oxazol-2-ylamine. White solid. MS (ISP): 331.1 ([M+H]$^+$)

Example 185

(S)-N-(4-(2-(2-Amino-4,5-dihydrooxazol-4-yl)ethyl) phenyl)-5-chloro-3-fluoropicolinamide

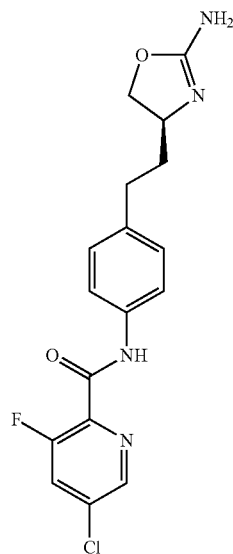

The title compound was obtained in analogy to example 83 starting from 5-chloro-3-fluoro2-pyridinecarboxylic acid and (S)-4-[2-(4-amino-phenyl)-ethyl]-4,5-dihydro-oxazol-2-ylamine. White solid. MS (ISP): 363.2 ([M+H]$^+$)

Example 186

2-{4-[2-((S)-2-Amino-4,5-dihydro-oxazol-4-yl)-ethyl]-phenyl}-6-chloro-2,3-dihydro-isoindol-1-one

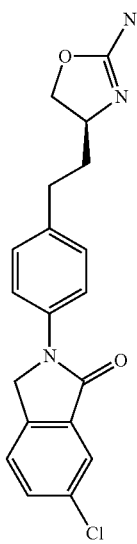

The title compound was obtained in analogy to example 177 starting from (S)-4-[(E)-2-(4-iodo-phenyl)-vinyl]-2,2-dimethyl-oxazolidine-3-carboxylic acid tert-butyl ester and 6-chloro-1-isoindolinone. White solid. 358.1 ([{$^{37}$Cl}M+H]$^+$), 356.1 ([{$^{35}$Cl}M+H]$^+$).

Example 187

(S)-2-(4-(2-(2-Amino-4,5-dihydrooxazol-4-yl)ethyl) phenyl)isoindolin-1-one hydrochloride

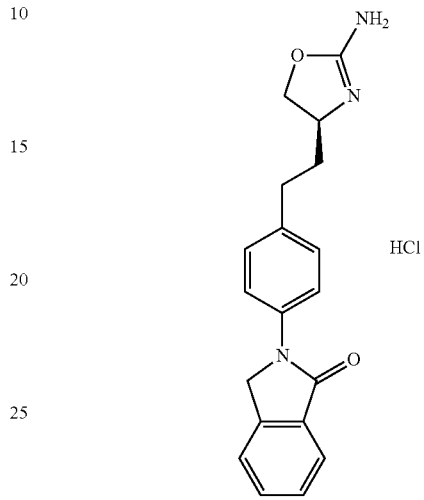

To a stirred solution of 2-{4-[2-((S)-2-amino-4,5-dihydro-oxazol-4-yl)-ethyl]-phenyl}-6-chloro-2,3-dihydro-isoindol-1-one (9 mg) in methanol (3 ml) was added 10% paladium on charcoal (2.7 mg) and the mixture was then stirred under an atmosphere of hydrogen at room temperature for 2 hours. The mixture was then filtered through celite and the filtrate was concentrated in vacuo to afford (S)-2-(4-(2-(2-amino-4,5-dihydrooxazol-4-yl)ethyl)phenyl)isoindolin-1-one hydrochloride (9 mg, 55%) as a white solid. MS (ISP): 322.2 ([M+H]$^+$)

Example 188

(S)-2-(4-(2-(2-Amino-4,5-dihydrooxazol-4-yl)ethyl) phenyl)-3,4-dihydroisoquinolin-1(2H)-one hydrochloride

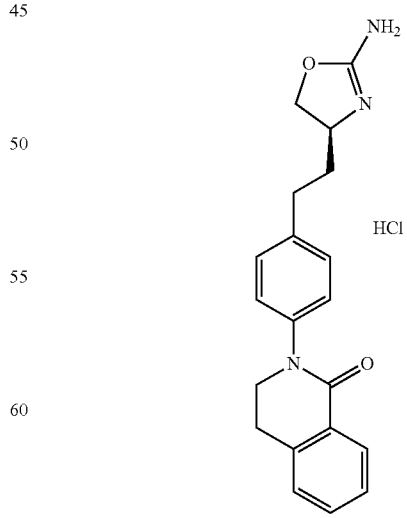

The title compound was obtained in analogy to example 187 starting from (S)-2-(4-(2-(2-amino-4,5-dihydrooxazol- 4-yl)ethyl)phenyl)-5,6-dichloro-3,4-dihydroisoquinolin-1 (2H)-one instead of 2-{4-[2-((S)-2-amino-4,5-dihydro-oxazol-4-yl)-ethyl]-phenyl}-6-chloro-2,3-dihydro-isoindol-1-one. Light yellow solid. MS (ISP): 336.3 ([M+H]$^+$)

Example 189

(S)-N-(4-(2-(2-Amino-4,5-dihydrooxazol-4-yl)ethyl)phenyl)-2-(dimethylamino)-5-isopropylthiazole-4-carboxamide

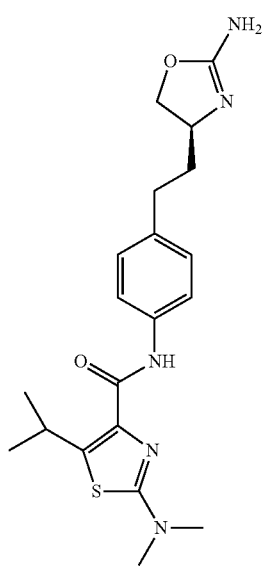 [SMILES: CC(C)c1sc(N(C)C)nc1C(=O)Nc1ccc(CC[C@H]2COC(N)=N2)cc1]

a)
2-(dimethylamino)-5-isopropylthiazole-4-carboxylic acid

Methyl 2-amino-5-isopropylthiazole-4-carboxylate (50 mg) was dissolved in acetonitrile (1 ml) to give a yellow solution. Sodium hydroxide (39.9 mg) and MeI (70.9 mg) were added and the reaction mixture was heated to 60° C. for 1 h. The crude reaction mixture was allowed to cool to RT and concentrated in vacuo. The residue was taken up in HCl 1N and extracted three times with AcOEt. The organic layers were combined, dried over Na$_2$SO$_4$ and concentrated in vacuo to afford title compound as a yellow oil (53 mg)

b) (S)-N-(4-(2-(2-Amino-4,5-dihydrooxazol-4-yl) ethyl)phenyl)-2-(dimethylamino)-5-isopropylthiazole-4-carboxamide The title compound was obtained in analogy to example 83 starting from 2-(dimethylamino)-5-isopropylthiazole-4-carboxylic acid and (S)-4-[2-(4-amino-phenyl)-ethyl]-4,5-dihydro-oxazol-2-ylamine. Light yellow solid. MS (ISP): 402.4 ([M+H]$^+$)

Example 190

(S)-N-(4-(2-(2-Amino-4,5-dihydrooxazol-4-yl)ethyl) phenyl)-2,6-dimethoxypyrimidine-4-carboxamide

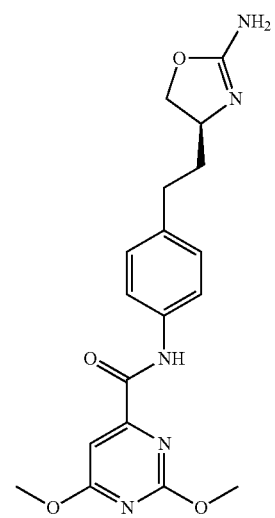 [SMILES: COc1cc(C(=O)Nc2ccc(CC[C@H]3COC(N)=N3)cc2)nc(OC)n1]

The title compound was obtained in analogy to example 83 starting from 2,6-dimethoxypyrimidine-4-carboxylic acid and (S)-4-[2-(4-amino-phenyl)-ethyl]-4,5-dihydro-oxazol-2-ylamine. White solid. MS (ISP): 372.2 ([M+H]$^+$)

Example 191

(S)-N-(4-(2-(2-Amino-4,5-dihydrooxazol-4-yl)ethyl) phenyl)-5-methyloxazole-4-carboxamide

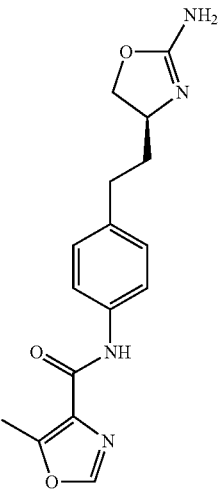 [SMILES: Cc1ocnc1C(=O)Nc1ccc(CC[C@H]2COC(N)=N2)cc1]

The title compound was obtained in analogy to example 83 starting from 5-methyl-1,3-oxazole-4-carboxylic acid and (S)-4-[2-(4-amino-phenyl)-ethyl]-4,5-dihydro-oxazol-2-ylamine. White solid. MS (ISP): 315.1 ([M+H]$^+$)

Example 192

(S)-2-(4-(2-(2-Amino-4,5-dihydrooxazol-4-yl)ethyl)phenyl)-6-chloro-3,4-dihydroisoquinolin-1(2H)-one

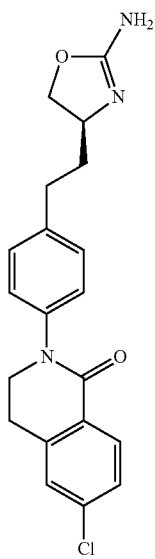 [SMILES: NC1=N[C@@H](CCc2ccc(N3CCc4cc(Cl)ccc4C3=O)cc2)CO1]

The title compound was obtained in analogy to example 177 starting from (S)-4-[(E)-2-(4-iodo-phenyl)-vinyl]-2,2-dimethyl-oxazolidine-3-carboxylic acid tert-butyl ester and 6-chloro-3,4-dihydroisoquinolin-1(2H)-one. White solid. 372.1 ([{$^{37}$Cl}M+H]$^+$), 370.1 ([{$^{35}$Cl}M+H]$^+$).

Example 193

(S)-N-(4-(2-(2-Amino-4,5-dihydrooxazol-4-yl)ethyl)phenyl)-1,5-dimethyl-1H-pyrazole-3-carboxamide

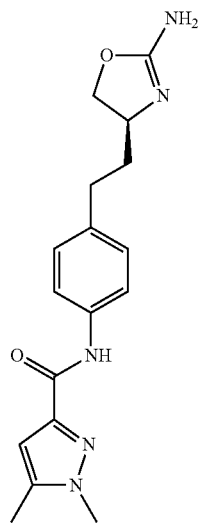 [SMILES: Cc1cc(C(=O)Nc2ccc(CC[C@H]3COC(N)=N3)cc2)nn1C]

The title compound was obtained in analogy to example 83 starting from 1,5-dimethyl-1H-pyrazole-3-carboxylic acid and (S)-4-[2-(4-amino-phenyl)-ethyl]-4,5-dihydro-oxazol-2-ylamine. White solid. MS (ISP): 328.2 ([M+H]$^+$)

Example 194

(S)-N-(4-(2-(2-Amino-4,5-dihydrooxazol-4-yl)ethyl)phenyl)-4-chloro-1-methyl-1H-pyrazole-3-carboxamide

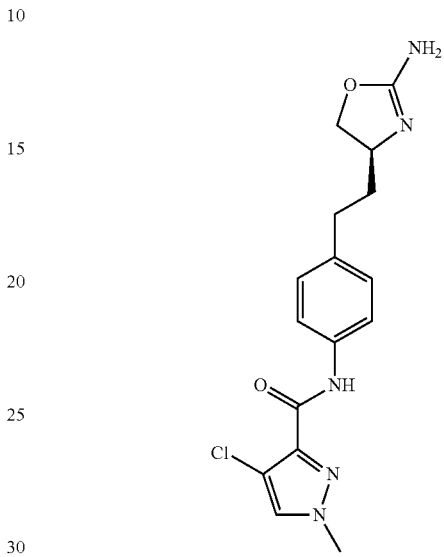

The title compound was obtained in analogy to example 83 starting from 4-chloro-1-methyl-1H-pyrazole-3-carboxylic acid and (S)-4-[2-(4-amino-phenyl)-ethyl]-4,5-dihydro-oxazol-2-ylamine. White solid. MS (ISP): 348.2 ([M+H]$^+$)

Example 195

(S)-N-(4-(2-(2-Amino-4,5-dihydrooxazol-4-yl)ethyl)phenyl)-1-(difluoromethyl)-1H-pyrazole-3-carboxamide

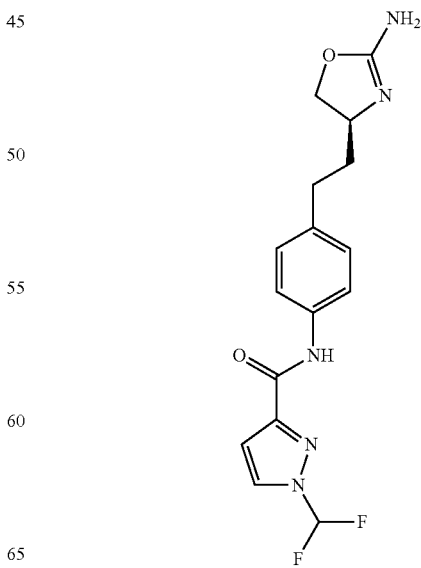

The title compound was obtained in analogy to example 83 starting from 1-(difluoromethyl)-1H-pyrazole-3-carboxylic acid and (S)-4-[2-(4-amino-phenyl)-ethyl]-4,5-dihydro-oxazol-2-ylamine. White solid. MS (ISP): 350.3 ([M+H]$^+$)

Example 196

(S)-N-(4-(2-(2-Amino-4,5-dihydrooxazol-4-yl)ethyl)phenyl)-1-methyl-1H-pyrazole-3-carboxamide

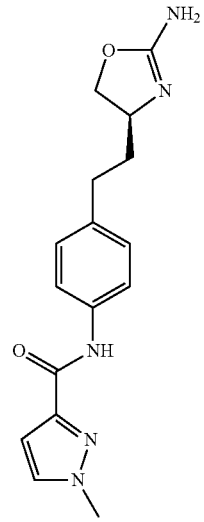 [SMILES: Cn1ccc(C(=O)Nc2ccc(CC[C@H]3COC(N)=N3)cc2)n1]

The title compound was obtained in analogy to example 83 starting from 1-methyl-1H-pyrazole-3-carboxylic acid and (S)-4-[2-(4-amino-phenyl)-ethyl]-4,5-dihydro-oxazol-2-ylamine. White solid. MS (ISP): 314.0 ([M+H]$^+$)

Example 197

(S)-N-(4-(2-(2-Amino-4,5-dihydrooxazol-4-yl)ethyl)phenyl)-2-tert-butylisonicotinamide

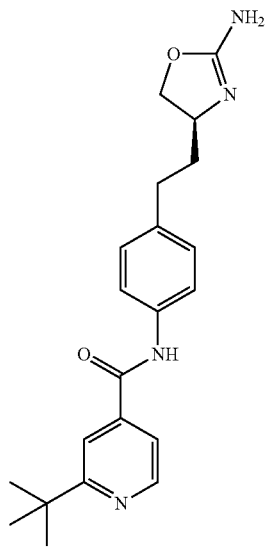 [SMILES: CC(C)(C)c1cc(C(=O)Nc2ccc(CC[C@H]3COC(N)=N3)cc2)ccn1]

The title compound was obtained in analogy to example 83 starting from 2-tert-butylisonicotinic acid and (S)-4-[2-(4-amino-phenyl)-ethyl]-4,5-dihydro-oxazol-2-ylamine. White solid. MS (ISP): 367.2 ([M+H]$^+$)

Example 198

(S)-N-(4-(2-(2-Amino-4,5-dihydrooxazol-4-yl)ethyl)phenyl)-2-isopropylisonicotinamide

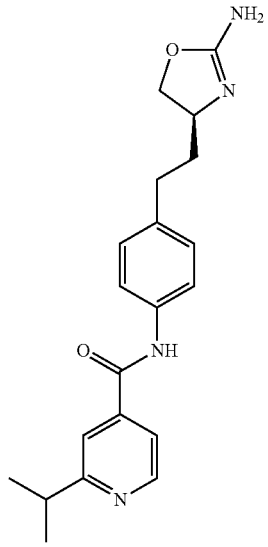 [SMILES: CC(C)c1cc(C(=O)Nc2ccc(CC[C@H]3COC(N)=N3)cc2)ccn1]

The title compound was obtained in analogy to example 83 starting from 2-isopropylisonicotinic acid and (S)-4-[2-(4-amino-phenyl)-ethyl]-4,5-dihydro-oxazol-2-ylamine. White solid. MS (ISP): 353.3 ([M+H]$^+$)

Example 199

(S)-N-(4-(2-(2-Amino-4,5-dihydrooxazol-4-yl)ethyl)phenyl)-2,4'-bipyridine-4-carboxamide

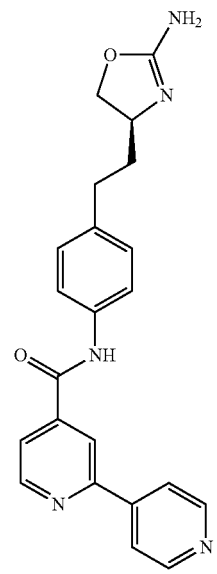 [SMILES: NC1=N[C@@H](CCc2ccc(NC(=O)c3ccnc(-c4ccncc4)c3)cc2)CO1]

The title compound was obtained in analogy to example 83 starting from 2,4'-bipyridine-4-carboxylic acid and (S)-4-[2-(4-amino-phenyl)-ethyl]-4,5-dihydro-oxazol-2-ylamine. White solid. MS (ISP): 388.2 ([M+H]$^+$)

Example 200

(R)—N-(4-(2-(2-Amino-4,5-dihydrooxazol-4-yl)ethyl)phenyl)-5-methylpyrazine-2-carboxamide

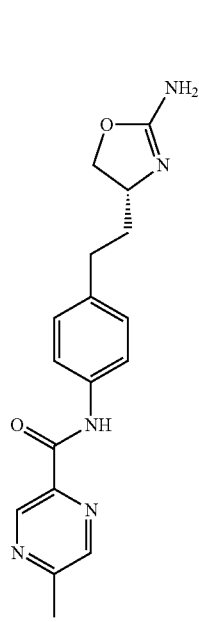 [SMILES: Cc1cnc(C(=O)Nc2ccc(CC[C@@H]3COC(N)=N3)cc2)cn1]

a) (R)-2,2-Dimethyl-4-[(E)-2-(4-nitro-phenyl)-vinyl]-oxazolidine-3-carboxylic acid tert-butyl ester The title compound was obtained in analogy to example 3(a) starting from (4-nitro-benzyl)-phosphonic acid diethyl ester (CAS 2609-49-6) instead of (4-iodo-benzyl)-phosphonic acid diethyl ester and (S)-4-formyl-2,2-dimethyl-oxazolidine-3-carboxylic acid tert-butyl ester (CAS 102308-32-7) instead of (R)-4-formyl-2,2-dimethyl-oxazolidine-3-carboxylic acid tert-butyl ester.

b) (R)-4-[2-(4-Amino-phenyl)-ethyl]-4,5-dihydro-oxazol-2-ylamine

The title compound was obtained in analogy to example 83 steps a)-c) starting from (R)-2,2-dimethyl-4-[(E)-2-(4-nitro-phenyl)-vinyl]-oxazolidine-3-carboxylic acid tert-butyl ester instead of (S)-2,2-dimethyl-4-[(E)-2-(4-nitro-phenyl)-vinyl]-oxazolidine-3-carboxylic acid tert-butyl ester.

c) (R)—N-(4-(2-(2-Amino-4,5-dihydrooxazol-4-yl)ethyl)phenyl)-5-methylpyrazine-2-carboxamide The title compound was obtained in analogy to example 83 step d) starting from 5-methylpyrazine-2-carboxylic acid and (R)-4-[2-(4-amino-phenyl)-ethyl]-4,5-dihydro-oxazol-2-ylamine. White solid. MS (ISP): 326.2 ([M+H]$^+$)

Example 201

(S)-N-(4-(2-(2-Amino-4,5-dihydrooxazol-4-yl)ethyl)phenyl)-5-methylthiophene-2-carboxamide

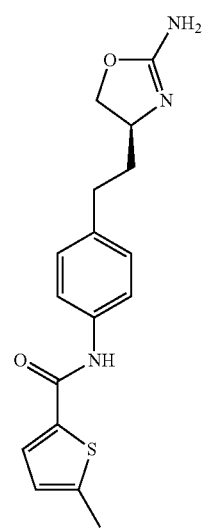 [SMILES: Cc1ccc(C(=O)Nc2ccc(CC[C@H]3COC(N)=N3)cc2)s1]

The title compound was obtained in analogy to example 83 starting from 5-methyl-thiophene-2-carboxylic acid and (S)-4-[2-(4-amino-phenyl)-ethyl]-4,5-dihydro-oxazol-2-ylamine. White solid. MS (ISP): 330.1 ([M+H]$^+$)

Example 202

(S)-N-(4-(2-(2-Amino-4,5-dihydrooxazol-4-yl)ethyl)phenyl)-4,5-dimethylthiophene-2-carboxamide

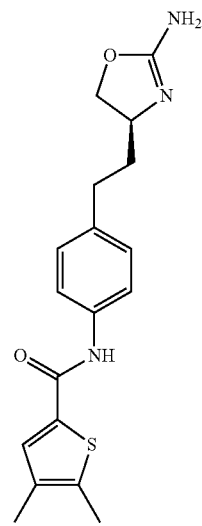 [SMILES: Cc1cc(C(=O)Nc2ccc(CC[C@H]3COC(N)=N3)cc2)sc1C]

The title compound was obtained in analogy to example 83 starting from 4,5-dimethyl-thiophene-2-carboxylic acid and (S)-4-[2-(4-amino-phenyl)-ethyl]-4,5-dihydro-oxazol-2-ylamine. White solid. MS (ISP): 344.1 ([M+H]+)

Example 203

2-Ethyl-6-methoxy-pyrimidine-4-carboxylic acid {4-[2-((S)-2-amino-4,5-dihydro-oxazol-4-yl)-ethyl]-phenyl}-amide

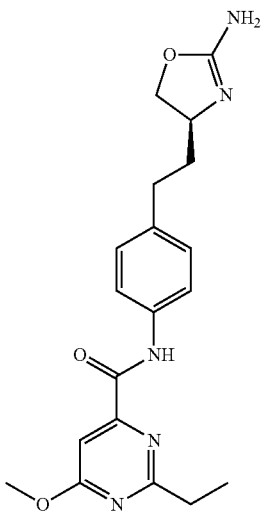

a) 2-Chloro-6-methoxy-pyrimidine-4-carboxylic acid methyl ester

Methyl 2,6-dichloropyrimidine-4-carboxylate (1 g) was combined with MeOH (20 ml) to give a light yellow solution. Potassium carbonate (668 mg) was added and the reaction mixture was stirred at RT for 6 h. The solvent was concentrated in vacuo and the residue was stirred in $Et_2O$. The suspension was filtered and the filtrate was concentrated in vacuo to afford title compound as a white solid. MS (ISP): 203.3 ([M+H]+)

b) 6-Methoxy-2-vinyl-pyrimidine-4-carboxylic acid methyl ester

2-Chloro-6-methoxy-pyrimidine-4-carboxylic acid methyl ester (300 mg) was combined with DMF (4 ml) to give a colorless solution. Argon was bubbled through the solution for 15 min. Cu(I)I (14.1 g), vinyltributylstannane (563 g) and tetrakis(triphenylphosphine)Pd (171 mg) were added successively. The reaction mixture was stirred at 100° C. overnight and then allowed to cool to RT before being poured into sat $NaHCO_3$ and extracted 3 times with EtOAc. The organic layers were combined, washed with sat NaCl, dried over $Na_2SO4$ and concentrated in vacuo. The crude material was purified by flash chromatography (silica gel, 0% to 20% EtOAc in heptane). The crude material was purified by flash chromatography (silica gel, 0% to 20% EtOAc in heptane) to give title compound a a light yellow solid. MS (ISP) 195.1 ([M+H]

c) 2-Ethyl-6-methoxy-pyrimidine-4-carboxylic acid methyl ester

6-Methoxy-2-vinyl-pyrimidine-4-carboxylic acid methyl ester (130 mg) was combined with MeOH (5 ml) to give a light yellow solution. Pd/C 10% (13 mg) was added and the reaction mixture was hydrogenated with a balloon at RT for 4 hours. The reaction mixture was filtered and the filtrate was concentrated in vacuo to give title compound as an off white solid. MS (ISP) 197.1 ([M+H]

d) 2-Ethyl-6-methoxy-pyrimidine-4-carboxylic acid

2-Ethyl-6-methoxy-pyrimidine-4-carboxylic acid was obtained from 2-ethyl-6-methoxy-pyrimidine-4-carboxylic acid methyl ester and lithium hydroxide in analogy to example 48 step a) and was used directly for the next step. MS (ISP) 181.1 ([M+H]

e) 2-Ethyl-6-methoxy-pyrimidine-4-carboxylic acid {4-[2-((S)-2-amino-4,5-dihydro-oxazol-4-yl)-ethyl]-phenyl}-amide The title compound was obtained in analogy to example 83 starting from 2-ethyl-6-methoxy-pyrimidine-4-carboxylic acid and (S)-4-[2-(4-amino-phenyl)-ethyl]-4,5-dihydro-oxazol-2-ylamine. White solid. MS (ISP): 370.2 ([M+H]+)

Example 204

(S)-N-(4-(2-(2-Amino-4,5-dihydrooxazol-4-yl)ethyl)phenyl)-5-methyl-1,2,4-oxadiazole-3-carboxamide

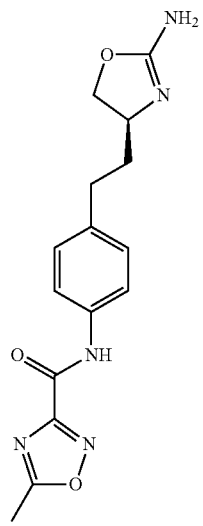 [SMILES: Cc1nc(C(=O)Nc2ccc(CC[C@H]3COC(N)=N3)cc2)no1]

The title compound was obtained in analogy to example 83 starting from 5-methyl-1,2,4-oxadiazole-3-carboxylic acid and (S)-4-[2-(4-amino-phenyl)-ethyl]-4,5-dihydro-oxazol-2-ylamine. White solid. MS (ISP): 316.1 ([M+H]+)

Example 205

N-(4-(2-((4S,5S)-2-Amino-5-methyl-4,5-dihydrooxazol-4-yl)ethyl)phenyl)-4-chlorobenzamide

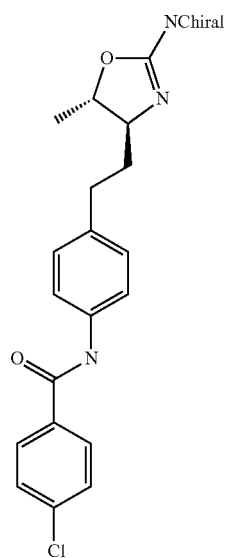

The title compound was obtained in analogy to example 218 using 4-chloro-benzoic acid in place of 5-ethoxypyrazine-2-carboxylic acid in step (j). White solid. MS (ISP) 360.1 ([$\{^{37}Cl\}$M+H]$^+$), 358.1 ([$\{^{35}Cl\}$M+H]$^+$).

Example 206

N-(4-(2-((4S,5R)-2-Amino-5-methyl-4,5-dihydrooxazol-4-yl)ethyl)phenyl)-4-chlorobenzamide

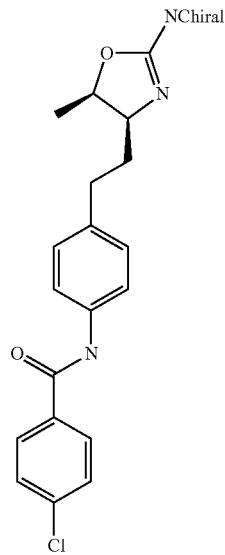

The title compound was obtained in analogy to example 218 using (4S,5R)-4-[2-(4-bromo-phenyl)-ethyl]-2,2,5-trimethyl-oxazolidine-3-carboxylic acid tert-butyl ester in place of (4S,5S)-4-[2-(4-bromo-phenyl)-ethyl]-2,2,5-trimethyl-oxazolidine-3-carboxylic acid tert-butyl ester in step (h) and then 4-chloro-benzoic acid in place of 5-ethoxypyrazine-2-carboxylic acid in step (j). White solid. MS (ISP) 360.1 ([$\{^{37}Cl\}$M+H]$^+$), 358.1 ([$\{^{35}Cl\}$M+H]$^+$).

Example 207

2-Isopropyl-6-methoxy-pyrimidine-4-carboxylic acid {4-[2-((S)-2-amino-4,5-dihydro-oxazol-4-yl)-ethyl]-phenyl}-amide

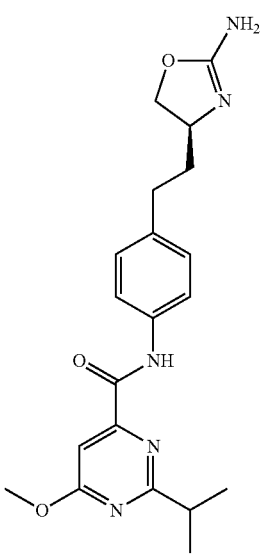 [SMILES: COc1cc(C(=O)Nc2ccc(CC[C@H]3COC(N)=N3)cc2)nc(C(C)C)n1]

a) 2-Isopropyl-6-methoxy-pyrimidine-4-carboxylic acid

2-Isopropyl-6-methoxy-pyrimidine-4-carboxylic acid was obtained in analogy to example 203 starting from 2-(tributyl-stannyl)propene and 2-chloro-6-methoxy-pyrimidine-4-carboxylic acid methyl ester in step b). White solid. MS (ISP): 195.0 ([M+H]$^+$)

b) 2-Isopropyl-6-methoxy-pyrimidine-4-carboxylic acid {4-[2-((S)-2-amino-4,5-dihydro-oxazol-4-yl)-ethyl]-phenyl}-amide The title compound was obtained in analogy to example 83 starting from 2-isopropyl-6-methoxy-pyrimidine-4-carboxylic acid and (S)-4-[2-(4-amino-phenyl)-ethyl]-4,5-dihydro-oxazol-2-ylamine. White solid. MS (ISP): 384.2 ([M+H]$^+$)

Example 208

(S)-N-(4-(2-(2-Amino-4,5-dihydrooxazol-4-yl)ethyl)phenyl)-5-ethylpyrazine-2-carboxamide

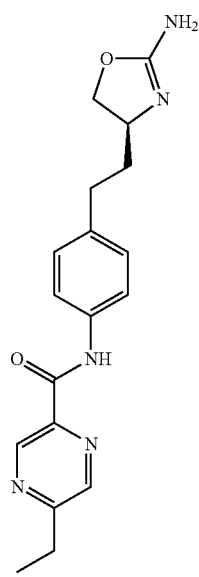

The title compound was obtained in analogy to example 83 starting from 5-ethylpyrazine-2-carboxylic acid and (S)-4-[2-(4-amino-phenyl)-ethyl]-4,5-dihydro-oxazol-2-ylamine. White solid. MS (ISP): 340.2 ([M+H]$^+$)

Example 209

(S)-N-(4-(2-(2-Amino-4,5-dihydrooxazol-4-yl)ethyl)phenyl)-4-cyclopropyl-2-(trifluoromethyl)pyrimidine-5-carboxamide

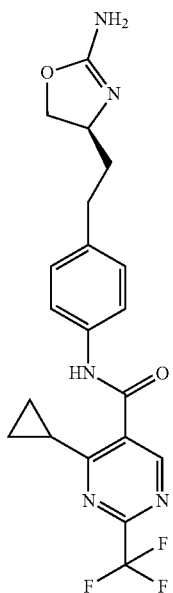 [SMILES: NC1=N[C@@H](CCc2ccc(NC(=O)c3cnc(C(F)(F)F)nc3C3CC3)cc2)CO1]

The title compound was obtained in analogy to example 83 starting from 4-cyclopropyl-2-(trifluoromethyl)pyrimidine-5-carboxylic acid and (S)-4-[2-(4-amino-phenyl)-ethyl]-4,5-dihydro-oxazol-2-ylamine. White solid. MS (ISP): 420.2 ([M+H]$^+$)

Example 210

2-Methoxy-4-trifluoromethyl-pyrimidine-5-carboxylic acid {4-[2-((S)-2-amino-4,5-dihydro-oxazol-4-yl)-ethyl]-phenyl}-amide

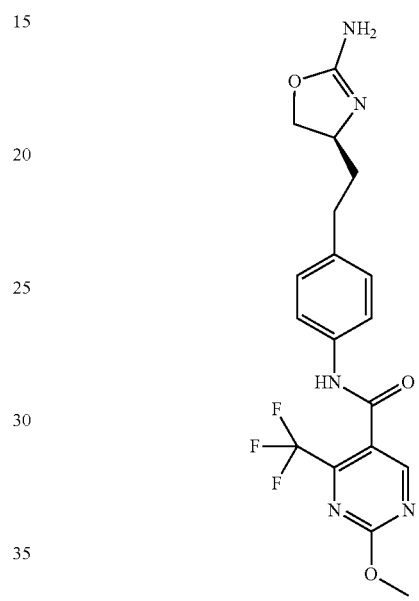

a) Methyl 2-methoxy-4-(trifluoromethyl)pyrimidine-5-carboxylate

Methyl 2-chloro-4-(trifluoromethyl)pyrimidine-5-carboxylate (1128 mg) was dissolved in MeOH (23 ml) before addition of sodium methoxide (380 mg), the reaction mixture was stirred for 2 hours in a sealed tube at 110° C. The solvent was evaporated, the product dissolved in ethyl acetate and washed with water, the organics were dried over Na$_2$SO$_4$, and concentrated in vacuo to afford title compound as a colourless oil. MS (ISP) 237.0 ([M+H]$^+$)

2-Methoxy-4-(trifluoromethyl)pyrimidine-5-carboxylic acid

2-Methoxy-4-(trifluoromethyl)pyrimidine-5-carboxylic acid was obtained from methyl 2-methoxy-4-(trifluoromethyl)pyrimidine-5-carboxylate and lithium hydroxide in analogy to example 48 step a) and was used directly for the next step. White solid. MS (ISP) 223.1 ([M+H]$^+$)

c) 2-M ethoxy-4-trifluoromethyl-pyrimidine-5-carboxylic acid {4-[2-((S)-2-amino-4,5-dihydro-oxazol-4-yl)-ethyl]-phenyl}-amide The title compound was obtained in analogy to example 83 starting from 2-methoxy-4-(trifluoromethyl)pyrimidine-5- carboxylic acid and (S)-4-[2-(4-amino-phenyl)-ethyl]-4,5-dihydro-oxazol-2-ylamine. White solid. MS (ISP): 410.2 ([M+H]$^+$)

Example 211

(S)-N-(4-(2-(2-Amino-4,5-dihydrooxazol-4-yl)ethyl)phenyl)-6-ethylpyrazine-2-carboxamide

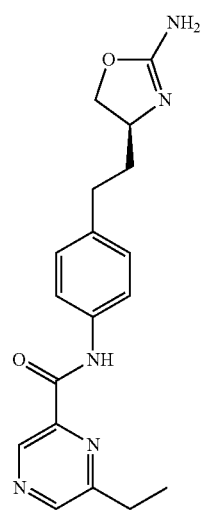 [SMILES: CCc1cncc(C(=O)Nc2ccc(CC[C@H]3COC(N)=N3)cc2)n1]

The title compound was obtained in analogy to example 83 starting from 6-ethylpyrazine-2-carboxylic acid and (S)-4-[2-(4-amino-phenyl)-ethyl]-4,5-dihydro-oxazol-2-ylamine. White solid. MS (ISP): 340.1 ([M+H]$^+$)

Example 212

(S)-N-(4-(2-(2-Amino-4,5-dihydrooxazol-4-yl)ethyl)phenyl)-5-(methylsulfonyl)picolinamide

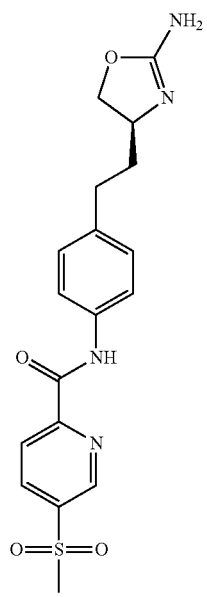 [SMILES: CS(=O)(=O)c1ccc(C(=O)Nc2ccc(CC[C@H]3COC(N)=N3)cc2)nc1]

The title compound was obtained in analogy to example 83 starting from 5-methylsulfonyl)-2-pyridinecarboxylic acid and (S)-4-[2-(4-amino-phenyl)-ethyl]-4,5-dihydro-oxazol-2-ylamine. White solid. MS (ISP): 389.2 ([M+H]$^+$)

Example 213

(S)-N-(4-(2-(2-Amino-4,5-dihydrooxazol-4-yl)ethyl)phenyl)-5-ethyloxazole-4-carboxamide

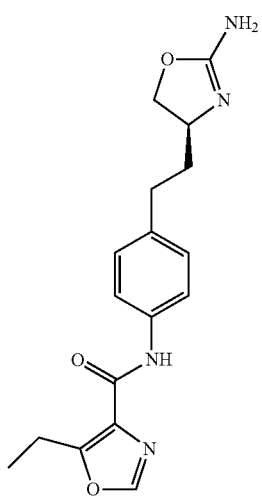 [SMILES: CCc1ocnc1C(=O)Nc1ccc(CC[C@H]2COC(N)=N2)cc1]

The title compound was obtained in analogy to example 83 starting from 5-ethyl-1,3-oxazole-4-carboxylic acid and (S)-4-[2-(4-amino-phenyl)-ethyl]-4,5-dihydro-oxazol-2-ylamine. White solid. MS (ISP): 329.2 ([M+H]$^+$)

Example 214

(S)-N-(4-(2-(2-Amino-4,5-dihydrooxazol-4-yl)ethyl)phenyl)-5-cyclopropyloxazole-4-carboxamide

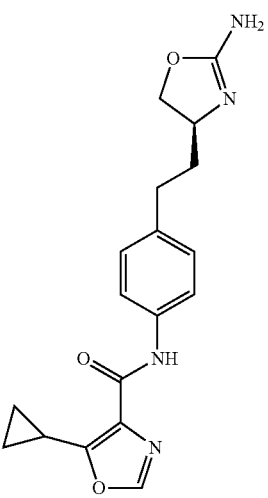 [SMILES: NC1=N[C@@H](CCc2ccc(NC(=O)c3ncoc3C3CC3)cc2)CO1]

The title compound was obtained in analogy to example 83 starting from 5-cyclopropyl-1,3-oxazole-4-carboxylic acid and (S)-4-[2-(4-amino-phenyl)-ethyl]-4,5-dihydro-oxazol-2-ylamine. White solid. MS (ISP): 341.1 ([M+H]+)

Example 215

(S)-N-(4-(2-(2-Amino-4,5-dihydrooxazol-4-yl)ethyl)phenyl)-5-isopropyloxazole-4-carboxamide

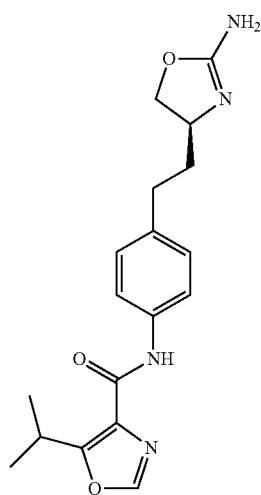 [SMILES: CC(C)c1ocnc1C(=O)Nc1ccc(CC[C@H]2COC(N)=N2)cc1]

The title compound was obtained in analogy to example 83 starting from 5-isopropyl-1,3-oxazole-4-carboxylic acid and (S)-4-[2-(4-amino-phenyl)-ethyl]-4,5-dihydro-oxazol-2-ylamine. White solid. MS (ISP): 343.2 ([M+H]+)

Example 216

(S)-N-(4-(2-(2-Amino-4,5-dihydrooxazol-4-yl)ethyl)phenyl)-2-methyl-5-(trifluoromethyl)oxazole-4-carboxamide

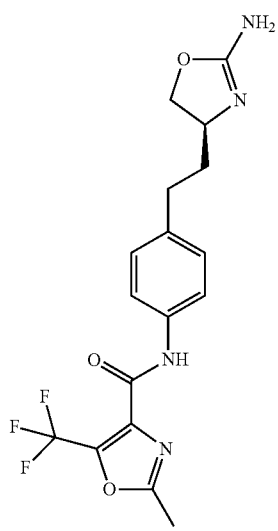 [SMILES: Cc1nc(C(=O)Nc2ccc(CC[C@H]3COC(N)=N3)cc2)c(C(F)(F)F)o1]

The title compound was obtained in analogy to example 83 starting from 2-methyl-5-(trifluoromethyl)oxazole-4-carboxylic acid and (S)-4-[2-(4-amino-phenyl)-ethyl]-4,5-dihydro-oxazol-2-ylamine. White solid. MS (ISP): 383.1 ([M+H]+)

Example 217

(S)-N-(4-(2-(2-Amino-4,5-dihydrooxazol-4-yl)ethyl)phenyl)-2-ethyloxazole-4-carboxamide

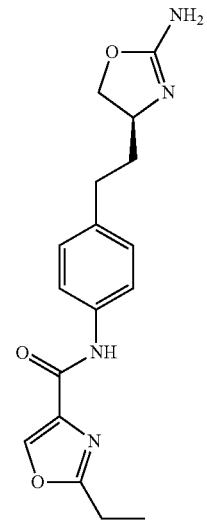 [SMILES: CCc1nc(C(=O)Nc2ccc(CC[C@H]3COC(N)=N3)cc2)co1]

The title compound was obtained in analogy to example 83 starting from 2-ethyl-1,3-oxazole-4-carboxylic acid and (S)-4-[2-(4-amino-phenyl)-ethyl]-4,5-dihydro-oxazol-2-ylamine. White solid. MS (ISP): 329.2 ([M+H]+)

Example 218

5-Ethoxy-pyrazine-2-carboxylic acid {4-[2-((4S,5S)-2-amino-5-methyl-4,5-dihydro-oxazol-4-yl)-ethyl]-phenyl}-amide

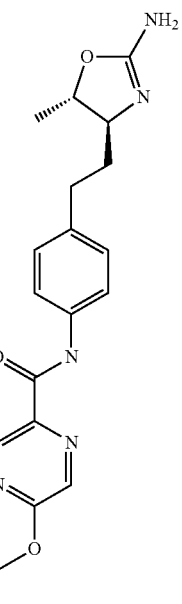

a) (S,E)-tert-Butyl 4-(4-bromostyryl)-2,2-dimethyloxazolidine-3-carboxylate

The title compound was obtained in analogy to example 3(a) using (4-bromo-benzyl)-phosphonic acid diethyl ester instead of (4-iodo-benzyl)-phosphonic acid diethyl ester. Yellow solid. MS (ISP): 284.0 ([{$^{81}$Br}M+H—C$_4$H$_8$—CO$_2$]$^+$), 282.0 ([{$^{79}$Br} M+H—C$_4$H$_8$—CO$_2$]$^+$).

b) (E)-(S)-2-Amino-4-(4-bromo-phenyl)-but-3-en-1-ol

To a solution of (S,E)-tert-butyl 4-(4-bromostyryl)-2,2-dimethyloxazolidine-3-carboxylate (13 g) in acetonitrile (30 ml) were added sequentially water (35 ml) and a solution of trifluoroacetic acid (18.3 ml) in water (50 ml). The mixture was heated at 80° C. for 3 hours. The mixture was then cooled to room temperature and diluted with ethyl acetate/THF (1:1). The resulting mixture was washed sequentially with 1 N aq. sodium hydroxide solution and saturated brine, the phases were then separated and the organic phase was dried over sodium sulphate and concentrated in vacuo. The residue was triturated in diethyl ether (40 ml) and the resulting crystals were collected by filtration to afford (E)-(S)-2-amino-4-(4-bromo-phenyl)-but-3-en-1-ol (5.59 g, 68%) as a brown solid. The filtrate was concentrated in vacuo and the residue was purified by column chromatography (SiO$_2$; gradient: 0-30% MeOH in dichloromethane) to afford a further amount of (E)-(S)-2-amino-4-(4-bromo-phenyl)-but-3-en-1-ol (2.21 g, 27%) as a brown solid. MS (ISP): 227.1 ([{$^{81}$Br}M+H—NH$_3$]$^+$), 225.1 ([{$^{79}$Br} M+H—NH$_3$]$^+$).

c) [(E)-(S)-3-(4-Bromo-phenyl)-1-hydroxymethyl-allyl]-carbamic acid tert-butyl ester (E)-(S)-2-amino-4-(4-bromo-phenyl)-but-3-en-1-ol (7.8 g) and N,N-diisopropylethylamine (11.1 ml) were combined with THF (150 ml) to give a colourless solution. The reaction mixture was cooled to 0° C. and di-tert-butyl carbonate (7.17 g) was added. The reaction mixture was stirred at room temperature overnight to afford a yellow solution. The reaction mixture was then poured into EtOAc and washed sequentially with 1 M aq. HCl, 1 M aq. NaOH and saturated brine. The organic layer was dried over Na2SO4, filtered, and the filtrate was then stirred over charcoal (2 g) for 30 min. The mixture was then filtered through celite and the filtrate was concentrated in vacuo to afford [(E)-(S)-3-(4-bromo-phenyl)-1-hydroxymethyl-allyl]-carbamic acid tert-butyl ester as an off-white solid (10.8 g, 98%). MS (ISP): 344.0 ([{$^{81}$Br}M+H]$^+$), 342.0 ([{$^{79}$Br} M+H]$^+$), 287.9 ([{$^{81}$Br}M+H—C$_4$H$_8$]$^+$), 286.0 ([{$^{79}$Br} M+H—C$_4$H$_8$]$^+$).

d) [(S)-3-(4-Bromo-phenyl)-1-hydroxymethyl-propyl]-carbamic acid tert-butyl ester To a solution of [(E)-(S)-3-(4-bromo-phenyl)-1-hydroxymethyl-allyl]-carbamic acid tert-butyl ester (14.7 g) in methanol (150 ml) was added 10% Pt/C (1.68 g) and the resulting mixture was stirred under a H$_2$ balloon at room temperature for 3 hours (whereby the reaction progress was checked continuously by $^1$H NMR). The reaction mixture was filtered through celite and the filtrate was concentrated in vacuo to afford [(S)-3-(4-bromo-phenyl)-1-hydroxymethyl-propyl]-carbamic acid tert-butyl ester as a yellow solid (11.5 g, 78%). MS (ISP): 346.0 ([{$^{81}$Br}M+H]$^+$), 344.0 ([{$^{79}$Br} M+H]$^+$), 289.9 ([{$^{81}$Br}M+H—C$_4$H$_8$]$^+$), 288.0 ([{$^{79}$Br} M+H—C$_4$H$_8$]$^+$), 246.1 ([{$^{81}$Br}M+H—C$_4$H$_8$—CO$_2$]$^+$), 244.1 ([{$^{79}$Br} M+H—C$_4$H$_8$—CO$_2$]$^+$).

e) [(S)-3-(4-Bromo-phenyl)-1-formyl-propyl]-carbamic acid tert-butyl ester

To a solution of [(S)-3-(4-bromo-phenyl)-1-hydroxymethyl-propyl]-carbamic acid tert-butyl ester (11.5 g) and triethylamine (27.9 ml) in DMSO (70 ml) was added dropwise sulfur trioxide-pyridine complex (16.0 g) while the reaction mixture was cooled in a ice bath. The mixture was then stirred at room temperature for 30 min to afford a yellow solution. The reaction mixture was poured into EtOAc and extracted sequentially with water and with saturated brine. The organic layer was dried over Na2SO4 and concentrated in vacuo. The residue was purified by column chromatography (silica gel, heptane/EtOAc 3/1) to afford [(S)-3-(4-bromo-phenyl)-1-formyl-propyl]-carbamic acid tert-butyl ester as a yellow oil (7.3 g, 64%). MS (EI): 343 ([{$^{81}$Br}M]$^+$), 341 ([{$^{79}$Br} M]$^+$), 287 ([{$^{81}$Br}M-C$_4$H$_8$]$^+$), 285 ([{$^{79}$Br} M-C$_4$H$_8$]$^+$), 214 ([{$^{81}$Br}M-C$_4$H$_8$—CO$_2$]$^+$), 212 ([{$^{79}$Br} M-C$_4$H$_8$—CO$_2$]$^+$), 171, 169, 103, 57 ([C$_4$H$_9$]$^+$).

f) {(1S,2RS)-1-[2-(4-Bromo-phenyl)-ethyl]-2-hydroxy-propyl}-carbamic acid tert-butyl ester To a stirred, cooled solution of [(S)-3-(4-bromo-phenyl)-1-formyl-propyl]-carbamic acid tert-butyl ester (7.3 g) in THF (40 ml) and Et2O (30 ml) at 0° C. was added dropwise over 30 min a solution of methylmagnesium bromide (20.0 ml, 3 M solution in Et2O). The reaction mixture was then stirred at room temperature for 4 hours before being quenched by dropwise addition of water (gas formation!). The reaction mixture was then poured into EtOAc, the layers were separated and the organic layer was washed sequentially with diluted aq. HCl (pH 5) and saturated brine, then dried over Na2SO4 and concentrated in vacuo. The residue was purified by flash chromatography (silica gel, gradient: 0% to 80% EtOAc in hexane) to afford {(1S,2RS)-1-[2-(4-bromo-phenyl)-ethyl]-2-hydroxy-propyl}-carbamic acid tert-butyl ester as a colourless amorphous solid comprising a mixture of epimers (5.1 g, 66%). MS (EI): 303 ([{$^{81}$Br}M-C$_4$H$_8$]$^+$), 301 ([{$^{79}$Br} M-C$_4$H$_8$]$^+$), 258([{$^{81}$Br}M-C$_4$H$_8$—CO$_2$H]$^+$), 256 ([{$^{79}$Br} M-C$_4$H$_8$—CO$_2$H]$^+$), 214, 212, 171, 169, 57 ([C$_4$H$_9$]$^+$).

g) (4S,5S)-4-[2-(4-Bromo-phenyl)-ethyl]-2,2,5-trimethyl-oxazolidine-3-carboxylic acid tert-butyl ester and (4S,5R)-4-[2-(4-Bromo-phenyl)-ethyl]-2,2,5-trimethyl-oxazolidine-3-carboxylic acid tert-butyl ester {(1S,2RS)-1-[2-(4-bromo-phenyl)-ethyl]-2-hydroxy-propyl}-carbamic acid tert-butyl ester (5.07 g), p-toluenesulfonic acid monohydrate (538 mg) and 2,2-dimethoxypropane (26.1 ml) were combined with CH2Cl2 (300 ml) to give a colourless solution. The reaction mixture was stirred at room temperature overnight before being washed with sat. aq. NaHCO3 solution. The layers were separated and the organic layer was dried over Na2SO4 and concentrated in vacuo. The residue was purified by flash chromatography (silica gel, gradient: 0% to 25% EtOAc in hexane) to afford (4S,5S)-4-[2-(4-bromo-phenyl)-ethyl]-2,2,5-trimethyl-oxazolidine-3-carboxylic acid tert-butyl ester as a yellow oil (2.85 g, 51%, fractions eluting first) and (4S,5R)-4-[2-(4-bromo-phenyl)-ethyl]-2,2,5-trimethyl-oxazolidine-3-carboxylic acid tert-butyl ester as a yellow oil (475 mg, 8%, fractions eluting last).

h) (4S,5S)-4-{2-[4-(Benzhydrylidene-amino)-phenyl]-ethyl}-2,2,5-trimethyl-oxazolidine-3-carboxylic acid tert-butyl ester To a solution of (4S,5S)-4-[2-(4-bromo-phenyl)-ethyl]-2,2,5-trimethyl-oxazolidine-3-carboxylic acid tert-butyl ester (3.13 g) in toluene (30 ml) were added diphenylmethanimine (1.71 g) and sodium tert-butoxide (1.06 g). The reaction mixture was degassed by bubbling argon through the mixture for several minutes. BINAP (489 mg) and Pd2(dba)3 (216 mg) were then added and the reaction mixture was stirred at 100° C. for 20 h. The reaction mixture was then cooled to room temperature, poured into EtOAc, and extracted with water. The organic layer was separated, dried over Na2SO4, and concentrated in vacuo. The residue was purified by flash chromatography (silica gel, gradient: 0% to 30% EtOAc in hexane) to afford (4S,5S)-4-{2-[4-(benzhydrylidene-amino)-phenyl]-ethyl}-2,2,5-trimethyl-oxazolidine-3-carboxylic acid tert-butyl ester as a yellow oil (3.2 g, 82%). MS (ISP): 499.3 ([M+H).

i) (4S,5S)-4-[2-(4-Amino-phenyl)-ethyl]-2,2,5-trimethyl-oxazolidine-3-carboxylic acid tert-butyl ester To a solution of (4S,5S)-4-{2-[4-(benzhydrylidene-amino)-phenyl]-ethyl}-2,2,5-trimethyl-oxazolidine-3-carboxylic acid tert-butyl ester (3.23 g) in methanol (50 ml) was added ammonium formate (6.13 g). The reaction mixture was degassed by bubbling argon through the mixture for several minutes. 10% Pd/C (207 mg) was added and the reaction mixture was stirred at 60° C. for 1 hour. TLC showed the reaction was complete. The reaction mixture was filtered through celite and concentrated in vacuo. The residue was purified by flash chromatography (silica gel, gradient: 0% to 100% EtOAc in hexane) to afford (4S,5S)-4-[2-(4-amino-phenyl)-ethyl]-2,2,5-trimethyl-oxazolidine-3-carboxylic acid tert-butyl ester as a yellow oil (1.76 g, 81%). MS (ISP): 335.2 ([M+H), 235.2 ([M-C4H8—CO2]+).

j) (4S,5S)-4-(2-{4-[(5-Ethoxy-pyrazine-2-carbonyl)-amino]-phenyl}-ethyl)-2,2,5-trimethyl-oxazolidine-3-carboxylic acid tert-butyl ester To a stirred solution of (4S,5S)-4-[2-(4-amino-phenyl)-ethyl]-2,2,5-trimethyl-oxazolidine-3-carboxylic acid tert-butyl ester (120 mg) and 5-ethoxypyrazine-2-carboxylic acid (72.4 mg) in THF (3 ml) were added N-methylmorpholine (158 µl) and TBTU (230 mg). The reaction mixture was capped and shaken at 50° C. overnight. The crude reaction mixture was concentrated in vacuo and the residue was purified by flash chromatography (silica gel, gradient: 0% to 70% EtOAc in hexane) to afford (4S,5S)-4-(2-{4-[(5-ethoxy-pyrazine-2-carbonyl)-amino]-phenyl}-ethyl)-2,2,5-trimethyl-oxazolidine-3-carboxylic acid tert-butyl ester as a white solid (167 mg, 96%). MS (ISP): 507.3 ([M+Na]+), 502.3 ([M+NH4]+), 485.3 ([M+H]+), 429.3 ([M-C4H8]+).

k) 5-Ethoxy-pyrazine-2-carboxylic acid {4-[2-((4S,5S)-2-amino-5-methyl-4,5-dihydro-oxazol-4-yl)-ethyl]-phenyl}-amide The title compound was obtained in analogy to example 1(g)-1(h) starting from (4S,5S)-4-(2-{4-[(5-ethoxy-pyrazine-2-carbonyl)-amino]-phenyl}-ethyl)-2,2,5-trimethyl-oxazolidine-3-carboxylic acid tert-butyl ester instead of (RS)-4-{4-[3-(4-chloro-phenyl)-ureido]-phenyl}-2,2-dimethyl-oxazolidine-3-carboxylic acid tert-butyl ester. White solid. MS (ISP): 370.2 ([M+H]+).

Example 219

2-Chloro-6-methoxy-pyrimidine-4-carboxylic acid {4-[2-((4S,5S)-2-amino-5-methyl-4,5-dihydro-oxazol-4-yl)-ethyl]-phenyl}-amide

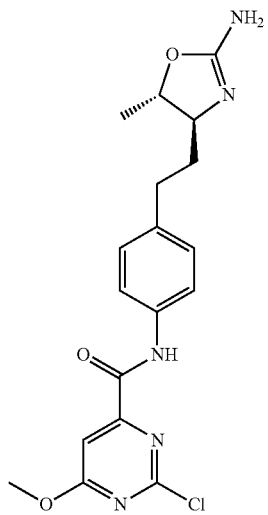 [SMILES: COc1cc(C(=O)Nc2ccc(CC[C@@H]3N=C(N)O[C@H]3C)cc2)nc(Cl)n1]

The title compound was obtained in analogy to example 218 using 2-chloro-6-methoxy-pyrimidine-4-carboxylic acid in place of 5-ethoxypyrazine-2-carboxylic acid in step (j). White solid. MS (ISP) 392.1 ([{37Cl}M+H]+), 390.1 ([{35Cl}M+H]+).

Example 220

N-{4-[2-((4S,5S)-2-Amino-5-methyl-4,5-dihydro-oxazol-4-yl)-ethyl]-phenyl}-2-fluoro-nicotinamide

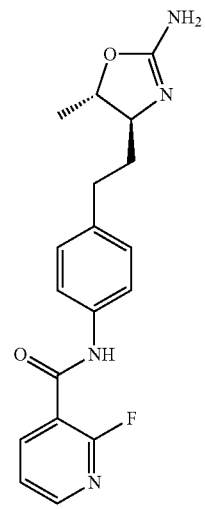 [SMILES: C[C@@H]1OC(N)=N[C@H]1CCc1ccc(NC(=O)c2cccnc2F)cc1]

The title compound was obtained in analogy to example 218 using 2-fluoro-nicotinic acid in place of 5-ethoxypyrazine-2-carboxylic acid in step (j). White solid. MS (ISP) 343.2 ([M+H]$^+$).

Example 221

6-Fluoro-pyridine-2-carboxylic acid {4-[2-((4S,5S)-2-amino-5-methyl-4,5-dihydro-oxazol-4-yl)-ethyl]-phenyl}-amide

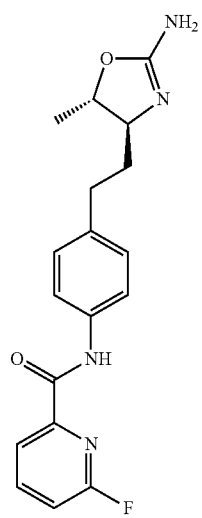 [SMILES: C[C@@H]1OC(N)=N[C@H]1CCc1ccc(NC(=O)c2cccc(F)n2)cc1]

The title compound was obtained in analogy to example 218 using 6-fluoro-nicotinic acid in place of 5-ethoxypyrazine-2-carboxylic acid in step (j). White solid. MS (ISP) 343.2 ([M+H]$^+$).

Example 222

5-Methyl-oxazole-4-carboxylic acid {4-[2-((4S,5S)-2-amino-5-methyl-4,5-dihydro-oxazol-4-yl)-ethyl]-phenyl}-amide

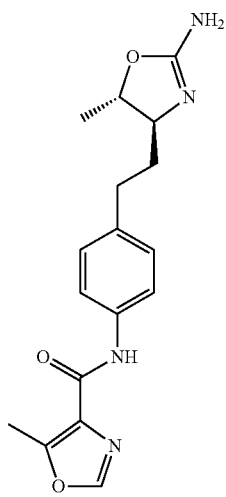 [SMILES: Cc1ocnc1C(=O)Nc1ccc(CC[C@@H]2N=C(N)O[C@H]2C)cc1]

The title compound was obtained in analogy to example 218 using 5-methyl-oxazole-4-carboxylic acid in place of 5-ethoxypyrazine-2-carboxylic acid in step (j). White solid. MS (ISP) 329.2 ([M+H]$^+$).

Example 223

2,5-Dimethyl-oxazole-4-carboxylic acid {4-[2-((4S,5S)-2-amino-5-methyl-4,5-dihydro-oxazol-4-yl)-ethyl]-phenyl}-amide

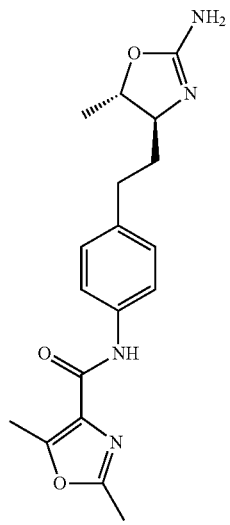 [SMILES: Cc1nc(C(=O)Nc2ccc(CC[C@@H]3N=C(N)O[C@H]3C)cc2)c(C)o1]

The title compound was obtained in analogy to example 218 using 2,5-dimethyl-oxazole-4-carboxylic acid in place of 5-ethoxypyrazine-2-carboxylic acid in step (j). White solid. MS (ISP) 343.2 ([M+H]$^+$).

Example 224

5-Methyl-pyrazine-2-carboxylic acid {4-[2-((4S,5S)-2-amino-5-methyl-4,5-dihydro-oxazol-4-yl)-ethyl]-phenyl}-amide

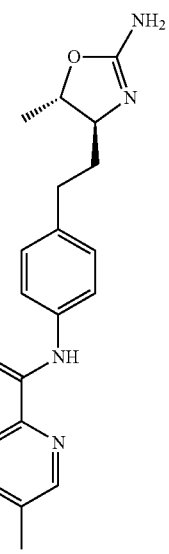

The title compound was obtained in analogy to example 218 using 5-methyl-pyrazine-2-carboxylic acid in place of 5-ethoxypyrazine-2-carboxylic acid in step (j). White solid. MS (ISP) 340.2 ([M+H]+).

Example 225

4,6-Dimethyl-pyridine-2-carboxylic acid {4-[2-((4S, 5S)-2-amino-5-methyl-4,5-dihydro-oxazol-4-yl)-ethyl]-phenyl}-amide

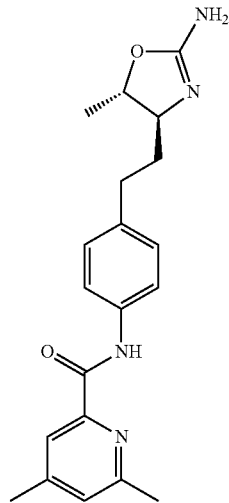 [SMILES: Cc1cc(C)nc(C(=O)Nc2ccc(CC[C@@H]3N=C(N)O[C@H]3C)cc2)c1]

The title compound was obtained in analogy to example 218 using 4,6-dimethyl-pyridine-2-carboxylic acid in place of 5-ethoxypyrazine-2-carboxylic acid in step (j). White solid. MS (ISP) 353.2 ([M+H]+).

Example 226

5-Trifluoromethyl-pyridine-2-carboxylic acid {4-[2-((4S,5S)-2-amino-5-methyl-4,5-dihydro-oxazol-4-yl)-ethyl]-phenyl}-amide

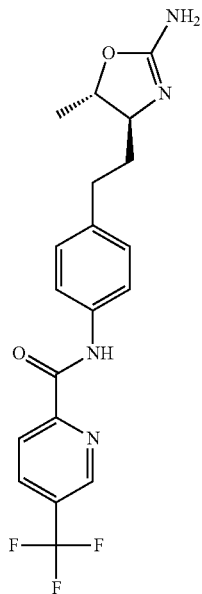 [SMILES: C[C@@H]1OC(N)=N[C@H]1CCc1ccc(NC(=O)c2ccc(C(F)(F)F)cn2)cc1]

The title compound was obtained in analogy to example 218 using 5-trifluoromethyl-pyridine-2-carboxylic acid in place of 5-ethoxypyrazine-2-carboxylic acid in step (j). White solid. MS (ISP) 393.2 ([M+H]+).

Example 227

5-Ethyl-pyrazine-2-carboxylic acid {4-[2-((4S,5S)-2-amino-5-methyl-4,5-dihydro-oxazol-4-yl)-ethyl]-phenyl}-amide

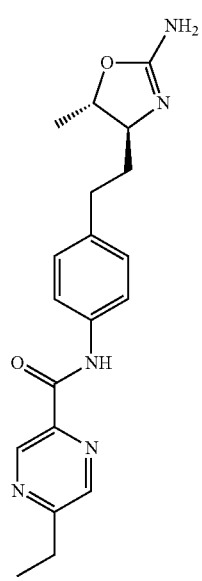 [SMILES: CCc1cnc(C(=O)Nc2ccc(CC[C@@H]3N=C(N)O[C@H]3C)cc2)cn1]

The title compound was obtained in analogy to example 218 using 5-ethyl-pyrazine-2-carboxylic acid in place of 5-ethoxypyrazine-2-carboxylic acid in step (j). White solid. MS (ISP) 354.2 ([M+H]+).

Example 228

(S)-N-(4-(2-(2-Amino-4,5-dihydrooxazol-4-yl)ethyl)phenyl)-2,6-dimethylpyrimidine-4-carboxamide

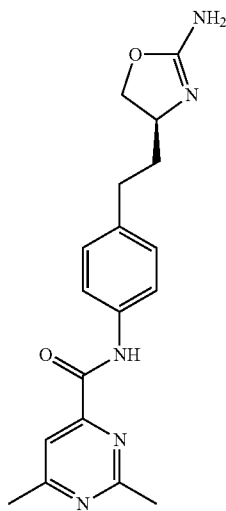 [SMILES: Cc1cc(C(=O)Nc2ccc(CC[C@H]3COC(N)=N3)cc2)nc(C)n1]

The title compound was obtained in analogy to example 83 starting from 2,6-dimethyl-pyrimidine-4-carboxylic acid and (S)-4-[2-(4-amino-phenyl)-ethyl]-4,5-dihydro-oxazol-2-ylamine. White solid. MS (ISP): 340.1 ([M+H]$^+$)

Example 229

(S)-N-(4-(2-(2-Amino-4,5-dihydrooxazol-4-yl)ethyl)phenyl)-5-isopropylpyrazine-2-carboxamide

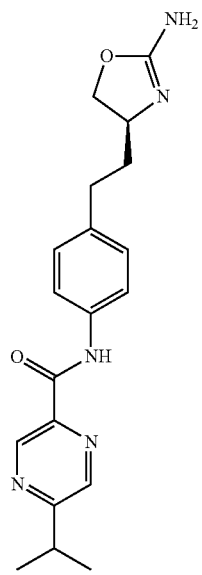

The title compound was obtained in analogy to example 83 starting from 5-isopropylpyrazine-2-carboxylic acid and (S)-4-[2-(4-amino-phenyl)-ethyl]-4,5-dihydro-oxazol-2-ylamine. White solid. MS (ISP): 354.3 ([M+H]$^+$)

Example 230

(S)-N-(4-(2-(2-Amino-4,5-dihydrooxazol-4-yl)ethyl)phenyl)-6-isopropylpyrazine-2-carboxamide

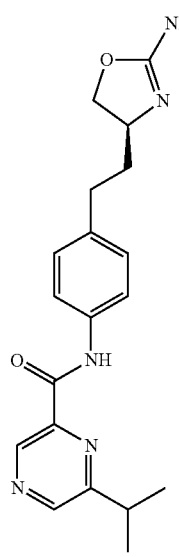

The title compound was obtained in analogy to example 83 starting from 6-isopropylpyrazine-2-carboxylic acid and (S)-4-[2-(4-amino-phenyl)-ethyl]-4,5-dihydro-oxazol-2-ylamine. White solid. MS (ISP): 354.3 ([M+H]$^+$)

Example 231

2-Chloro-6-methoxy-pyrimidine-4-carboxylic acid {4-[2-((S)-2-amino-4,5-dihydro-oxazol-4-yl)-ethyl]-phenyl}-amide

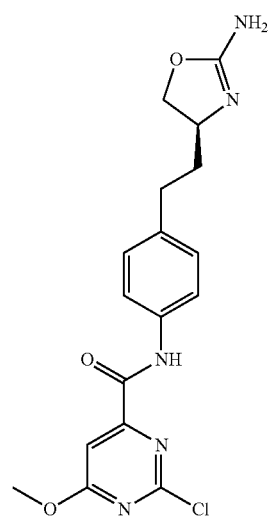 [SMILES: COc1cc(C(=O)Nc2ccc(CC[C@H]3COC(N)=N3)cc2)nc(Cl)n1]

The title compound was obtained in analogy to example 83 starting from 2-chloro-6-methoxy-pyrimidine-4-carboxylic acid and (S)-4-[2-(4-amino-phenyl)-ethyl]-4,5-dihydro-oxazol-2-ylamine. White solid. MS (ISP): 376.3 ([M+H]$^+$)

Example 232

(S)-4-(2-(2-Amino-4,5-dihydrooxazol-4-yl)ethyl)-N-cyclohexylbenzamide

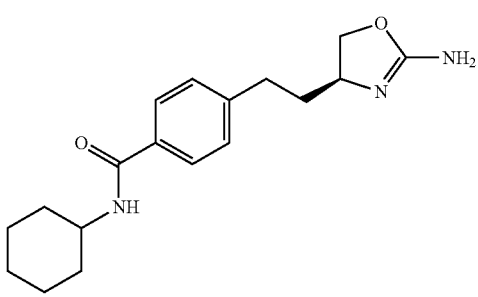 [SMILES: NC1=N[C@@H](CCc2ccc(C(=O)NC3CCCCC3)cc2)CO1]

The title compound was obtained in analogy to example 84 step c and d starting from (S)-4-[2-(4-carboxy-phenyl)-ethyl]-2,2-dimethyl-oxazolidine-3-carboxylic acid tert-butyl ester (this acid is described in example 48) and cyclohexy- Example 233

(S)-4-(2-(2-Amino-4,5-dihydrooxazol-4-yl)ethyl)-N-phenylbenzamide

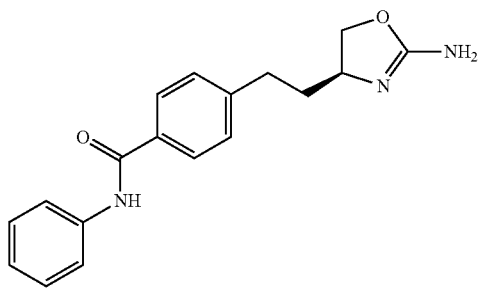 [SMILES: NC1=N[C@@H](CCc2ccc(C(=O)Nc3ccccc3)cc2)CO1]

The title compound was obtained in analogy to example 84 step c and d starting from (5)-4-[2-(4-carboxy-phenyl)-ethyl]-2,2-dimethyl-oxazolidine-3-carboxylic acid tert-butyl ester (this acid is described in example 48) and aniline, using HATU and DIPEA in DMF for the amide coupling step. White solid. MS (ISP): 310.2 ([M+H]$^+$)

The invention claimed is:
1. A compound of formula I

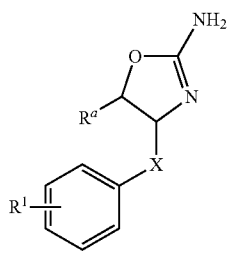

I wherein
$R^a$ is hydrogen or lower alkyl;
$R^1$ is

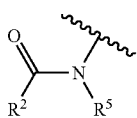

$R^8$ is hydrogen, halogen or aryl optionally substituted by halogen;
X is, —(CH$_2$)$_n$—, —CHRCH$_2$,
R is lower alkyl or lower alkyl substituted by halogen;
$R^2$ is
  a) heterocycloalkyl, optionally substituted by halogen or lower alkyl substituted by halogen; or
  b) (CR'R")$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen;
R' and R" are each independently hydrogen, lower alkoxy or lower alkyl; or together with the C-atom to which they are attached form a cycloalkyl group;
$R^5$ is hydrogen, lower alkyl or aryl substituted by halogen:
$R^6$ and $R^7$ are each independently hydrogen, lower alkyl or (CH$_2$)$_2$—O-lower alkyl;
m is 0, 1 or 2; and
n is 1, 2 or 3;
or a pharmaceutically suitable acid addition salt thereof.
2. The compound of claim 1, having formula IA

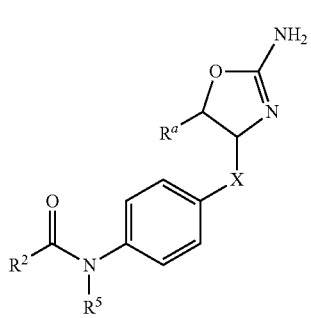

IA $R^a$ is hydrogen or lower alkyl;
X is, —(CH$_2$)$_n$—, —CHRCH$_2$,
R is lower alkyl or lower alkyl substituted by halogen;
$R^2$ is
  a) heterocycloalkyl, optionally substituted by halogen or lower alkyl substituted by halogen; or
  b) (CR'R")$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen;
R' and R" are each independently from each other hydrogen, lower alkoxy or lower alkyl; or together with the C-atom to which they are attached form a cycloalkyl group;
$R^5$ is hydrogen, lower alkyl or aryl substituted by halogen:
$R^6$ and $R^7$ are each independently hydrogen, lower alkyl or (CH$_2$)$_2$—O-lower alkyl;
m is 0, 1 or 2; and
n is 1, 2 or 3;
or a pharmaceutically suitable acid addition salt thereof.
3. The compound of claim 2, wherein X is —(CH$_2$)$_n$—.
4. The compound of claim 3, selected from the group consisting of
1-{4-[2-((S)-2-amino-4,5-dihydro-oxazol-4-yl)-ethyl]-phenyl}-3-(4-chloro-phenyl)-urea;
N-{4-[3-((S)-2-amino-4,5-dihydro-oxazol-4-yl)-propyl]-phenyl}-4-chloro-benzamide;
N-{4-[2-((S)-2-amino-4,5-dihydro-oxazol-4-yl)-ethyl]-phenyl}-4-chloro-benzamide;
1-{4-[2-((S)-2-amino-4,5-dihydro-oxazol-4-yl)-ethyl]-phenyl}-3-(3,4-dichloro-phenyl)-urea;
1-{4-[2-((S)-2-amino-4,5-dihydro-oxazol-4-yl)-ethyl]-phenyl}-3-(4-trifluoromethyl-phenyl)-urea;
N-{4-[2-((S)-2-amino-4,5-dihydro-oxazol-4-yl)-ethyl]-phenyl}-4-fluoro-benzamide;
N-{4-[2-((S)-2-amino-4,5-dihydro-oxazol-4-yl)-ethyl]-phenyl}-4-trifluoromethyl-benzamide;

N-{4-[2-((S)-2-amino-4,5-dihydro-oxazol-4-yl)-ethyl]-phenyl}-3-chloro-benzamide;
N-{4-[2-((S)-2-amino-4,5-dihydro-oxazol-4-yl)-ethyl]-phenyl}-6-chloro-nicotinamide; and
5-chloro-pyridine-2-carboxylic acid {4-[2-((S)-2-amino-4,5-dihydro-oxazol-4-yl)-ethyl]-phenyl}-amide.

5. The compound of claim 3, selected from the group consisting of 5-chloro-pyrimidine-2-carboxylic acid {4-[2-((S)-2-amino-4,5-dihydro-oxazol-4-yl)-ethyl]-phenyl}-amide;
1-{4-[2-((S)-2-amino-4,5-dihydro-oxazol-4-yl)-ethyl]-phenyl}-3-(5-chloro-pyridin-2-yl)-urea;
1-{4-[2-((S)-2-amino-4,5-dihydro-oxazol-4-yl)-ethyl]-phenyl}-3-(6-chloro-pyridin-3-yl)-urea;
4,4-difluoro-cyclohexanecarboxylic acid {4-[2-((S)-2-amino-4,5-dihydro-oxazol-4-yl)-ethyl]-phenyl}-amide;
1-methyl-cyclopropanecarboxylic acid {4-[2-((S)-2-amino-4,5-dihydro-oxazol-4-yl)-ethyl]-phenyl}-amide;
cyclopentanecarboxylic acid {4-[2-((S)-2-amino-4,5-dihydro-oxazol-4-yl)-ethyl]-phenyl}-amide;
3,3-difluoro-cyclobutanecarboxylic acid {4-[2-((S)-2-amino-4,5-dihydro-oxazol-4-yl)-ethyl]-phenyl}-amide;
cyclobutanecarboxylic acid {4-[2-((S)-2-amino-4,5-dihydro-oxazol-4-yl)-ethyl]-phenyl}-amide;
cyclopropanecarboxylic acid {4-[2-((S)-2-amino-4,5-dihydro-oxazol-4-yl)-ethyl]-phenyl}-amide; and
cyclohexanecarboxylic acid {4-[2-((S)-2-amino-4,5-dihydro-oxazol-4-yl)-ethyl]-phenyl}-amide.

6. The compound of claim 3, selected from the group consisting of 1-trifluoromethyl-cyclopropanecarboxylic acid {4-[2-((S)-2-amino-4,5-dihydro-oxazol-4-yl)-ethyl]-phenyl}-amide;
1-(4-chloro-phenyl)-cyclopropanecarboxylic acid {4-[2-((S)-2-amino-4,5-dihydro-oxazol-4-yl)-ethyl]-phenyl}-amide;
5-trifluoromethyl-pyridine-2-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-trifluoromethyl-nicotinamide;
1-{4-[2-((S)-2-amino-4,5-dihydro-oxazol-4-yl)-ethyl]-phenyl}-3-(4-fluoro-phenyl)-imidazolidin-2-one;
N-{4-[2-((S)-2-amino-4,5-dihydro-oxazol-4-yl)-ethyl]-phenyl}-2-(4-chloro-phenyl)-propionamide;
N-{4-[2-((S)-2-amino-4,5-dihydro-oxazol-4-yl)-ethyl]-phenyl}-4-cyano-benzamide;
N-{4-[2-((S)-2-amino-4,5-dihydro-oxazol-4-yl)-ethyl]-phenyl}-4-ethoxy-benzamide;
N-{4-[2-((S)-2-amino-4,5-dihydro-oxazol-4-yl)-ethyl]-phenyl}-4-propyl-benzamide; and
N-{4-[2-((S)-2-amino-4,5-dihydro-oxazol-4-yl)-ethyl]-phenyl}-4-ethynyl-benzamide.

7. The compound of claim 3, selected from the group consisting of
N-{4-[2-((S)-2-amino-4,5-dihydro-oxazol-4-yl)-ethyl]-phenyl}-4-methoxymethyl-benzamide;
N-{4-[2-((S)-2-amino-4,5-dihydro-oxazol-4-yl)-ethyl]-phenyl}-2-(4-ethoxy-phenyl)-acetamide;
N-{4-[2-((S)-2-amino-4,5-dihydro-oxazol-4-yl)-ethyl]-phenyl}-2-(4-methoxy-phenyl)-acetamide;
N-{4-[2-((S)-2-amino-4,5-dihydro-oxazol-4-yl)-ethyl]-phenyl}-2-(4-fluoro-phenyl)-acetamide;
N-{4-[2-((S)-2-amino-4,5-dihydro-oxazol-4-yl)-ethyl]-phenyl}-2-(4-chloro-phenyl)-acetamide;
N-{4-[2-((S)-2-amino-4,5-dihydro-oxazol-4-yl)-ethyl]-phenyl}-4-methoxy-benzamide;
N-{4-[2-((S)-2-amino-4,5-dihydro-oxazol-4-yl)-ethyl]-phenyl}-2-(4-chloro-phenyl)-isobutyramide;
N-{4-[2-((S)-2-amino-4,5-dihydro-oxazol-4-yl)-ethyl]-phenyl}-2-(4-bromo-phenyl)-2-methoxy-acetamide;
(S)-N-{4-[2-((S)-2-amino-4,5-dihydro-oxazol-4-yl)-ethyl]-phenyl}-2-methoxy-2-phenyl-acetamide; and
N-{4-[2-((S)-2-amino-4,5-dihydro-oxazol-4-yl)-ethyl]-phenyl}-2-(4-chloro-phenyl)-2-methoxy-acetamide.

8. The compound of claim 3, selected from the group consisting of
4-trifluoromethyl-cyclohexanecarboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-3-(2-chloro-phenyl)-propionamide;
N-{4-[2-((S)-2-amino-4,5-dihydro-oxazol-4-yl)-ethyl]-phenyl}-2-(3-trifluoromethyl-phenyl)-propionamide;
N-{4-[2-((S)-2-amino-4,5-dihydro-oxazol-4-yl)-ethyl]-phenyl}-2-(3-trifluoromethoxy-phenyl)-propionamide;
2-methoxy-pyrimidine-5-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-pyrazol-1-yl-nicotinamide;
1H-benzoimidazole-2-carboxylic acid {4-[2-((S)-2-amino-4,5-dihydro-oxazol-4-yl)-ethyl]-phenyl}-amide;
3,5-difluoro-pyridine-2-carboxylic acid {4-[2-((S)-2-amino-4,5-dihydro-oxazol-4-yl)-ethyl]-phenyl}-amide;
6-fluoro-pyridine-2-carboxylic acid {4-[2-((S)-2-amino-4,5-dihydro-oxazol-4-yl)-ethyl]-phenyl}-amide; and
6-chloro-3-fluoro-pyridine-2-carboxylic acid {4-[2-((S)-2-amino-4,5-dihydro-oxazol-4-yl)-ethyl]-phenyl}-amide.

9. The compound of claim 3, selected from the group consisting of
4-chloro-pyridine-2-carboxylic acid {4-[2-((S)-2-amino-4,5-dihydro-oxazol-4-yl)-ethyl]-phenyl}-amide;
quinoline-2-carboxylic acid {4-[2-((S)-2-amino-4,5-dihydro-oxazol-4-yl)-ethyl]-phenyl}-amide;
5-bromo-pyridine-2-carboxylic acid {4-[2-((S)-2-amino-4,5-dihydro-oxazol-4-yl)-ethyl]-phenyl}-amide;
isoquinoline-1-carboxylic acid {4-[2-((S)-2-amino-4,5-dihydro-oxazol-4-yl)-ethyl]-phenyl}-amide;
1-{4-[2-((S)-2-amino-4,5-dihydro-oxazol-4-yl)-ethyl]-phenyl}-3-(4-fluoro-phenyl)-urea;
1-{4-[2-((S)-2-amino-4,5-dihydro-oxazol-4-yl)-ethyl]-phenyl}-3-(3-chloro-phenyl)-urea;
(S)-N-(4-(2-(2-amino-4,5-dihydrooxazol-4-yl)ethyl)phenyl)-5-fluoropicolinamide;
N-{4-[2-((S)-2-amino-4,5-dihydro-oxazol-4-yl)-ethyl]-phenyl}-6-methoxy-nicotinamide;
N-{4-[2-((S)-2-amino-4,5-dihydro-oxazol-4-yl)-ethyl]-phenyl}-6-methyl-nicotinamide; and
(S)-N-(4-(2-(2-amino-4,5-dihydrooxazol-4-yl)ethyl)phenyl)-2-fluoronicotinamide.

10. The compound of claim 3, selected from the group consisting of
N-{4-[2-((S)-2-amino-4,5-dihydro-oxazol-4-yl)-ethyl]-phenyl}-5-fluoro-nicotinamide;
3-chloro-5-trifluoromethyl-pyridine-2-carboxylic acid {4-[2-((S)-2-amino-4,5-dihydro-oxazol-4-yl)-ethyl]-phenyl}-amide;

[1,6]naphthyridine-2-carboxylic acid {4-[2-((S)-2-amino-4,5-dihydro-oxazol-4-yl)-ethyl]-phenyl}-amide;
[1,8]naphthyridine-2-carboxylic acid {4-[2-((S)-2-amino-4,5-dihydro-oxazol-4-yl)-ethyl]-phenyl}-amide;
N-{4-[2-((S)-2-amino-4,5-dihydro-oxazol-4-yl)-ethyl]-phenyl}-6-bromo-nicotinamide;
N-{4-[2-((S)-2-amino-4,5-dihydro-oxazol-4-yl)-ethyl]-phenyl}-2,5-difluoro-nicotinamide;
N-{4-[2-((S)-2-amino-4,5-dihydro-oxazol-4-yl)-ethyl]-phenyl}-5,6-dichloro-nicotinamide;
N-{4-[2-((S)-2-amino-4,5-dihydro-oxazol-4-yl)-ethyl]-phenyl}-2,6-difluoro-nicotinamide;
N-{4-[2-((S)-2-amino-4,5-dihydro-oxazol-4-yl)-ethyl]-phenyl}-6-cyano-nicotinamide; and
6-bromo-pyridine-2-carboxylic acid {4-[2-((S)-2-amino-4,5-dihydro-oxazol-4-yl)-ethyl]-phenyl}-amide.

11. The compound of claim 3, selected from the group consisting of
N-{4-[2-((S)-2-amino-4,5-dihydro-oxazol-4-yl)-ethyl]-phenyl}-6-(2,2,2-trifluoro-ethoxy)-nicotinamide;
N-{4-[2-((S)-2-amino-4,5-dihydro-oxazol-4-yl)-ethyl]-phenyl}-2-methoxy-nicotinamide;
(S)-N-(4-(2-(2-amino-4,5-dihydrooxazol-4-yl)ethyl)phenyl)-5-methoxypicolinamide;
(S)-N-(4-(2-(2-amino-4,5-dihydrooxazol-4-yl)ethyl)phenyl)-5-cyanopicolinamide;
(S)-N-(4-(2-(2-amino-4,5-dihydrooxazol-4-yl)ethyl)phenyl)-6-fluoronicotinamide;
(S)-N-(4-(2-(2-amino-4,5-dihydrooxazol-4-yl)ethyl)phenyl)-6-chloropyridazine-3-carboxamide;
(S)-N-(4-(2-(2-amino-4,5-dihydrooxazol-4-yl)ethyl)phenyl)-2-(piperidin-1-yl)pyrimidine-5-carboxamide;
(S)-N-(4-(2-(2-amino-4,5-dihydrooxazol-4-yl)ethyl)phenyl)-5-chloronicotinamide;
(S)-N-(4-(2-(2-amino-4,5-dihydrooxazol-4-yl)ethyl)phenyl)-2-(3,4-dichlorophenyl)-2,2-difluoroacetamide; and
(S)-N-(4-(2-(2-amino-4,5-dihydrooxazol-4-yl)ethyl)phenyl)-5-chloropyrazine-2-carboxamide.

12. The compound of claim 3, selected from the group consisting of
(S)-N-(4-(2-(2-amino-4,5-dihydrooxazol-4-yl)ethyl)phenyl)-5-methoxypyrazine-2-carboxamide;
(S)-N-(4-(2-(2-amino-4,5-dihydrooxazol-4-yl)ethyl)phenyl)-6-methoxypyrazine-2-carboxamide;
(S)-N-(4-(2-(2-amino-4,5-dihydrooxazol-4-yl)ethyl)phenyl)-5-methylpyrazine-2-carboxamide;
(S)-4-(2-(2-amino-4,5-dihydrooxazol-4-yl)ethyl)-N-(5-chloropyridin-2-yl)benzamide;
(S)-N-(4-(2-(2-amino-4,5-dihydrooxazol-4-yl)ethyl)phenyl)-4-chloro-2-fluorobenzamide;
(S)-N-(4-(2-(2-amino-4,5-dihydrooxazol-4-yl)ethyl)phenyl)-2,4-dichlorobenzamide;
(S)-N-(4-(2-(2-amino-4,5-dihydrooxazol-4-yl)ethyl)phenyl)-4-chloro-2-methoxybenzamide;
(S)-4-(2-(2-amino-4,5-dihydrooxazol-4-yl)ethyl)-N-(4-cyanophenyl)benzamide;
(S)-4-(2-(2-amino-4,5-dihydrooxazol-4-yl)ethyl)-N-(4-ethynylphenyl)benzamide; and
{4-[2-((S)-2-amino-4,5-dihydro-oxazol-4-yl)-ethyl]-phenyl}-carbamic acid 4-chloro-benzyl ester.

13. The compound of claim 3, selected from the group consisting of
{4-[2-((S)-2-amino-4,5-dihydro-oxazol-4-yl)-ethyl]-phenyl}-carbamic acid 4-methoxy-phenyl ester;
{4-[2-((S)-2-amino-4,5-dihydro-oxazol-4-yl)-ethyl]-phenyl}-carbamic acid 4-fluoro-phenyl ester;
{4-[2-((S)-2-amino-4,5-dihydro-oxazol-4-yl)-ethyl]-phenyl}-carbamic acid 3-trifluoromethyl-phenyl ester;
1-{4-[2-((S)-2-amino-4,5-dihydro-oxazol-4-yl)-ethyl]-phenyl}-3-(5-chloro-pyrimidin-2-yl)-urea;
(S)-N-(4-(2-(2-amino-4,5-dihydrooxazol-4-yl)ethyl)phenyl)-5-ethoxypicolinamide;
(S)-N-(4-(2-(2-amino-4,5-dihydrooxazol-4-yl)ethyl)phenyl)-5-chloro-4-methylpicolinamide;
(S)-N-(4-(2-(2-amino-4,5-dihydrooxazol-4-yl)ethyl)phenyl)-4-chloro-6-methylpicolinamide;
(S)-N-(4-(2-(2-amino-4,5-dihydrooxazol-4-yl)ethyl)phenyl)-4,6-dimethylpicolinamide;
(S)-N-(4-(2-(2-amino-4,5-dihydrooxazol-4-yl)ethyl)phenyl)-4,6-dichloropicolinamide; and
(S)-N-(4-(2-(2-amino-4,5-dihydrooxazol-4-yl)ethyl)phenyl)-5-(trifluoromethyl)pyrazine-2-carboxamide.

14. The compound of claim 3, selected from the group consisting of
(S)-N-(4-(2-(2-amino-4,5-dihydrooxazol-4-yl)ethyl)phenyl)-6-chloropyrazine-2-carboxamide;
(S)-N-(4-(2-(2-amino-4,5-dihydrooxazol-4-yl)ethyl)phenyl)-5-ethoxypyrazine-2-carboxamide;
(S)-N-(4-(2-(2-amino-4,5-dihydrooxazol-4-yl)ethyl)phenyl)-5-morpholinopyrazine-2-carboxamide;
(S)-N-(4-(2-(2-amino-4,5-dihydrooxazol-4-yl)ethyl)phenyl)-6-chloro-5-methoxypicolinamide;
(S)-N-(4-(2-(2-amino-4,5-dihydrooxazol-4-yl)ethyl)phenyl)-5-chlorothiophene-2-carboxamide;
(S)-N-(4-(2-(2-amino-4,5-dihydrooxazol-4-yl)ethyl)phenyl)-3-cyclopropylpropanamide;
(S)-N-(4-(2-(2-amino-4,5-dihydrooxazol-4-yl)ethyl)phenyl)-5-methylpicolinamide;
(S)-N-(4-(2-(2-amino-4,5-dihydrooxazol-4-yl)ethyl)phenyl)-2-methylisonicotinamide;
(S)-N-(4-(2-(2-amino-4,5-dihydrooxazol-4-yl)ethyl)phenyl)-2-chloroisonicotinamide; and
(S)-N-(4-(2-(2-amino-4,5-dihydrooxazol-4-yl)ethyl)phenyl)-2-chloro-3-fluoroisonicotinamide.

15. The compound of claim 3, selected from the group consisting of
(S)-N-(4-(2-(2-amino-4,5-dihydrooxazol-4-yl)ethyl)phenyl)-2,6-dichloroisonicotinamide;
(S)-N-(4-(2-(2-amino-4,5-dihydrooxazol-4-yl)ethyl)phenyl)-5-ethylpicolinamide;
(S)-N-(4-(2-(2-amino-4,5-dihydrooxazol-4-yl)ethyl)phenyl)-2,5-dimethyloxazole-4-carboxamide;
(S)-N-(4-(2-(2-amino-4,5-dihydrooxazol-4-yl)ethyl)phenyl)-2-(dimethylamino)-5-isopropylthiazole-4-carboxamide;
(S)-N-(4-(2-(2-amino-4,5-dihydrooxazol-4-yl)ethyl)phenyl)-2,6-dimethoxypyrimidine-4-carboxamide;
(S)-N-(4-(2-(2-amino-4,5-dihydrooxazol-4-yl)ethyl)phenyl)-5-methyloxazole-4-carboxamide;
(S)-N-(4-(2-(2-amino-4,5-dihydrooxazol-4-yl)ethyl)phenyl)-4-chloro-1-methyl-1H-pyrazole-3-carboxamide;
(S)-N-(4-(2-(2-amino-4,5-dihydrooxazol-4-yl)ethyl)phenyl)-1-(difluoromethyl)-1H-pyrazole-3-carboxamide;
(S)-N-(4-(2-(2-amino-4,5-dihydrooxazol-4-yl)ethyl)phenyl)-2-tert-butylisonicotinamide; and
(S)-N-(4-(2-(2-amino-4,5-dihydrooxazol-4-yl)ethyl)phenyl)-2-isopropylisonicotinamide.

16. The compound of claim 3, selected from the group consisting of
(S)-N-(4-(2-(2-amino-4,5-dihydrooxazol-4-yl)ethyl)phenyl)-2,4'-bipyridine-4-carboxamide;
(S)-N-(4-(2-(2-amino-4,5-dihydrooxazol-4-yl)ethyl)phenyl)-5-methylthiophene-2-carboxamide;

(S)-N-(4-(2-(2-amino-4,5-dihydrooxazol-4-yl)ethyl)phenyl)-4,5-dimethylthiophene-2-carboxamide;
2-ethyl-6-methoxy-pyrimidine-4-carboxylic acid {4-[2-((S)-2-amino-4,5-dihydro-oxazol-4-yl)-ethyl]-phenyl}-amide;
N-(4-(2-((4S,5S)-2-amino-5-methyl-4,5-dihydrooxazol-4-yl)ethyl)phenyl)-4-chlorobenzamide;
N-(4-(2-((4S,5R)-2-amino-5-methyl-4,5-dihydrooxazol-4-yl)ethyl)phenyl)-4-chlorobenzamide;
2-isopropyl-6-methoxy-pyrimidine-4-carboxylic acid {4-[2-((S)-2-amino-4,5-dihydro-oxazo-4-yl)-ethyl]-phenyl}-amide;
(S)-N-(4-(2-(2-amino-4,5-dihydrooxazol-4-yl)ethyl)phenyl)-5-ethylpyrazine-2-carboxamide;
(S)-N-(4-(2-(2-amino-4,5-dihydrooxazol-4-yl)ethyl)phenyl)-4-cyclopropyl-2-(trifluoromethyl)pyrimidine-5-carboxamide;
(S)-N-(4-(2-(2-amino-4,5-dihydrooxazol-4-yl)ethyl)phenyl)-6-ethylpyrazine-2-carboxamide; and
(S)-N-(4-(2-(2-amino-4,5-dihydrooxazol-4-yl)ethyl)phenyl)-5-ethyloxazole-4-carboxamide.

17. The compound of claim 3, selected from the group consisting of
(S)-N-(4-(2-(2-amino-4,5-dihydrooxazol-4-yl)ethyl)phenyl)-5-cyclopropyloxazole-4-carboxamide;
(S)-N-(4-(2-(2-amino-4,5-dihydrooxazol-4-yl)ethyl)phenyl)-5-isopropyloxazole-4-carboxamide;
(S)-N-(4-(2-(2-amino-4,5-dihydrooxazol-4-yl)ethyl)phenyl)-2-methyl-5-(trifluoromethyl)oxazole-4-carboxamide;
(S)-N-(4-(2-(2-amino-4,5-dihydrooxazol-4-yl)ethyl)phenyl)-2-ethyloxazole-4-carboxamide;
5-ethoxy-pyrazine-2-carboxylic acid {4-[2-((4S,5S)-2-amino-5-methyl-4,5-dihydro-oxazol-4-yl)-ethyl]-phenyl}-amide;
2-chloro-6-methoxy-pyrimidine-4-carboxylic acid {4-[2-((4S,5S)-2-amino-5-methyl-4,5-dihydro-oxazol-4-yl)-ethyl]-phenyl}-amide;
5-methyl-oxazole-4-carboxylic acid {4-[2-((4S,5S)-2-amino-5-methyl-4,5-dihydro-oxazol-4-yl)-ethyl]-phenyl}-amide;
5-trifluoromethyl-pyridine-2-carboxylic acid {4-[2-((4S,5S)-2-amino-5-methyl-4,5-dihydro-oxazol-4-yl)-ethyl]-phenyl}-amide;
5-ethyl-pyrazine-2-carboxylic acid {4-[2-((4S,5S)-2-amino-5-methyl-4,5-dihydro-oxazol-4-yl)-ethyl]-phenyl}-amide;
(S)-N-(4-(2-(2-amino-4,5-dihydrooxazol-4-yl)ethyl)phenyl)-6-isopropylpyrazine-2-carboxamide;
and
2-chloro-6-methoxy-pyrimidine-4-carboxylic acid {4-[2-((S)-2-amino-4,5-dihydro-oxazol-4-yl)-ethyl]-phenyl}-amide.

18. The compound of claim 2, wherein X is —CHRCH$_2$—.

19. The compound of claim 18, selected from the group consisting of
1-{4-[(S)-1-((S)-2-amino-4,5-dihydro-oxazol-4-ylmethyl)-propyl]-phenyl}-3-(4-fluoro-phenyl)-urea and
1-{4-[(S)-1-((S)-2-amino-4,5-dihydro-oxazol-4-ylmethyl)-propyl]-phenyl}-3-(4-trifluoromethyl-phenyl)-urea.

20. A pharmaceutical composition comprising a therapeutically effective amount of a compound of formula I

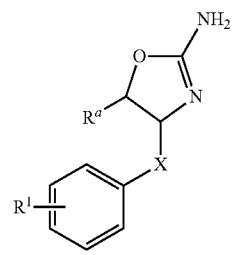

wherein
$R^a$ is hydrogen or lower alkyl;
$R^1$ is

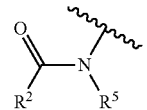

X is, —(CH$_2$)$_n$—, —CHRCH$_2$,
R is lower alkyl or lower alkyl substituted by halogen;
$R^2$ is
 a) heterocycloalkyl, optionally substituted by halogen or lower alkyl substituted by halogen; or
 b) (CR'R")$_m$-heteroaryl, optionally substituted by halogen, lower alkoxy, lower alkyl substituted by halogen, lower alkoxy substituted by halogen, lower alkyl, cycloalkyl, NHC(O)-lower alkyl, cyano, S(O)$_2$-lower alkyl, NR$^6$R$^7$, or by heteroaryl or heterocycloalkyl each of which is optionally substituted by halogen;
R' and R" are each independently hydrogen, lower alkoxy or lower alkyl; or together with the C-atom to which they are attached form a cycloalkyl group;
$R^5$ is hydrogen, lower alkyl or aryl substituted by halogen:
$R^6$ and $R^7$ are each independently hydrogen, lower alkyl or (CH$_2$)$_2$—O-lower alkyl;
m is 0, 1 or 2; and
n is 1, 2 or 3;
or a pharmaceutically suitable acid addition salt thereof and a pharmaceutically acceptable carrier.

* * * * *